(12) United States Patent
Carlberg et al.

(10) Patent No.: US 12,279,647 B2
(45) Date of Patent: Apr. 22, 2025

(54) VAPORIZER CARTRIDGE

(71) Applicant: Pax Labs, Inc., San Francisco, CA (US)

(72) Inventors: David Carlberg, Portland, OR (US); Andrew Cushing, Baltimore, MD (US); Philipe Manoux, Oakland, CA (US); Robyn Nariyoshi, San Francisco, CA (US); Alexander Weiss, Oakland, CA (US)

(73) Assignee: Pax Labs, Inc., San Francisco, CA (US)

( * ) Notice: Subject to any disclaimer, the term of this patent is extended or adjusted under 35 U.S.C. 154(b) by 918 days.

(21) Appl. No.: 17/131,614

(22) Filed: Dec. 22, 2020

(65) Prior Publication Data

US 2021/0219608 A1    Jul. 22, 2021

Related U.S. Application Data

(60) Provisional application No. 63/081,150, filed on Sep. 21, 2020, provisional application No. 63/058,125, filed on Jul. 29, 2020, provisional application No. 62/985,314, filed on Mar. 4, 2020, provisional application No. 62/968,888, filed on Jan. 31, 2020, provisional application No. 62/953,172, filed on Dec. 23, 2019.

(51) Int. Cl.
*A24F 40/42* (2020.01)
*A24F 40/10* (2020.01)
*A24F 40/44* (2020.01)
*A24F 40/46* (2020.01)
*A24F 40/70* (2020.01)

(52) U.S. Cl.
CPC .............. *A24F 40/42* (2020.01); *A24F 40/10* (2020.01); *A24F 40/44* (2020.01); *A24F 40/46* (2020.01); *A24F 40/70* (2020.01)

(58) Field of Classification Search
CPC ........... A24F 40/42; A24F 40/44; A24F 40/46
See application file for complete search history.

(56) References Cited

U.S. PATENT DOCUMENTS

| | | |
|---|---|---|
| 7,258,868 B2 | 8/2007 | Welch et al. |
| 8,479,747 B2 | 7/2013 | O'Connell |
| D690,461 S | 9/2013 | Chen |

(Continued)

FOREIGN PATENT DOCUMENTS

| | | |
|---|---|---|
| WO | WO-2017139595 A1 | 8/2017 |
| WO | WO-2019119612 A1 | 6/2019 |

(Continued)

*Primary Examiner* — Michael J Felton
*Assistant Examiner* — Courtney G Culbert
(74) *Attorney, Agent, or Firm* — Mintz, Levin, Cohn, Ferris, Glovsky and Popeo, P.C.

(57) ABSTRACT

A cartridge includes an atomizer assembly, a reservoir, and a mouthpiece. The atomizer assembly may heat a vaporizable material to generate an inhalable vapor. The reservoir may store the vaporizable material and include a wick housing and a reservoir body. The wick housing may surround at least a portion of the atomizer assembly and form a proximal wall of the reservoir. The reservoir body may be coupled to the wick housing and form a distal wall of the reservoir. The mouthpiece may deliver the inhalable vapor.

20 Claims, 63 Drawing Sheets

(56) References Cited

U.S. PATENT DOCUMENTS

| | | |
|---|---|---|
| 8,550,068 B2 | 10/2013 | Terry et al. |
| 8,757,147 B2 | 6/2014 | Terry et al. |
| 8,757,169 B2 | 6/2014 | Gysland |
| 8,899,239 B2 | 12/2014 | Hon |
| 8,955,522 B1 | 2/2015 | Bowen et al. |
| D730,571 S | 5/2015 | Chen |
| 9,095,175 B2 | 8/2015 | Terry et al. |
| 9,226,525 B2 | 1/2016 | Liu |
| D749,261 S | 2/2016 | Chen |
| D750,321 S | 2/2016 | Chen |
| 9,308,336 B2 | 4/2016 | Newton |
| D769,519 S | 10/2016 | Chen |
| 9,497,993 B2 | 11/2016 | Vallar |
| 9,497,998 B2 | 11/2016 | Chen |
| D774,247 S | 12/2016 | Chen |
| 9,555,203 B2 | 1/2017 | Terry et al. |
| D778,831 S | 2/2017 | Chen |
| 9,572,373 B2 | 2/2017 | Chen |
| 9,603,389 B2 | 3/2017 | Chen |
| 9,603,390 B2 | 3/2017 | Li et al. |
| 9,648,909 B2 | 5/2017 | Zhou et al. |
| 9,655,890 B2 | 5/2017 | Hearn et al. |
| 9,668,520 B2 | 6/2017 | Boldrini |
| 9,675,118 B2 | 6/2017 | Chen |
| 9,693,584 B2 | 7/2017 | Hearn et al. |
| 9,723,870 B2 | 8/2017 | Hearn |
| 9,743,691 B2 | 8/2017 | Minskoff et al. |
| 9,750,282 B2 | 9/2017 | Liu |
| 9,770,054 B2 | 9/2017 | Chen |
| D800,381 S | 10/2017 | Chen |
| 9,795,167 B2 | 10/2017 | Chen |
| 9,795,169 B1 | 10/2017 | Zhu |
| 9,795,170 B1 | 10/2017 | Zhu |
| 9,814,264 B2 | 11/2017 | Coelho Belo Fernandes De Carvalho |
| 9,826,781 B1 | 11/2017 | Zhu |
| 9,848,646 B2 | 12/2017 | Liu |
| 9,861,129 B2 | 1/2018 | Liu et al. |
| 9,861,134 B2 | 1/2018 | Zhu |
| 9,861,135 B2 | 1/2018 | Chen |
| 9,877,517 B2 | 1/2018 | Liu |
| 9,883,698 B2 | 2/2018 | Zhu |
| 9,883,699 B2 | 2/2018 | Zhu |
| 9,888,722 B2 | 2/2018 | Chen |
| 9,888,727 B2 | 2/2018 | Li et al. |
| 9,901,119 B2 | 2/2018 | Liu |
| 9,907,341 B1 | 3/2018 | Zhu |
| 9,927,452 B2 | 3/2018 | Watson et al. |
| 9,936,731 B2 | 4/2018 | Hopps |
| 9,943,108 B2 | 4/2018 | Lord |
| 9,949,511 B2 | 4/2018 | Liu |
| D817,544 S | 5/2018 | Chen |
| 9,955,726 B2 | 5/2018 | Brinkley et al. |
| 9,961,940 B2 | 5/2018 | Anderson, Jr. et al. |
| 9,974,335 B2 | 5/2018 | Lord |
| 9,980,513 B2 | 5/2018 | Chen |
| 9,980,517 B2 | 5/2018 | Zhu |
| 9,980,520 B2 | 5/2018 | Hearn et al. |
| 9,993,028 B2 | 6/2018 | Li et al. |
| 9,999,245 B1 | 6/2018 | Zhu |
| 9,999,248 B2 | 6/2018 | Liu |
| 9,999,255 B2 | 6/2018 | Li et al. |
| 10,004,270 B2 | 6/2018 | Li et al. |
| 10,004,271 B2 | 6/2018 | Li et al. |
| 10,004,272 B2 | 6/2018 | Li et al. |
| 10,004,274 B2 | 6/2018 | Li et al. |
| D823,534 S | 7/2018 | Chen |
| D823,536 S | 7/2018 | Lai |
| 10,015,989 B2 | 7/2018 | Davis et al. |
| 10,034,494 B2 | 7/2018 | Ampolini et al. |
| D825,834 S | 8/2018 | Chen |
| D826,471 S | 8/2018 | Wang |
| D827,195 S | 8/2018 | Chen |
| 10,039,326 B2 | 8/2018 | Wu |
| 10,051,889 B2 | 8/2018 | Chen |
| 10,058,126 B2 | 8/2018 | Chen |
| D828,953 S | 9/2018 | Chen |
| 10,070,668 B2 | 9/2018 | Li et al. |
| 10,080,387 B2 | 9/2018 | Phillips et al. |
| D829,648 S | 10/2018 | Chen |
| D829,982 S | 10/2018 | Wang |
| D829,983 S | 10/2018 | Wang |
| 10,111,469 B2 | 10/2018 | Zhu |
| 10,117,461 B2 | 11/2018 | Chen |
| 10,123,568 B1 | 11/2018 | Zhu |
| 10,136,675 B2 | 11/2018 | Li et al. |
| 10,149,496 B2 | 12/2018 | Chen |
| 10,172,393 B2 | 1/2019 | Li et al. |
| 10,178,880 B2 | 1/2019 | Dubief |
| 10,182,599 B2 | 1/2019 | Zhu |
| 10,188,146 B2 | 1/2019 | Chen |
| 10,188,148 B2 | 1/2019 | Althorpe et al. |
| 10,194,694 B2 | 2/2019 | Davis et al. |
| 10,195,370 B2 | 2/2019 | Chen |
| 10,207,914 B2 | 2/2019 | Murison et al. |
| 10,219,546 B2 | 3/2019 | Li et al. |
| D846,796 S | 4/2019 | Pan |
| 10,264,821 B2 | 4/2019 | Lipowicz |
| 10,279,934 B2 | 5/2019 | Christensen et al. |
| 10,285,436 B2 | 5/2019 | Branton |
| 10,285,444 B2 | 5/2019 | Clemens et al. |
| 10,285,445 B2 | 5/2019 | Metz et al. |
| 10,287,155 B2 | 5/2019 | Murison et al. |
| 10,292,430 B2 | 5/2019 | Zhang et al. |
| 10,300,225 B2 | 5/2019 | Terry et al. |
| 10,301,077 B1 | 5/2019 | Finlow-Bates |
| 10,306,930 B2 | 6/2019 | Qiu |
| 10,314,340 B2 | 6/2019 | Davis et al. |
| 10,321,712 B2 | 6/2019 | Lipowicz |
| 10,321,722 B2 | 6/2019 | Qiu |
| D853,635 S | 7/2019 | Chen |
| 10,349,682 B2 | 7/2019 | Hon |
| 10,349,684 B2 | 7/2019 | Ampolini et al. |
| 10,357,058 B1 | 7/2019 | Contreras |
| 10,357,064 B1 | 7/2019 | Kleizo et al. |
| 10,357,623 B2 | 7/2019 | Fang |
| 10,368,582 B2 | 8/2019 | Lord |
| 10,383,368 B2 | 8/2019 | Larson |
| 10,390,566 B2 | 8/2019 | Hu et al. |
| D861,239 S | 9/2019 | Chen |
| 10,398,174 B2 | 9/2019 | Phillips et al. |
| 10,398,178 B2 | 9/2019 | Scatterday |
| 10,407,196 B2 | 9/2019 | Slurink |
| 10,412,996 B2 | 9/2019 | Bright et al. |
| D861,549 S | 10/2019 | Lai |
| D861,594 S | 10/2019 | Lai |
| D861,978 S | 10/2019 | Lai |
| D863,673 S | 10/2019 | Lai |
| 10,433,583 B2 | 10/2019 | Wang et al. |
| 10,440,989 B2 | 10/2019 | Gardella et al. |
| 10,440,991 B2 | 10/2019 | Levitz et al. |
| 10,463,078 B2 | 11/2019 | Davis et al. |
| 10,470,499 B2 | 11/2019 | Clemens et al. |
| 10,477,895 B2 | 11/2019 | Wang et al. |
| D869,086 S | 12/2019 | Pan |
| D870,034 S | 12/2019 | Lai |
| 10,492,539 B2 | 12/2019 | Chen |
| 10,506,831 B2 | 12/2019 | Shen et al. |
| 10,506,834 B2 | 12/2019 | Liu |
| 10,512,284 B2 | 12/2019 | Wang et al. |
| 10,512,738 B2 | 12/2019 | Fornarelli |
| 10,524,504 B2 | 1/2020 | Li et al. |
| 10,525,217 B2 | 1/2020 | Morris |
| 10,542,780 B2 | 1/2020 | Chung |
| D874,721 S | 2/2020 | Lai |
| D875,302 S | 2/2020 | Pan |
| D875,303 S | 2/2020 | Pan |
| D875,305 S | 2/2020 | Lai |
| D875,306 S | 2/2020 | Pan |
| 10,555,557 B2 | 2/2020 | Liu |
| D877,976 S | 3/2020 | Ding et al. |
| D877,977 S | 3/2020 | Ding et al. |
| D879,708 S | 3/2020 | Chen |
| D880,053 S | 3/2020 | Han |

(56) References Cited

U.S. PATENT DOCUMENTS

| | | |
|---|---|---|
| D880,060 S | 3/2020 | Chen |
| D881,460 S | 4/2020 | Han |
| D882,065 S | 4/2020 | Wang |
| 10,624,391 B2 | 4/2020 | Chen |
| 10,631,578 B2 | 4/2020 | Chen |
| D883,563 S | 5/2020 | Pan |
| D883,567 S | 5/2020 | Liu |
| D883,780 S | 5/2020 | Wu |
| D884,266 S | 5/2020 | Wang |
| D884,267 S | 5/2020 | Wang |
| D885,652 S | 5/2020 | Ding et al. |
| D885,654 S | 5/2020 | Ding |
| D885,655 S | 5/2020 | Ding |
| D885,657 S | 5/2020 | Lai |
| 10,721,971 B2 | 7/2020 | Barbaric et al. |
| 10,822,123 B2 | 11/2020 | Barbaric et al. |
| 2009/0126745 A1 | 5/2009 | Hon |
| 2012/0111347 A1 | 5/2012 | Hon |
| 2012/0325228 A1 | 12/2012 | Williams |
| 2013/0056012 A1 | 3/2013 | Hearn et al. |
| 2013/0087160 A1 | 4/2013 | Gherghe |
| 2013/0220316 A1 | 8/2013 | Oglesby et al. |
| 2014/0109921 A1 | 4/2014 | Chen |
| 2014/0123989 A1 | 5/2014 | LaMothe |
| 2014/0209109 A1 | 7/2014 | Larson |
| 2014/0246016 A1 | 9/2014 | Terry et al. |
| 2014/0283854 A1 | 9/2014 | Magne |
| 2014/0283946 A1 | 9/2014 | Kribs |
| 2014/0360517 A1 | 12/2014 | Taggart et al. |
| 2015/0090281 A1 | 4/2015 | Chen |
| 2015/0157055 A1 | 6/2015 | Lord |
| 2015/0272218 A1 | 10/2015 | Chen |
| 2015/0314085 A1 | 11/2015 | Banoun |
| 2015/0359261 A1 | 12/2015 | Li et al. |
| 2016/0157522 A1 | 6/2016 | Zhu |
| 2016/0192710 A1 | 7/2016 | Liu |
| 2016/0198770 A1 | 7/2016 | Alarcon |
| 2016/0221707 A1 | 8/2016 | Xu et al. |
| 2016/0278163 A1 | 9/2016 | Chen |
| 2016/0309785 A1 | 10/2016 | Holtz |
| 2016/0332754 A1 | 11/2016 | Brown et al. |
| 2016/0345630 A1 | 12/2016 | Mironov et al. |
| 2017/0013880 A1 | 1/2017 | O'Brien et al. |
| 2017/0020191 A1* | 1/2017 | Lamb .................. A24F 40/53 |
| 2017/0048930 A1 | 2/2017 | Marsh et al. |
| 2017/0049153 A1 | 2/2017 | Guo et al. |
| 2017/0056368 A1 | 3/2017 | Hearn et al. |
| 2017/0086496 A1 | 3/2017 | Cameron |
| 2017/0094999 A1 | 4/2017 | Hearn et al. |
| 2017/0105448 A1 | 4/2017 | Scarpulla |
| 2017/0105455 A1 | 4/2017 | Qiu |
| 2017/0135398 A1 | 5/2017 | Scott et al. |
| 2017/0188636 A1 | 7/2017 | Li et al. |
| 2017/0208870 A1 | 7/2017 | Liu |
| 2017/0231274 A1 | 8/2017 | Davis et al. |
| 2017/0233114 A1* | 8/2017 | Christensen .............. B65B 3/14 141/2 |
| 2017/0241857 A1 | 8/2017 | Hearn et al. |
| 2017/0245549 A1 | 8/2017 | Nedelman |
| 2017/0258143 A1 | 9/2017 | Lederer |
| 2017/0280773 A1 | 10/2017 | Force |
| 2017/0280778 A1 | 10/2017 | Force |
| 2017/0283154 A1 | 10/2017 | Karles et al. |
| 2017/0295848 A1 | 10/2017 | LaMothe |
| 2017/0340011 A1* | 11/2017 | Batista .................. A24F 40/44 |
| 2017/0347709 A1 | 12/2017 | Laakso et al. |
| 2017/0367405 A1 | 12/2017 | Zhu |
| 2018/0007741 A1 | 1/2018 | Metz et al. |
| 2018/0014575 A1 | 1/2018 | Fursa |
| 2018/0016040 A1 | 1/2018 | Ewing et al. |
| 2018/0020722 A1 | 1/2018 | Davis et al. |
| 2018/0020723 A1 | 1/2018 | Davis et al. |
| 2018/0020726 A1 | 1/2018 | Alarcon et al. |
| 2018/0029866 A1 | 2/2018 | Scott et al. |
| 2018/0042301 A1 | 2/2018 | Rostami |
| 2018/0070632 A1 | 3/2018 | Sur et al. |
| 2018/0070637 A1 | 3/2018 | Deng et al. |
| 2018/0077967 A1* | 3/2018 | Hatton .................. A61M 15/06 |
| 2018/0116288 A1 | 5/2018 | Hu et al. |
| 2018/0140018 A1 | 5/2018 | Hu et al. |
| 2018/0153208 A1 | 6/2018 | Schaller et al. |
| 2018/0153218 A1 | 6/2018 | Verleur et al. |
| 2018/0160737 A1 | 6/2018 | Verleur et al. |
| 2018/0170588 A1 | 6/2018 | Boldrini |
| 2018/0184714 A1 | 7/2018 | Liu |
| 2018/0184717 A1 | 7/2018 | Jiang et al. |
| 2018/0192705 A1 | 7/2018 | Lord |
| 2018/0235281 A1 | 8/2018 | Wang et al. |
| 2018/0235284 A1 | 8/2018 | Lord |
| 2018/0279672 A1 | 10/2018 | Davis et al. |
| 2018/0279684 A1 | 10/2018 | Hon |
| 2018/0280636 A1 | 10/2018 | Jiang et al. |
| 2018/0289067 A1 | 10/2018 | Courbat et al. |
| 2018/0292250 A1 | 10/2018 | Colotte et al. |
| 2018/0296777 A1 | 10/2018 | Terry et al. |
| 2018/0303158 A1 | 10/2018 | Chen |
| 2018/0310615 A1 | 11/2018 | Zhu |
| 2018/0310626 A1 | 11/2018 | Zhou et al. |
| 2018/0310628 A1 | 11/2018 | Qiu |
| 2018/0317550 A1 | 11/2018 | Zhu |
| 2018/0317559 A1 | 11/2018 | Qiu |
| 2018/0325171 A1 | 11/2018 | Zhu |
| 2018/0332896 A1 | 11/2018 | Wang et al. |
| 2018/0338536 A1 | 11/2018 | Hu et al. |
| 2018/0360113 A1 | 12/2018 | Reinitz et al. |
| 2018/0360119 A1 | 12/2018 | Kuwa et al. |
| 2018/0360120 A1 | 12/2018 | Huang et al. |
| 2018/0368474 A1 | 12/2018 | Bache et al. |
| 2019/0000143 A1 | 1/2019 | Zhu |
| 2019/0006866 A1 | 1/2019 | Zhu |
| 2019/0022345 A1 | 1/2019 | Kotch |
| 2019/0031407 A1 | 1/2019 | Biel et al. |
| 2019/0038553 A1 | 2/2019 | Engqvist |
| 2019/0046743 A1 | 2/2019 | Engqvist |
| 2019/0046745 A1 | 2/2019 | Nettenstrom et al. |
| 2019/0090544 A1 | 3/2019 | Minskoff et al. |
| 2019/0098932 A1* | 4/2019 | Fan .................. A24F 7/00 |
| 2019/0099562 A1* | 4/2019 | Nettenstrom .......... A24F 40/485 |
| 2019/0124991 A1 | 5/2019 | Davis et al. |
| 2019/0133186 A1 | 5/2019 | Fraser |
| 2019/0142066 A1 | 5/2019 | Gill et al. |
| 2019/0166912 A1 | 6/2019 | Ding et al. |
| 2019/0166913 A1 | 6/2019 | Trzecieski |
| 2019/0174826 A1 | 6/2019 | Zhu |
| 2019/0174832 A1 | 6/2019 | Lin et al. |
| 2019/0208811 A1 | 7/2019 | Biel et al. |
| 2019/0216132 A1 | 7/2019 | Phan et al. |
| 2019/0223502 A1 | 7/2019 | Qiu et al. |
| 2019/0223504 A1 | 7/2019 | Chen |
| 2019/0223513 A1 | 7/2019 | Clemens et al. |
| 2019/0246692 A1 | 8/2019 | Li et al. |
| 2019/0246698 A1 | 8/2019 | Nakano et al. |
| 2019/0246701 A1 | 8/2019 | Nakano et al. |
| 2019/0246703 A1 | 8/2019 | Nakano et al. |
| 2019/0274356 A1 | 9/2019 | Deng et al. |
| 2019/0276167 A1 | 9/2019 | Brown et al. |
| 2019/0281892 A1 | 9/2019 | Hejazi et al. |
| 2019/0289920 A1 | 9/2019 | Lord |
| 2019/0313696 A1 | 10/2019 | Ding et al. |
| 2019/0321570 A1 | 10/2019 | Rubin |
| 2019/0321572 A1 | 10/2019 | Stalder et al. |
| 2019/0335809 A1 | 11/2019 | Han |
| 2019/0335812 A1 | 11/2019 | Ampolini et al. |
| 2019/0335815 A1 | 11/2019 | Scatterday |
| 2019/0350256 A1 | 11/2019 | Hejazi |
| 2019/0357595 A1 | 11/2019 | Liu |
| 2019/0364967 A1 | 12/2019 | Wu |
| 2019/0364968 A1 | 12/2019 | Fu et al. |
| 2019/0364972 A1 | 12/2019 | Lin et al. |
| 2019/0369127 A1 | 12/2019 | Fu et al. |
| 2019/0373679 A1 | 12/2019 | Fu et al. |
| 2019/0373949 A1 | 12/2019 | Pan |
| 2019/0373959 A1 | 12/2019 | Nakano et al. |
| 2019/0387797 A1 | 12/2019 | Christensen et al. |

(56) References Cited

U.S. PATENT DOCUMENTS

| | | |
|---|---|---|
| 2019/0387801 A1 | 12/2019 | Takeuchi et al. |
| 2020/0000151 A1 | 1/2020 | Fraser et al. |
| 2020/0008475 A1 | 1/2020 | Lai et al. |
| 2020/0037663 A1 | 2/2020 | Chau et al. |
| 2020/0046024 A1 | 2/2020 | Chen |
| 2020/0054077 A1 | 2/2020 | Chen |
| 2020/0068951 A1 | 3/2020 | Li et al. |
| 2020/0077710 A1 | 3/2020 | Volodarsky et al. |
| 2020/0085108 A1 | 3/2020 | Li et al. |
| 2020/0086067 A1 | 3/2020 | Li et al. |
| 2020/0093172 A1 | 3/2020 | Liu |
| 2020/0107583 A1 | 4/2020 | Wu et al. |
| 2020/0107584 A1 | 4/2020 | Li et al. |
| 2020/0113246 A1 | 4/2020 | Barbaric et al. |
| 2020/0120983 A1 | 4/2020 | Chen |
| 2022/0046993 A1* | 2/2022 | Liu .......................... A24F 7/00 |

FOREIGN PATENT DOCUMENTS

| | | |
|---|---|---|
| WO | WO-2019127811 A1 | 7/2019 |
| WO | WO-2019179004 A1 | 9/2019 |
| WO | WO-2019/232086 A1 | 12/2019 |
| WO | WO-2020030033 A1 | 2/2020 |
| WO | WO-2020093746 A1 | 5/2020 |

\* cited by examiner

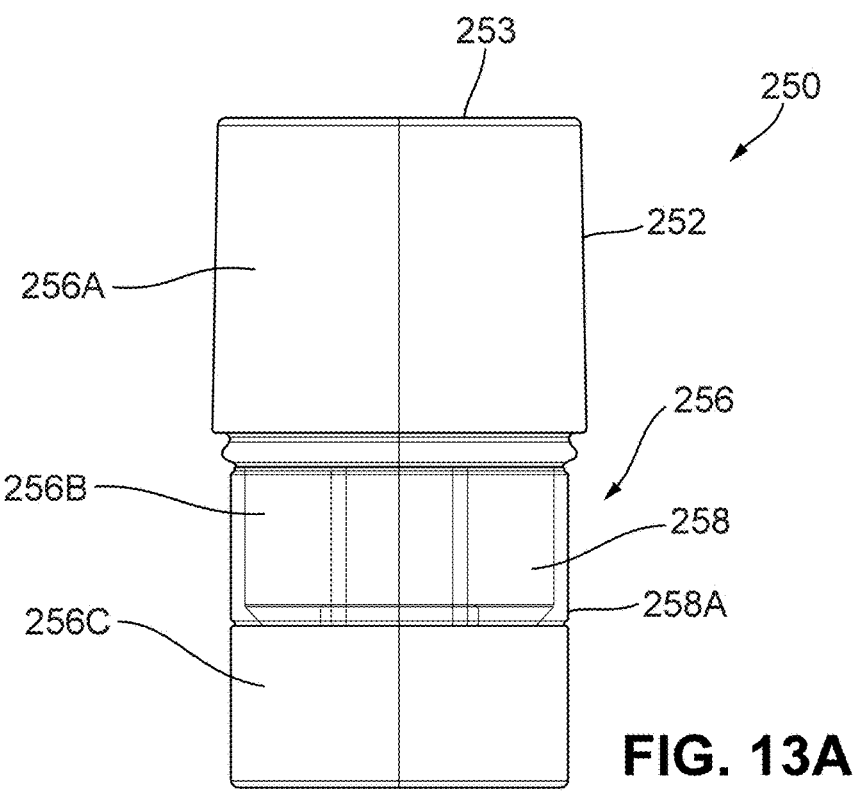
FIG. 13A
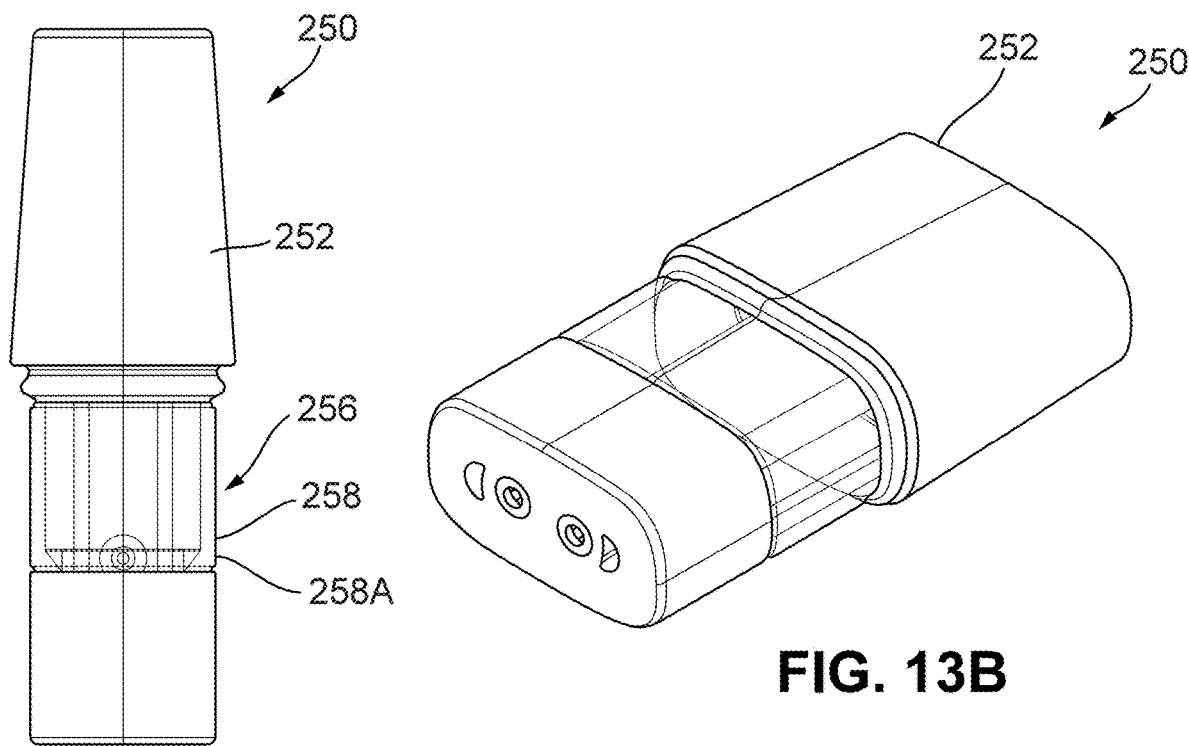
FIG. 13B
FIG. 13C

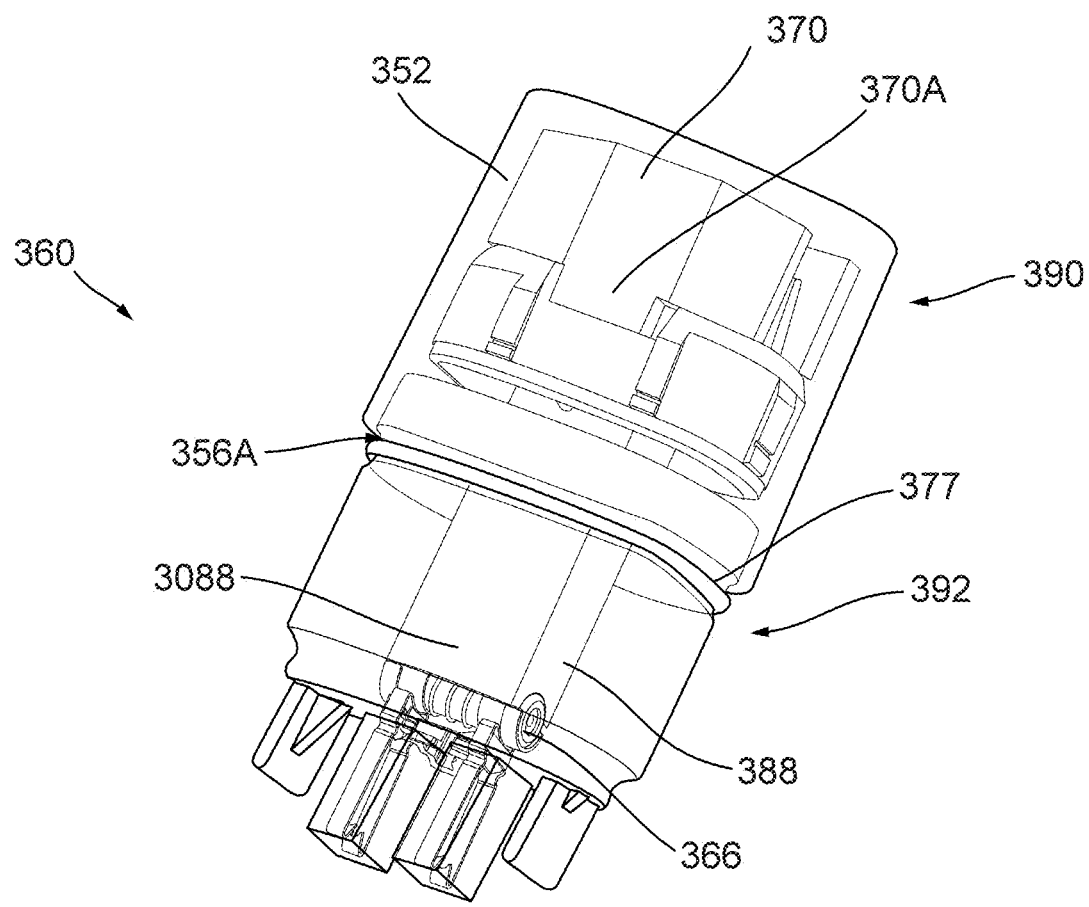
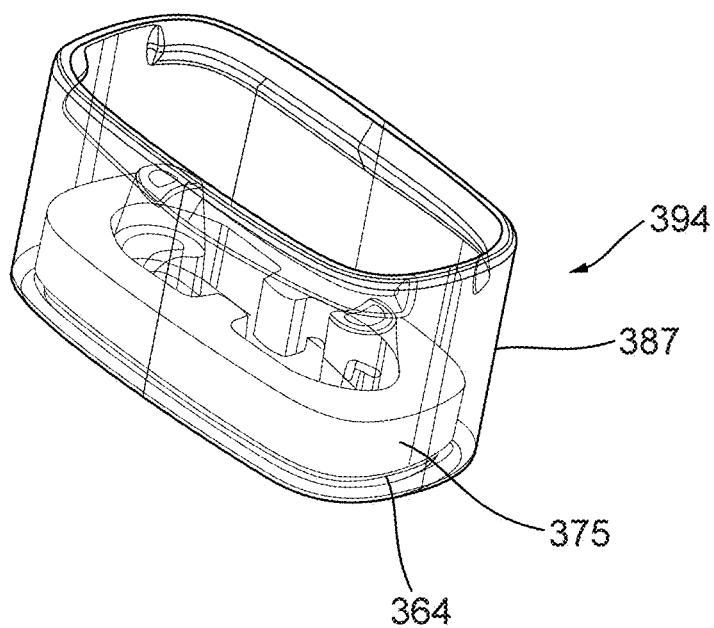
FIG. 24E

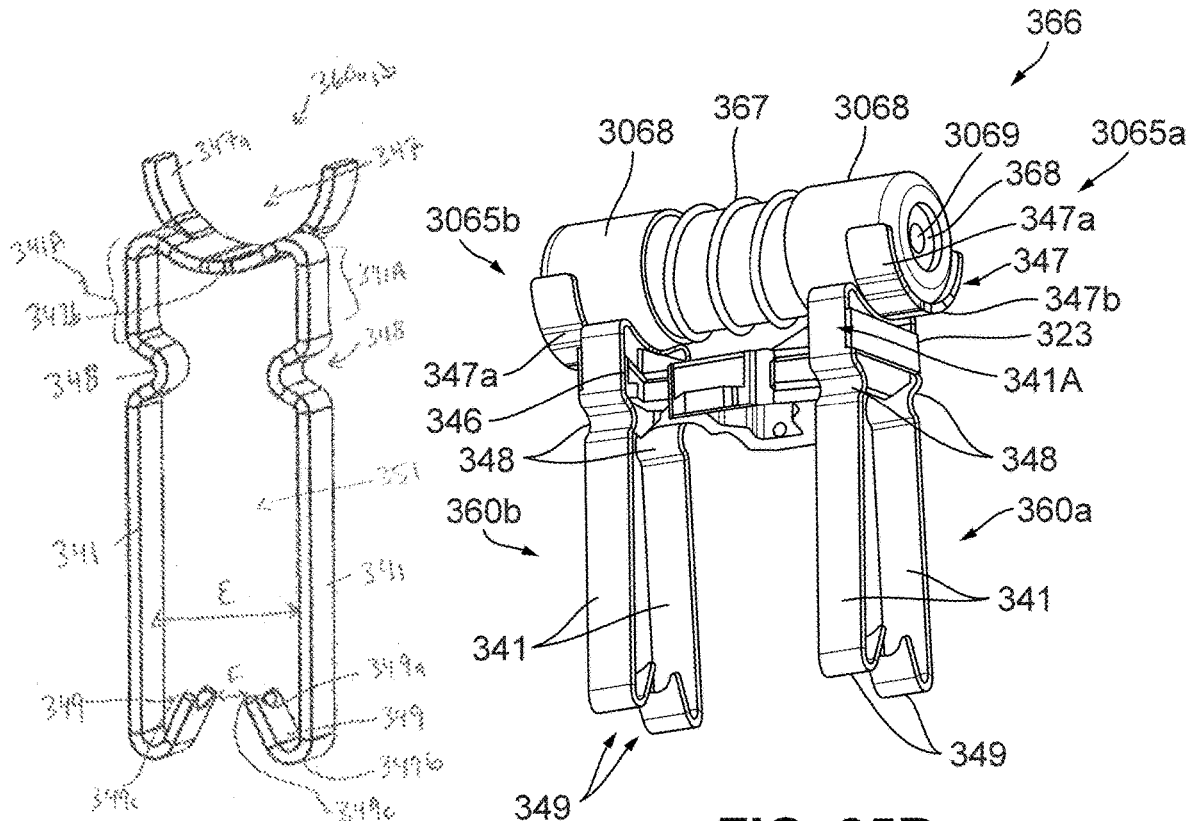
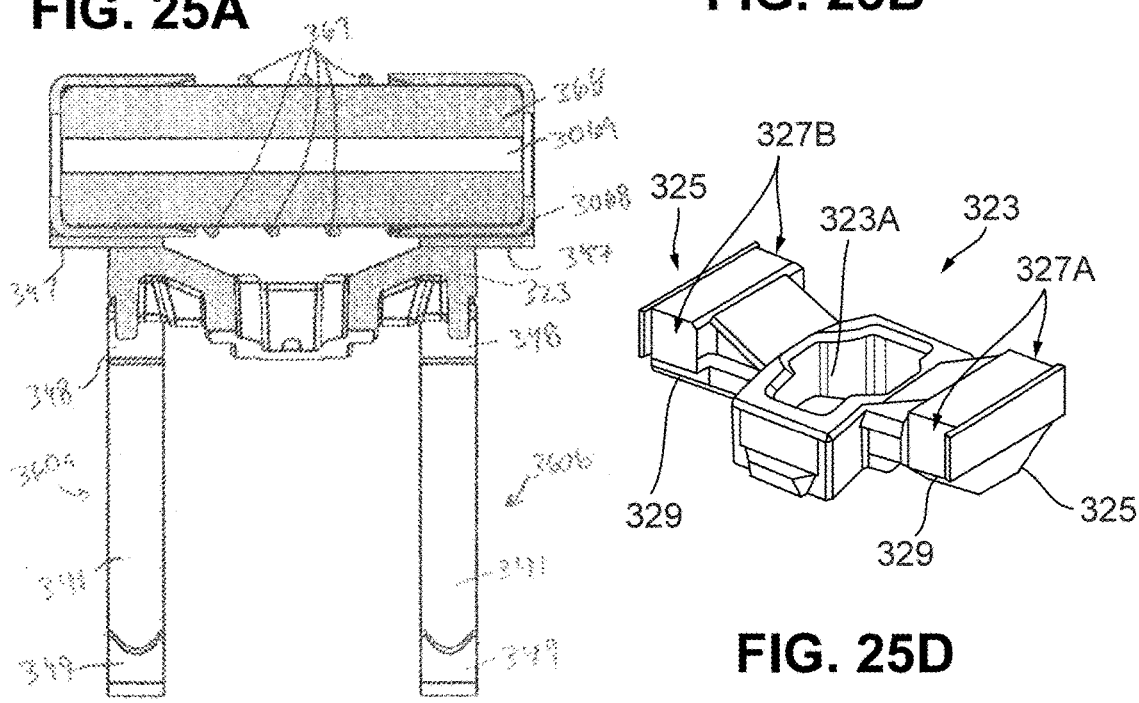
FIG. 25A
FIG. 25B
FIG. 25C
FIG. 25D

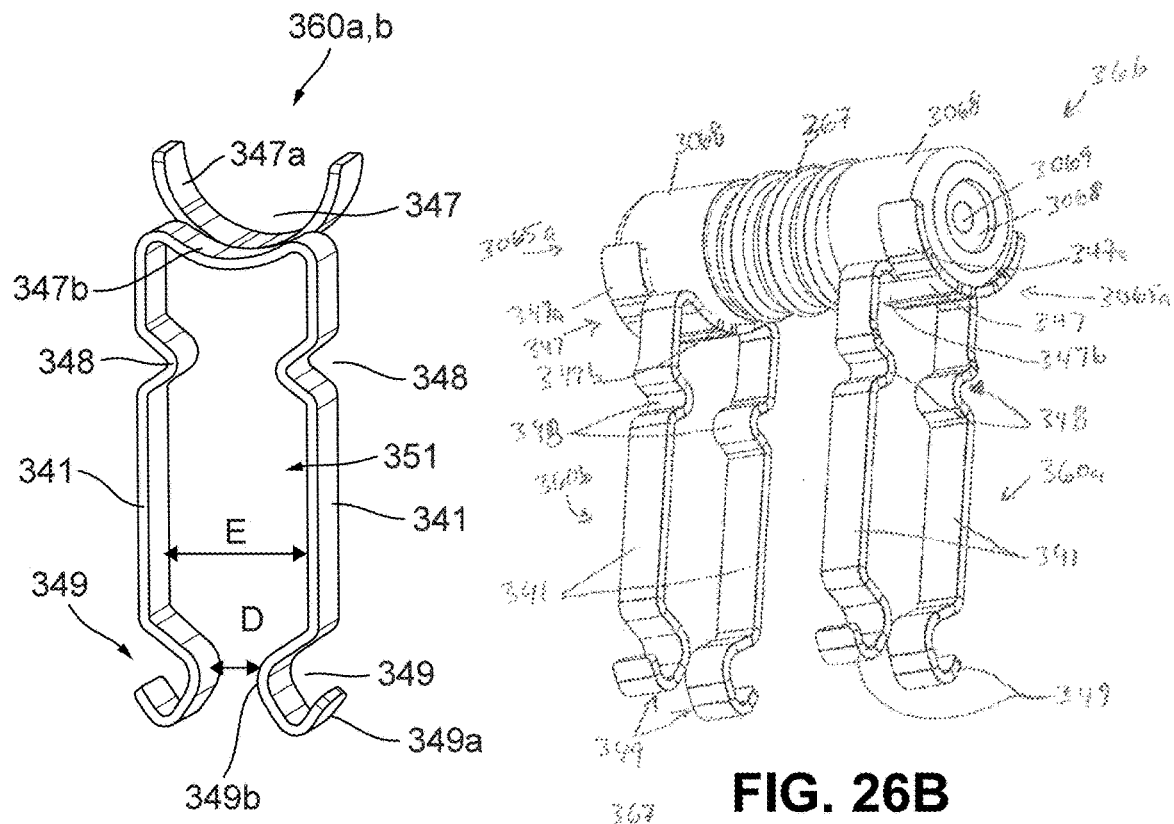
FIG. 26B
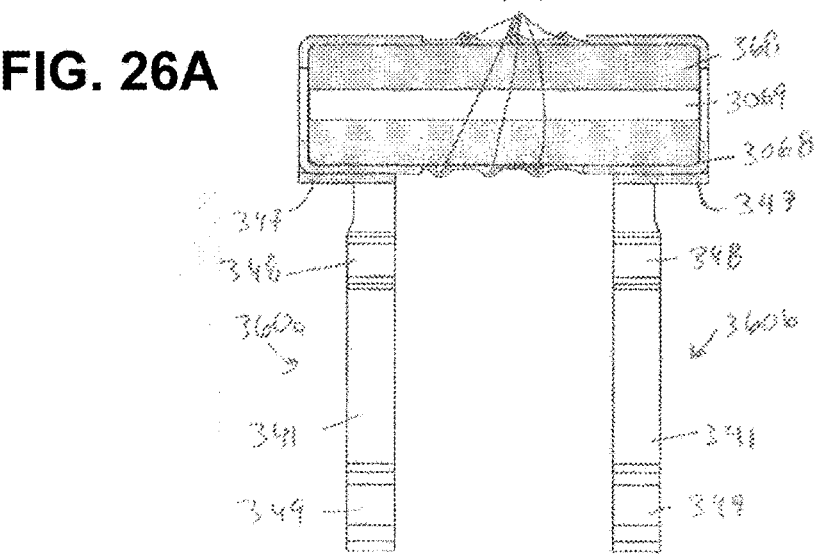
FIG. 26A
FIG. 26C

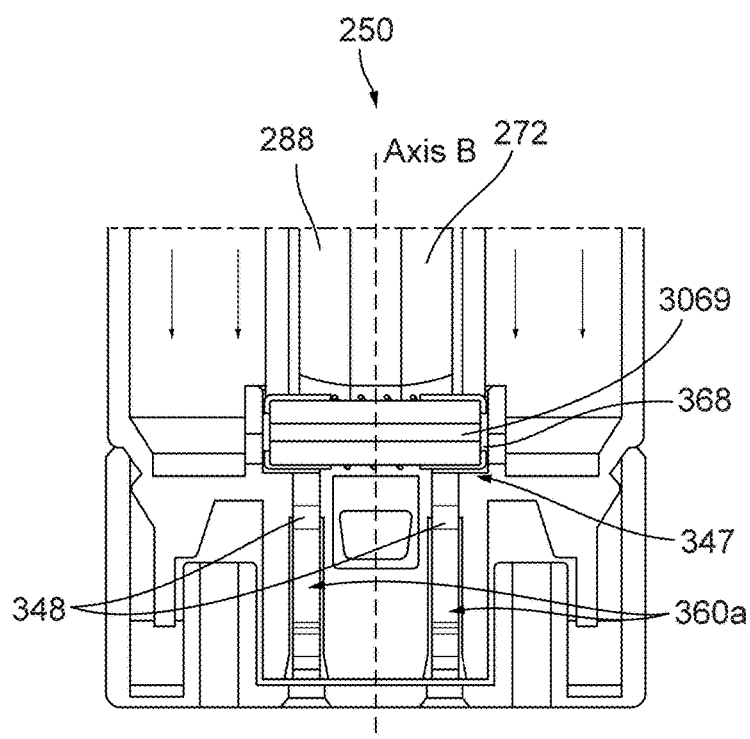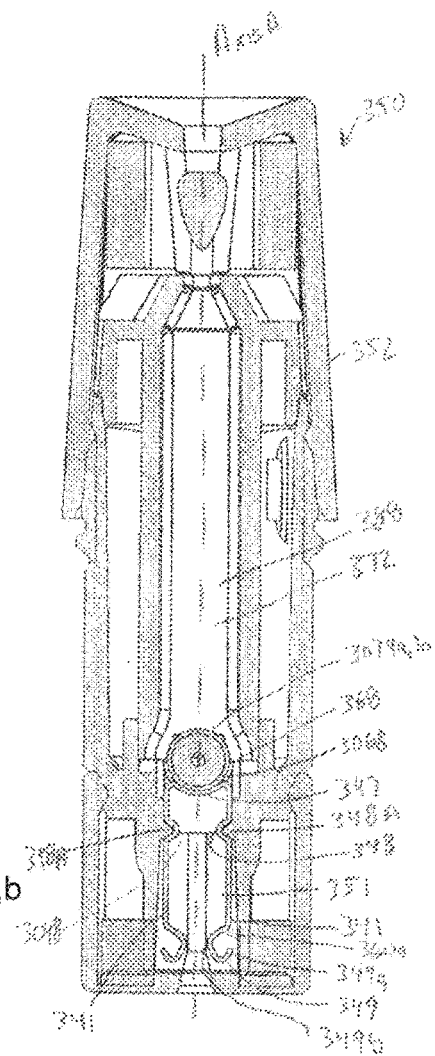
FIG. 26D
FIG. 26E

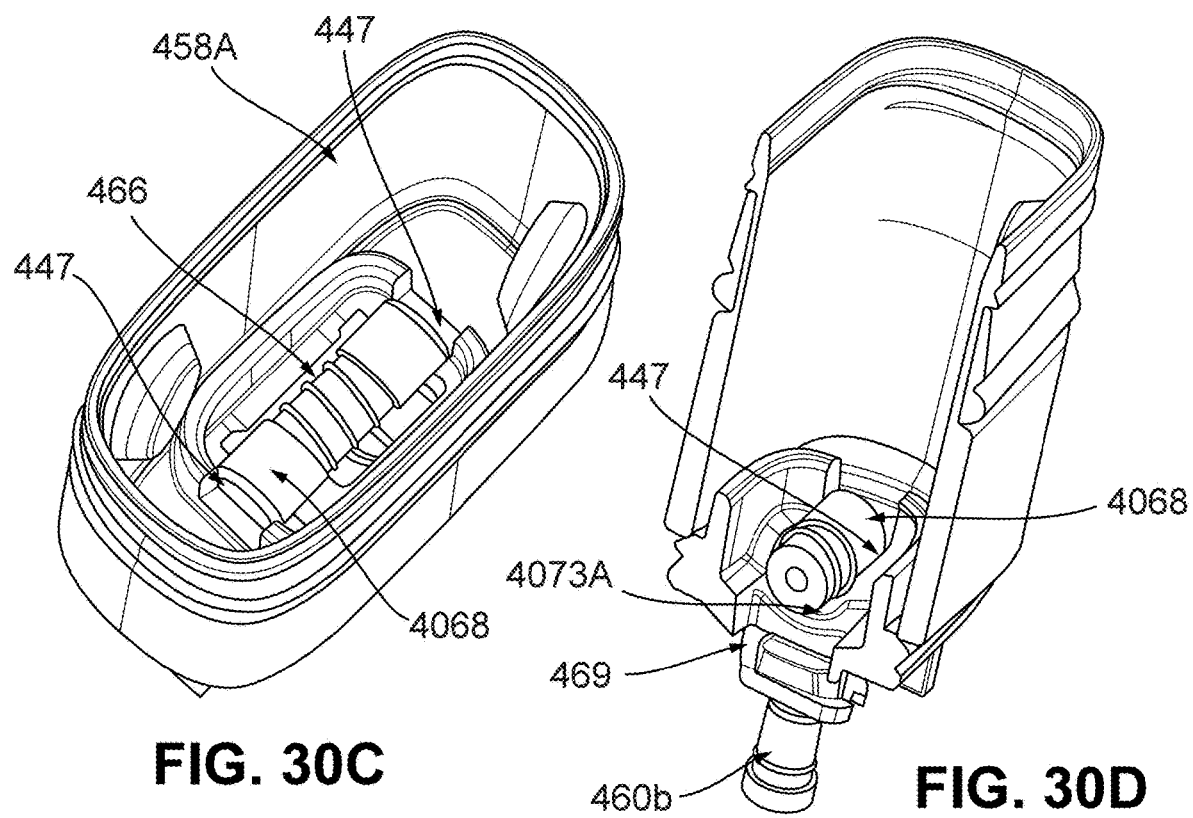
FIG. 30C
FIG. 30D
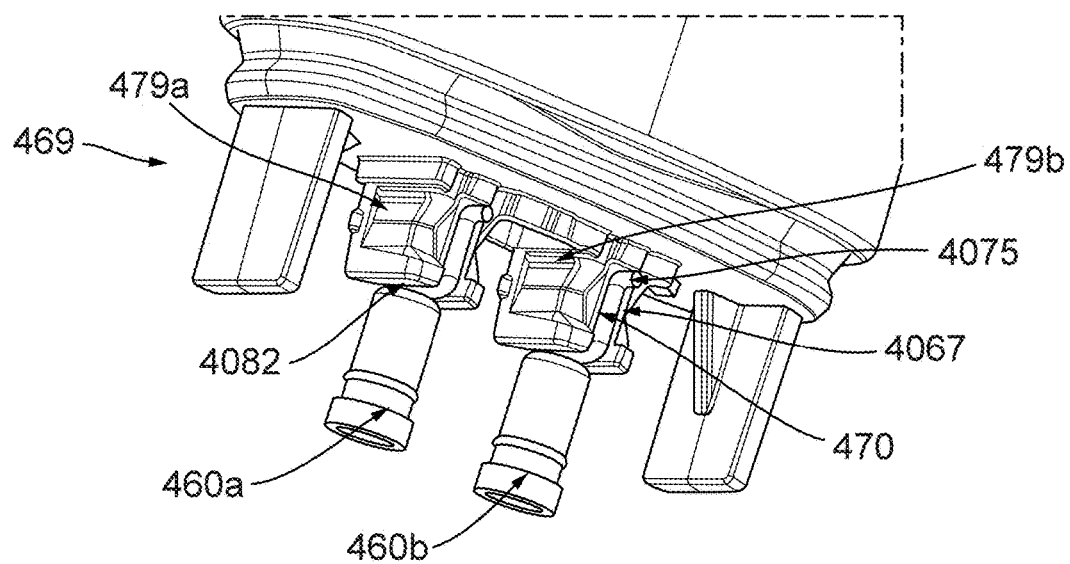
FIG. 30E

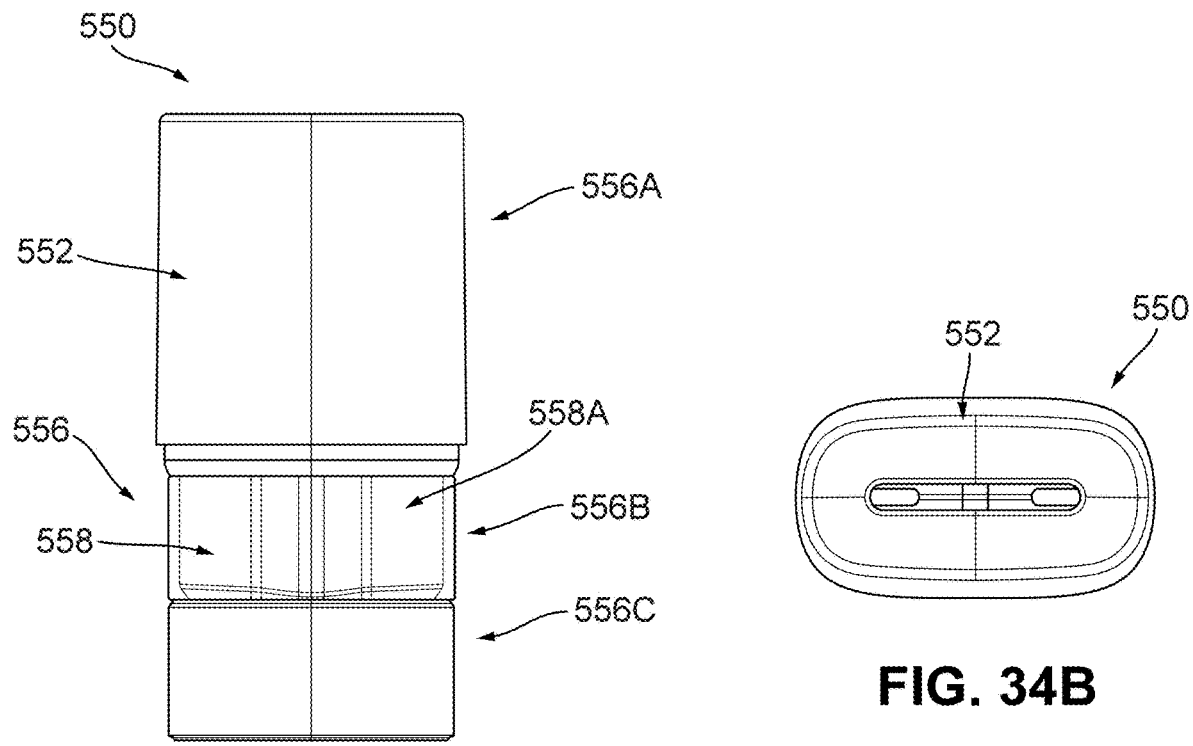
FIG. 34A
FIG. 34B
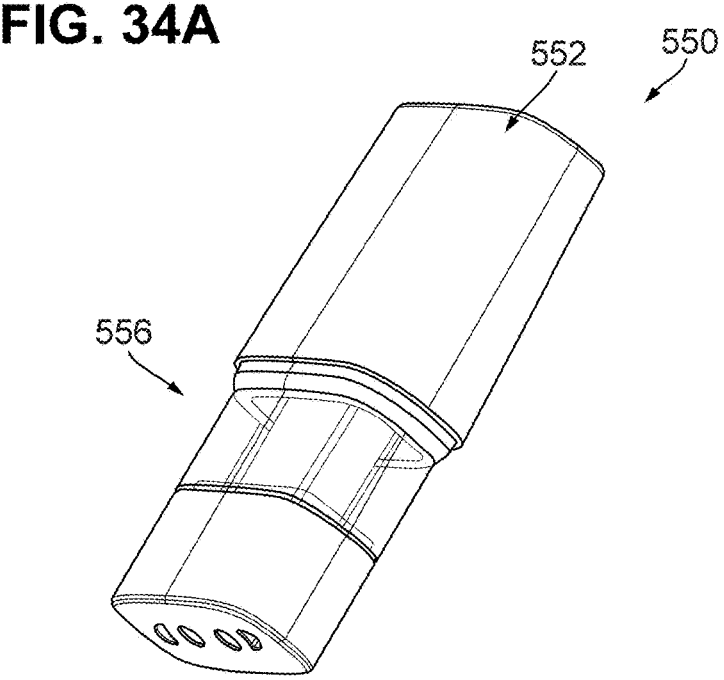
FIG. 34C

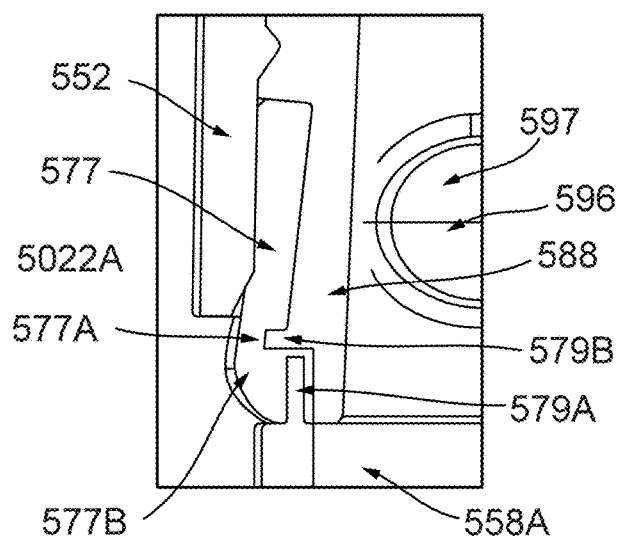
FIG. 35B
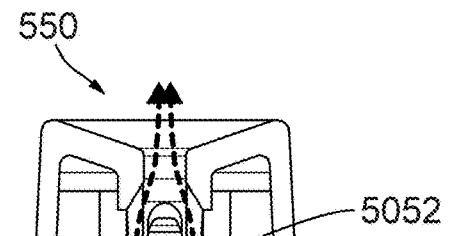
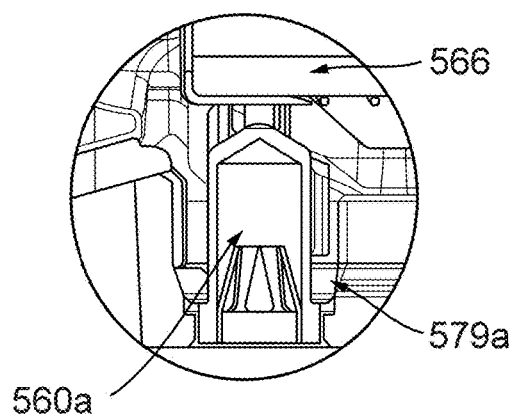
FIG. 35C
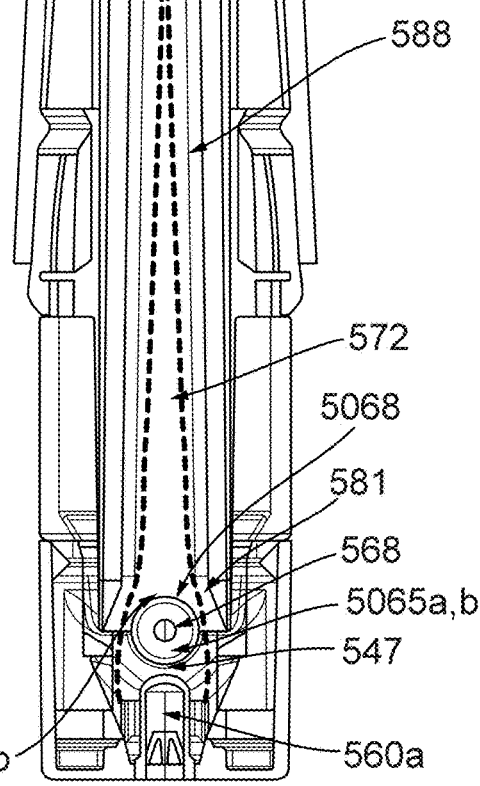
FIG. 35E
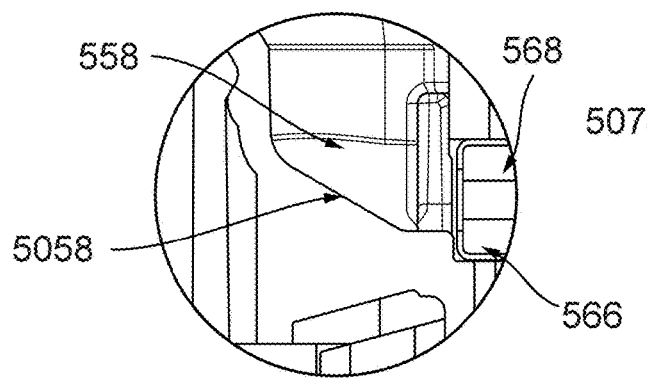
FIG. 35D

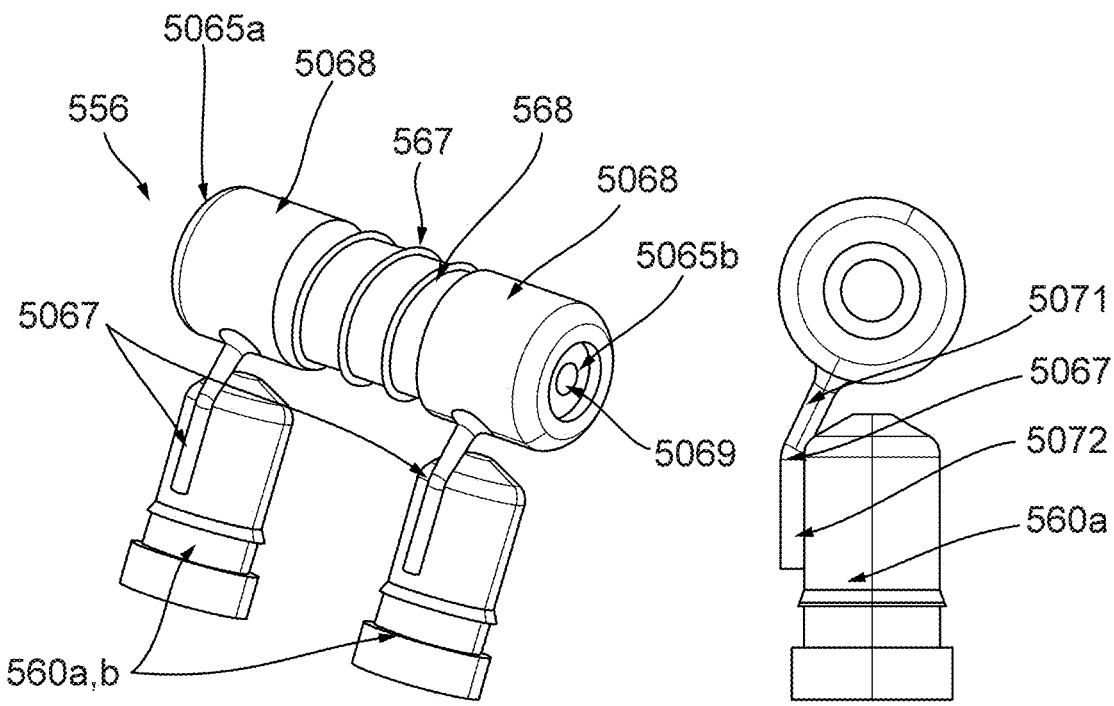
FIG. 37A
FIG. 37B
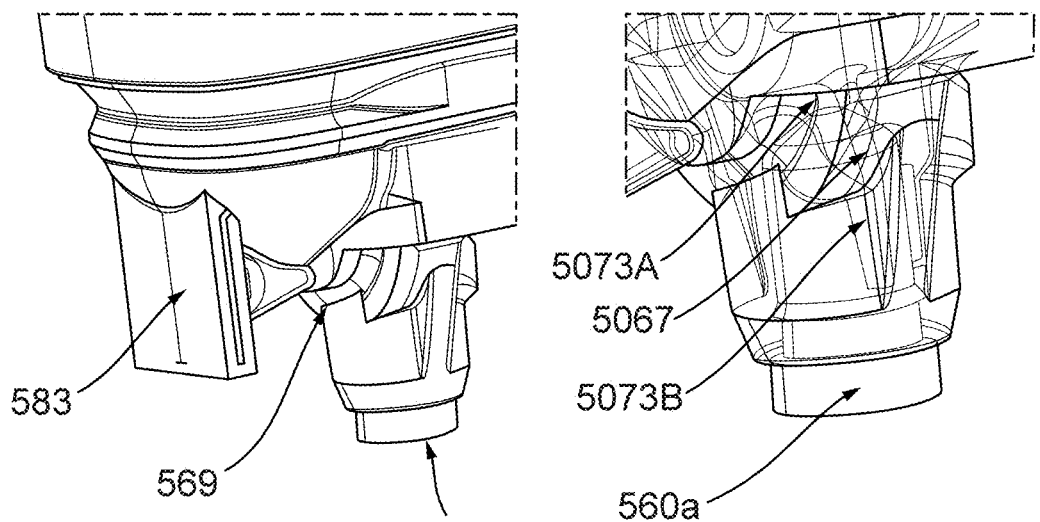
FIG. 37C
FIG. 37D

VAPORIZER CARTRIDGE

CROSS-REFERENCE TO RELATED APPLICATIONS

This application claims priority to U.S. Provisional Application No. 63/081,150, filed on Sep. 21, 2020, U.S. Provisional Application No. 63/058,125, filed on Jul. 29, 2020, U.S. Provisional Application No. 62/985,314, filed on Mar. 4, 2020, U.S. Provisional Application No. 62/968,888, filed on Jan. 31, 2020, and U.S. Provisional Application No. 62/953,172, filed on Dec. 23, 2019, the entirety of each of which is incorporated by reference herein.

TECHNICAL FIELD

The current subject matter described herein relates generally to vaporizer devices, such as portable, personal vaporizer devices for generating and delivering an inhalable aerosol from one or more vaporizable materials.

BACKGROUND

Vaporizing devices, including electronic vaporizers or e-vaporizer devices, allow the delivery of vapor containing one or more active ingredients by inhalation of the vapor. Electronic vaporizer devices are gaining increasing popularity both for prescriptive medical use, in delivering medicaments, and for consumption of nicotine, tobacco, other liquid-based substances, and other plant-based smokeable materials, such as *cannabis*, including solid (e.g., loose-leaf) materials, solid/liquid (e.g., suspensions, liquid-coated) materials, wax extracts, and prefilled pods (cartridges, wrapped containers, etc.) of such materials. Electronic vaporizer devices in particular may be portable, self-contained, and convenient for use.

SUMMARY

Aspects of the current subject matter relate to a vaporizer cartridge for use with a vaporizer body to provide a vaporizable aerosol for consumption by a user.

According to some aspects, a cartridge may operatively couple with a vaporizer. The cartridge may include a cartridge body, a vaporizing assembly, a mouthpiece, and at least one absorbent pad. The cartridge body may define, at least in part, a reservoir configured to contain vaporizable material. The vaporizing assembly may be positioned within the cartridge body in fluid communication with the reservoir. The vaporizing assembly may vaporize the vaporizable material. The mouthpiece may be coupled to a proximal end region of the cartridge body. The mouthpiece may include an internal volume and an external surface defining at least one mouthpiece opening that opens into the internal volume. The at least one absorbent pad may be wedged within the internal volume of the mouthpiece. The at least one absorbent pad may include an annular shape having a central opening that aligns with the at least one mouthpiece opening. A central, upper element may define, at least in part a top surface of the cartridge body. The central upper element extends across a major axis of the cartridge body between sidewalls of the cartridge body and includes a side cross-sectional profile having a sharpened end that is configured to split vapor flow around the central, upper element and to the mouthpiece such that particles within the vapor flow are entrained in the at least one absorbent pad.

In some aspects, the at least one absorbent pad includes one absorbent pad surrounding the at least one mouthpiece opening. The at least one mouthpiece opening may be a narrow, elongate slit. The central opening of the one absorbent pad may have a shape that substantially corresponds to a shape of the slit. In some aspects, the one absorbent pad is wedged within the internal volume of the mouthpiece to avoid blocking gas flow through the at least one mouthpiece opening.

In some aspects, the one absorbent pad has an outer perimeter wall sized and shaped to engage with an inner wall of the mouthpiece.

In some aspects, the at least one absorbent pad interfaces with at least a portion of the top surface of the cartridge body.

In some aspects, the vaporizing assembly includes a ceramic porous wick and a vaporization chamber. The ceramic porous wick includes a central bore along a length thereof. The ceramic porous wick may passively draw the vaporizable material contained in the reservoir towards the vaporization chamber.

According to some aspects, a cartridge may operatively couple with a vaporizer. The cartridge may include a cartridge body. A mouthpiece, a cannula, and a ceramic porous wick. The cartridge body may define, at least in part, a reservoir configured to contain vaporizable material. The mouthpiece may be coupled to a proximal end region of the cartridge body. The mouthpiece may include an internal volume and an external surface defining at least one mouthpiece opening that opens into the internal volume. The cannula may define a vaporization chamber extending through the cartridge body. The vaporization chamber may be in fluid communication with the at least one opening of the mouthpiece. The ceramic porous wick may include a central bore along a length thereof. The ceramic porous wick may passively draw the vaporizable material in the reservoir towards the vaporization chamber.

In some aspects, the porous wick includes a central region positioned within the vaporization chamber, a first end positioned outside the vaporization chamber and within the first volume of the reservoir, and a second, opposite end positioned outside the vaporization chamber and within the second volume of the reservoir.

In some aspects, the cartridge further includes a first end cap positioned over the first end of the wick and a second end cap positioned over the second end of the wick. The first end cap and the second end cap may connect to respective electrical leads.

In some aspects, the cartridge further includes at least one absorbent pad wedged within the internal volume of the mouthpiece. The at least one absorbent pad may include an annular shape having a central opening that aligns with the at least one mouthpiece opening. A central, upper element may define in part a top surface of the cartridge body. The central upper element may extend across a major axis of the cartridge body between sidewalls of the cartridge body and include a side cross-sectional profile having a sharpened end that is configured to split vapor flow around the central, upper element and to the mouthpiece such that particles within the vapor flow are entrained in the at least one absorbent pad.

In some aspects, the cartridge includes at least two absorbent pads wedged within the internal volume of the mouthpiece. The at least two absorbent pads may define a central opening therebetween that aligns with the at least one mouthpiece opening. A central, upper element may define in part a top surface of the cartridge body. The central upper element extends across a major axis of the cartridge body between sidewalls of the cartridge body and includes a side cross-sectional profile having a sharpened end that is configured to split vapor flow around the central, upper element and to the mouthpiece such that particles within the vapor flow are entrained in the at least one absorbent pad.

In some aspects, the cartridge body comprises a fill port, through which the reservoir may be filled.

In some aspects, the mouthpiece is configured to cover the fill port to prevent access to the fill port.

In some aspects, the mouthpiece is configured to slide along the cartridge body from a first position to a second position. When the mouthpiece is coupled to the cartridge in the first position, the fill port is accessible, and when the mouthpiece is coupled to the cartridge in the second position, the fill port is inaccessible.

In some aspects, the mouthpiece is coupled to the cartridge in the first position when an inwardly-projecting feature of the mouthpiece is engaged with a first recess of a wick housing of the cartridge body. The mouthpiece may be coupled to the cartridge in the second position when the inwardly-projecting feature of the mouthpiece is engaged with a second recess formed within a reservoir body of the reservoir.

In some aspects, the cartridge includes a data tag positioned within an interior of the cartridge. The data tag may wirelessly communicate with the vaporizer.

In some aspects, the cartridge body further comprises a wick housing and a reservoir body. The reservoir may defined by a combination of an interior volume of the wick housing and an interior volume of the reservoir body.

In some aspects, the reservoir body and the wick housing are laser-welded to one another.

In some aspects, the cannula includes a rectangular cross-sectional shape.

According to some aspects, an atomizer assembly for a cartridge may operatively couple with a vaporizer. The atomizer assembly may include a wick, a heating coil, a pair of opposing end caps, and a pair of receptacles. The wick may passively draw vaporizable material stored within the cartridge. The heating coil may be wrapped around at least a portion of the wick. The pair of opposing end caps may be positioned over opposing ends of the wick. The pair of opposing end caps may be electrically coupled to the heating coil. The pair of receptacles may receive power from a power supply of the vaporizer.

In some aspects, the wick includes a ceramic porous material.

In some aspects, the wick includes a central bore along a length of the wick.

In some aspects, each receptacle of the pair of receptacles includes at least two opposing contact arms. Each contact arm includes a proximal end and a distal end. Each receptacle may include an end cap contact configured to engage with a corresponding end cap of the pair of opposing end caps. The end cap contact may be positioned at the proximal end. Each receptacle may include a power supply contact configured to contact the power supply of the vaporizer. The power supply contact may be positioned at the distal end.

In some aspects, the at least two opposing contact arms define an interior volume in which the power supply is configured to be inserted.

In some aspects, the at least two opposing contact arms are configured to deflect when the power supply is inserted within the interior volume.

In some aspects, each of the at least two opposing contact arms includes a locking feature. The locking feature may secure the receptacles within the cartridge.

In some aspects, the locking feature includes a recess configured to receive a corresponding protrusion within the cartridge.

In some aspects, at least a portion of the end cap contact includes a circular shape having an end cap contact radius. The end cap contact radius may be smaller than an end cap radius of the corresponding end cap.

According to some aspects, an atomizer assembly for a cartridge operatively couples with a vaporizer. The atomizer assembly may include a wick, a heating coil, an end cap, a lead, and a receptacle. The wick may passively draw vaporizable material stored within the cartridge. The heating coil may be wrapped around at least a portion of the wick. The end cap may be positioned over an end of the wick. The end cap may be electrically coupled to the heating coil. The lead may extend from the end cap. The lead may include a bend. The receptacle may receive power from a power supply of the vaporizer.

In some aspects, the lead contacts at least two surfaces of the receptacle.

In some aspects, the lead includes a first portion extending away from the end cap, a second portion configured to contact the at least two surfaces of the receptacle, and a third portion extending towards the end cap.

In some aspects, the second portion includes a first contact portion and a second contact portion. The first contact portion may contact an end surface of the receptacle, and the second contact portion may contact a side surface of the receptacle.

In some aspects, the receptacle includes a lead connector portion and at least two opposing contact arms extending from opposing sides of the lead connector portion.

In some aspects, the at least two opposing contact arms define an interior volume in which the power supply is configured to be inserted.

In some aspects, the at least two opposing contact arms are configured to deflect when the power supply is inserted within the interior volume.

In some aspects, the lead connector portion includes a locking feature. The locking feature may secure the receptacle within the cartridge.

In some aspects, the locking feature includes an opening configured to receive a corresponding protrusion from within the cartridge.

In some aspects, the lead connector portion includes a recess configured to contact an end portion of the lead to establish an electrical connection between the lead and the receptacle.

According to some aspects, the cartridge includes an atomizer assembly and a lead guide. The lead guide may receive and surround at least a portion of the lead.

In some aspects, the lead guide includes a bore, and at least a portion of the lead is configured to pass through the bore.

In some aspects, the lead guide includes a recess configured to receive an end portion of the lead.

In some aspects, the receptacle may be at least partially inserted into the bore. The insertion of the receptacle into the bore may seal the bore to prevent vaporizable material from passing through the bore.

In some aspects, the locking feature of the receptacle secures the receptacle to a protrusion extending from the lead guide.

In some aspects, the lead connector portion wraps around at least a portion of the lead guide.

In some aspects, the lead connector portion is configured to snap to at least a portion of the lead guide.

According to some aspects, a cartridge includes an atomizer assembly and a reservoir. The atomizer assembly heats a vaporizable material to generate an inhalable vapor. The reservoir stores the vaporizable material. The reservoir includes a wick housing configured to surround at least a portion of the atomizer assembly and form at least one wall of the reservoir, a reservoir body coupled to the wick housing and configured to form at least another wall of the reservoir, and a mouthpiece configured to deliver the inhalable vapor.

In some aspects, the wick housing and the reservoir body are coupled at a joining interface via laser-welding.

In some aspects, the cartridge further includes a mouthpiece seal.

In some aspects, the wick housing includes a joining rib extending from an exterior surface of the wick housing. The joining rib engages a corresponding joining recess on the mouthpiece seal to thereby strengthen the mouthpiece seal.

In some aspects, a length of the mouthpiece indicates a volume of the vaporizable material stored within the reservoir.

In some aspects, the length of the mouthpiece is 19 mm.

In some aspects, the cartridge further includes a mouthpiece seal. The mouthpiece seal may surround at least a portion of the joining interface.

In some aspects, the cartridge further includes a mouthpiece seal. The mouthpiece seal is positioned in contact with a portion of the reservoir body opposite the joining interface.

In some aspects, the mouthpiece seal includes a region of increased thickness positioned in contact with the portion of the reservoir body opposite the joining interface.

In some aspects, the region of increased thickness extends between a proximal end of the reservoir body and a distal end of the mouthpiece.

In some aspects, the cartridge also includes a base assembly coupled to a distal end of the reservoir. The base assembly includes a base, an absorbent pad positioned within the base, and a data tag positioned within the base.

In some aspects, the atomizer assembly is positioned within an interior volume of the base assembly.

In some aspects, at least a portion of the reservoir is transparent and at least a portion of the base assembly is opaque. In some aspects, at least a portion of the atomizer assembly is hidden from view from external to the cartridge.

In some aspects, the atomizer assembly includes a wick configured to passively draw the vaporizable material, a heating element in contact with the wick, and an end cap positioned over an end of the wick. The end cap may be electrically coupled to the heating element. The atomizer assembly may also include a lead extending from the end cap. The lead may include a bend. The atomizer assembly may also include a receptacle that may receive power from a power supply of the vaporizer.

In some aspects, the lead contacts a side surface of the receptacle.

In some aspects, the receptacle is press-fit into contact with the lead.

In some aspects, a distal side of the reservoir is tapered. The distal side encourages the vaporizable material from within the reservoir towards the atomizer assembly.

According to some aspects, a cartridge includes an atomizer assembly, a reservoir, and a mouthpiece. The atomizer assembly may heat a vaporizable material to generate an inhalable vapor. The reservoir may store the vaporizable material and include a wick housing and a reservoir body. The wick housing may surround at least a portion of the atomizer assembly and form a proximal wall of the reservoir. The reservoir body may be coupled to the wick housing and form a distal wall of the reservoir. The mouthpiece may deliver the inhalable vapor.

The details of one or more variations of the subject matter described herein are set forth in the accompanying drawings and the description below. Other features and advantages of the subject matter described herein will be apparent from the description and drawings, and from the claims.

DESCRIPTION OF DRAWINGS

The accompanying drawings, which are incorporated in and constitute a part of this specification, show certain aspects of the subject matter disclosed herein and, together with the description, help explain some of the principles associated with the disclosed implementations. In the drawings:

FIGS. 13A-13C illustrate an example of a cartridge of a vaporizer device consistent with implementations of the current subject matter;

FIGS. 15A-15B illustrate cross-sectional views of a cartridge consistent with implementations of the current subject matter;

FIG. 17A illustrates a partial view of a cartridge consistent with implementations of the current subject matter;

FIG. 24E illustrates a partial exploded view of a cartridge consistent with implementations of the current subject matter;

FIGS. 25A-25D illustrate features of a heater of a cartridge consistent with implementations of the current subject matter;

FIGS. 26A-26C illustrate features of a heater of a cartridge consistent with implementations of the current subject matter;

FIGS. 26D-26E illustrate cross-sectional views of a cartridge consistent with implementations of the current subject matter;

FIGS. 30C-30E illustrate partial views of a cartridge consistent with implementations of the current subject matter;

FIGS. 34A-34C illustrate an example of a cartridge of a vaporizer device consistent with implementations of the current subject matter;

FIGS. 35A-35E illustrate cross-sectional views of a cartridge consistent with implementations of the current subject matter;

FIGS. 37A-37D illustrate features of a heater of a cartridge consistent with implementations of the current subject matter;

When practical, similar reference numbers denote similar structures, features, or elements.

DETAILED DESCRIPTION

Figure 1A:
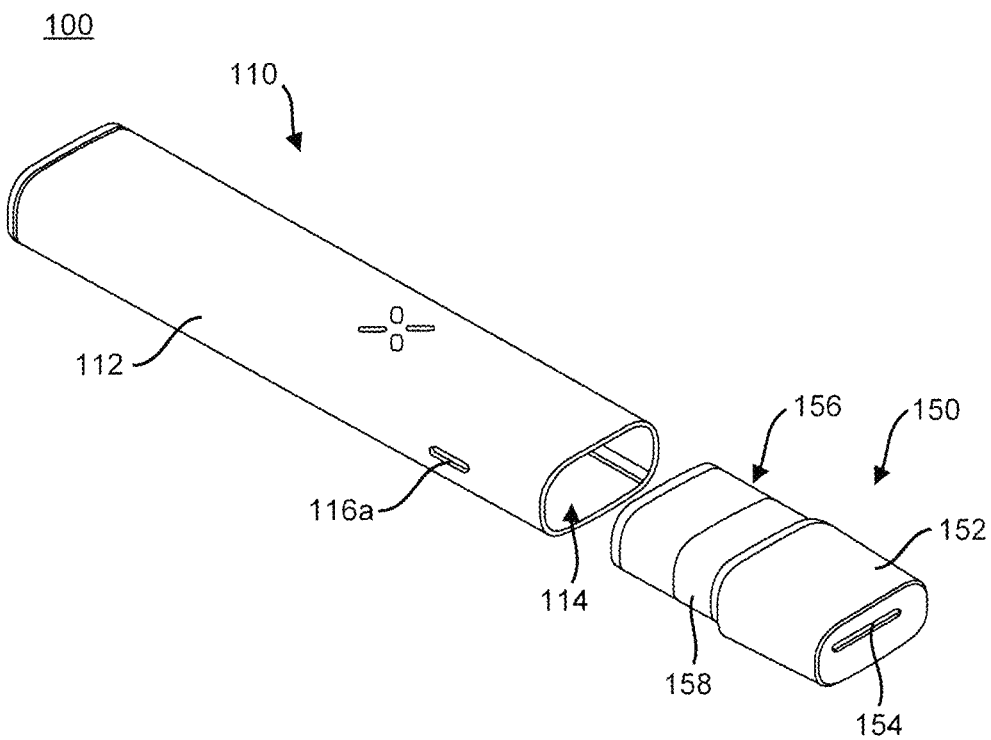
FIG. 1A-FIG. 1F illustrate features of a vaporizer device including a vaporizer body and a cartridge consistent with implementations of the current subject matter.

According to aspects of the current subject matter, a cartridge, in which vaporizable material is contained for producing a vaporizable aerosol and which couples to a vaporizer body, includes various seals, internal structures, and absorbent padding to contain the vaporizable material, prevent leakage of the vaporizable material, and provide enhanced air flow. According to aspects of the current subject matter, a cartridge may have a reservoir in which approximately 1.0 grams of vaporizable material may be contained. According to aspects of the current subject matter, a cartridge may include a porous ceramic wick configured to draw the vaporizable material in the reservoir towards the vaporization chamber.

Implementations of the current subject matter include devices relating to vaporizing of one or more materials for inhalation by a user. The term "vaporizer" may be used generically in the following description and refers to a vaporizer device, such as, for example, an electronic vaporizer. Examples of vaporizers consistent with implementations of the current subject matter include electronic vaporizers, electronic cigarettes, e-cigarettes, or the like. In general, such vaporizers are often portable, hand-held devices that heat a vaporizable material to provide an inhalable dose of the material.

Vaporizer devices consistent with the current subject matter may be referred to by various terms such as, for example, inhalable aerosol devices, aerosolizers, vaporization devices, electronic vaping devices, electronic vaporizers, vape pens, etc.

An apparatus and/or method consistent with implementations of the current subject matter involves heating of a vaporizable material to result in production of one or more gas-phase components of the vaporizable material. A vaporizable material may include liquid and/or oil-type plant materials. The gas-phase components of the vaporizable material may condense after being vaporized such that an aerosol is formed in a flowing air stream that is deliverable for inhalation by a user. Such vaporizer devices may in some implementations of the current subject matter be particularly adapted for use with an oil-based vaporizable material, such as, for example, *cannabis* oils.

One or more features of the current subject matter, including one or more of a cartridge (also referred to as vaporizer cartridges and pods) and a reusable vaporizer device body (also referred to as a vaporizer device base, a body, a base, etc.), may be employed with a suitable vaporizable material (where suitable refers in this context to being usable with a device whose properties, settings, etc. are configured or configurable to be compatible for use with the vaporizable material). The vaporizable material can include one or more liquids, such as, for example, oils, extracts, aqueous or other solutions, etc., of one or more substances that may be desirably provided in the form of an inhalable aerosol.

In some implementations, the vaporizable material is *cannabis* oil. *cannabis* oils may present particular challenges when vaporized using a cartridge and a vaporizer device. For example, *cannabis* oil is relatively sticky and viscous, particularly once it dries out. Thus, leakage may be a more serious consideration and challenge compared to other aqueous vaporizable materials. In particular, leakage of *cannabis* oil may result in clogging of the device and disturbing the electrical components, particularly the electrical contacts. The dried oil may also disrupt the electrical control of the vaporizer device due to its electrically insulating properties. The cartridges described herein may provide robust leak-resistant designs and may be configured to be used with viscous oil-based vaporizable materials, such as *cannabis* oil that may have a viscosity at room temperature of between about 40 cP and 113 KcP.

Before providing additional details regarding the cartridge (also referred to as a "pod"), the following provides a description of some example of vaporizer devices.

Figure 1B:
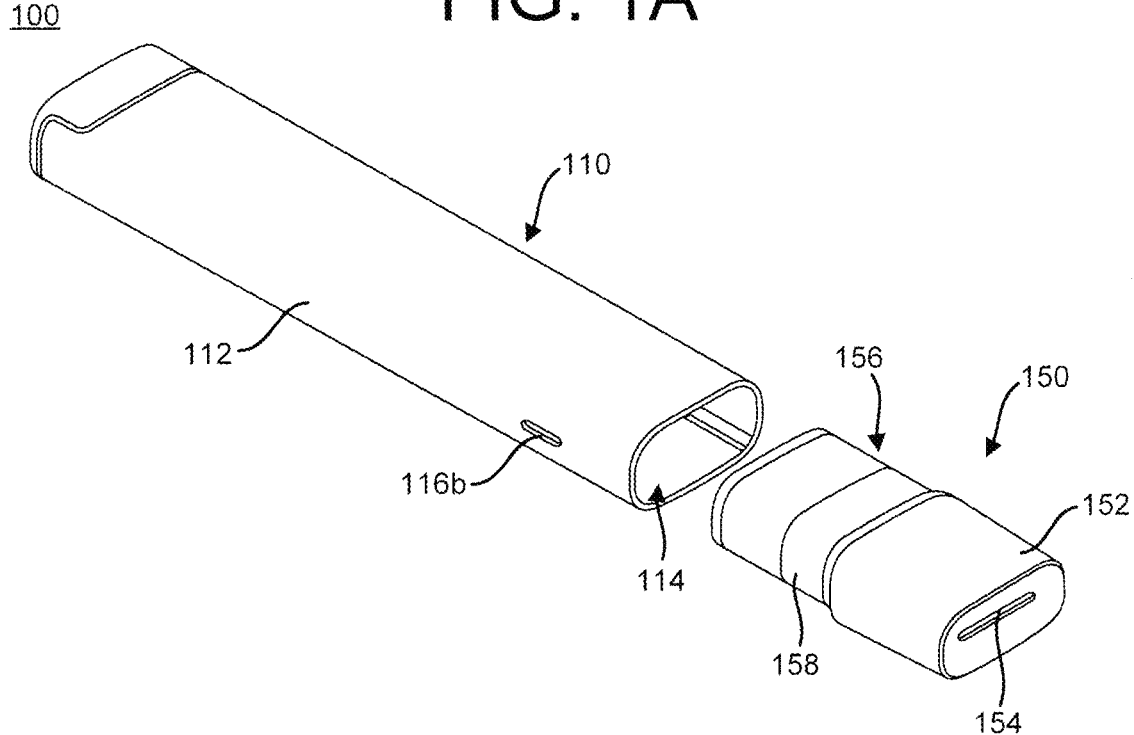
Figure 1C:
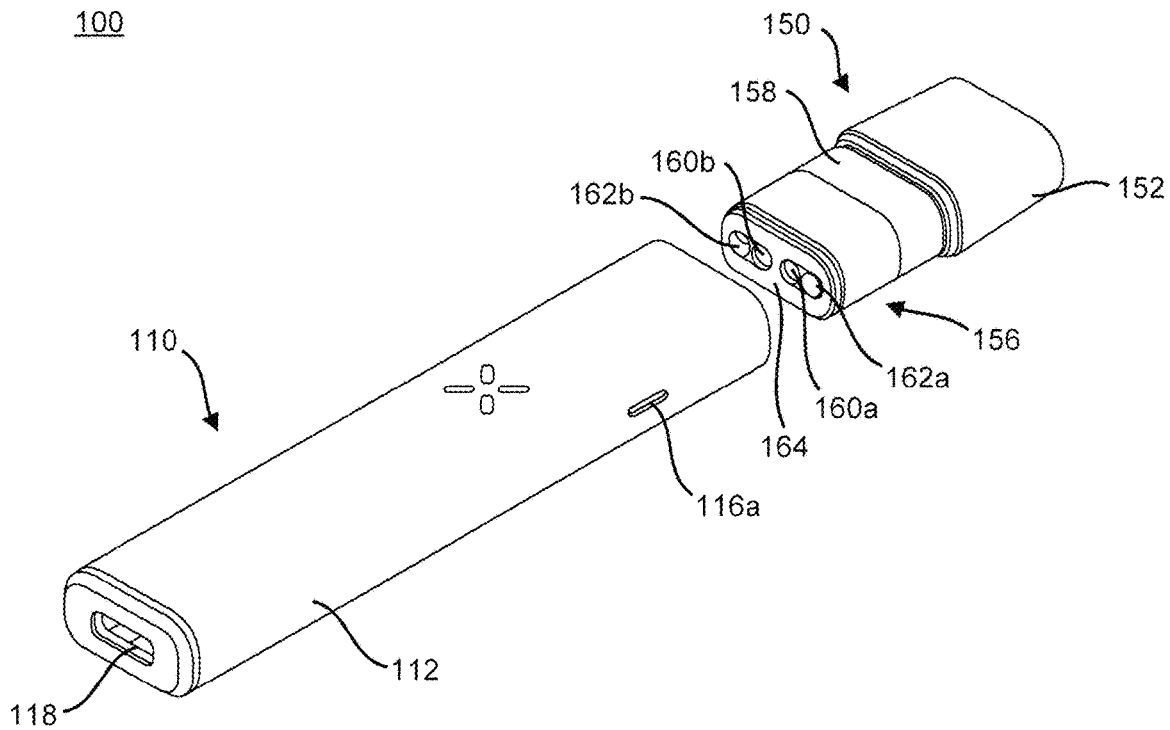
Figure 1D:
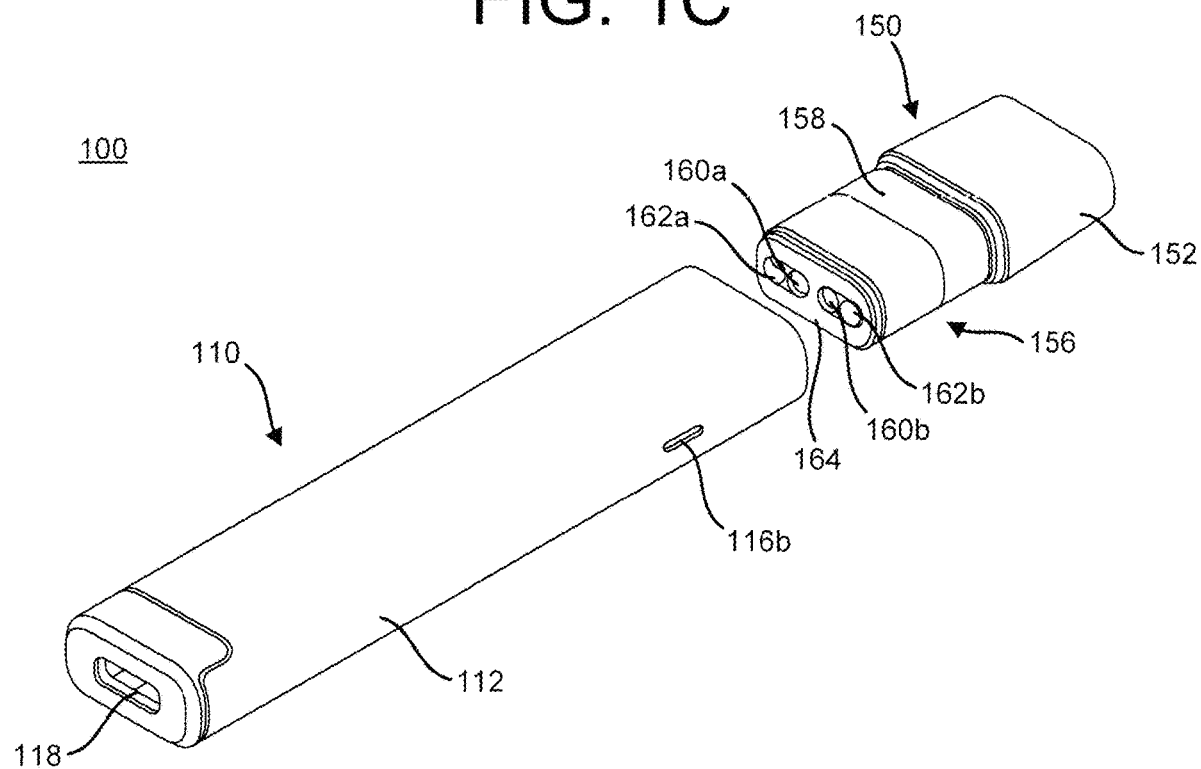
Figure 1E:
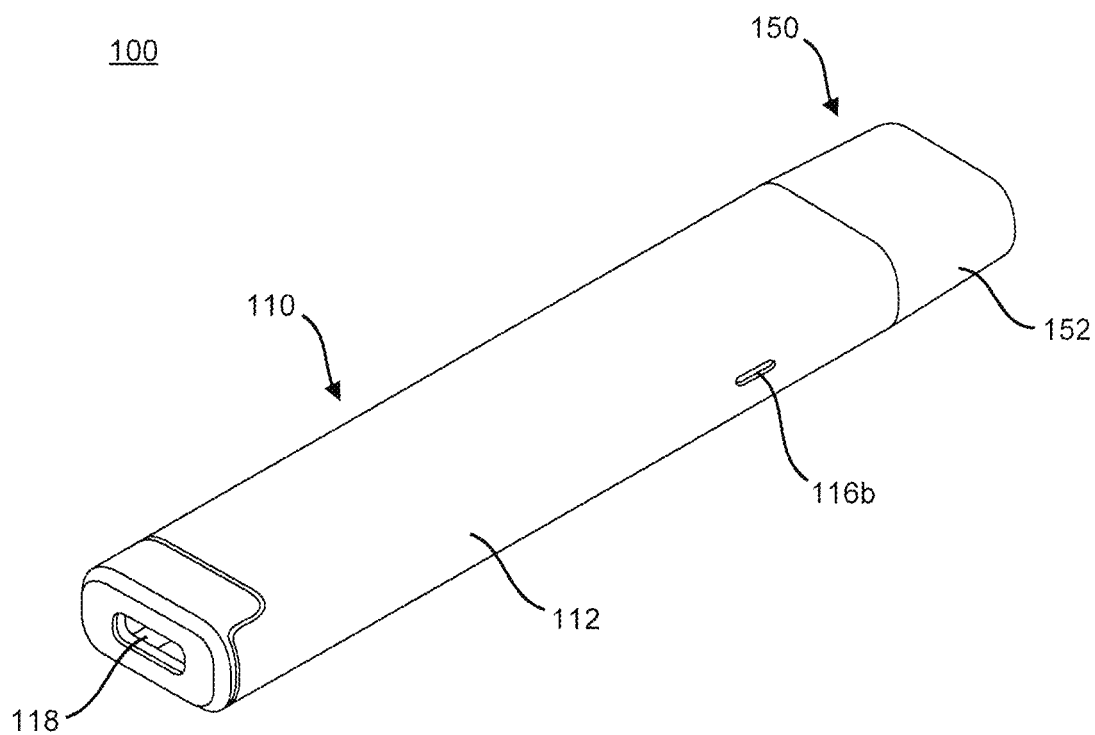
Figure 1F:
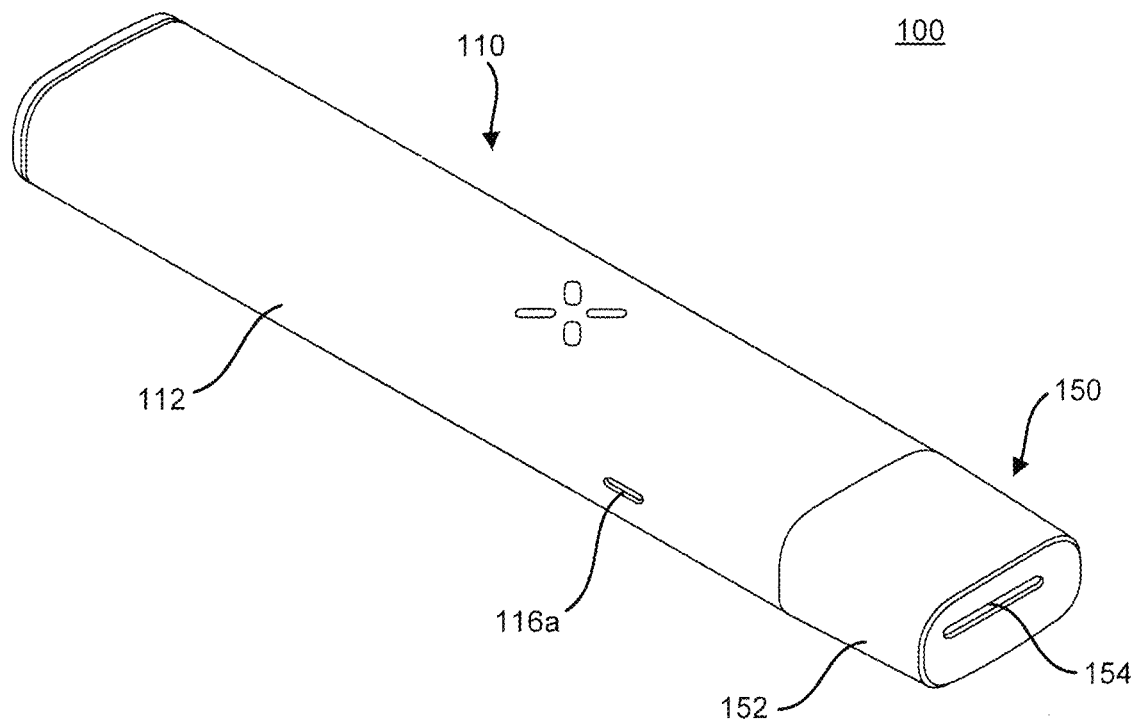

FIG. 1A-FIG. 1F illustrates features of a vaporizer device 100 including a vaporizer body 110 and a cartridge 150 consistent with implementations of the current subject matter. FIG. 1A is a bottom perspective view, and FIG. 1B is a top perspective view of the vaporizer device 100 with the cartridge 150 separated from a cartridge receptacle 114 on the vaporizer body 110. Both of the views in FIG. 1A and FIG. 1B are shown looking towards a mouthpiece 152 of the cartridge 150. FIG. 1C is a bottom perspective view, and FIG. 1D is a top perspective view of the vaporizer device with the cartridge 150 separated from the cartridge receptacle 114 of the vaporizer body 110. FIGS. 1C and 1D are shown looking toward the distal end of the vaporizer body 110. FIG. 1E is a top perspective view, and FIG. 1F is a bottom perspective view of the vaporizer device 100 with the cartridge 150 engaged for use with the vaporizer body 110.

As shown in FIGS. 1A-1D, the cartridge 150 includes, at the proximal end, a mouthpiece 152 that is attached over a cartridge body 156 that forms a reservoir (or tank) 158 that holds a vaporizable material. The cartridge body 156 may be transparent, translucent, opaque, or a combination thereof. The mouthpiece 152 may include one or more openings 154 (see FIGS. 1A, 1B, 1F) at the proximal end out of which vapor may be inhaled, by drawing breath through the vaporizer device 100. The distal end of the cartridge body 156 may couple to and be secured to the vaporizer body 110 within the cartridge receptacle 114 of the vaporizer body 110. Power pin receptacles 160a,b (see FIGS. 1C, 1D) of the cartridge 150 mate with respective power pins (or contacts) 122a,b of the vaporizer body 110 that extend into the cartridge receptacle 114. The cartridge 150 also includes air flow inlets (or air flow openings) 162a,b on the distal end of the cartridge body 156.

A tag 164, such as a data tag, a near-field communication (NFC) tag, or other type of wireless transceiver or communication tag, may be positioned on at least a portion of the distal end of the cartridge body 156. As shown in FIGS. 1C and 1D, the tag 164 may substantially surround the power pin receptacles 160a,b and the air flow inlets 162a,b, although other configurations of the tag 164 may be implemented as well. For example, the tag 164 may be positioned between the power pin receptacle 160a and the power pin receptacle 160b, or the tag 164 may be shaped as a circle, partial circle, oval, partial oval, or any polygonal shape encircling or partially encircling the power pin receptacles 160a,b and the air flow inlets 162a,b or a portion thereof.

In the example of FIG. 1A, the vaporizer body 110 has an outer shell (or cover) 112 that may be made of various types of materials, including for example aluminum (e.g., AL6063), stainless steel, glass, ceramic, titanium, plastic (e.g., Acrylonitrile Butadiene Styrene (ABS), Nylon, Polycarbonate (PC), Polyethersulfone (PESU), and the like), and any hard, durable material. The proximal end of the vaporizer body 110 includes an opening forming the cartridge receptacle 114, and the distal end of the vaporizer body 110 includes a connection 118, such as, for example, a universal serial bus Type C (USB-C) connection and/or the like. The cartridge receptacle 114 portion of the vaporizer body 110 includes one or more air inlets (or openings) 116a,b that extend through the outer shell 112 to allow airflow therein, as described in more detail below. The vaporizer body 110 as shown has an elongated, flattened tubular shape that is curvature-continuous, although the vaporizer body 110 is not limited to such a shape. The vaporizer body 110 may take the form of other shapes, such as, for example, a rectangular box, a cylinder, and the like.

The cartridge 150 may fit within the cartridge receptacle 114 by a friction fit, snap fit, and/or other types of secure connection. The cartridge 150 may have a rim, ridge, protrusion, and/or the like for engaging a complimentary portion of the vaporizer body 110. While fitted within the cartridge receptacle 114, the cartridge 150 may be held securely within but still allow for being easily withdrawn to remove the cartridge 150.

Figure 2:
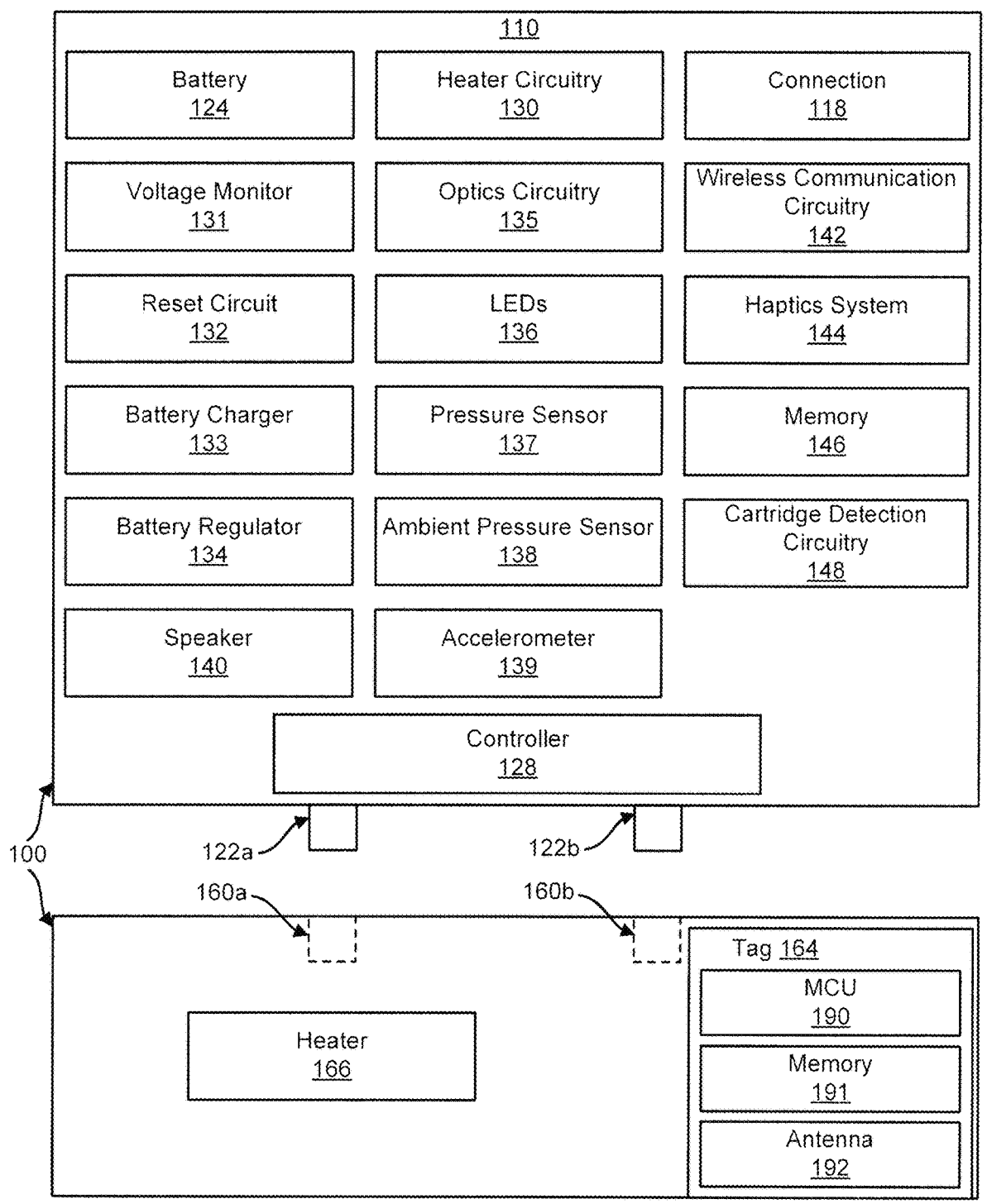
FIG. 2 is a schematic block diagram illustrating features of a vaporizer device having a cartridge and a vaporizer body consistent with implementations of the current subject matter.

FIG. 2 is a schematic block diagram illustrating components of a vaporizer device 100 having a cartridge 150 and a vaporizer body 110 consistent with implementations of the current subject matter. Included in the vaporizer body 110 is a controller 128 that includes at least one processor and/or at least one memory configured to control and manage various operations among the components of the vaporizer device 100 described herein.

Heater control circuitry 130 of the vaporizer body 110 controls a heater 166 of the cartridge 150. The heater 166 may generate heat to provide vaporization of the vaporizable material. For example, the heater 166 may include a heating coil (e.g., a resistive heater) in thermal contact with a wick, as described in further detail below.

A battery 124 is included in the vaporizer body 110, and the controller 128 may control and/or communicate with a voltage monitor 131 circuitry configured to monitor the battery voltage, a reset circuit 132 configured to reset (e.g., shut down the vaporizer device 100 and/or restart the vaporizer device 100 in a certain state), a battery charger 133, and a battery regulator 134 (which may regulate the battery output, regulate charging/discharging of the battery, and provide alerts to indicate when the battery charge is low, etc.).

The power pins 122*a,b* of the vaporizer body 110 engage complementary power pin receptacles 160*a,b* of the cartridge 150 when the cartridge 150 is engaged with the vaporizer body 110. Alternatively, the power pins may be part of the cartridge 150 for engaging complementary power pin receptacles of the vaporizer body 110. The engagement allows for the transfer of energy from an internal power source (e.g., the battery 124) to the heater 166 in the cartridge 150. The controller 128 may regulate the power flow (e.g., an amount or current and/or a voltage amount) to control a temperature at which the heater 166 heats a vaporizable material contained in the reservoir 158. According to implementations of the current subject matter, a variety of electrical connectors other than a pogo-pin and complementary pin receptacle configuration may be used to electrically connect the vaporizer body 110 and the cartridge 150, such as for example, a plug and socket connector.

The controller 128 may control and/or communicate with optics circuitry 135 (which controls and/or communicates with one or more displays such as LEDs 136), a pressure sensor 137, an ambient pressure sensor 138, an accelerometer 139, and/or a speaker 140 configured to generate sound or other feedback to a user.

The pressure sensor 137 may be configured to sense a user drawing (i.e., inhaling) on the mouthpiece 152 and activate the heater control circuitry 130 of the vaporizer body 110 to accordingly control the heater 166 of the cartridge 150. In this way, the amount of current supplied to the heater 166 may be varied according the user's draw (e.g., additional current may be supplied during a draw, but reduced when there is not a draw taking place). The ambient pressure sensor 138 may be included for atmospheric reference to reduce sensitivity to ambient pressure changes and may be utilized to reduce false positives potentially detected by the pressure sensor 137 when measuring draws from the mouthpiece 152.

The accelerometer 139 (and/or other motion sensors, capacitive sensors, flow sensors, strain gauge(s), or the like) may be used to detect user handling and interaction, for example, to detect movement of the vaporizer body 110 (such as, for example, tapping, rolling, and/or any other deliberate movement associated with the vaporizer body 110). The detected movements may be interpreted by the controller 128 as one or more predefined user commands. For example, one particular movement may be a user command to gradually increase the temperature of the heater 166 as the user intends to begin using the vaporizer device 100.

The vaporizer body 110, as shown in FIG. 2, includes wireless communication circuitry 142 that is connected to and/or controlled by the controller 128. The wireless communication circuitry 142 may include a near-field communication (NFC) antenna that is configured to read from and/or write to the tag 164 of the cartridge 150 and also automatically detect a cartridge 150. The wireless communication circuitry 142 may include additional components/circuitry for other communication modes, such as, for example, Bluetooth, Bluetooth Low Energy, and/or Wi-Fi chips and associated circuitry (e.g., control circuitry), for communication with other devices. For example, the vaporizer body 110 may be configured to wirelessly communicate with a remote processor (e.g., smartphone, tablet, wearable electronics, cloud server, and/or the like) through the wireless communication circuitry 142, and through this communication may receive control information and/or configuration parameters (e.g., information or parameters for setting temperature (i.e., a predetermined temperature), setting a dose (i.e., a predetermined dose), resetting a dose counter, etc.) from and/or transmit output information (e.g., dose information, operational information, error information, temperature setting information, charge/battery information, etc.) to one or more of the remote processors.

The tag 164, as previously described, may be a type of wireless transceiver and may include a microcontroller unit (MCU) 190, a memory 191, and an antenna 192 (e.g., an NFC antenna) to perform the various functionalities described below with further reference to FIG. 3. The tag 164 may be, for example, a 1 Kbit or a 2 Kbit NFC tag that is of type ISO/IEC 15693. NFC tags with other specifications may also be used.

Figure 3:
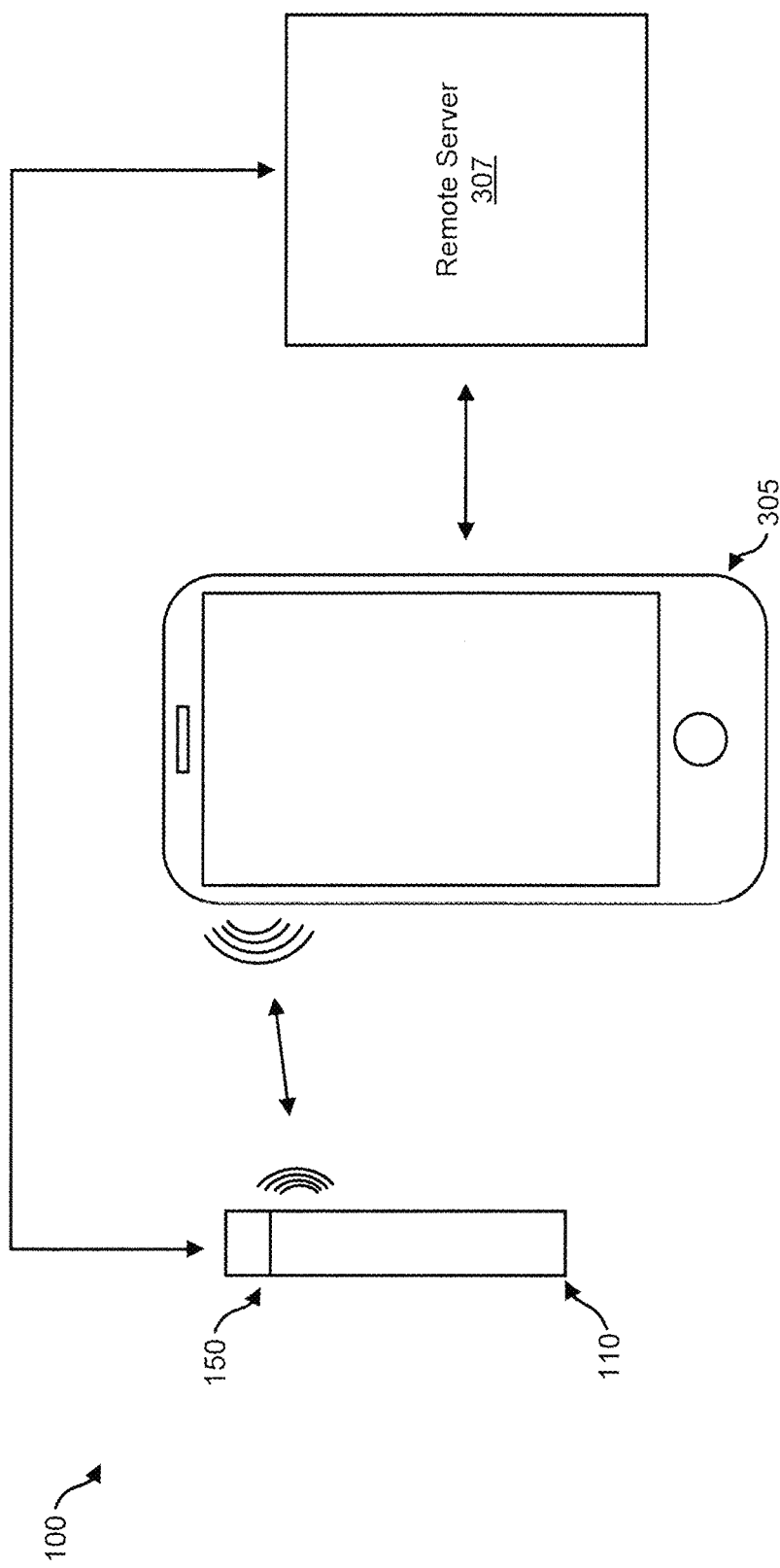
FIG. 3 illustrates communication between a vaporizer device, a user device, and a server consistent with implementations of the current subject matter.

FIG. 3 illustrates communication between a vaporizer device 100 (including the vaporizer body 110 and the cartridge 150), a user device 305 (e.g., a smartphone, tablet, laptop, and/or the like), and a remote server 307 (e.g., a server coupled to a network, a cloud server, and/or the like) consistent with implementations of the current subject matter. The user device 305 wirelessly communicates with the vaporizer device 100. A remote server 307 may communicate directly with the vaporizer device 100 or through the user device 305. The vaporizer body 110 may communicate with the user device 305 and/or the remote server 307 through the wireless communication circuitry 142. In some implementations, the cartridge 150 may establish communication with the user device 305 and/or the remote server 307 through the tag 164.

An application software ("app") running on at least one of the remote processors (the user device 305 and/or the remote server 307) may be configured to control operational aspects of the vaporizer device 100 and receive information relating to operation of the vaporizer device 100. For example, the app may provide a user with capabilities to input or set desired properties or effects, such as, for example, a particular temperature or desired dose, which is then communicated to the controller 128 of the vaporizer body 110 through the wireless communication circuitry 142. The app may also provide a user with functionality to select one or more sets of suggested properties or effects that may be based on the particular type of vaporizable material in the cartridge 150. For example, the app may allow adjusting heating based on the type of vaporizable material, the user's (of the vaporizer device 100) preferences or desired experience, and/or the like.

The app may allow a user to perform a hard-reset of the vaporizer device 100. For example, a user may indicate through the app that the vaporizer device should be reset, which may cause the vaporizer device 100 to shut down, which may be performed by the reset circuit 132. Following shut-down, the vaporizer device 100 may enter a standby mode or may resume operation, depending upon a variety of factors, such as for example the reason (if known) for the reset.

The input and/or user selections may act as control signals for the controller 128 to perform a corresponding function (e.g., reach and hold a defined temperature, provide a certain dose, reduce heat after a certain time period, reset, etc.). Likewise, the controller 128 may transmit information, through the wireless communication circuitry 142, to one of the remote processors for display via the app. For example, a summary of use of the vaporizer device 100 throughout a day may be tracked and sent to the user device 305.

Data read from the tag 164 from the wireless communication circuitry 142 of the vaporizer body 110 may be transferred to one or more of the remote processors (e.g., the user device 305 and/or the remote server 307) to which it is connected, which allows for the app running on the one or more processors to access and utilize the read data for a variety of purposes. For example, the read data relating to the cartridge 150 may be used for providing recommended temperatures, dose control, usage tracking, and/or assembly information.

Additionally, the cartridge 150 may communicate directly, through the tag 164, with one or more remote processors (e.g., the user device 305), such as, for example, a smartphone, tablet, assembly equipment, and/or filling equipment. This enables data relating to the cartridge to be written to/read from the tag 164, without interfacing with the vaporizer body 110. The tag 164 thus allows for identifying information related to the cartridge 150 to be associated with the cartridge 150 by one or more remote processors. For example, when the cartridge 150 is filled with a certain type of vaporizable material, this information may be transmitted to the tag 164 by filling equipment. Then, the vaporizer body 110 is able to obtain this information from the tag 164 to identify the vaporizable material currently being used and accordingly adjust the controller 128 based on, for example, user-defined criteria or pre-set configuration parameters associated with the particular type of vaporizable material (set by a manufacturer or as determined based upon user experiences/feedback aggregated from other users). For example, a user may establish (via the app) a set of criteria relating to desired effects for or usage of one or more types of vaporizable materials. When a certain vaporizable material is identified, based on communication via the tag 164, the controller 128 accordingly adopts the established set of criteria, which may include, for example, temperature and dose, for that particular vaporizable material.

Other information related to the cartridge 150 may be transmitted to and stored on the tag 164, such as information relating to components of the cartridge 150, for example heating components. The controller 128 of the vaporizer body 110 may use this information to control a usage session for a user. A manufacturer may thus transmit manufacturing information to the tag 164 for storage for subsequent use by the controller 128 or other remote processors (e.g., the user device 305 and/or the remote server 307).

Types of data that may be stored on the tag 164 include manufacturing data (e.g., tag serial number, tag manufacturer identifier, tag IC product code, cartridge serial number, cartridge hardware revision code, date of assembly, manufacture (MFG) lot code, MFG test equipment serial number (S/N), MFG test data (e.g., coil resistance, leak/flow rate test, cosmetic check, etc.), MFG test parameters, material logging (e.g., coil type, wick type, etc.), and/or mass of empty cartridge); filler data (which may be added after the cartridge is filled with a vaporizable material, for example, batch identifier (ID), vendor ID, product ID, strain code, mass of filled cartridge, viscosity, default/min/max temperature setting, tetrahydrocannabinol (THC) content percentage (%), cannabidiol (CBD) %, terpene %, extraction method, and/or fill date); and/or usage data (e.g., total puffs taken, total puff time, drop count, total energy delivered to cartridge (joules), date of first/most recent puff, cartridge lock (for locking cartridge to specific device/child lock), cartridge kill (initiating lock out of cartridge), min/max temperature set by user/device, min/max "baseline" resistance measured, count of bad connections (where cartridge did not properly dock and measure baseline resistance), and/or various device error codes). As previously described, the data stored on the tag 164 may also include pre-set or user-established configuration parameters relating to operation of the vaporizer body 110 with respect to the particular cartridge 150 and/or the particular type of vaporizable material (e.g., a predetermined temperature and/or parameters associated with a dose). The tag data may be encrypted and/or hashed, and the tag 164 may be password protected.

Returning to FIG. 2, the vaporizer body may include a haptics system 144, such as, for example, an actuator, a linear resonant actuator (LRA), an eccentric rotating mass (ERM) motor, or the like that provide haptic feedback such as, for example, a vibration as a "find my device" feature or as a control or other type of user feedback signal. For example, using an app running on a user device (such as, for example, the user device 305), a user may indicate that he/she cannot locate his/her vaporizer device 100. Through communication via the wireless communication circuitry 142, the controller 128 sends a signal to the haptics system 144, instructing the haptics system 144 to provide haptic feedback (e.g., a vibration). The controller 128 could additionally or alternatively provide a signal to the speaker 140 to emit a sound or series of sounds. The haptics system 144 and/or speaker 140 may also provide control and usage feedback to the user of the vaporizer device 100; for example, providing haptic and/or audio feedback when a particular amount of a vaporizable material has been used or when a period of time since last use has elapsed. Alternatively or additionally, haptic and/or audio feedback may be provided as a user cycles through various settings of the vaporizer device 100. Alternatively or additionally, the haptics system 144 and/or speaker 140 may signal when a certain amount of battery power is left (e.g., a low battery warning and recharge needed warning) and/or when a certain amount of vaporizable material remains (e.g., a low vaporizable material warning and/or time to replace the cartridge).

The vaporizer body 110 also includes the connection (e.g., USB-C connection, micro-USB connection, and/or other types of connectors) 118 for coupling the vaporizer body to a charger to enable charging the battery 124. Alternatively or additionally, electrical inductive charging (also referred to as wireless charging) may be used, in which case the vaporizer body 110 would include inductive charging circuitry to enable charging. The connection 118 at FIG. 2 may also be used for a data connection between a computing device and the controller 128, which may facilitate development activities such as, for example, programming and debugging, for example.

The vaporizer body 110 may also include a memory 146 that is part of the controller 128 or is in communication with the controller 128. The memory 146 may include volatile and/or non-volatile memory or provide data storage. In some implementations, the memory 146 may include 8 Mbit of flash memory, although the memory is not limited to this and other types of memory may be implemented as well.

As mentioned above, the vaporizer device 100 includes the cartridge 150 configured to operatively couple with the vaporizer body 110. In some implementations, the cartridge 150 is disposable whereas the vaporizer body 110 is durable and/or re-usable. The cartridge 150 may also be configured to be reused as described elsewhere herein.

FIGS. 4-46C illustrate various examples of a cartridge 150, 250, 350, 450, 550 consistent with implementations of the current subject matter. The features, properties, and/or components of each of the cartridges 150, 250, 350, 450, 550 described herein may be implemented on one or more the other disclosed cartridges 150, 250, 350, 450, 550. For example, the features, properties, and/or components of the cartridge 150 may be implemented in the cartridge 250, 350, 450, 550 and/or the features, properties, and/or components of the cartridge 250 may be implemented in the cartridge 150, 350, 450, 550 and/or the features, properties, and/or components of the cartridge 350 may be implemented in the cartridge 150, 250, 450, 550 and/or the features, properties, and/or components of the cartridge 450 may be implemented in the cartridge 150, 250, 350, 550, and/or components of the cartridge 550 may be implemented in the cartridge 150, 250, 350, 450.

FIG. 4, FIG. 5A, FIG. 5B, and FIG. 6 illustrate features of a cartridge 150 of a vaporizer device 100 consistent with implementations of the current subject matter. The cartridge 150 may include the cartridge body 156 defining, at least in part, a reservoir 158 configured to contain vaporizable material, a mouthpiece 152, and a vaporizing assembly of vapor-generating components positioned within the cartridge body 156 and configured to vaporize the vaporizable material. Each will be described in more detail below.

The cartridge body 156 can be divided, generally, into a proximal end region 156A, a central region 156B, and a distal end region 156C. The proximal end region 156A of the cartridge body 156 can be coupled to the mouthpiece 152 configured to deliver the vapor to the user. A tank or reservoir 158 is defined, at least in part by, the proximal end region 156A and the central region 156B of the cartridge body 156 and is configured to contain an amount of the vaporizable material. The distal end region 156C of the cartridge body 156 may house one or more components configured to vaporize the material from the reservoir 158 into a vaporization chamber 1005 (see, e.g., FIG. 5A and FIG. 5B). The mouthpiece 152 is configured to interface with the user to release the vapor from the vaporization chamber 1005 to the user through one or more openings 154 in the mouthpiece 152, for example, upon the user drawing a breath through the vaporizer device 100. Each of these components will be described in more detail below.

In some implementations, the vaporizable material is *cannabis* oil. *Cannabis* oils can present particular challenges when vaporized using a cartridge and a vaporizer device. For example, *cannabis* oil is relatively sticky and viscous, particularly once it dries out. Thus, leakage may be a more serious consideration and challenge compared to other aqueous vaporizable materials. In particular, leakage of *cannabis* oil may result in clogging of the device and disturbing the electrical components, particularly the electrical contacts. The dried oil can also disrupt the electrical control of the vaporizer device due to its electrically insulating properties. The cartridges described herein may in certain implementations provide robust leak-resistant designs and may be configured to be used with viscous oil-based vaporizable materials, such as *cannabis* oil that can have a viscosity at room temperature of between about 40 cP and 113 KcP.

Figure 4:
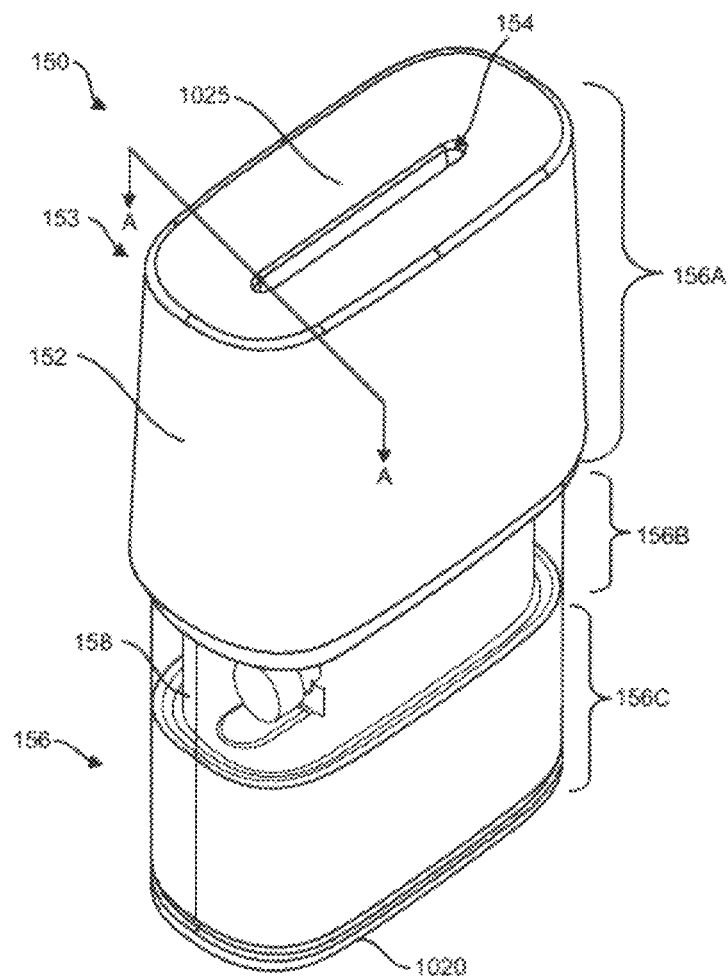
FIG. 4 illustrates a cartridge of a vaporizer device consistent with implementations of the current subject matter.

As mentioned, the cartridge body 156 can be divided generally into the upper, proximal end region 156A, the lower, distal end region 156C, and the central region 156B located between the proximal and distal end regions 156A, 156C (see FIG. 4). The upper, proximal end region 156A of the cartridge body 156 is configured to couple with the mouthpiece 152, for example, by inserting within an internal volume 1010 of the mouthpiece 152 such that an exterior surface of the cartridge body 156 near the upper proximal end region 156A seals with an inner surface of the mouthpiece 152. The proximal end region 156A of the cartridge body 156 can define a central channel 1015 for directing vapor from the vaporization chamber 1005 towards the one or more openings 154 through the mouthpiece 152. The lower, distal end region 156C of the cartridge body 156 may house components configured to couple with the vaporizer body 110, for example, by inserting within the cartridge receptacle 114, which will also be described in more detail below. The reservoir 158 is defined by hollow portions of the central region 156B and the proximal end region 156A of the cartridge body 156.

As mentioned, the distal end region 156C of the cartridge body 156 may be configured to couple to and be secured with the vaporizer body 110, for example, by inserting within the cartridge receptacle 114 (see FIG. 1A and FIG. 1B). The cartridge receptacle 114 may have a proximal opening and an inner diameter sufficient to receive the outer diameter of the distal end region 156C of the cartridge body 156. Additionally, the cartridge receptacle 114 may have a depth sufficient to slide the cartridge body 156 into the cartridge receptacle 114 up to about the level of the mouthpiece 152. Thus, the walls of the cartridge receptacle 114 may surround the cartridge body 156 on the distal end 1020 and all four sides of the distal end region 156C and the central region 156B. Other configurations of coupling between the cartridge body 156 and the vaporizer body 110 are considered herein. For example, in some implementations, the cartridge body 156 may insert within the cartridge receptacle 114 from a side opening rather than from a proximal opening. Alternatively, in some implementations, the cartridge body 156 need not insert within a receptacle that fully surrounds the distal end region 156C of the cartridge body 156, for example, if the cartridge body 156 and vaporizer body 110 form a seal sufficient to sense a pressure drop. The cartridge body 156 may include a receptacle configured to receive a proximal end region of the vaporizer device 100. In another implementation, the cartridge body 156 may insert within a slot of the vaporizer body 110 such that at least one wall of the distal end region 156C of the cartridge body 156 forms an outer surface and completes the outer contour of the vaporizer device 100 upon coupling between the cartridge 150 and the vaporizer body 110. The cartridge body 156 and the vaporizer body 110 may also snap together on their respective distal and proximal ends without the exterior walls of the cartridge body 156 being contained by or covered by a receptacle wall of the vaporizer body 110. For example, the distal end 1020 of the cartridge body 156 may include a coupling mechanism configured to fixedly attach and seal with the proximal end of the vaporizer body 110.

The cartridge 150 can couple within the cartridge receptacle 114 by a friction-fit, snap-fit, and/or other types of secure connection. In some implementations, any of a variety of complementary coupling features may be incorporated, including but not limited to tab, indent, magnetic lock, channel, rim, lip, ridge, protrusion, groove, rib, etc., that are configured to engage with a complementary feature (not shown) of the vaporizer body 110. For example, in some implementations the cartridge 150 and vaporizer body 110 may incorporate one or more coupling features having corresponding male and female parts that allow the cartridge 150 to snap into place in operable contact with the vaporizer body 110. The distal end region 156C of the cartridge body 156 may include substantially straight or inwardly tapered sides and include one or more coupling features that secure the cartridge 150 within the cartridge receptacle 114 of the vaporizer body 110. The one or more coupling features may be configured to engage with a complementary feature on the vaporizer body 110, such as within the cartridge receptacle 114, when the cartridge 150 engages with the vaporizer body 110. For example, the one or more coupling features may be male parts such as a pair of tabs or a circumferential rib on an outer surface of the distal end region 156C of the cartridge body 156 that inserts within a complementary female part such as a pair of indents or a circumferential groove on an inner surface of the cartridge receptacle 114. The male parts may snap into the female parts upon downward insertion of the cartridge 150 within the cartridge receptacle 114 to provide a secure fit and reversed upon withdrawing the cartridge 150 upward out of the cartridge receptacle 114.

In some implementations, the one or more coupling features is a circumferential rib on an outer surface of the cartridge 150, for example, near where proximal end region 156A meets the central region 156B (see FIG. 13). The circumferential rib may be an elastomeric element configured to provide an interference fit with an inner surface of the cartridge receptacle 114 such that the cartridge 150 securely couples with the vaporizer body 110 without needing to engage with a corresponding feature on the inner surface of the cartridge receptacle 114. The circumferential rib may be part of a mouthpiece seal 177 positioned between and configured to seal between an inner surface of the mouthpiece 152 and an outer surface of the cartridge body 156. The compliant material of the mouthpiece seal 177 may wedge against and engage with the inner surface of the cartridge receptacle 114 providing a secure fit. The mouthpiece seal 177 may provide a snap-fit feel upon seating the cartridge 150 within the cartridge receptacle 114 of the vaporizer device.

The cartridge 150 may have an elongate and flattened tubular body extending in a distal to a proximal axis (longitudinal axis A). The cartridge 150 may be described as having a length (sometimes referred to herein as a height), a width, and a depth (sometimes referred to herein as a thickness). The height is a length from the proximal end to the distal end of the cartridge 150 along the longitudinal axis A (see, for example, FIG. 13). The width of the cartridge is measured transverse the longitudinal axis A along a major axis of the cartridge 150 and thus refers to the length of the longer sides of the cartridge. The depth of the cartridge 150 is also measured transverse the longitudinal axis A, but along the minor axis of the cartridge 150 and thus refers to the length of the shorter sides. The width may be 1.2 times, 1.3 times, 1.4 times, 1.5 times, 1.6 times, 1.7 times, 1.8 times, 1.9 times, etc. or greater than the depth. The cartridge 150 may be between about 1 cm and 10 cm long, between about 2 cm and 7 cm long, between 3 cm and 5 cm long. The length of the cartridge 150 may be less than 8 cm, less than 7 cm, less than 6 cm, less than 5.5 cm, less than 5 cm, etc. In some implementations, the cartridge 150 may have a total length of about 3.3 cm, a width (i.e., across the major axis of the cartridge) of about 1.7 cm, and a depth (i.e., across the minor axis of the cartridge) of about 0.85 cm.

The cross-sectional shape of the cartridge body 156 may be any of a variety of shapes, including circular, round, or non-round shapes, such as an approximately oval, elliptical, rectangular, square, trapezoidal, or other cross-sectional shape. The cross-sectional shape may be geometric or free-form shape. Non-round shapes, particularly flattened shapes may be preferred to prevent rolling when the vaporizer device 100 is placed on its side. The shape of the cartridge 150, including the cartridge body 156 and the mouthpiece 152, resembles or is a continuation of the general shape of the vaporizer body 110 such that upon coupling the cartridge 150 and the vaporizer body 110 together, the vaporizer device 100 has a substantially sleek profile. The coupling between the cartridge 150 and the vaporizer body 110 may allow for the vaporizer device 100 to have continuous edges that provide a seamless unibody profile from end to end.

Because the overall shape of the cartridge 150 may be somewhat flattened, the coupling between the cartridge 150 and the vaporizer body 110 may occur upon relative sliding along the longitudinal axis A of the vaporizer device 100 as shown at FIG. 13. However, depending on the shape and configuration of the cartridge body 156 and the cartridge receptacle 114, other relative movements are considered herein, such as rotation around the longitudinal axis A or side-to-side movements orthogonal to the longitudinal axis A of the vaporizer device 100. In some implementations, the cartridge receptacle 114 and the cartridge 150 have bilateral symmetry such that the cartridge 150 may be flipped horizontally relative to the cartridge receptacle 114 and still operatively couple with the vaporizer body 110. In other implementations, the cartridge receptacle 114 and cartridge 150 have lateral dissymmetry such that they engage with one another in only a single orientation.

The fit between the cartridge body 156 and the vaporizer body 110 may be sufficient to provide a secure fit to prevent inadvertent uncoupling, but may still allow for the cartridge 150 to be easily withdrawn or disengaged from the vaporizer body 110 to remove and replace the cartridge 150. In some implementations, the engagement between the cartridge body 156 and the vaporizer body 110 may include a release button or other feature that is configured to actively disengage the cartridge 150 from the device. The outer surface of the cartridge 150 may incorporate one or more three-dimensional features such as slots, knurling, or other type of finger grips that aid a user during installation and removal of the cartridge 150 from the vaporizer body 110. The coupling, such as a snap-fit coupling, may provide a visual, audible and/or tactile confirmation that the cartridge body 156 is positioned properly relative to the vaporizer body 110.

Again with respect to FIG. 4, FIG. 5A, FIG. 5B, and FIG. 6, the proximal end region 156A of the cartridge body 156 is configured to couple with the mouthpiece 152. The mouthpiece 152 can include the internal volume 1010 sized such that the mouthpiece 152 may be attached over the proximal end region 156A of the cartridge body 156. As such, the mouthpiece 152 may form the proximal end of the cartridge 150. The mouthpiece 152 may have an external surface that is generally amenable to a user placing their lips over the proximal end 153 of the mouthpiece 152 to inhale the vapor. The external surface of the mouthpiece 152 may have a variety of configurations. In some implementations, the external surface may have smooth edges that are pleasing to the lips and tongue. The mouthpiece may also have a length along the longitudinal axis A sufficient to be inserted a distance between the lips for inhaling. As mentioned above, the cartridge 150 may have a total length along the longitudinal axis A from the proximal end to the distal end that is between about 3 cm and 5 cm, a width (i.e., across the major axis of the cartridge) of between about 1 cm and about 2 cm, and a depth (i.e., across the minor axis of the cartridge) of between about 0.5 cm and about 1 cm. In some implementations, the mouthpiece 152 may have a length along the longitudinal axis A that is about 0.5 cm, about 0.75 cm, about 1 cm, about 1.25 cm, about 1.5 cm, about 1.75 cm, about 2.0 cm, about 2.25 cm, about 2.5 cm, up to about 3.0 cm in length. The length of the mouthpiece 152 along the longitudinal axis A may be a fraction of the total length of the cartridge 150 as a whole, for example, at least 25%, at least 30%, at least 35%, at least 40%, up to about 50% the total length of the cartridge 150. As described elsewhere herein, the cartridge 150 may be somewhat flattened in shape creating a rectangular shape such that a width of the cartridge 150 is greater than the depth. The mouthpiece 152 of the cartridge may also have a somewhat flattened shape. For example, the mouthpiece 152 may have a length that is about 1.5 cm, a width (across the major axis) that is about 1.7 cm, and a depth (across the minor axis) that is about 0.85 cm. It should be appreciated that the proximal end region of the mouthpiece 152 may taper slightly such that the thickness of the mouthpiece 152 across the minor axis may be less at the proximal end than the thickness at the distal end of the mouthpiece 152.

One or more openings 154 may extend through the proximal end surface 1025 into the internal volume 1010 of the mouthpiece 152. The one or more openings 154 allow for the vapor produced within the cartridge 150 to be inhaled by the user. The one or more openings 154 may be aligned with the central, longitudinal axis A of the device or positioned off-set from the longitudinal axis A. The proximal end surface 1025 of the mouthpiece 152 may be sloped inwardly away from the outer edges towards the one or more openings 154. The relative size of the one or more openings 154 may be minimized to hide from view internal components positioned beneath the mouthpiece 152 from the proximal end 153 of the cartridge 150 and aid in reducing the amount of dirt/lint that may enter the mouthpiece 152, while at the same time being of sufficient size to permit the sufficient flow of vapor to the user. In some implementations, the one or more openings 154 through the proximal end surface 1025 of the mouthpiece 152 is a single, elongate slot that has a relatively narrow width providing a generally thin, rectangular shape to the opening 154. However, other shapes, sizes, and/or configurations of the mouthpiece opening 154 may be utilized. For example, the mouthpiece opening 154 may be an oval shape, or two more openings of the same or different shapes may be used.

In some implementations, the elongate opening 154 may have a length along the major axis of the mouthpiece 152 that is a fraction of the total width of the mouthpiece 152 along the major axis. For example, the opening 154 may have a length that is at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, up to at least about 90% of the total width of the mouthpiece along the major axis. The elongate opening 154 may have a narrow width along the minor axis of the mouthpiece 152. For example, the opening 154 may have a width that is no greater than 50%, no greater than 45%, no greater than 40%, no greater than 35%, no greater than 30%, no greater than 25%, no greater than 20%, no greater than 15%, or no greater than 10% of the total width of the mouthpiece along the minor axis. For example, the width of the mouthpiece 152 along the major axis may be about 2 cm and the width of the mouthpiece 152 along the minor axis may be about 1 cm. The opening 154 of the mouthpiece 152 may have a length along the major axis that is about 0.5 cm to about 1.8 cm and a width along the minor axis that is about 0.1 cm to about 0.5 cm. In some implementations, the opening 154 of the mouthpiece 152 has a length that is about 10 mm, about 11 m, about 12 mm, about 13 mm, about 14 mm, up to about 15 mm and has a width of about 1 mm, 1.25 mm, about 1.5 mm, about 1.75 mm, about 2 mm, about 2.25 mm, about 2.5 mm, up to about 3 mm. The dimensions of the opening 154 may vary. The dimensions of the opening 154 may be sufficient to allow vapor to be easily drawn through the opening 154 while the internal components within the cartridge 150 are substantially hidden from view.

The mouthpiece 152 may couple (e.g., snap-fit) onto the proximal end region 156A of the cartridge body 156 to snugly mate with the cartridge body 156. The configuration of the coupling between the cartridge body 156 and the mouthpiece 152 may vary. The coupling may incorporate corresponding male and female parts configured to mate together. For example, an inner surface of the mouthpiece 152 (or the external surface of the cartridge body 156) may incorporate a lip, flange, rib, or other outwardly projecting coupling feature configured to slide past and/or into a corresponding feature on an exterior surface of the cartridge body 156 (or the inner surface of the mouthpiece 152).

The mouthpiece 152 may be permanently affixed to the cartridge body 156 by the coupling or may be configured to be removed by a user. For example, the mouthpiece 152 may be removed from the cartridge body 156 in order to refill the reservoir and attached again following refilling for reuse. The cartridge 150 may be disposable and not configured to be refilled. It should be appreciated that the mouthpiece 152 need not be a part of the cartridge 150 itself. For example, the cartridge 150 may include a reservoir and be configured to attach with the vaporizer body 110 independent of the mouthpiece 152.

Mating between the mouthpiece 152 and the proximal end region 156A of the cartridge body 156 may provide a seal with an exterior surface of the cartridge body 156. For example, the mouthpiece seal 177 may be incorporated between where the mouthpiece 152 and the proximal end region 156A of the cartridge body 156 couple together. The sealing of the mouthpiece seal 177 may eliminate, or at least aid in reduction of, air leaks at the junction between the mouthpiece 152 and the cartridge body 156. Preventing air flow leaks into the mouthpiece 152 at this junction, in turn, may improve drawing vapor through the at least one opening in the mouthpiece by blocking gas flow between the inner surface of the mouthpiece and the outer surface of the cartridge body and thereby may increase air flow through the cartridge 150, which will be described in more detail below. The sealing may also eliminate, or aid in the reduction of, vapor leaks from the mouthpiece 152.

As mentioned above, the mouthpiece seal 177 may be incorporated between where the mouthpiece 152 and the cartridge body 156 couple together. The mouthpiece seal 177 may be dual-purpose in that it may provide a seal or barrier between the mouthpiece 152 and the cartridge body 156 to prevent leaks as discussed above. The mouthpiece seal 177 also may aid in coupling the cartridge 150 to the cartridge receptacle 114 of the vaporizer body 110 by providing a seal between the cartridge 150 and the cartridge receptacle 114. Thus, the mouthpiece seal 177 simplifies manufacturing in that a single element may perform more than a single function. In some implementations, the mouthpiece seal 177 may be an elastomeric element such as an O-ring or flattened band positioned over the exterior surface of the cartridge body 156. In other implementations, the mouthpiece seal 177 may be formed around (e.g., by overmolding) the exterior surface of the cartridge body 156. The mouthpiece seal 177 may be an elastomeric element that encircles the exterior surface of the cartridge body 156 near the proximal end region 156A, for example where the proximal end region 156A meets the central region 156B of the cartridge body 156. The mouthpiece seal 177 may engage the internal surface of the mouthpiece 152 near its distal end region 1030. The mouthpiece seal 177 may be a generally annular feature having a flat inner diameter configured to be affixed or engaged flush with the external surface of the cartridge body 156. The outer surface of the mouthpiece seal 177 may have at least one, two, three, or more circumferential sealing beads or ribs 1035 (see FIG. 5A and FIG. 5B). The ribs 1035 may provide a redundancy to the sealing between the mouthpiece 152 and the cartridge body 156 as well as a redundancy to the coupling between the cartridge 150 and the vaporizer body 110. The ribs 1035 may provide a maximum outer diameter for the mouthpiece seal 177 that is slightly oversized compared to an inner diameter of the distal end region 1030 of the mouthpiece 152. Thus, when the mouthpiece 152 is inserted over the proximal end region 156A of the cartridge body 156, the inner diameter of the mouthpiece 152 slightly compresses one or more of the ribs 1035 of the mouthpiece seal 177, thereby providing an airtight, circumferential seal between the two components. In some implementations, the mouthpiece seal 177 is an over-molded element on the proximal end region of the cartridge body 156 thereby eliminating a hand assembly step in production. The over-molded design may also improve performance of the seal in that the mouthpiece seal 177 is less likely to twist or roll relative to the cartridge body 156 that might occur with an O-ring. In some implementations, the mouthpiece seal 177 may be positioned or over-molded within a groove formed in the exterior surface to provide better fixation of the mouthpiece seal 177 to the exterior surface of the cartridge body 156. The groove in the exterior surface of the cartridge body 156 may have a surface that is conducive to coupling with the inner diameter of the mouthpiece seal 177. For example, the surface of the groove may be etched or otherwise textured. In some implementations, the inner surface of the distal end region 1030 of the mouthpiece 152 may have an inwardly-projecting feature configured to snap over and position within a groove between the ribs 1035 of the mouthpiece seal 177. The mouthpiece seal 177 may be positioned on the cartridge body 156 near where the distal end region 1030 of the mouthpiece 152 encircles the cartridge body 156. This allows for the mouthpiece seal 177 to provide sealing between the mouthpiece 152 and the cartridge body 156 as well as between the cartridge 150 and the cartridge receptacle 114 of the vaporizer body 110 upon coupling of the two. For example, the mouthpiece seal 177 may have width such that one or more of the ribs 1035 near a proximal end of the mouthpiece seal 177 may engage with the distal end region 1030 of the mouthpiece 152 and block gas flow between the inner surface of the mouthpiece 152 and the outer surface of the cartridge body 156, and one or more of the ribs 1035 near a distal end of the mouthpiece seal 177 remain available and seal within the opening of the cartridge receptacle 114 upon coupling with the vaporizer body 110.

The second sealing rib 1035 may be configured to provide an interference fit between the outer surface of the cartridge body 156 and the inner surface of the cartridge receptacle 114 of the vaporizer device. The second sealing rib 1035 may provide a snap-fit with the cartridge receptacle 114 when inserted within the cartridge receptacle 114. It should be appreciated that the position of the mouthpiece seal 177 relative to the mouthpiece 152 may vary. Additionally, the mouthpiece 152 may incorporate more than the mouthpiece seal 177, for example, the mouthpiece seal 177 near the distal end region 1030 as well as a seal (such as an O-ring) closer to the proximal end 153 of the mouthpiece 152.

Again with respect to FIG. 5A, FIG. 5B, and FIG. 6, the mouthpiece 152 may be coupled to the proximal end region 156A of the cartridge body 156. The mouthpiece 152 may include an internal volume 1010 and an external surface defining at least one opening 154 into the internal volume 1010. The at least one opening 154 may be configured to release vapor from the vaporizing assembly in the cartridge. The internal volume 1010 of the mouthpiece 152 may be mostly filled by the proximal end region 156A of the cartridge body 156. The internal volume 1010 of the mouthpiece 152 may include a region, for example, near the proximal end 153 of the cartridge 150 adjacent the one or more openings 154 of the mouthpiece 152, that is configured to contain one or more absorbent pads 170 within the internal volume 1010. The one or more pads 170 may be positioned within the internal volume 1010 of the mouthpiece 152 near or proximate to the one or more openings 154 through which vapor may be inhaled, e.g., by drawing breath through the vaporizer device 100, such that it may capture moisture just prior to inhalation by the user. The one or more absorbent pads 170 may prevent or reduce the flow of fluid, such as the vaporizable material, into and out of the one or more openings 154. The one or more pads 170 may be pushed against the interior surface of the mouthpiece 152 or may be pulled away from interior walls so as to maximize the surface area available for moisture absorption. The pads may have any of a variety of shapes including rectangular, circular, ovoid, triangular, square, ring, or other shape. The size and shape of the pads 170 may be selected to minimize interference with the vapor path through the openings 154 while maximizing moisture and particle collection. Thus, the pads 170 may capture deposited and/or condensed liquid from the vapor flowing through the cartridge 150 without requiring the vapor to pass through the pads 170.

In an implementation, the absorbent pad 170 is configured to be positioned within the internal volume 1010 of the mouthpiece 152 near the opening 154 without obstructing vapor flow through the opening 154. The pad 170 may be positioned within the mouthpiece 152 such that the pad 170 is generally off-axis relative to the opening 154 allowing unobstructed vapor flow through the opening 154. In other implementations, the pad 170 may be coaxial with the opening 154 and the shape of the pad 170 allows the pad to avoid obstructing vapor flow through the opening 154.

Figures 5A, 5B:
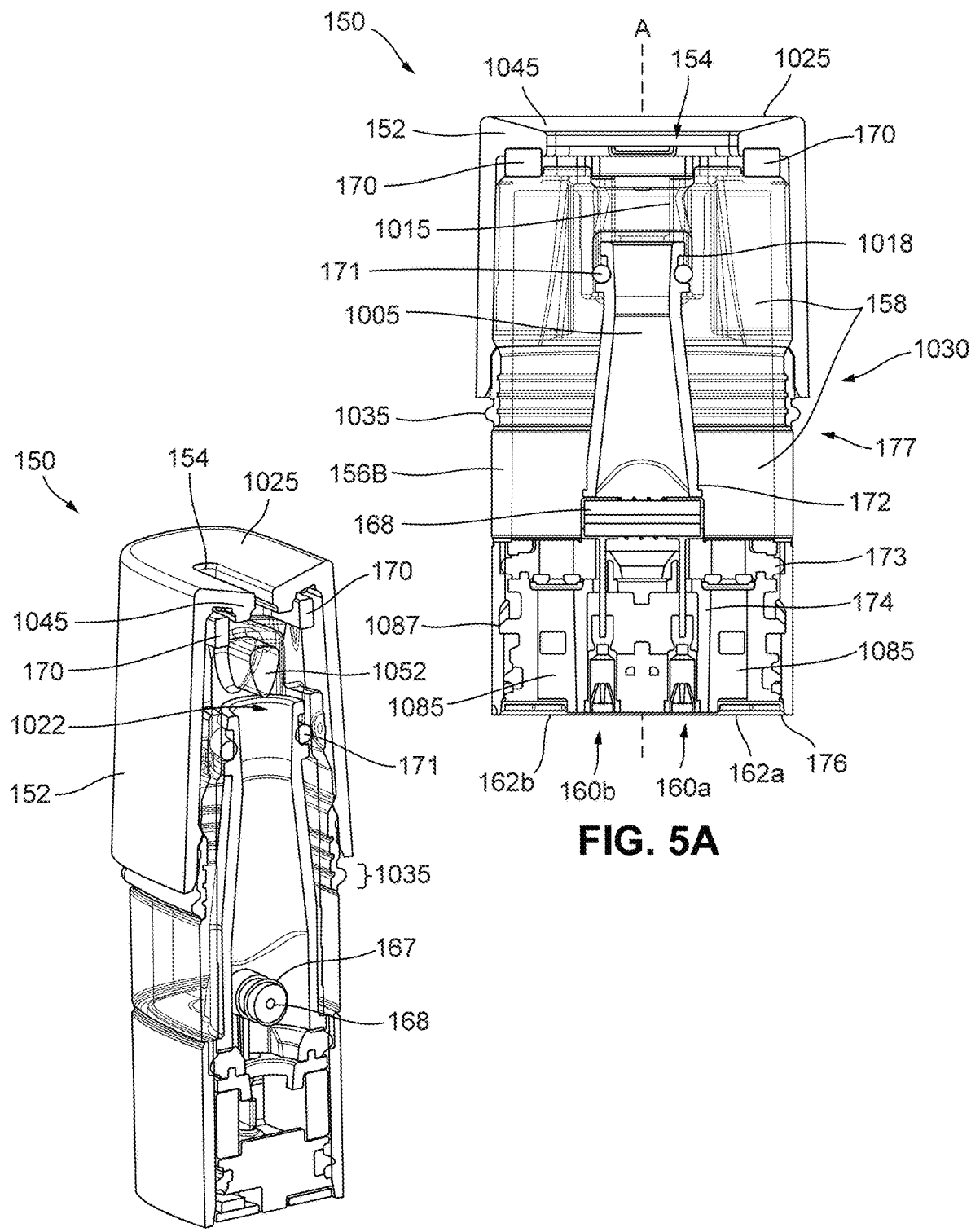
FIGS. 5A-5B illustrate cross-sectional views of a cartridge consistent with implementations of the current subject matter.
Figure 6:
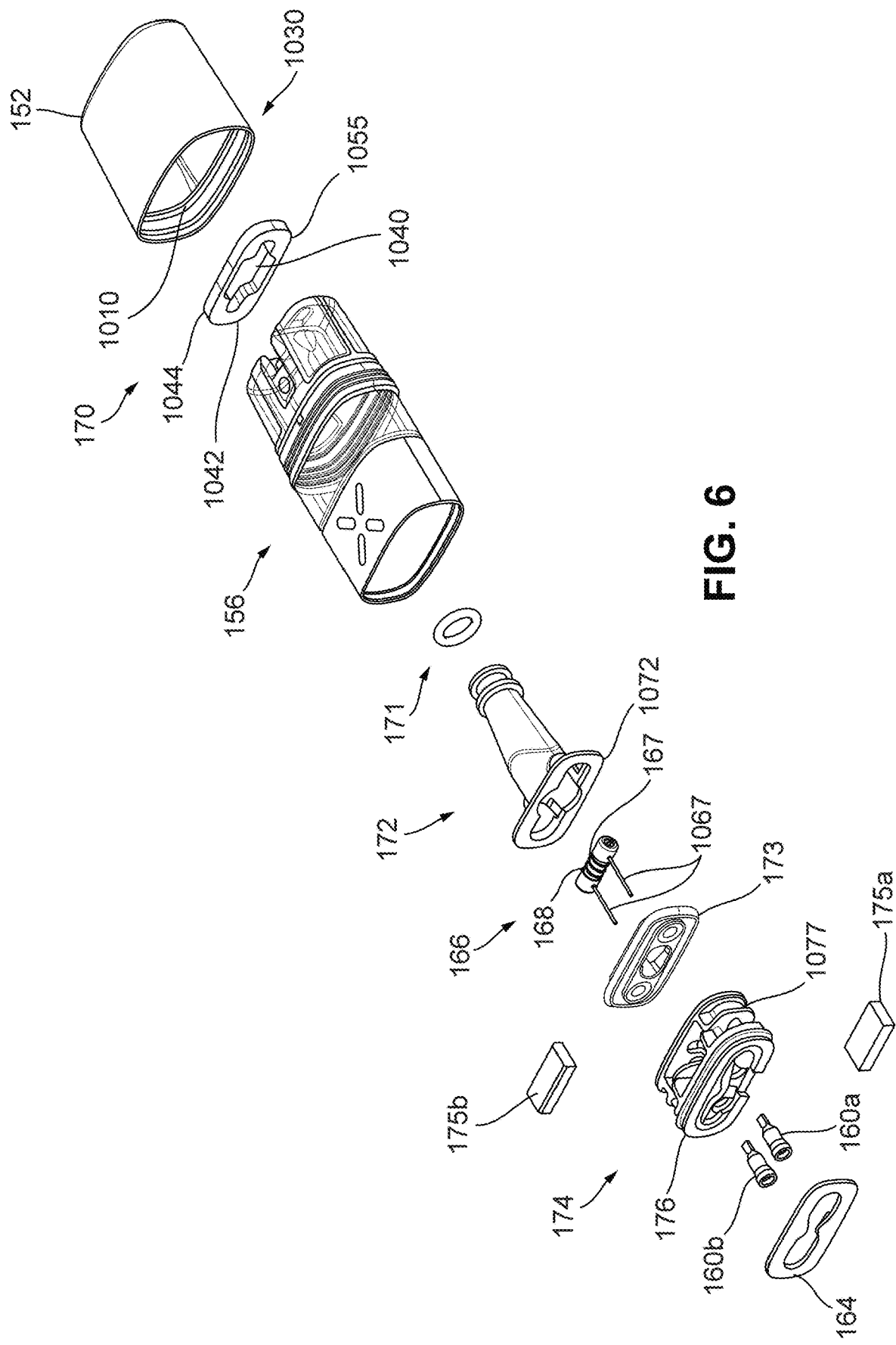
FIG. 6 illustrates an exploded view of a cartridge consistent with implementations of the current subject matter.

FIG. 6 illustrates that the pad 170 may be a flattened disk defining a central opening 1040 and thus, has a ring-like shape. In an implementation, an external surface of the mouthpiece 152 may define the opening 154 into the internal volume as a narrow, elongate slit. The central opening 1040 of the pad 170 may have a shape that corresponds or substantially corresponds to a shape of the opening 154 such that it may surround the opening 154. The pad 170 may be wedged within the internal volume of the mouthpiece to avoid blocking gas flow through the opening 154. The ring-shaped pad 170 may have an inner perimeter or wall 1042 defining the central opening 1040 that is sized and shaped to surround the opening 154 through the upper end of the mouthpiece 152. The pad 170 may also have an outer perimeter or wall 1044 sized and shape to engage with the inner sides of the mouthpiece 152. It should be appreciated the pad 170 may have a ring shape, but need not be a circular ring-shaped object. Rather, the absorbent pad 170 may be a flat, non-circular ring having a perimeter in the shape of an oval, ellipse, or rectangle. The outer wall 1044 may have a shape configured to mate with an inner surface of the mouthpiece 152. In some implementations, the outer wall 1044 of the pad 170 may engage with the internal surfaces or inner sides of the mouthpiece 152 (e.g., the major sides of the generally flattened shape of the mouthpiece 152) such that the outer wall 1044 generally matches the flattened cross-sectional geometry of the mouthpiece 152. For example, if the cross-sectional geometry of the mouthpiece 152 is a flattened oval or rectangular, the geometry defined by the outer wall 1044 of the pad 170 is likewise a flattened oval or rectangular. Likewise, the inner wall 1042 of the pad 170 defining the central opening 1040 may have a shape configured to mirror the shape of the opening 154 through the mouthpiece 152 such that the pad 170 does not obstruct vapor flow through the opening 154. The mouthpiece 152 may include a projecting flat collar forming an internal flange 1045 surrounding the opening 154 (see FIG. 5A and FIG. 5B) and extending into the internal volume 1010 of the mouthpiece 152. The internal flange 1045 may have an inner diameter and an outer diameter. The inner wall 1042 of the pad 170 may be sized to engage with the outer diameter of the internal flange 1045 such that the central opening 1040 of the pad 170 aligns generally with the opening 154 of the mouthpiece 152.

As mentioned above, the mouthpiece 152 may be attached over the proximal end region 156A of the cartridge body 156. The pad 170 may be positioned (e.g., sandwiched) against an upper, proximal surface 1050 of the cartridge body 156 (see FIG. 7A). The upper, proximal surface 1050 of the cartridge body 156 abuts against the lower surface 1055 of the pad 170 such that the pad 170 is wedged between the internal flange 1045, the inner sides of the mouthpiece 152, and the proximal surface 1050 of the cartridge body 156. The pad 170 may be wedged into place and affixed without an adhesive although it should be appreciated that adhesives may also be used to affix the pad 170. The upper, proximal surface 1050 of the cartridge body 156 may also include a central, upper element 1052 sized to be inserted through the central opening 1040 of the absorbent pad 170. The absorbent pad 170 thereby encircles the central, upper element 1052, which in turn, projects through central opening 1040 of the absorbent pad 170 (see FIG. 7A). The shape of the pad 170 along with its wedged coupling with the internal flange 1045 of the mouthpiece and the proximal surface 1050 and upper element 1052 of the cartridge body 156 prevent shifting of the pad 170 during use and handling. Shifting of the pad 170 may cause the pad 170 to obstruct vapor flow through the device.

The pad 170 need not be formed by a single absorbent element. Rather, the pad 170 may be formed by multiple absorbent elements positioned relative to the opening 154 to provide absorption without impeding, restricting, or blocking vapor flow through the openings 154 in the mouthpiece 152. Use of the term "pad" is not intended to be limiting. The pad 170 may be any absorbent member (e.g., sponge, pad, felts, fiber, fabric, etc.) that may absorb an amount of a fluid. The one or more pads 170 may include any absorbent material configured to wick moisture relatively quickly and allow it to disperse quickly therethrough. The absorbent material may be hydrophilic, including cotton, non-woven cotton linter paper, felt, cellulose, or hydrophilic polymers. The pad 170 may be formed of thin sheets of layered material.

The configuration of the pad 170 in which the opening 1040 is generally aligned with the central channel 1015 and off-axis from the opening 154 of the mouthpiece 152 may result in the capture of large particles yet allow smaller particles through to the opening 154. In some implementations, a large particle may have a diameter of at least about 10 microns. In some implementations, a large particle may have a dimeter of at least about 8 microns, about 9 microns, about 10 microns, about 11 microns, up to about 12 microns. As larger particles have more inertia, the larger particles will hit the pad 170 whereas smaller particles will curl around the central, upper element 1052 to exit the mouthpiece 152, as further described below.

Figure 7A:
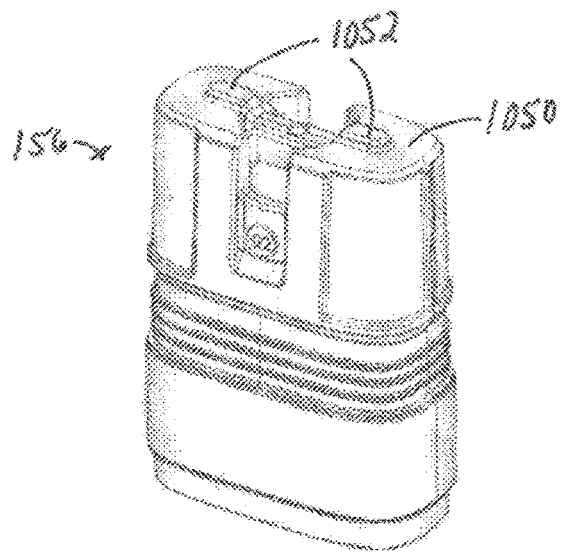
FIGS. 7A-7G illustrate portions of a cartridge consistent with implementations of the current subject matter.
Figure 7B:
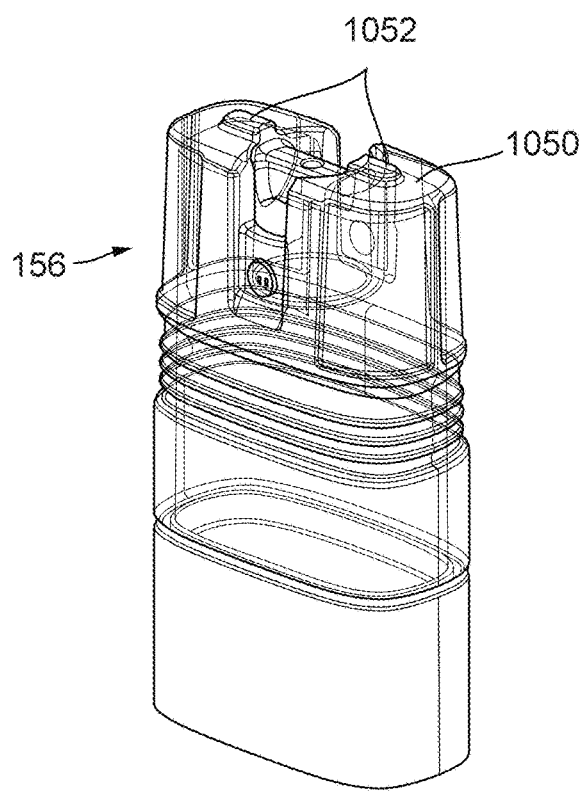
Figure 7C:
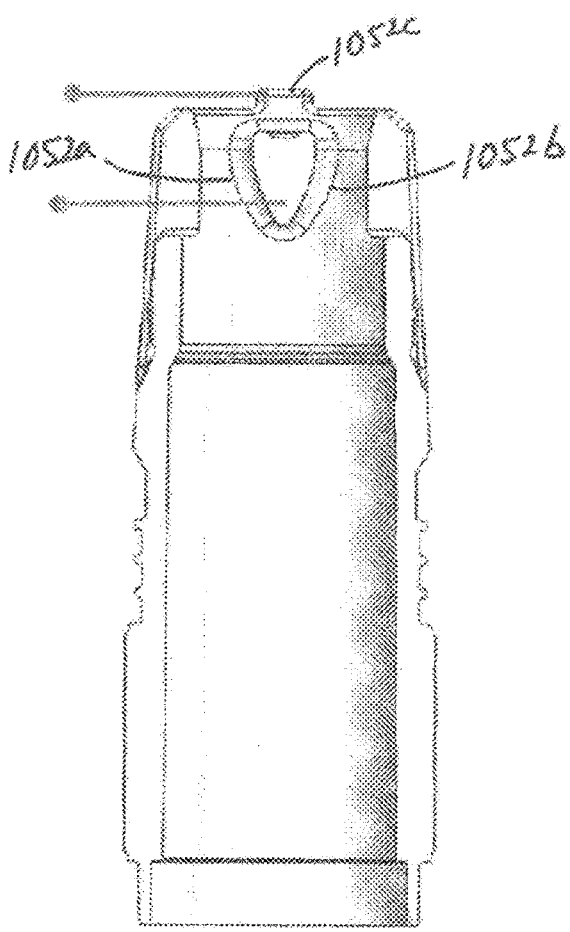

FIG. 5B. FIG. 7B, and FIG. 7C illustrate features of the central, upper element 1052 that extends across the major axis of the upper, proximal surface 1050 of the cartridge body 156, consistent with implementations of the current subject matter. FIG. 5B is a perspective, cross-sectional view of the cartridge 150, FIG. 7B is front perspective view of the cartridge body 156, and FIG. 7C is a side cross-sectional view of the cartridge body 156. As shown, the central, upper element 1052 is positioned above the top end portion of a central cannula 172 in the central channel 1015. In some implementations, the central, upper element 1052 is about 0 mm, about 0.1 mm, about 0.2 mm, about 0.3 mm, about 0.4 mm, about 0.5 mm, about 0.6 mm, about 0.7 mm, about 0.8 mm, about 0.9 mm, about 1.0 mm, about 1.1 mm, about 1.2 mm, about 1.3 mm, about 1.4 mm, about 1.5 mm, about 1.6 mm, about 1.7 mm, about 1.8 mm, about 1.9 mm, up to about 2.0 mm above the top end portion of the central cannula 172.

The size and shape of the central, upper element 1052 may aesthetically block off the internal components from a user (e.g., through the opening 154 of the mouthpiece 152) as well as direct or split vapor flow around it. By directing the flow around the central, upper element 1052, larger particles are trapped in the pad 170 due to their inherent inertial properties described above. The central, upper element 1052 thus splits the vapor flow to allow for flow around the central, upper element 1052 and thereby reduces the amount of excess material that is collected on the central, upper element 1052 and elsewhere in the cartridge body 156.

In an implementation, as shown in FIG. 5B and FIG. 7C, the central, upper element 1052 has a side cross-sectional profile with a sharpened end, curved and angled sides, and a blunt top that splits. Due to the sharpened end and the curved and angled sides, the flow of vapor around the central, upper element 1052 provides for larger particles to be captured and entrained by the pad 170, which is off-axis with respect to direction of the vapor flow. The central, upper element 1052 may be an airfoil with a leading edge and a closed trailing edge. The side cross-sectional profile of the central, upper element 1052 may be parabolic or triangular, as shown in FIG. 5B and FIG. 7C, with a flat top surface 1052c and with angled side portions 1052a and 1052b that meet at the sharpened end. This configuration may prevent vapor impaction on surfaces within the cartridge body 156 (including the central, upper element 1052 itself), which can lead to a build-up of oil condensation. In some implementations, the angled side portions 1052a,b may be, with respect to the flat top surface 1052c, at an angle of about 45 degrees, about 50 degrees, about 55 degrees, about 60 degrees, about 65 degrees, about 70 degrees, about 75 degrees, up to about 80 degrees. A bounding box defining the side cross-sectional area of the central, upper element 1052 may have a length of about 1.5 mm, about 1.6 mm, about 1.7 mm, about 1.8 mm, about 1.9 mm, up to about 2.0 mm, and may have a height of about 2.0 mm, about 2.1 mm, about 2.2 mm, about 2.3 mm, about 2.4 mm, about 2.5 mm, about 2.6 mm, up to about 2.7 mm.

In some implementations, other side cross-sectional profiles as well as variations of those described herein may be used for the central, upper element 1052, where such profiles aid in the splitting and directing of the flow of vapor, such as other shapes with a sharpened or pointed end, including for example a diamond, a teardrop, an arrow, or a round or rounded edge profile.

Again with respect to FIG. 4, FIG. 5A, FIG. 5B, and FIG. 6, the cartridge body 156 includes the tank or reservoir 158 (defined by the central region 156B and the proximal end region 156A), where the reservoir 158 is configured to hold an amount of vaporizable material within the cartridge 150. The reservoir 158 may be sealed on a distal or bottom end by an internal sealing gasket 173 positioned within the distal end region 156C of the cartridge body 156. For example and with reference to FIG. 7D, the reservoir 158 may be sealed on a proximal or top end by a sealing ring 171. The central cannula 172 may extend through the reservoir 158 from near the distal end region 156C of the cartridge body 156 to the proximal end region 156A of the cartridge body 156. As best shown in FIG. 5A and in FIG. 7D, the proximal end region 156A of the cartridge body 156 defines a central channel 1015 that extends to an opening that may be coaxially aligned with the opening 154 through the proximal end surface of the mouthpiece 152. A proximal tap 1018 of the central cannula 172 encircled by the sealing ring 171 may extend into the central channel 1015. The sealing ring 171 may seal with the surface of the central channel 1015 and thereby seal the reservoir 158 on the upper end.

The sealing ring 171 may provide a seal between the central cannula 172 and the mouthpiece 152 to prevent or reduce the likelihood of fluid, such as the vaporizable material, from flowing into and out of the mouthpiece opening 154. The sealing ring 171 may be any of a variety of sealing element and can, but need not, have an annular shape. The shape of the sealing ring 171 may be configured to match the shape of the proximal tap 1018 of the central cannula 172 on its inner diameter and match the shape of the central channel 1015 on its outer diameter. In some implementations, the sealing ring 171 may be an elastomeric material configured to be compressed slightly upon insertion of the central cannula 172 into the central channel 1015 thereby providing fluid sealing and preventing the vaporizable fluid stored in the reservoir 158 from exiting the cartridge 150 through the central channel 1015.

The reservoir 158 may be arranged to surround the central cannula 172, which may be positioned coaxial with the longitudinal axis A of the cartridge 150. The reservoir 158 may thereby be generally ring-shaped such that the outer wall(s) of the reservoir 158 are formed by the cartridge body 156 and the inner wall(s) of the reservoir 158 are formed by the central cannula 172 extending through the reservoir 158. The reservoir 158 need not be arranged symmetrically around the longitudinal axis A of the cartridge 150 with the central cannula 172 extending through it. Other configurations are considered herein.

Figure 7E:
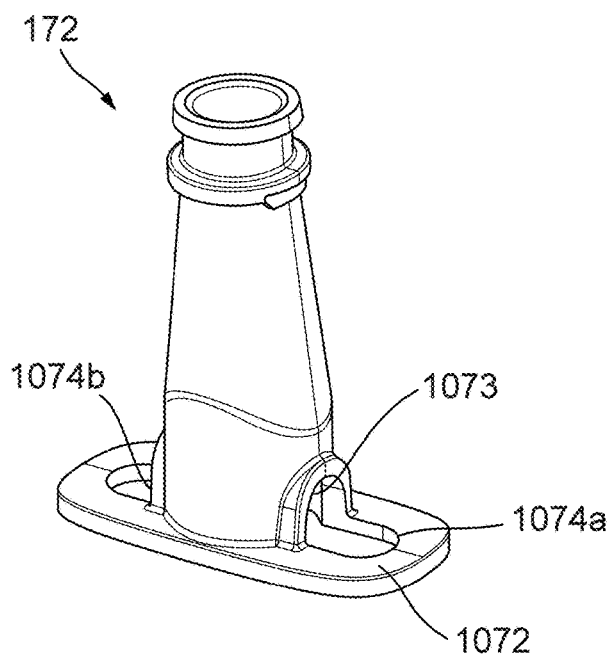
Figure 7D:
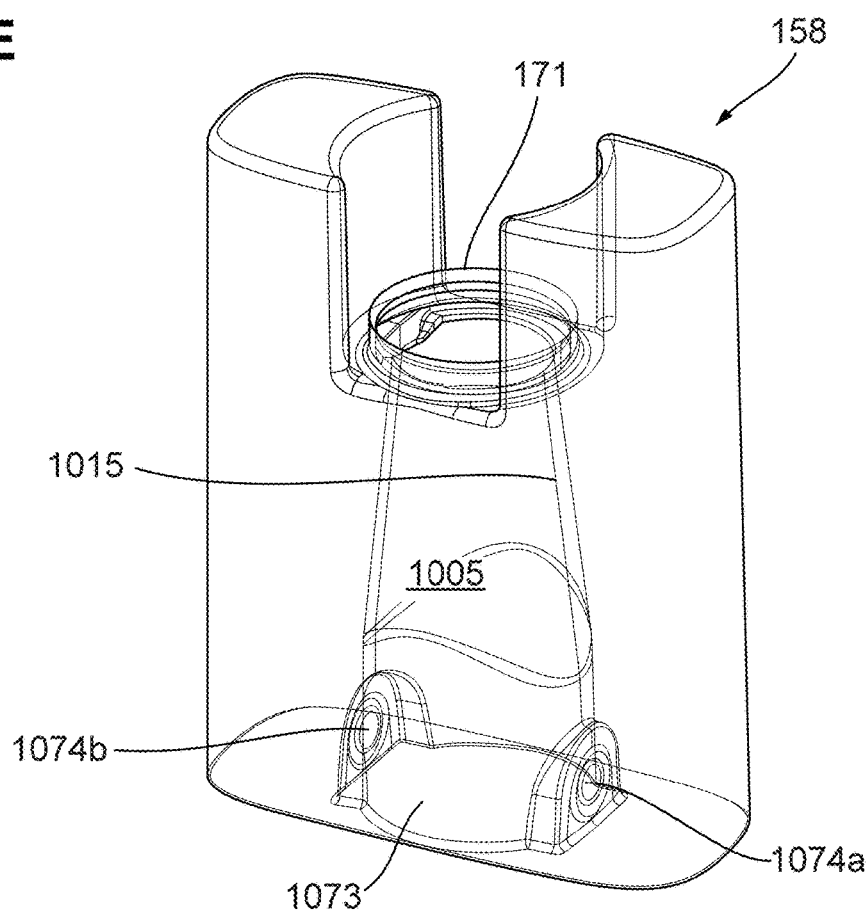
Figure 7F:
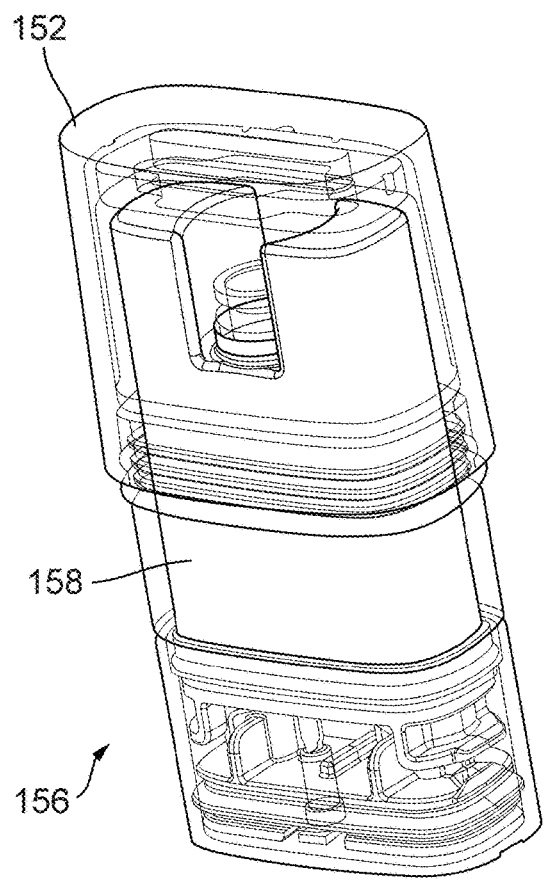
Figure 7G:
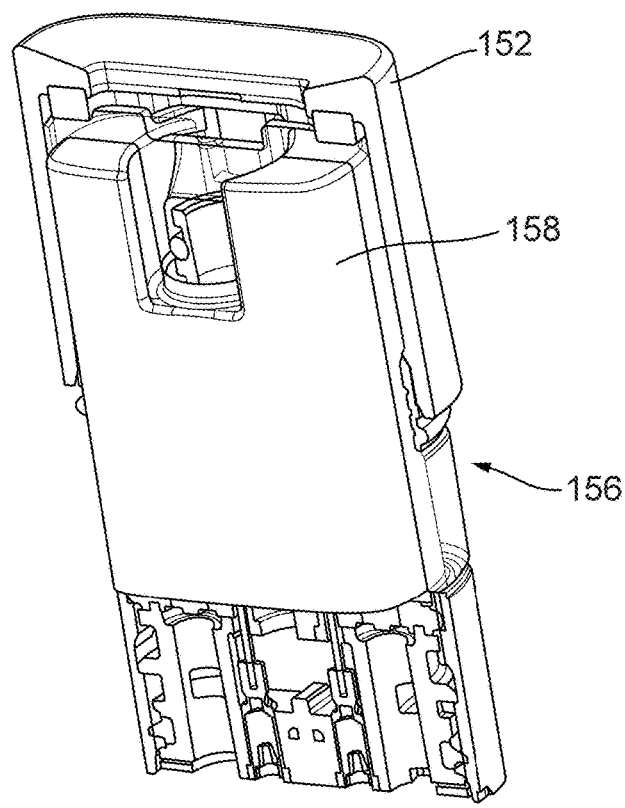

FIG. 7F and FIG. 7G illustrate placement and positioning of the reservoir 158 with respect to the mouthpiece 152. As shown, the reservoir 158 fits snugly within the mouthpiece 152, providing for a large reservoir size to accommodate the vaporizable material contained therein.

As mentioned above, at least a portion of the cartridge body 156 may be transparent, translucent, opaque, or a combination thereof. The cartridge body 156 may include one or more regions formed of an opaque material such that the contents are not visible from outside the device as well as one or more regions formed of a translucent or transparent material such that the contents are visible from outside the device. For example, the central region 156B of the cartridge body 156 may be translucent to transparent such that the reservoir 158 contained within this portion of the cartridge body 156 may remain visible to a user from outside the cartridge 150. The distal end region 156C of the cartridge body 156 may be opaque such that a majority of the components within this region remain hidden from view. Similarly, the mouthpiece 152 positioned over the proximal end region 156A of the cartridge body 156 may be opaque.

The volume of the reservoir 158 may vary, but is generally sized to hold sufficient vaporizable material for delivering at least one dose of the material. The volume of the reservoir 158 may be between about 0.2 mL to about 2 mL, in other implementations between 0.4 mL to about 1.2 mL, in other implementations between about 0.4 mL to about 0.8 mL, or in still other implementations between about 0.6 mL to about 1 mL. The reservoir 158 may be pre-filled or filled prior to, during, and after use as well be described more below.

Again with respect to FIG. 4, FIG. 5A, FIG. 5B, and FIG. 6, the central cannula 172 extending through the reservoir 158 defines the vaporization chamber 1005 that together with the central channel 1015 directs vapor flow towards the mouthpiece 152. The central cannula 172 defining the vaporizing chamber may be a generally cylindrical element extending from a bottom plate 1072 to the proximal tap 1018. The central cannula 172 may extend coaxial with the longitudinal axis A of the cartridge 150 up through the reservoir 158 such that the reservoir 158 surrounds the central cannula 172. The base region of the vaporization chamber 1005 may have an enlarged volume and a greater inner diameter compared to an inner diameter of the proximal tap 1018. As described above, the proximal tap 1018 may insert into and seal (i.e., via the sealing ring 171) with the central channel 1015 of the proximal end region 156A of the cartridge body 156. The proximal tap 1018 may define an opening 1022 near its upper-most end such that the vaporization chamber 1005 of the central cannula 172 may be in fluid communication with the central channel 1015 via the opening 1022. Vapor from the vaporization chamber 1005 may flow through the opening 1022 in the proximal tap 1018 into the central channel 1015 and out the one or more openings 154 of the mouthpiece 152.

The enlarged base of the central cannula 172 may be coupled to a bottom plate 1072 (as shown in FIG. 7E). The bottom plate 1072 may be a generally planar feature coupled to the base of the central cannula 172 that forms a rim around the base. The lower surface of the bottom plate 1072 may include distal extensions configured to extend through the internal sealing gasket 173. The upper surface of the bottom plate 1072 may define, at least in part, a lower surface of the reservoir 158 and the lower surface of the bottom plate 1072 may abut against the internal sealing gasket 173. As best shown in FIG. 6 and FIG. 7E, the bottom plate 1072 may include a central aperture 1073 such that the vaporization chamber 1005 remains open on a distal end to provide a vapor flow passageway through the cartridge body 156 to the mouthpiece 152. The central aperture 1073 may be elongated such that it forms an oval, elliptical, or other elongate shape having a minor axis and a major axis. A middle portion of the central aperture 1073 may be aligned with the vaporization chamber 1005 and at least partially encircled by the central cannula 172. As such, the middle portion of the central aperture 1073 may be generally rounded or circular in shape similar to a cross-sectional shape of the base of the central cannula 172. Two outer portions of the central aperture 1073 (i.e., along the major axis) may extend beyond the base of the central cannula 172 due to the elongate shape of the central aperture 1073. These outer portions of the central aperture 1073 may be narrower than the middle portion providing the central aperture 1073 with a keyhole shape. The central aperture 1073 may have other shapes and may also be made up of a plurality of openings through the bottom plate 1072.

The cartridge 150 may include a vaporizing assembly of vapor-generating components. The vapor-generating components may include a heater 166 configured to heat the vaporizable material to a sufficient temperature that it may vaporize. The vapor-generating components may be arranged as an atomizer or cartomizer or oven. The vapor may be released to a vaporization chamber where the gas phase vapor may condense, forming an aerosol cloud having typical liquid vapor particles with particles having a diameter of average mass of approximately 1 micron or greater. In some cases, the diameter of average mass may be approximately 0.1-1 micron.

The heater 166 of the vaporizing assembly may cause the vaporizable material to be converted from a condensed form (e.g., a solid, a liquid, a solution, a suspension, a part of an at least partially unprocessed plant material, etc.) to the gas phase. After conversion of the vaporizable material to the gas phase, and depending on the type of vaporizer, the physical and chemical properties of the vaporizable material, and/or other factors, at least some of the gas-phase vaporizable material may condense to form particulate matter in at least a partial local equilibrium with the gas phase as part of an aerosol, which may form some or all of an inhalable dose provided by the vaporizer for a given puff or draw on the vaporizer. It will be understood that the interplay between gas and condensed phases in an aerosol generated by a vaporizer may be complex and dynamic, as factors such as ambient temperature, relative humidity, chemistry, flow conditions in airflow paths (both inside the vaporizer and in the airways of a human or other animal), mixing of the gas-phase or aerosol-phase vaporizable material with other air streams, etc., may affect one or more physical parameters of an aerosol. In some vaporizers, and particularly for vaporizers for delivery of more volatile vaporizable materials, the inhalable dose may exist predominantly in the gas phase (i.e., formation of condensed phase particles may be very limited).

Vaporizers for use with liquid vaporizable materials (e.g., neat liquids, suspensions, solutions, mixtures, etc.) typically include an atomizer in which a wicking element (also referred to herein as a wick 168), which may include any material capable of causing passive fluid motion, for example, by capillary pressure) conveys an amount of a liquid vaporizable material to a part of the atomizer that includes the heating element. The wicking element is generally configured to draw liquid vaporizable material from the reservoir configured to contain (and that may in use contain) the liquid vaporizable material such that the liquid vaporizable material may be vaporized by heat delivered from the heating element.

The heater 166 may be or include one or more of a conductive heater, a radiative heater, and a convective heater. One type of vaporizing heating element is a resistive heating element, which may be constructed of or at least include a material (e.g., a metal or alloy, for example a nickel-chromium alloy, or a non-metallic resistor) configured to dissipate electrical power in the form of heat when electrical current is passed through one or more resistive segments of the heating element. In some implementations of the current subject matter, an atomizer may include a vaporizing heating element that includes resistive coil or other heating element wrapped around, positioned within, integrated into a bulk shape of, pressed into thermal contact with, or otherwise arranged to deliver heat to a wicking element to cause a liquid vaporizable material drawn by the wicking element from a reservoir to be vaporized for subsequent inhalation by a user in a gas and/or a condensed (e.g., aerosol particles or droplets) phase. Other wicking element, heating element, and/or atomizer assembly configurations are also possible, as discussed further below.

Certain vaporizers may also or alternatively be configured to create an inhalable dose of gas-phase and/or aerosol-phase vaporizable material via heating of a non-liquid vaporizable material, such as for example a solid-phase vaporizable material or plant material containing the vaporizable material. In such vaporizers, a resistive heating element may be part of or otherwise incorporated into or in thermal contact with the walls of an oven or other heating chamber into which the non-liquid vaporizable material is placed. Alternatively, a resistive heating element or elements may be used to heat air passing through or past the non-liquid vaporizable material to cause convective heating of the non-liquid vaporizable material. In still other examples, a resistive heating element or elements may be disposed in intimate contact with plant material such that direct conductive heating of the plant material occurs from within a mass of the plant material (e.g., as opposed to only by conduction inward from walls of an oven).

Figure 8A:
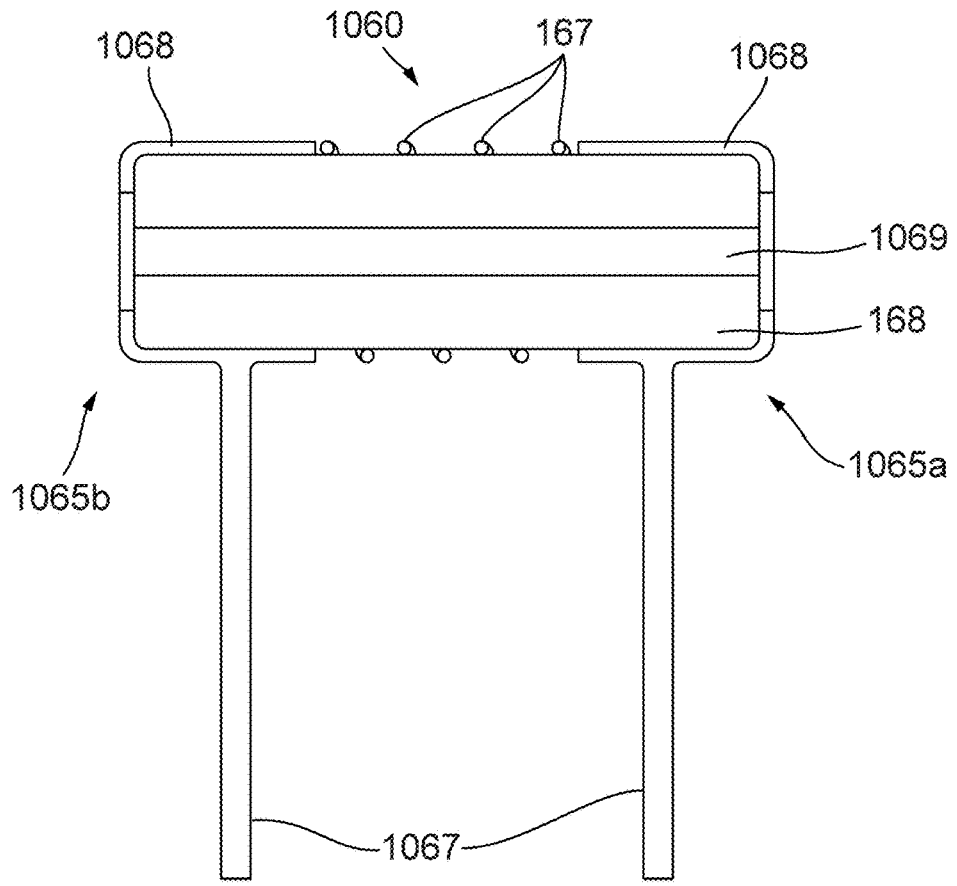
FIGS. 8A-8B illustrate an example heater of a cartridge consistent with implementations of the current subject matter.
Figure 8B:
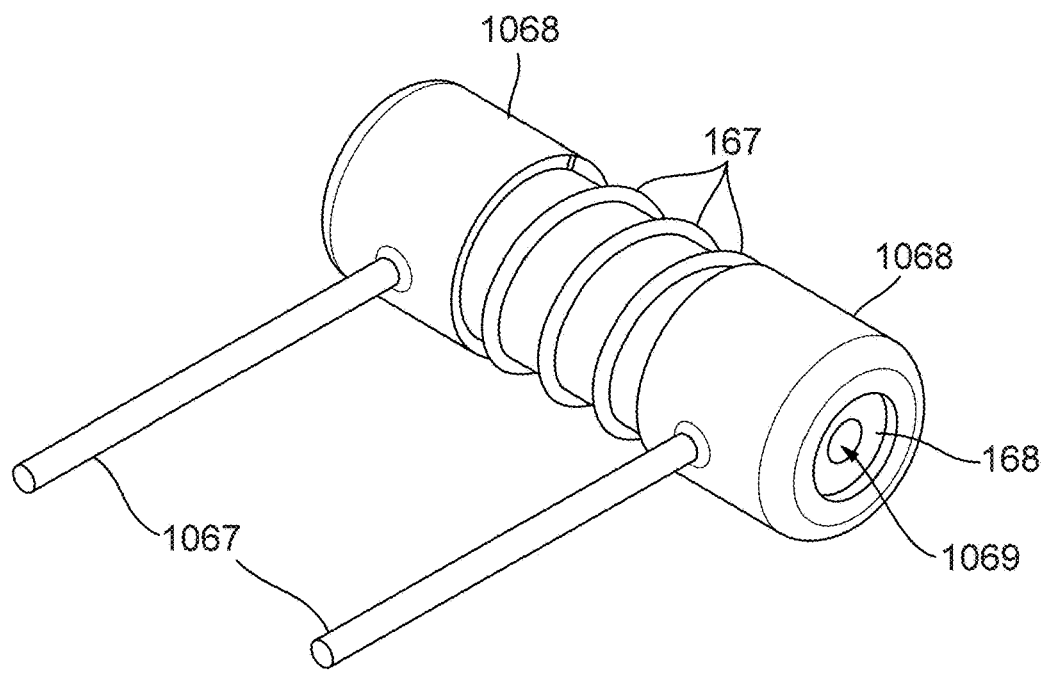
Figure 8C:
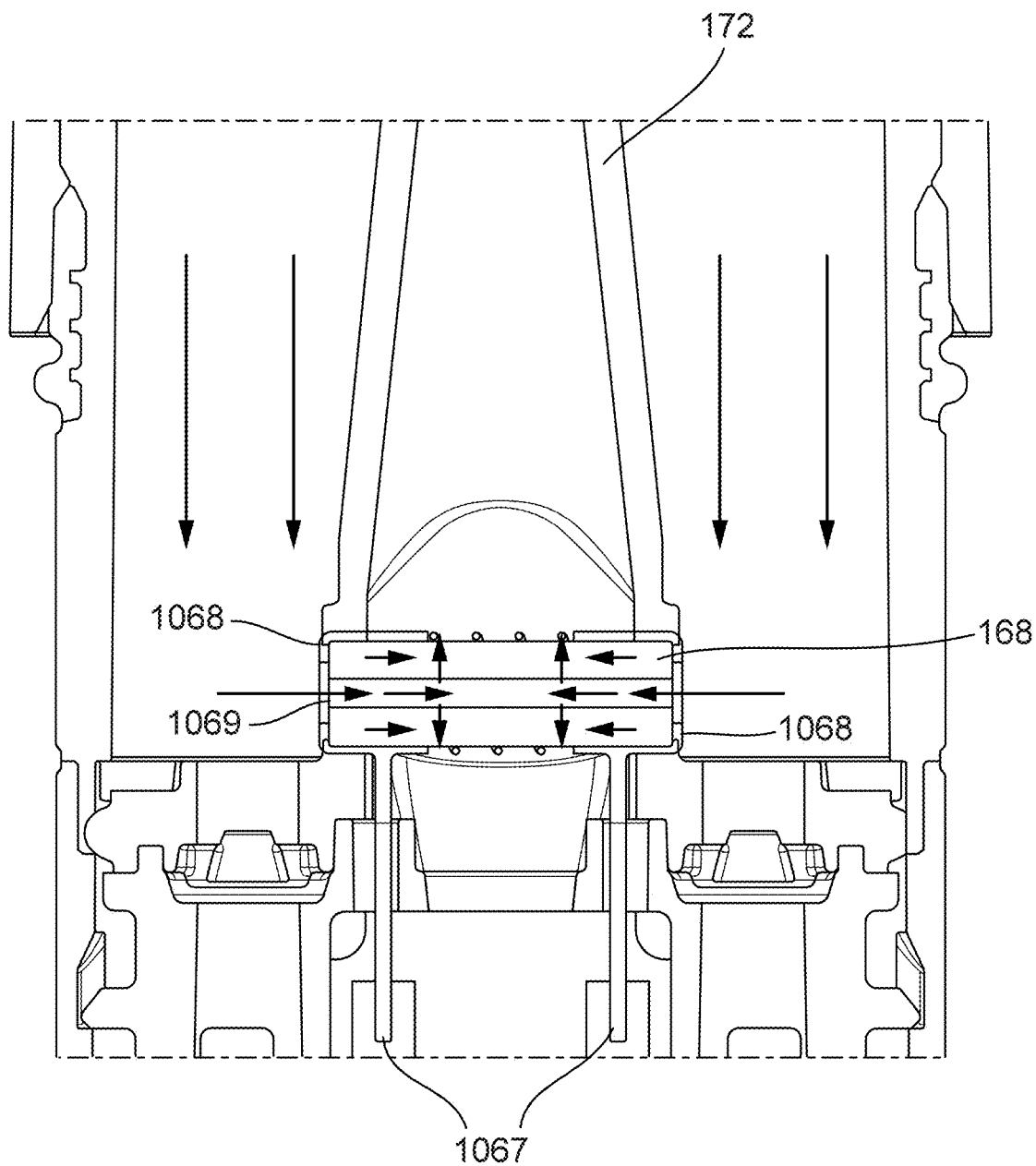
FIG. 8C illustrates a partial cross-sectional view of a cartridge consistent with implementations of the current subject matter.

Still with respect to FIG. 5A, FIG. 5B, FIG. 6, and also FIG. 8A and FIG. 8B, the heater 166 may be configured to heat and/or vaporize at least a portion of the vaporizable material drawn towards the heater 166 from the reservoir 158. The central cannula 172 defining the vaporization chamber 1005 is configured to couple to the heater 166 configured to generate heat to provide vaporization of the vaporizable material contained in the reservoir 158. In some implementations, the heater 166 of the vaporizing assembly may include a resistive element such as a heating coil 167 in thermal contact with a wick 168 of the vaporizing assembly.

The wick 168 may be formed of any of a variety of materials, including metals, polymer, natural fibers, synthetic fibers, or combinations of these. For example, the wick 168 may be formed of silica fibers, cotton, ceramic, mullite, hemp, stainless steel mesh, rope cables, and/or any porous medium, such as for example sintered glass beads. The wick 168 is porous and provides a capillary pathway for fluid within the reservoir 158 through and into the wick 168. The capillary pathway is generally large enough to permit wicking of sufficient material to replace vaporized liquid transferred from the reservoir 158 by capillary action (wicking) during vaporization, but may be small enough to prevent leakage of the vaporizable material out of the cartridge during normal operation, including when pressure is applied to outside the cartridge 150. The wick 168 may have a size configured to handle high viscosity liquids. In some implementations, the wick 168 may have a diameter that is at least about 1.5 mm. The wick may be larger than 1.5 mm in diameter (e.g., about 1.9 mm or larger, about 2.0 mm or larger, about 2.1 mm or larger, about 2.2 mm or larger, about 2.3 mm or larger, about 2.4 mm or larger, about 2.5 mm or larger, etc., including between about 1.8 mm and about 5 mm, between about 1.9 mm and about 4 mm, between about 2 mm and about 4 mm, etc.). The material of the wick 168 is configured to draw the liquid vaporizable material from the reservoir 158 into the vaporization chamber 1005 without the need for a pump or other mechanical moving part. In some implementations, the tension of the heating coil 167 wound around the wick 168 may vary. Winding the heating coil 167 tighter and/or with additional windings may create a larger heating surface area to create more intense or concentrated heating of the vaporizable material. Likewise, reducing the diameter of the wick may also create more intense or concentrated heating of the vaporizable material.

Consistent with implementations of the current subject matter and as shown in FIG. 8A and FIG. 8B, the wick 168 may be made of a porous material, such as ceramic, in which the pores of the porous material facilitate wicking of the vaporizable material along the length of the wick 168. A central bore 1069 may extend through a length of the wick 168 to further facilitate wicking (see FIG. 8C, which illustrates movement of the vaporizable material through the reservoir 158 and along the wick 168).

The heating coil 167 may be a resistance wire wrapped around the wick 168 and connected to a positive and negative pole of a current source. The coil 167 may increase in temperature as a result of the current flowing through the wire to generate heat. The heat may be transferred to at least a portion of the vaporizable material through conductive, convective, and/or radiative heat transfer such that at least a portion of the vaporizable material vaporizes. Air drawn into the vaporization chamber 1005 may carry the vapor away from the heater 166.

The wick 168 may include end caps 1068 that provide a connection between the heating coil 167 and respective leads 1067 (e.g., for facilitating the electrical connection of the coil 167 with the vaporizer body 110). The end caps 1068 may be made of various materials, such as copper, stainless steel, other metals, or combinations thereof. The end caps 1068 may securely and snugly fit over respective ends of the wick 168 (e.g., opposing ends 1065a,b described below). For example, the end caps 1068 may be thin sleeves that fit over the respective ends of the wick 168. End portions of each of the end caps 1068 have an opening that aligns with the central bore 1069. The openings may be of a larger diameter than that of the central bore 1069 to further promote wicking of the vaporizable material along the length of the wick 168.

The heater 166 may extend across the air path within the vaporization chamber 1005, such as in a transverse direction. Still with respect to FIG. 5A, FIG. 5B, FIG. 6, and also FIG. 8A and FIG. 8B, the central cannula 172 may be arranged coaxial with the longitudinal axis A of the device and the wick 168 may extend orthogonal to the longitudinal axis A through the central cannula 172. The wick 168 is preferably positioned near a distal-most end region of the reservoir 158 such that the vaporizable material in the reservoir 158 may be fully used. A pair of lateral openings 1074a,b may extend through the walls of the central cannula 172 near its base where the central cannula 172 couples to the bottom plate 1072. The pair of lateral openings 1074a,b may be aligned across from one another on opposing sides of the central cannula 172. The openings 1074a,b are provided and sized for coupling to the heater 166. As described above, the bottom plate 1072 and the central aperture 1073 extending through the bottom plate 1072 may have a major axis and a minor axis. The elongate shape of the central aperture 1073 provides for two outer portions along the major axis of the bottom plate 1072 to extend beyond the base of the central cannula 172. The two outer portions of the central aperture 1073 may be aligned with the lateral openings 1074a,b of the central cannula 172 thereby forming an enlarged slot near the base of the central cannula 172 where it couples with the bottom plate 1072. The wick 168 may extend through these lateral openings 1074a,b and within this slot.

In some implementations, the wick 168 of the heater 166 may include a central portion 1060 and opposing ends 1065a,b. The heating coil 167 may be wrapped around the central portion 1060 of the wick 168, which in turn may be positioned within the vaporization chamber 1005. The opposing ends 1065a,b of the wick 168 may be positioned outside the vaporization chamber 1005 by extending laterally outward through the lateral openings 1074a,b of the central cannula 172. As such, the opposing ends 1065a,b may be positioned within the internal volume of the reservoir 158 whereas the central portion 1060 of the wick 168 wrapped by the heating coil 167 may be positioned inside the vaporization chamber 1005 of the central cannula 172. The leads 1067 of the heating coil 167 may extend away from the central portion 1060 of the wick 168 and down through the central aperture 1073 of the bottom plate 1072 out of the vaporization chamber 1005. The leads 1067 may extend into the distal end region 156C of the cartridge body 156 where the leads 1067 may electrically couple with the power pin receptacles 160a,b.

As mentioned, the distal end region 156C of the cartridge body 156 may house the internal sealing gasket 173 coupled to a lower support structure 174. The internal sealing gasket 173 may be positioned generally under the bottom plate 1072 of the central cannula 172 and attached to an upper surface of the lower support structure 174. This placement of the internal sealing gasket 173 serves to seal the reservoir 158 on the distal or bottom end and thereby reduce or eliminate leaking of vaporizable material out of the reservoir 158, for example, into the electrical components contained in the distal end region 156C of the cartridge 150 as well as the vaporizer body 110. The internal sealing gasket 173 may be, in some implementations, an oversized elastic or rubberized material that plugs various openings in a distal end region of the device and forms a seal between the reservoir 158 and the lower support structure 174 when under compression. Thus, the internal sealing gasket 173 may be sized and shaped to fit between the reservoir 158 and the lower support structure 174 to seal any openings therebetween.

Now with respect to FIG. 9, FIG. 10, FIG. 11A, and FIG. 11B, the internal sealing gasket 173 may be defined generally by an upper region and a lower region separated by a midline region. A central opening 195 may extend through the internal sealing gasket 173, thus providing the internal sealing gasket 173 with a generally annular structure. The central opening 195 may align with the middle portion of the central aperture 1073 through the bottom plate 1072 to allow for air flow through the internal sealing gasket 173 into the vaporization chamber 1005. When the upper region of the internal sealing gasket 173 abuts against the bottom plate 1072 of the central cannula 172, the distal extensions of the central cannula 172 projecting from the lower surface of the bottom plate 1072 extend down through the central opening 195 of the internal sealing gasket 173. As discussed above, the leads 1067 of the heating coil 167 may extend away from the central portion 1060 of the wick 168 and down through the central aperture 1073 of the bottom plate 1072 and through the central opening 195 of the internal sealing gasket 173 in order to electrically couple with the power pin receptacles 160*a,b*, within the lower support structure 174 which will be described in more detail below.

The upper region of the internal sealing gasket 173 is configured to seal the distal end region of the reservoir 158, the lower region of the internal sealing gasket 173 is configured to seal with the lower support structure 174, and the midline region of the internal sealing gasket 173 is configured to seal with an inner surface of the distal end region 156C of the cartridge body 156. The upper region of the internal sealing gasket 173 may include a pair of surface features projecting upward from a generally planar upper surface (see FIG. 11B). The generally planar upper surface is configured to abut against the generally planar lower surface of the bottom plate 1072 of the central cannula 172. When the upper surface of the internal sealing gasket 173 abuts against the lower surface of the bottom plate 1072, the surface features may project through the outer portions of the central aperture 1073 of the bottom plate 1072. The middle portion of the central aperture 1073 is aligned with the longitudinal axis A of the cartridge and at least partially encircled by the central cannula 172. The central aperture 1073 may additionally include two outer portions on either side of the middle portion that are positioned generally outside the perimeter of the central cannula 172 base (i.e., along the major axis of the plate). The pair of surface features projecting from the upper surface of the internal sealing gasket 173 extends up through the outer portions of the central aperture 1073 on either side of the central cannula 172 thereby sealing these outer portions of the central aperture 1073. At the same time, the distal extensions of the central cannula 172 on the lower surface of the bottom plate 1072 may extend down through the central opening 195 in the internal sealing gasket 173. This provides a tight fit coupling between the bottom plate 1072 of the central cannula 172 and the internal sealing gasket 173. The pair of surface features projecting from the upper surface of the internal sealing gasket 173 may include a region configured to interface with and laterally support the heater 166. For example, the opposing ends 1065*a,b* of the wick 168 extending through the lateral openings 1074*a,b* may engage with at least a portion of the pair of surface features. The pair of surface features may also seal with the wick 168. As such, the pair of surface features may generally align with the location of the lateral openings 1074*a,b* of the central cannula 172 through which the opposing ends 1065*a,b* of the wick 168 extend.

As described above, the wick 168 may extend orthogonal to the longitudinal axis A at the base of the reservoir 158. The opposing ends 1065*a,b* of the wick 168 may be positioned within the reservoir 158 and the central portion 1060 of the wick 168 wound by the heating coil 167 may be positioned within the vaporization chamber 1005. The upper half of the wick 168 may be sealed by the walls of the central cannula 172 defining the lateral openings 1074*a,b*. The lower half of the wick 168 may engage and seal with the pair surface features of the internal sealing gasket 173. The pair of surface features may be sized and shaped to insert through the central aperture 1073 of the bottom plate 1072 helping to seal the central aperture 1073 (see FIG. 9, FIG. 11A, and FIG. 11B). At least a portion of the pair of surface features extends a distance toward the opposing ends 1065*a,b* of the wick 168. This portion of the pair of surface features may include a wick mating surface sized and shape to complement the cylindrical surface of the wick 168. For example, the portion may have a semi-circular wick mating surface configured to seal with the cylindrical outer surface of a region of the wick 168. The portion of the pair of surface features may also laterally support the opposing ends 1065*a,b* of the wick 168.

As mentioned, the internal sealing gasket 173 also may include a midline region between the upper and lower regions. The midline region of the internal sealing gasket 173 may seal with the internal surface of the cartridge body 156. In an implementation, the midline region of the internal sealing gasket 173 may be encircled by a seal having dual sealing beads 198. The dual sealing beads 198 are configured to provide a circumferential seal with the distal end region 156C of the cartridge body 156 (see FIG. 11B). For example, the dual sealing bands 198 may be provided for redundancy, to prevent vaporizable material from leaking from the reservoir 158.

Figure 9:
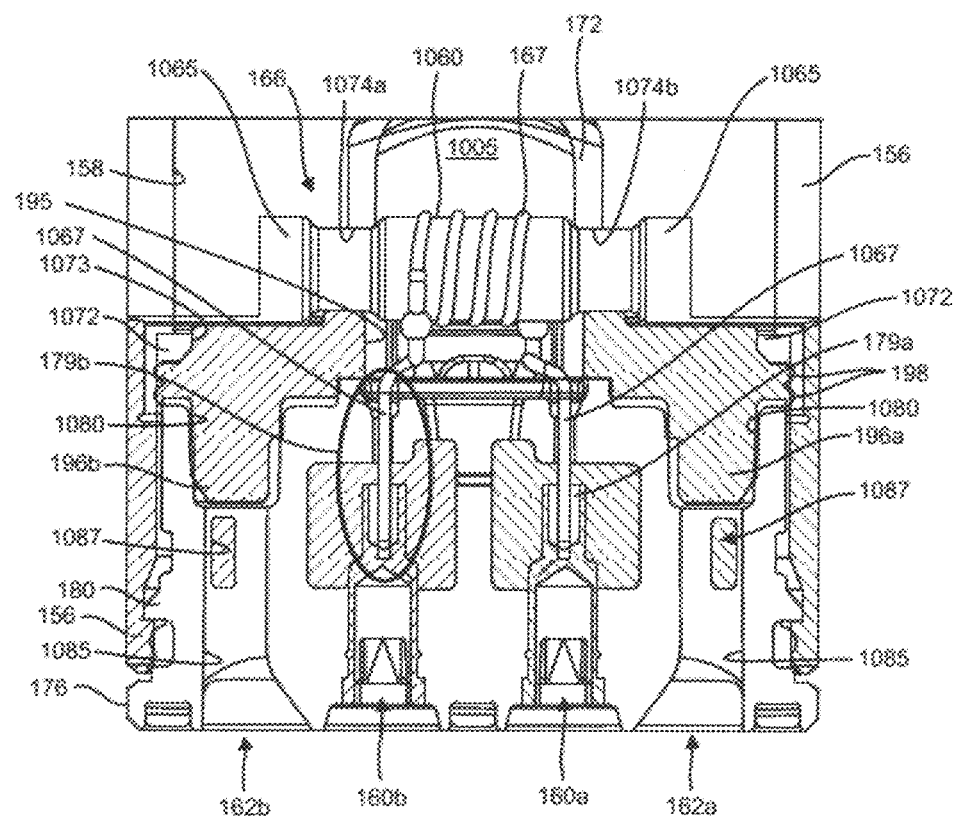
FIG. 9 illustrates a partial cross-sectional view of a cartridge consistent with implementations of the current subject matter.
Figure 11A:
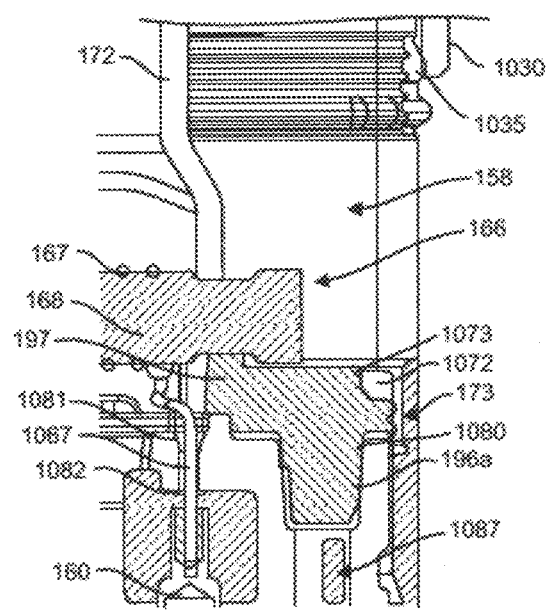
FIG. 11A illustrates a partial cross-sectional view of a cartridge consistent with implementations of the current subject matter.
Figure 11B:
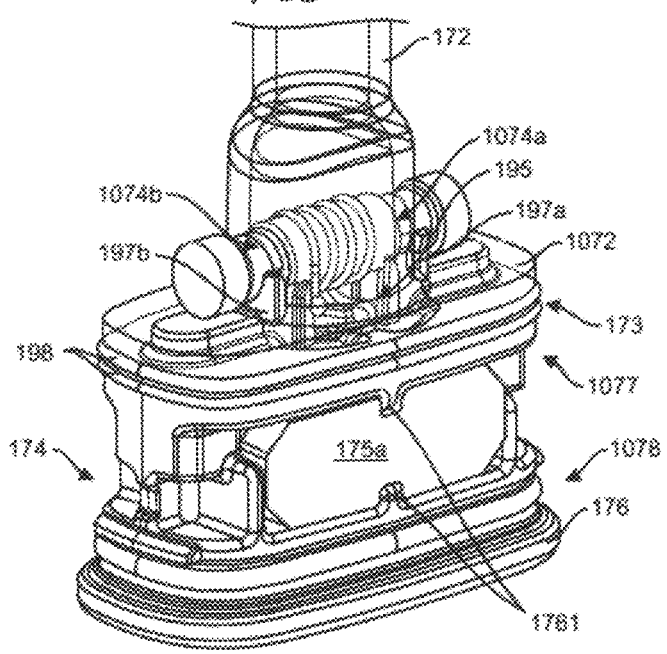
FIGS. 11B-11C illustrate portions of a cartridge consistent with implementations of the current subject matter.

Still with respect to FIG. 9, FIG. 11A, and FIG. 11B, the lower region of the internal sealing gasket 173 may include a pair of penetrable surface features projecting downward from the lower surface of the internal sealing gasket 173. When the lower surface of the internal sealing gasket 173 abuts against an upper surface of the lower support structure 174, the pair of penetrable surface features extend distally and insert within corresponding ones of the pair of openings 1080 in the upper surface of the lower support structure 174, as will be described in more detail below.

The various features of the internal sealing gasket 173 on the upper, lower, and perimeter surfaces form an integrated sealing element that may seal a variety of locations within the cartridge 150 (i.e., the filling ports, the wick, and the distal end of the reservoir 158). The integrated seals provided by the internal sealing gasket 173 may simplify assembly and manufacturing.

As mentioned, the distal end region 156C of the cartridge body 156 may house the lower support structure 174. The lower support structure 174 may include an upper region 1077 and a lower region 1078 (see FIG. 11B). The upper region 1077 is configured to mate with the lower region of the internal sealing gasket 173. For example, the upper region 1077 may include the pair of openings 1080 in the upper surface that are sized and shaped to receive the pair of penetrable surface features projecting downward from the lower surface of the internal sealing gasket 173. The upper region 1077 of the lower support structure 174 may also include a central aperture 1079 extending through its thickness that is configured to align with the central opening 195 of the internal sealing gasket 173 that, in turn, aligns with the central aperture 1073 extending through the bottom plate 1072. The central aperture 1073 in the bottom plate 1072, the central opening 195 in the internal sealing gasket 173, and the central aperture 1079 of the lower support structure 174 are configured to receive distal extensions of the central cannula 172 and align with the vaporization chamber 1005 to allow for air flow through the distal end region 156C of the cartridge body 156.

A pair of air flow channels 1085 may extend through the lower support structure 174. The air flow channels 1085 each communicate on a distal end with a respective one of a pair of the air flow inlets 162*a,b* configured to remain in fluid communication with the atmosphere during use of the device. The distal end of the lower support structure 174 may define the air flow inlets 162*a,b* into the air flow channels 1085 extending through the lower support structure 174. The air flow channels 1085 extend from the air flow inlets 162*a,b* through the lower region 1078 of the lower support structure into the upper region 1077 of the lower support structure 174. The air flow channels 1085 extend to the pair of openings 1080 in the upper region 1077 of the lower support structure 174. Thus, the pair of air flow channels 1085 may extend through the entire thickness of the lower support structure 174 between the air flow inlets 162a,b in the lower surface to the pair of openings 1080 in the upper surface. The internal sealing gasket 173 may be positioned in the distal end region 156C of the cartridge body 156 providing sealing between the reservoir 158 and the air flow channels 1085 of the lower support structure 174. The pair of penetrable surface features projecting downward from the lower surface of the internal sealing gasket 173 insert through the pair of openings 1080 and seat within an upper portion or proximal end of the air flow channels 1085 thereby sealing the upper end of the air flow channels 1085 preventing leaking of the vaporizable material out of the reservoir 158 through the air flow channels 1085. The pair of air flow inlets 162a,b through the lower surface of the lower support structure 174 into the air flow channels 1085 remain unobstructed. The air flow inlets 162a,b may align with or be positioned in fluid communication with the side air inlets 116a,b, which will be described in more detail below. Each of the air flow channels 1085 extending through the lower support structure 174 from the lower air flow inlets 162a,b to the pair of openings 1080 may additionally include a side channel outlet 1087. The side channel outlet 1087 may be positioned a distance distal to the pair of penetrable surface features projecting into the air flow channels 1085 and a distance proximal to the lower air flow inlets 162a,b into the air flow channels 1085. The length of the air flow channels 1085 allows for the positioning of these side channel outlets 1087 away from the lower air flow inlets 162a,b such that, in the event of a leak into the bottom volume of the cartridge body 156, the air flow channels 1085 avoid being significantly filled in a manner that could block the air flow through or cause leaking out of the side channel outlets 1087.

The air flow inlets 162a,b into the air flow channels 1085 form an entry point for air into the cartridge 150 as well as an entry point for a filler to fill the reservoir 158 with vaporizable material.

Figure 10:
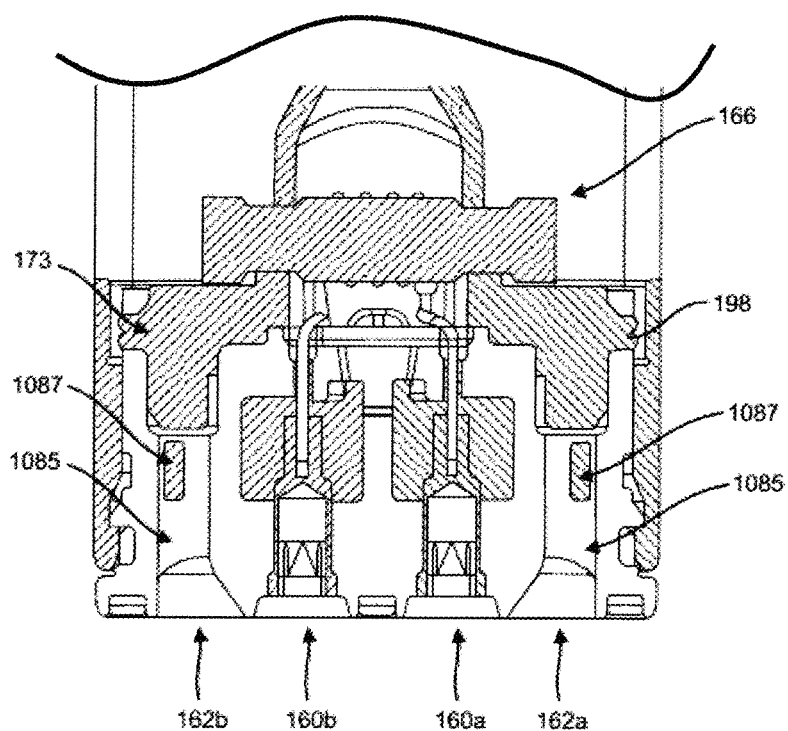
FIG. 10 illustrates a partial cross-sectional view of a cartridge consistent with implementations of the current subject matter.
Figure 12C:
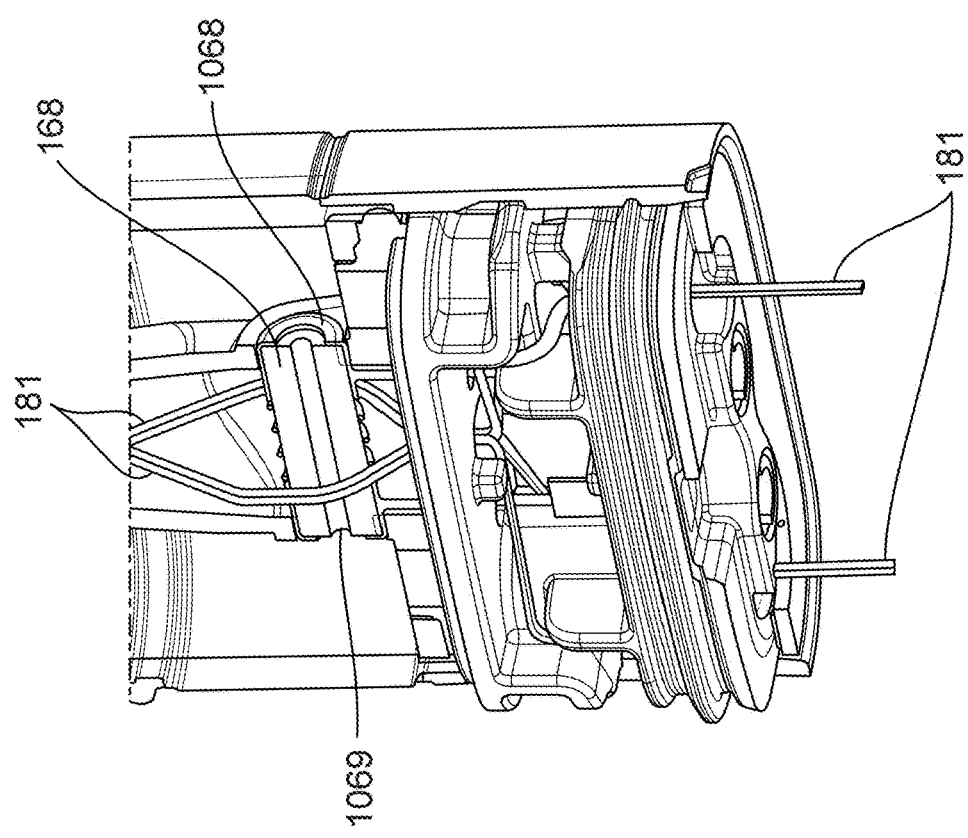
FIGS. 12A-12C illustrate a cartridge consistent with implementations of the current subject matter.
Figure 12B:
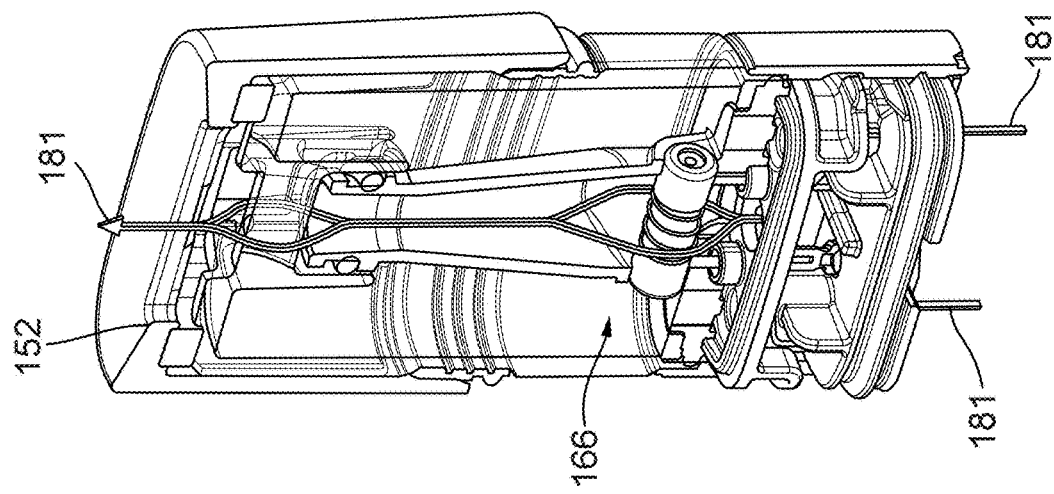
Figure 12A:
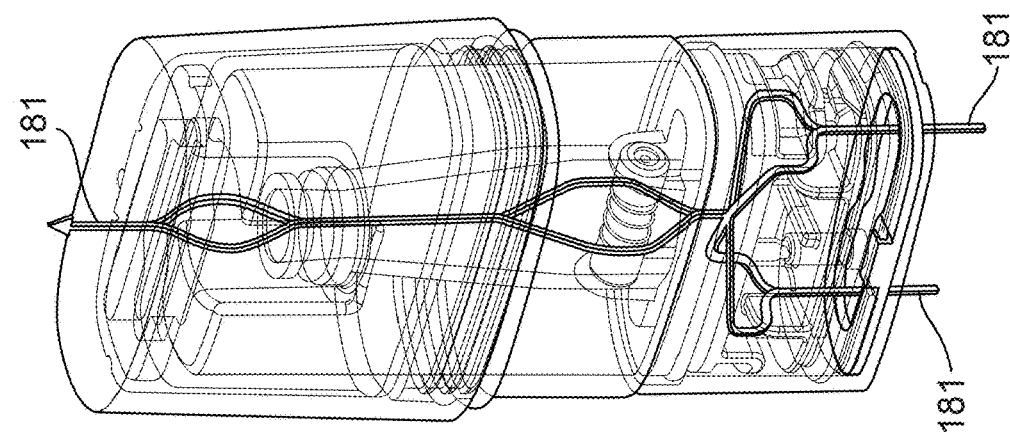
Figure 14:
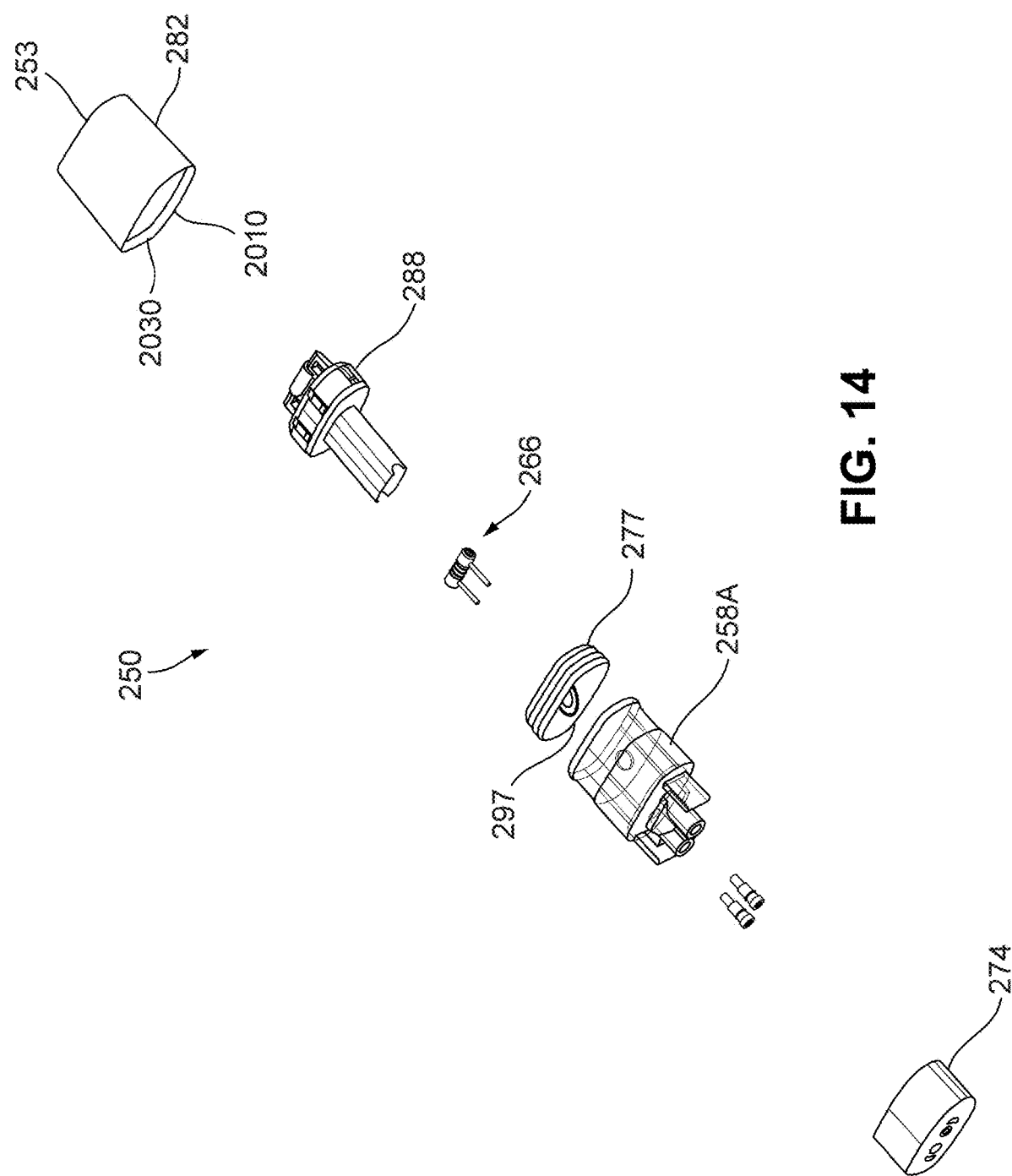
FIG. 14 illustrates an exploded view of a cartridge consistent with implementations of the current subject matter.

FIG. 12A-FIG. 12C illustrate air flow path 181 through the cartridge 150 upon coupling the cartridge 150 to a vaporizer body 110. As described elsewhere herein, the outer shell 112 of the cartridge receptacle 114 of the vaporizer body 110 may include one or more side air inlets 116a,b (see also FIG. 1C and FIG. 1D). The air inlets 116a,b may be aligned with or positioned in fluid communication with the lower air flow inlets 162a,b leading into the air flow channels 1085 from the lower region 1078 of the lower support structure 174. Air may enter the cartridge 150 through the air inlets 116a,b and continue through the lower air flow inlets 162a,b and into the air flow channels 1085 of the lower region 1078 of the lower support structure 174. FIG. 12A-FIG. 12C and also FIG. 10 and FIG. 11A-FIG. 11B show air may pass from the air flow channels 1085 of the lower region 1078 of the lower support structure 174 through the side channel outlets 1087 before passing up through the upper region 1077 into the vaporization chamber 1005. The lower support structure 174 may act as a plenum for the air, which is then directed through the central opening 195 in the internal sealing gasket 173, past the wick 168 and heating coil 167, and through the vaporization chamber 1005 of the central cannula 172. The air flow path 181 may continue through the opening 1022 of the proximal tap 1018, into the central channel 1015 of the proximal end region 156A of the cartridge body 156 and out the opening 154 of the mouthpiece 152. The vapor may then be inhaled by a user. The mouthpiece 152 may incorporate a baffle near the opening 154 to allow the vapor to cool via a longer, turbulent flow path before entering the mouth of a user (see FIG. 12B).

The lower region 1078 of the lower support structure 174 is configured to mate with the distal end region 156C of the cartridge body 156. As a further leak protection in this region of the cartridge, the lower region 1078 of the lower support structure 174 may include a bottom tank seal 176 extending circumferentially around its perimeter (see FIG. 12B and FIG. 12C). The bottom tank seal 176 may further block any material that leaks from the wick 168 into the distal end region 156C of the cartridge body 156 from leaking out of the cartridge body 156. The bottom tank seal 176 may be over-molded around the distal end of the lower region 1078.

In another implementation, the bottom tank seal 176 may incorporate an outward protruding rib along its circumference. The material of the bottom tank seal 176 may be such that it absorbs material that is being blocked and may thus need room to expand to account for this absorption. For example, the bottom tank seal 176 may be a Liquid Silicone Rubber (LSR). The ribbed design provides for absorption and expansion of the bottom tank seal 176 through the rib 176a while still blocking leaked material from the distal end region 156C of the cartridge body 156.

The internal sealing gasket 173 and the lower support structure 174 may provide redundant sealing to prevent liquid leaks from the reservoir. As described above, the internal sealing gasket 173 positioned in a distal end region 156C of the cartridge body 156 may include an upper region configured to seal a bottom end of the reservoir 158, a midline region that may include the first circumferential perimeter seal (e.g. 198) that is configured to seal with an inner surface of the cartridge body 156, and a lower region. The lower support structure 174 may also be positioned in the distal end region 156C of the cartridge body 156. The lower support structure 174 may include the upper region 1077 configured to seal with the lower region of the internal sealing gasket 173 and the lower region 1078. The lower region 1078 of the lower support structure 174 may include the second circumferential perimeter seal (e.g., bottom tank seal 176) that is configured to seal with an inner surface of the cartridge body 156. The first circumferential perimeter seal provided by the dual sealing beads 198 and the second circumferential perimeter seal provided by the bottom tank seal 176 provide redundant sealing to prevent liquid leaks from the reservoir 158 and out of the cartridge 150.

One or more absorbent pads 175a,b may be positioned within the distal end region 156C of the cartridge body 156 to prevent leakage of the vaporizable material from the reservoir 158 (see, for example, FIG. 6, FIG. 11A, FIG. 11B, and FIG. 11C). The pads 175a,b in addition to the bottom tank seal 176 add a layer of redundancy against vaporizable material leaking from the cartridge 150. The pads 175a,b may be oriented to prevent leakage in this region of the cartridge 150 without disrupting airflow or formation of vapor. For example, the absorbent pads 175a,b may be positioned and fitted within the lower support structure 174 off-axis from the air flow path 181. The configuration of the pads 175a,b may vary. In some implementations, the cartridge 150 may include a pair of absorbent pads 175a,b that are attached to opposing sides of the lower support structure 174, for example, between the upper and lower regions 1077, 1078 to absorb excess vaporizable material. The pads 175a,b may be wedged between the lower support structure 174 and the long, interior walls of the distal end region 156C of the cartridge body 156. The pads 175a,b may align generally parallel to each other and to the flat sides of the device. The pads 175a,b may be spaced away from one another creating a gap between them that prevents the pads from interfering with the air flow path 181 through the distal end region 156C of the cartridge body 156. The pads 175a,b may have any of a variety of shapes configured to fill this region of the cartridge 150 including rectangular, circular, ovoid, triangular, square, rings, or other shape. The size and shape of the pads 175a,b may be selected to minimize interference with the air path through the cartridge 150 while maximizing moisture and particle collection. Also, the size and shape of the pads 175a,b may be configured to fit within open spaces of the lower support structure 174 thereby filling the distal end region 156C of the cartridge body 156. For example, FIG. 11B illustrates the pads 175a,b may incorporate a keyed shape or a keying feature 1761. The pads 175a,b having the keyed shape or keying feature 1761 may be configured to wedge within a respective keyed recess 1762 located between the upper region 1077 and the lower region 1078. The keyed recess 1762 may have a shape corresponding to the keyed shape or keying feature 1761 of the respective one of the pads 175a,b. The lower support structure 174 may have a first keyed recess 1762 on a first side configured to receive a first pad 175a and a second keyed recess 1762 on a second side configured to receive a second pad 175b such that each of the first and second keyed recesses may have their own respective pad 175a,b wedged therein. The keying feature 1761 of the pads 175a,b provides a snug, wedged fit with the lower support structure 174 thereby preventing shifting of the pads relative to the device that could impact air flow through the device. As discussed above, air may pass from the air flow channels 1085 of the lower region 1078 of the lower support structure 174 through the side channel outlets 1087 before passing up through the upper region 1077 into the vaporization chamber 1005. The snug, wedged fit of the pads 175a,b prevents the pads from encroaching on this air flow path that could result in blocking the air flow path or reducing the efficiency of the path.

Figure 11C:
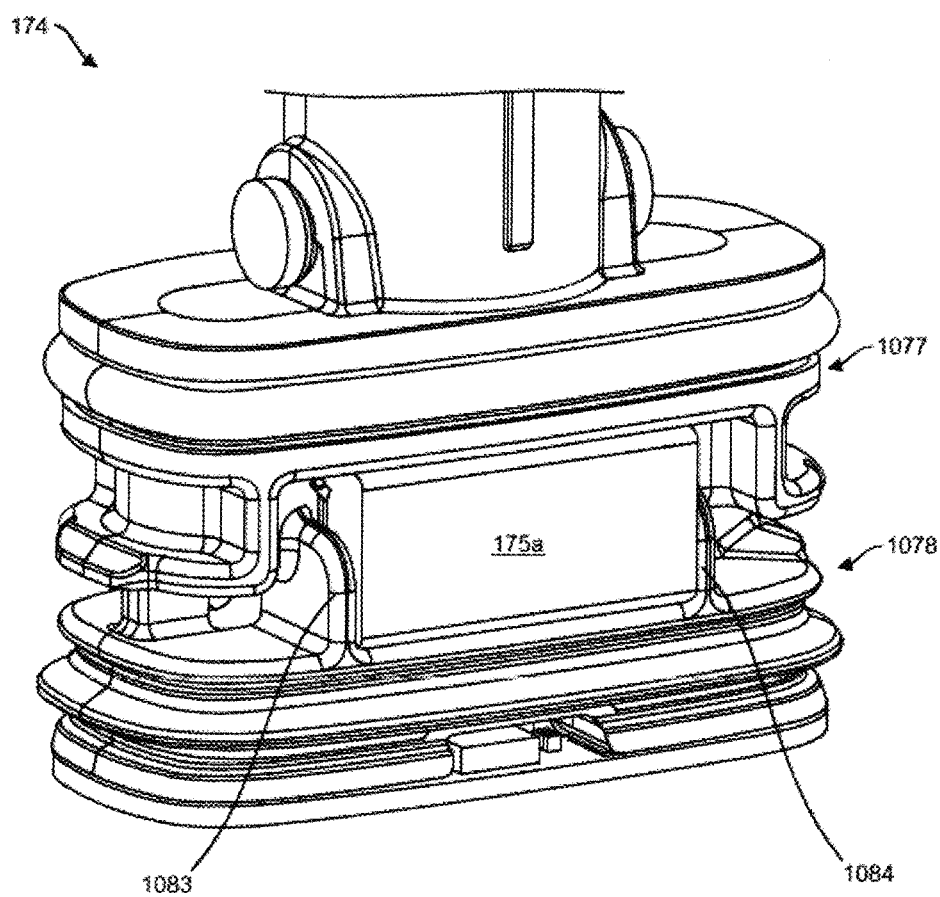

FIG. 11C illustrates an additional implementation consistent with the current subject matter in which the first absorbent pad 175a is positioned and fitted within the lower support structure 174 without the use of the keying feature 1761 shown in FIG. 11B. As shown in FIG. 11C, the first absorbent pad 175a is fitted between the upper and lower regions 1077, 1078 and between side regions 1083, 1084 of the lower support structure 174 to provide a snug, wedged fit with the lower support structure 174. The side regions 1083, 1084 extend upward from the lower region 1078 of the lower support structure 174. The first absorbent pad 175a thus occupies an area into which excess vaporizable material may flow, thereby preventing excess vaporizable material from leaking into the air flow path.

The opposing side of the lower support structure 174 may have a similar configuration and geometry, and may include an absorbent pad and side regions for aiding in holding the absorbent pad to perform the same or similar functions with respect to excess vaporizable material.

Although sets of absorbent pads are shown and described in certain configurations, it should be appreciated that fewer or more pads may be incorporated within the cartridge 150. For example, the absorbent pad 170 in the proximal end region of the cartridge 150 may be formed by more than a single ring-shaped pad (e.g., 2, 3, 4, 5 or more). Similarly, the pair of absorbent pads 175a,b in the distal end region of the cartridge 150 may be a single pad or greater than two pads. Additionally, the absorbent pads may be located in only one region of the cartridge 150.

As mentioned above, the leads 1067 of the heating coil 167 extend through the central aperture 1073 of the bottom plate 1072 as well as through the central opening 195 of the internal sealing gasket 173 into the lower support structure 174. The leads 1067 of the heating coil 167 may electrically couple with the power pin receptacles 160a,b within the lower region 1078 of the lower support structure 174. The power pin receptacles 160a,b may be power pin receptacles configured to mate with the respective power pins (or contacts) 122a,b of the vaporizer body 110, for example, pins projecting upward from a bottom end of the receptacle, as described elsewhere herein. The power pins 122a,b are configured to insert into the respective power pin receptacles 160a,b; the engagement between the power pins 122a,b and the power pin receptacles 160a,b allowing for the transfer of energy from an internal power source of the vaporizer body 110 to the leads 1067 of the heating coil 167. However, the wick 168 and coil 167 assembly performed by hand may pose difficult in ensuring the leads 1067 of the coil 167 are properly inserted into the power pin receptacles 160a,b. Thus, the upper region 1077 of the lower support structure 174 may include a pair of coil guides 179a,b aligned with the central opening 195 and the power pin receptacles 160a,b (see FIG. 9 and FIG. 11A). The coil guides 179a,b are configured to receive and securely hold the leads 1067 of the heating coil 167 as well as reduce the free space between the wick/coil assembly within the vaporization chamber 1005 and the power pin receptacles 160a,b to improve assembly.

The upper surface of the lower support structure 174 may abut against a lower surface of the internal sealing gasket 173 such that the pair of coil guides 179a,b are aligned with and positioned below the central opening 195. The pair of coil guides 179a,b, in turn, may be aligned with and positioned above their respective power pin receptacles 160a,b. The built-in coil guides 179a,b may be provided within an upper region of a respective one or the power pin receptacles 160a,b. The coil guides 179a,b may include a bore extending through a thickness of the upper region 1077 of the lower support structure 174 from a generally circular opening 1081 on the upper surface of the upper region 1077 to another generally circular opening 1082 leading towards the power pin receptacles 160a,b within the lower support structure 174. The bore of the coil guides 179a,b may be cylindrical and have an inner diameter sized to receive and mate with the outer surface of the leads 1067 such that the leads 1067 are securely held within the coil guides 179a,b. The opening 1081 into the bore of the coil guides 179a,b on the upper surface may have an inner diameter that is slightly larger than the inner diameter of the bore. For example, the opening 1081 into the bore of the coil guide 179a,b may be funnel-shaped to ease insertion of each the leads 1067 into their respective coil guides 179a,b. The coil guides 179a,b may advantageously eliminate the cumbersome installation by hand of properly inserting the leads 1067 of the coil 167 into the power pin receptacles 160a,b. The coil guides 179a,b and also the power pin receptacles 160a,b may be insert-molded into the lower support structure 174.

FIGS. 13A-29 illustrate features of a cartridge 250 of a vaporizer device 100 consistent with implementations of the current subject matter. The cartridge 250 may include the same or similar features as the cartridge 150 described herein. The cartridge 250 may include a cartridge body 256 defining, at least in part, a reservoir 258 configured to contain vaporizable material, a mouthpiece 252, and a vaporizing assembly of vapor-generating components positioned within the cartridge body 256 and configured to vaporize the vaporizable material.

The cartridge 250 may include one or more assemblies that may be coupled together, such as via snap-fit, laser-welding, adhesives, and/or the like. For example, the cartridge 250 may include a mouthpiece assembly 290, a cartridge body assembly 292, and a base assembly 294. The cartridge body assembly 292 may include the cartridge body 256, which may be divided, generally, into a proximal end region 256A, a central region 256B, and a distal end region 256C. The proximal end region 256A of the cartridge body 256 can be coupled to the mouthpiece 252 configured to deliver the vapor to the user. A tank or reservoir 258 is defined, at least in part by, the proximal end region 256A and the central region 256B of the cartridge body 256 and is configured to contain an amount of the vaporizable material. The distal end region 256C (alone or together with the central region 256B) of the cartridge body 256 may house one or more components configured to vaporize the material from the reservoir 258 into a vaporization chamber 2005 (see, e.g., FIG. 15A and FIG. 15B). The mouthpiece 252 is configured to interface with the user to release the vapor from the vaporization chamber 2005 to the user through one or more openings 254 in the mouthpiece 252, for example, upon the user drawing a breath through the vaporizer device. Each of these components will be described in more detail below.

As noted above with respect to FIGS. 4-12C, in some implementations, the vaporizable material is *cannabis* oil, which can present particular challenges when vaporized using a cartridge and a vaporizer device. For example, *cannabis* oil is relatively sticky and viscous, particularly once it dries out. Thus, leakage may be a more serious consideration and challenge compared to other aqueous vaporizable materials. In particular, leakage of *cannabis* oil may result in clogging of the device and disturbing the electrical components, particularly the electrical contacts. The dried oil can also disrupt the electrical control of the vaporizer device due to its electrically insulating properties. The cartridges described herein may in certain implementations provide robust leak-resistant designs and may be configured to be used with viscous oil-based vaporizable materials, such as *cannabis* oil that can have a viscosity at room temperature of between about 40 cP and 113 KcP.

As mentioned, the cartridge body 256 can be divided generally into the upper, proximal end region 256A, the lower, distal end region 256C, and the central region 256B located between the proximal and distal end regions 256A, 256C (see FIGS. 13A-13C). The upper, proximal end region 256A of the cartridge body 256 is configured to couple with the mouthpiece 252, for example, by inserting within an internal volume 2010 of the mouthpiece 252 such that an exterior surface of the cartridge body 256, such as a portion of a wick housing 288, near the proximal end region 256A seals with an inner surface of the mouthpiece 252. The proximal end region 256A of the cartridge body 256 can define a central channel 2015 (see FIG. 15A) for directing vapor from the vaporization chamber 2005 towards the one or more openings 254 through the mouthpiece 252. The lower, distal end region 256C of the cartridge body 256 may house components configured to couple with the vaporizer body 110, for example, by inserting the cartridge 250 within the cartridge receptacle 114, which will also be described in more detail below.

As mentioned, the distal end region 256C of the cartridge body 256 may be configured to couple to and be secured with the vaporizer body 110, for example, by inserting the cartridge 250 within the cartridge receptacle 114 (see FIG. 1A and FIG. 1B), as described above with respect to the cartridge 150 (shown in FIGS. 4-12C). The cartridge 250 can couple within the cartridge receptacle 114 by a friction-fit, snap-fit, and/or other types of secure connection. In some implementations, any of a variety of complementary coupling features may be incorporated, including but not limited to tab, indent, magnetic lock, channel, rim, lip, ridge, protrusion, groove, rib, etc., that are configured to engage with a complementary feature (not shown) of the vaporizer body 110. For example, in some implementations the cartridge 250 and vaporizer body 110 may incorporate one or more coupling features having corresponding male and female parts that allow the cartridge 250 to snap into place in operable contact with the vaporizer body 110. The one or more coupling features may be configured to engage with a complementary feature on the vaporizer body 110, such as within the cartridge receptacle 114, when the cartridge 250 engages with the vaporizer body 110.

In some implementations, the one or more coupling features is a circumferential rib on an outer surface of the cartridge 250, for example, near where proximal end region 256A meets the central region 256B. The circumferential rib may be an elastomeric element configured to provide an interference fit with an inner surface of the cartridge receptacle 114 such that the cartridge 250 securely couples with the vaporizer body 110 without needing to engage with a corresponding feature on the inner surface of the cartridge receptacle 114. The circumferential rib may be part of a mouthpiece seal 277 positioned between and configured to seal between an inner surface of the mouthpiece 252 and an outer surface of the cartridge body 256. The compliant material of the mouthpiece seal 277 may wedge against and engage with the inner surface of the cartridge receptacle 114 providing a secure fit. The mouthpiece seal 277 may provide a snap-fit feel upon seating the cartridge 250 within the cartridge receptacle 114 of the vaporizer device.

The cartridge 250 may have an elongate and flattened tubular body extending in a distal to a proximal axis (longitudinal axis A). The cartridge 250 may be described as having a length (sometimes referred to herein as a height), a width, and a depth (sometimes referred to herein as a thickness). The height is a length from the proximal end to the distal end of the cartridge 250 along the longitudinal axis A (see FIG. 15A). The width of the cartridge is measured transverse the longitudinal axis A along a major axis of the cartridge 250 and thus refers to the length of the longer sides of the cartridge. The depth of the cartridge 250 is also measured transverse the longitudinal axis A, but along the minor axis of the cartridge 250 and thus refers to the length of the shorter sides. The width may be 1.2 times, 1.3 times, 1.4 times, 1.5 times, 1.6 times, 1.7 times, 1.8 times, 1.9 times, etc. or greater than the depth. The cartridge 250 may be between about 1 cm and 10 cm long, between about 2 cm and 7 cm long, between 3 cm and 5 cm long. The length of the cartridge 250 may be less than 8 cm, less than 7 cm, less than 6 cm, less than 5.5 cm, less than 5 cm, etc. In some implementations, the cartridge 250 may have a total length of about 3.3 cm, a width (i.e., across the major axis of the cartridge) of about 1.7 cm, and a depth (i.e., across the minor axis of the cartridge) of about 0.85 cm.

Similar to the cartridge body 156, the cross-sectional shape of the cartridge body 256 may be any of a variety of shapes, including circular, round, or non-round shapes, such as an approximately oval, elliptical, rectangular, square, trapezoidal, or other cross-sectional shape.

Again with respect to FIGS. 13A-15B, the proximal end region 256A of the cartridge body 256 is configured to couple with the mouthpiece 252 of the mouthpiece assembly 290. The mouthpiece 252 can include the internal volume 2010 sized such that the mouthpiece 252 may be attached over the proximal end region 256A of the cartridge body 256. As such, the mouthpiece 252 may form the proximal end of the cartridge 250. The mouthpiece 252 may have an external surface that is generally amenable to a user placing their lips over the proximal end 253 of the mouthpiece 252 to inhale the vapor. As noted above with respect to the mouthpiece 152, the external surface of the mouthpiece 252 may have a variety of configurations, shapes, and/or sizes.

One or more openings 254 may extend through a proximal end surface 2025 into the internal volume 2010 of the mouthpiece 252. The one or more openings 254 allow for the vapor produced within the cartridge 250 to be inhaled by the user. The one or more openings 254 may be aligned with the central, longitudinal axis A of the device or positioned off-set from the longitudinal axis A. The proximal end surface 2025 of the mouthpiece 252 may be sloped inwardly away from the outer edges towards the one or more openings 254. The relative size of the one or more openings 254 may be minimized to hide from view internal components positioned beneath the mouthpiece 252 from the proximal end 253 of the cartridge 250 and aid in reducing the amount of dirt/lint that may enter the mouthpiece 252, while at the same time being of sufficient size to permit the sufficient flow of vapor to the user. In some implementations, the one or more openings 254 through the proximal end surface 2025 of the mouthpiece 252 is a single, elongate slot that has a relatively narrow width providing a generally thin, rectangular shape to the opening 254. However, other shapes, sizes, and/or configurations of the mouthpiece opening 254 may be utilized. For example, the mouthpiece opening 254 may be an oval shape, or two more openings of the same or different shapes may be used.

The mouthpiece 252 may couple (e.g., snap-fit) onto the proximal end region 256A of the cartridge body 256 to snugly mate with the cartridge body 256. The configuration of the coupling between the cartridge body 256 and the mouthpiece 252 may vary. The coupling may incorporate corresponding male and female parts configured to mate together. For example, an inner surface of the mouthpiece 252 (or the external surface of the cartridge body 256) may incorporate a lip, flange, rib, or other outwardly projecting coupling feature configured to slide past and/or into a corresponding feature on an exterior surface of the cartridge body 256 (or the inner surface of the mouthpiece 252).

In some embodiments, the mouthpiece 252 may be permanently affixed to the cartridge body 256. In some embodiments, the cartridge 250 may be disposable and not configured to be refilled. It should be appreciated that the mouthpiece 252 need not be a part of the cartridge 250 itself. For example, the cartridge 250 may include a reservoir and be configured to attach with the vaporizer body 110 independent of the mouthpiece 252.

Mating the mouthpiece 252 with the proximal end region 256A of the cartridge body 256 may provide a seal with an exterior surface of the cartridge body 256. For example, the mouthpiece seal 277, which may be the same or similar to the mouthpiece seal 177, be incorporated between where the mouthpiece 252 and the proximal end region 256A of the cartridge body 256 couple together. As noted above with respect to the cartridge 150, the sealing of the mouthpiece seal 277 may eliminate, or at least aid in reduction of, air leaks at the junction between the mouthpiece 252 and the cartridge body 256.

The mouthpiece seal 277 may engage the internal surface of the mouthpiece 252 near its distal end region 2030. For example, the mouthpiece seal 277 may be positioned on the cartridge body 256 near where the distal end region 2030 of the mouthpiece 252 encircles the cartridge body 256.

The mouthpiece seal 277 may be a generally annular feature having a flat inner diameter configured to be affixed or engaged flush with the external surface of the cartridge body 256. The mouthpiece seal 277 may include a fill port seal 296 that aligns with a fill port 297 that extends through a side of the reservoir body 258A (see FIG. 15A). The fill port 297 may form an opening in the reservoir body 258A. In some implementations, the fill port 297 forms a circular opening through the side of the reservoir body 258A. In other implementations, the fill port 297 is oval, triangular, square, rectangular, and/or the like. Through the fill port 297, the cartridge 250 may be filled with the vaporizable material. As noted above, the fill port seal 296 may align with the fill port 297. The fill port seal 296 may define an opening in the mouthpiece seal 277 that allows a needle, syringe, or other filling mechanism to pass through the mouthpiece seal 277 and fill port 297 to fill the cartridge 250 with the vaporizable material. The fill port seal 296 may include a septum, such as a self-sealing septum that allows the filling mechanism to pierce the septum, and pass through the fill port seal 296 to fill the cartridge 250, such as in a first direction (e.g., a direction extending from the exterior of the cartridge 250 to the interior of the cartridge 250). In some implementations, the septum may be pre-cut to enable blunt needle filling. In some implementations, the septum of the fill port seal 296 does not allow the vaporizable material to flow out of the reservoir 258 through the fill port 297 and/or fill port seal 296. For example, the septum of the fill port seal 296 may close when the filling mechanism is removed from the fill port 297 and/or passes by or through the fill port seal 296 in a second direction (e.g., a direction extending from the interior of the cartridge 250 to the exterior of the cartridge 250) opposite the first direction. The fill port seal 296 may include a self-healing seal, such as a 50 A durometer self-healing seal.

Figure 15A:
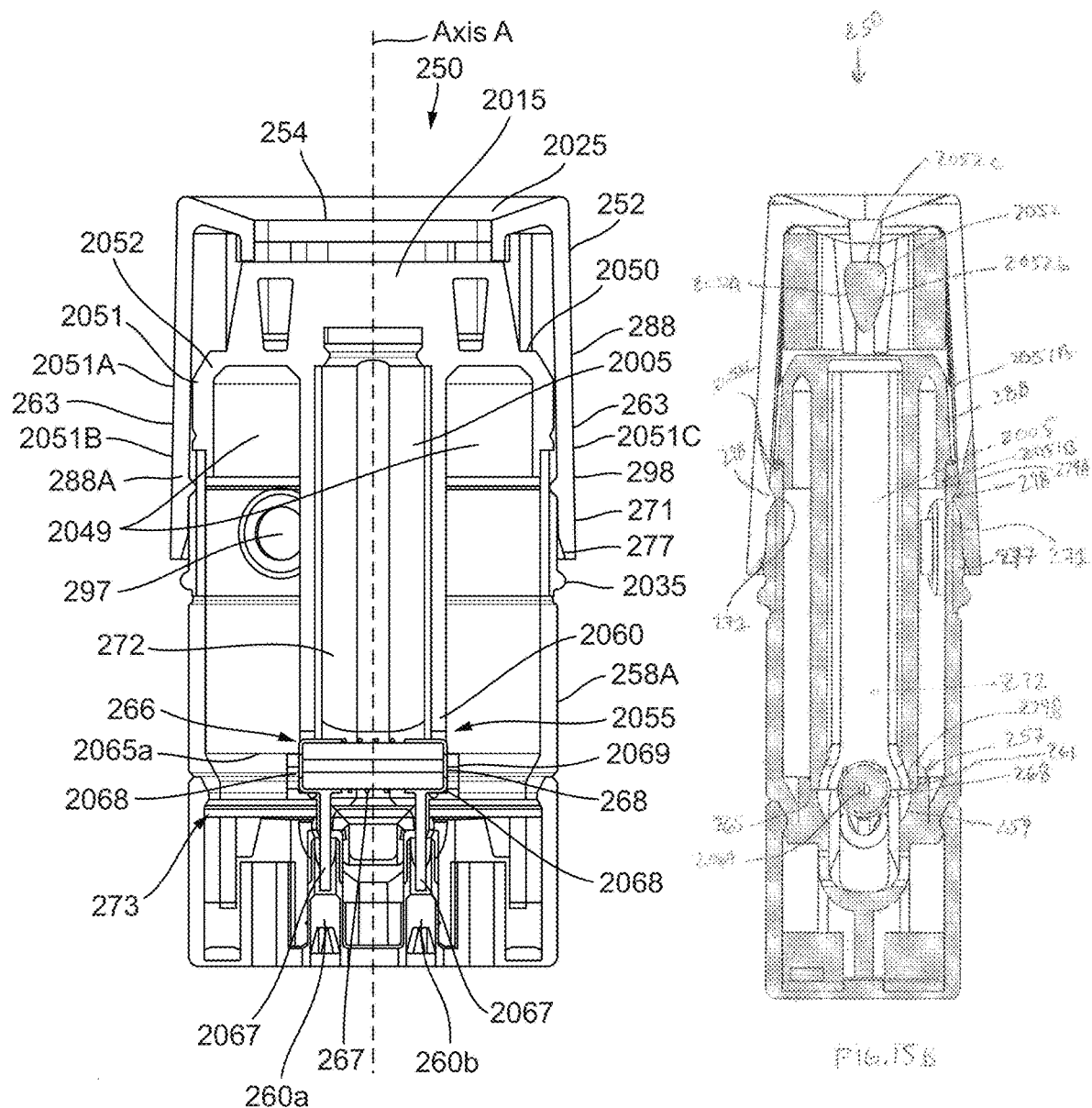
Figure 17:
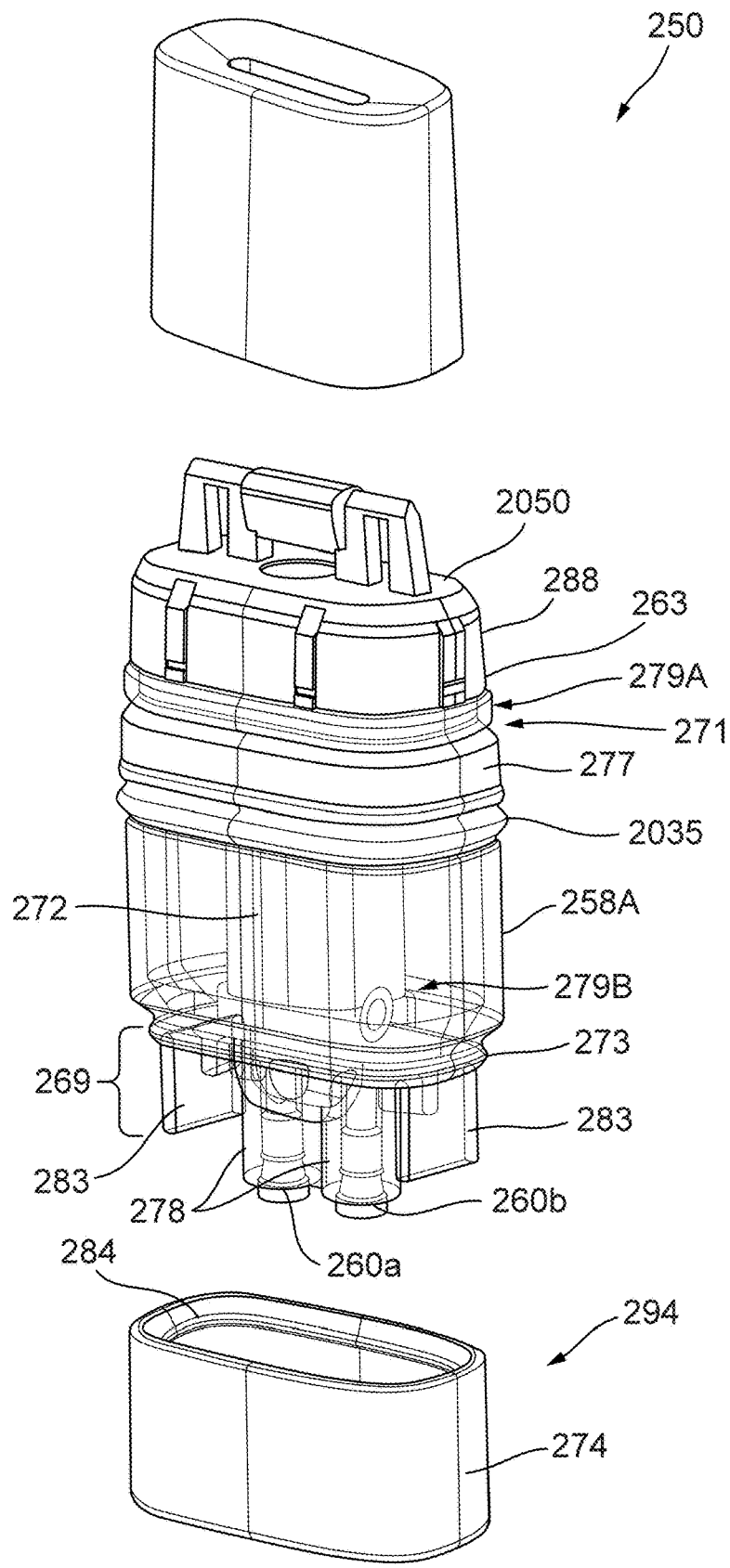
FIG. 17 illustrates a partial exploded view of a cartridge consistent with implementations of the current subject matter.
Figure 77A:
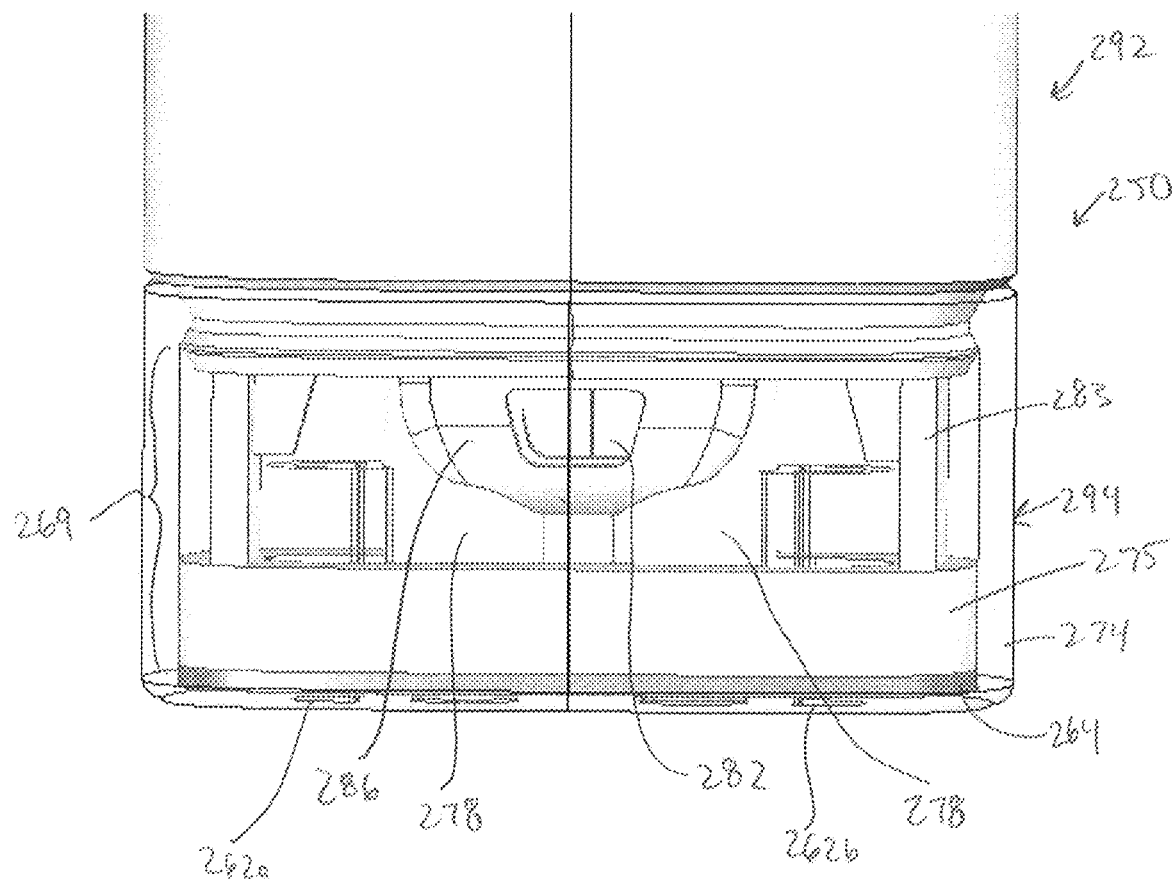
Figure 18:
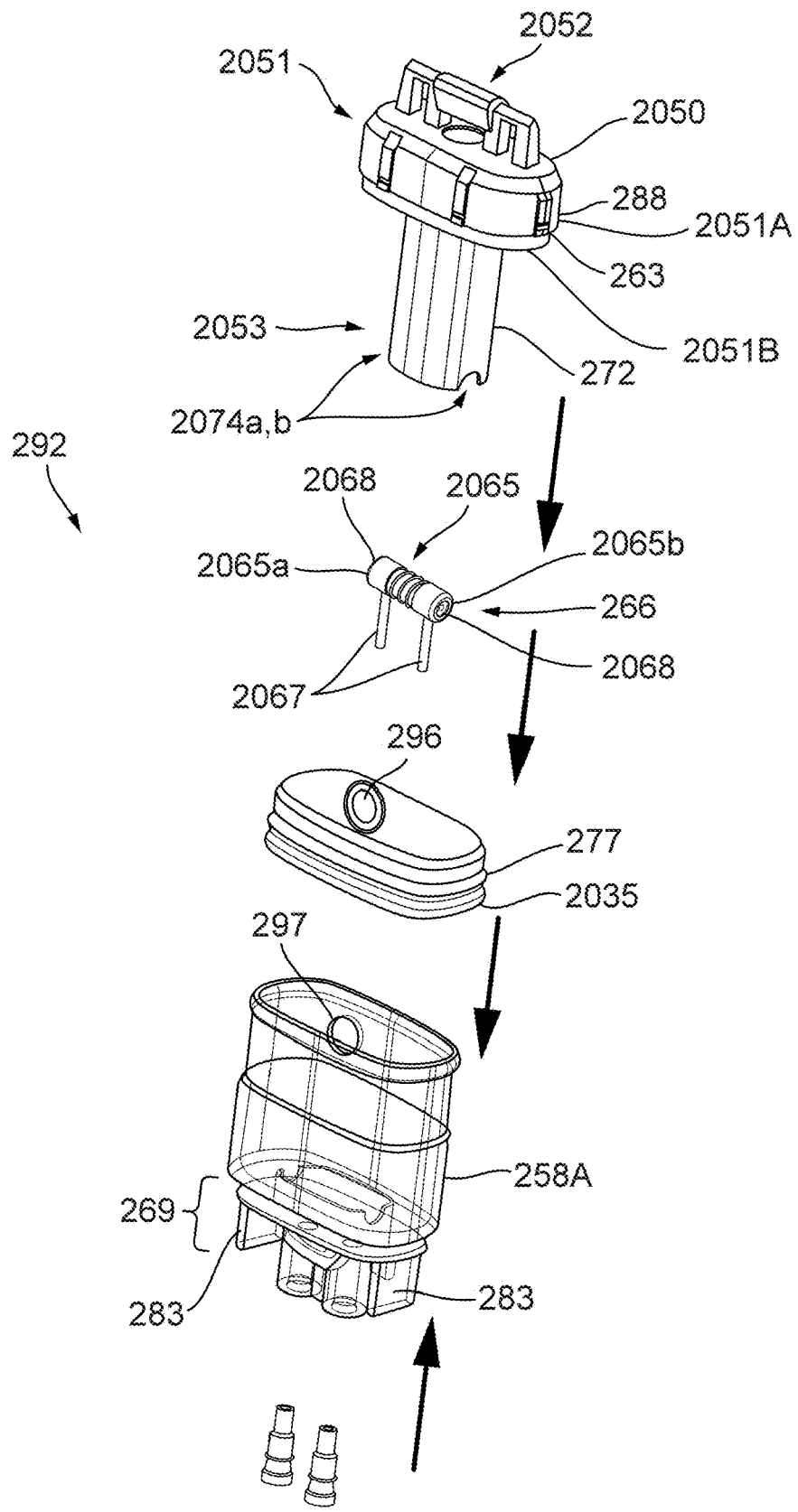
FIG. 18 illustrates a partial exploded view of a cartridge consistent with implementations of the current subject matter.

Referring to FIGS. 15A, 17, and 18, the outer surface of the mouthpiece seal 277 may have at least one, two, three, or more circumferential sealing beads or ribs 2035. As noted above with respect to the mouthpiece seal 177, the ribs 2035 may provide a redundancy to the sealing between the mouthpiece 252 and the cartridge body 256 as well as a redundancy to the coupling between the cartridge 250 and the vaporizer body 110. In some implementations, the mouthpiece seal 277 may be positioned or over-molded within a groove or recessed portion formed in the exterior surface of the cartridge body 256 (e.g., of the reservoir body 258A) to provide better fixation of the mouthpiece seal 277 to the exterior surface of the cartridge body 256. The groove in the exterior surface of the cartridge body 256 may have a surface that is conducive to coupling with the inner diameter of the mouthpiece seal 277. For example, the surface of the groove may be etched or otherwise textured.

In some implementations, an inner surface of the distal end region 2030 of the mouthpiece 252 may have an inwardly-projecting feature 298. In some implementations, such as is shown in FIGS. 15A-15B, the inwardly-projecting feature 298 may be configured to couple with (e.g., snap over and position within) a wick housing groove 263 formed along at least a portion of the wick housing 288 of the cartridge body assembly 292, and/or a reservoir body groove 271 formed on the cartridge body assembly 292 between the mouthpiece seal 277 and a proximal end of the reservoir body 268A on one side of the recessed portion formed in the exterior surface of the cartridge body 156. As described in more detail below, the mouthpiece 252 may be configured to slide from a first mouthpiece position (see FIG. 22B), in which the inwardly-projecting feature 298 is positioned within the groove 263 and the fill port 297 and/or fill port seal 296 are accessible for filling the cartridge 250, to a second mouthpiece position (see FIG. 13A, 15A), in which the inwardly-projecting feature 298 is positioned within the groove 271 and the fill port 297 and/or fill port seal 296 are not accessible for filling the cartridge 250. Mating the inwardly-projecting feature 298 with the groove 271 also closes off the fill port 297 from the exterior of the cartridge 250. Accordingly, mating the inwardly-projecting feature 298 with the groove 263 after the reservoir has been filled helps to ensure that vaporizable material does not leak from the fill port 297. In some implementations, the engagement between the inwardly-projecting feature 298 of the mouthpiece 252 and the groove 263 and/or the groove 271 additionally and/or alternatively blocks gas flow between the inner surface of the mouthpiece 252 and the outer surface of the cartridge body 256. Such configurations of the mouthpiece seal 277 may only include a single sealing rib (e.g., the sealing rib 2035), which may help to reduce the amount of materials required to form the mouthpiece seal 277.

Again with respect to FIGS. 13A-15B, the mouthpiece 252 may be coupled to the proximal end region 256A of the cartridge body 256. The mouthpiece 252 may include an internal volume 2010 and an external surface defining at least one opening 254 into the internal volume 2010. The at least one opening 254 may be configured to release vapor from the vaporizing assembly in the cartridge. The internal volume 2010 of the mouthpiece 252 may include a region, for example, near the proximal end 253 of the cartridge 250 adjacent the one or more openings 254 of the mouthpiece 252, that is configured to contain one or more (e.g., one, two, three, four or more) pads (e.g., absorbent pads) 270 within the internal volume 2010 (see FIG. 20). The one or more pads 270 may be positioned within the internal volume 2010 of the mouthpiece 252 near or proximate to the one or more openings 254 through which vapor may be inhaled, e.g., by drawing breath through the vaporizer device 100, such that the pads may capture moisture just prior to inhalation by the user. The one or more absorbent pads 270 may prevent or reduce the flow of fluid, such as the vaporizable material, into and out of the one or more openings 254. The one or more pads 270 may be pushed against the interior surface of the mouthpiece 252 or may be pulled away from interior walls so as to maximize the surface area available for moisture absorption. The pads may have any of a variety of shapes including rectangular, circular, ovoid, triangular, square, ring, or other shape. The size and shape of the one or more pads 270 may be selected to minimize interference with the vapor path through the openings 254 while maximizing moisture and particle collection. Thus, the one or more pads 270 may capture deposited and/or condensed liquid from the vapor flowing through the cartridge 250 without requiring the vapor to pass through the pads 270.

In some implementations, the one or more pads 270 are configured to be positioned within the internal volume 2010 of the mouthpiece 252 near the opening 254 without obstructing vapor flow through the opening 254. The one or more pads 270 may be positioned within the mouthpiece 252 such that the one or more pads 270 surround at least a portion of the vapor path and are generally off-axis relative to the opening 254, allowing unobstructed vapor flow through the opening 254. In other implementations, the one or more pads 270 may be coaxial with the opening 254 and the shape of the one or more pads 270 allows the one or more pads 270 to avoid obstructing vapor flow through the opening 254.

Figure 20:
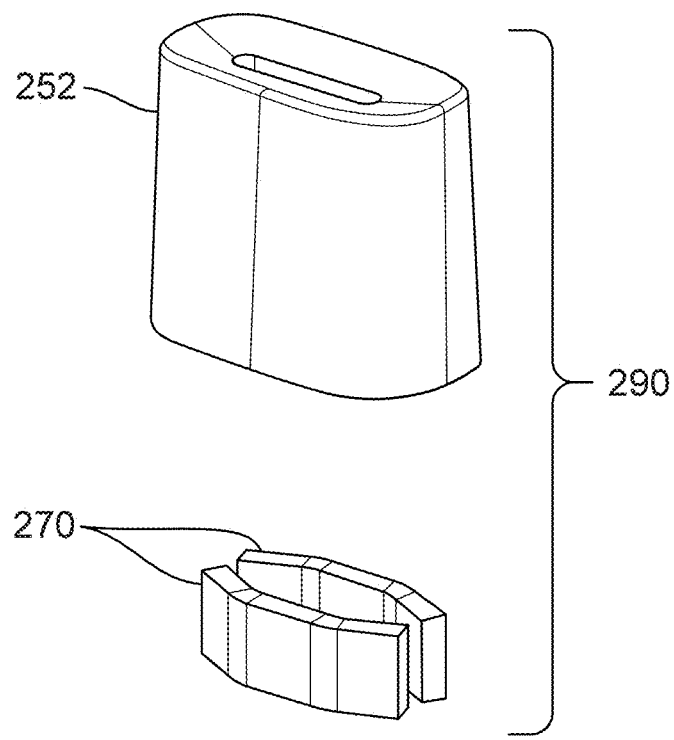
FIG. 20 illustrates a partial exploded view of a cartridge consistent with implementations of the current subject matter.
Figure 21A:
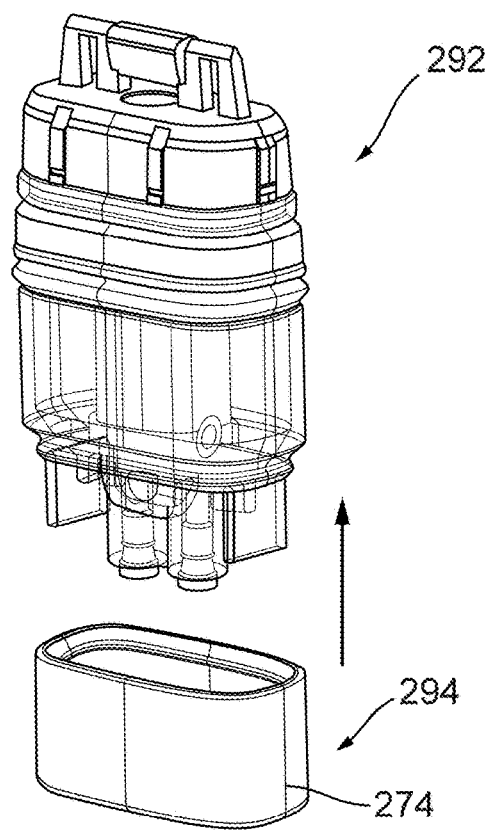
FIGS. 21A-21B illustrate examples of assembling a cartridge consistent with implementations of the current subject matter.
Figure 21B:
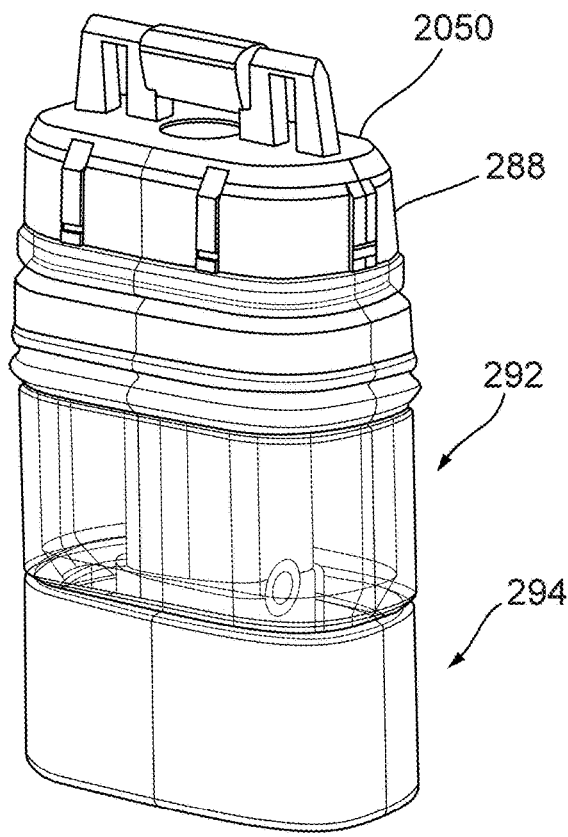

FIG. 20 illustrates that the one or more pads 270 may include two pads 270. The two pads 270 may include a rectangular shape and may be bent. Each of the two pads 270 may be positioned opposite one another within the interior of the mouthpiece 252 such that an opening is formed between the two pads. The two pads may be shaped to correspond to an interior surface of the mouthpiece 252. The opening between the two pads 270 may have a shape that corresponds or substantially corresponds to a shape of the opening 254 such that it may surround the opening 254. The two pads 270 may be wedged within the internal volume of the mouthpiece and against the internal surface of the mouthpiece 252 to avoid blocking gas flow through the opening 254. In some implementations, an outer wall of the pads 270 may engage with the internal surfaces or inner sides of the mouthpiece 252 (e.g., the major sides of the generally flattened shape of the mouthpiece 252) such that the outer wall generally matches the flattened cross-sectional geometry of the mouthpiece 252. For example, if the cross-sectional geometry of the mouthpiece 252 is a flattened oval or rectangular, the geometry defined by the outer wall of the pad 270 is likewise a flattened oval or rectangular.

As mentioned above, the mouthpiece 252 may be attached over the proximal end region 256A of the cartridge body 256. The pad 270 may be positioned (e.g., sandwiched) against an upper, proximal surface 2050 of the cartridge body 256 (e.g., of the wick housing 288). The upper, proximal surface 2050 of the cartridge body 256 abuts against a lower surface 2055 of the pads 270 such that the pad 270 is wedged between a proximal portion of the mouthpiece 252, the inner sides of the mouthpiece 252, and the proximal surface 2050 of the cartridge body 256. The pads 270 may be wedged into place and affixed without an adhesive although it should be appreciated that adhesives may also be used to affix the pads 270.

The upper, proximal surface 2050 of the cartridge body 256 (e.g., of the wick housing 288) may also include a central, upper element 2052 sized to be inserted through the opening formed between the two pads 270. The pads 270 thereby encircles at least a portion of the central, upper element 2052, which in turn, projects through opening formed between the pads 270. The shape of the pads 270 along with the wedged coupling with the mouthpiece 252, and the proximal surface 2050 and upper element 2052 of the cartridge body 256 prevent shifting of the pads 270 during use and handling. Shifting of the pads 270 may cause the pads 270 to obstruct vapor flow through the device. Use of the term "pad" is not intended to be limiting. The pads 270 may be any absorbent member (e.g., sponge, pad, felts, fiber, fabric, etc.) that may absorb an amount of a fluid. The one or more pads 270 may include any absorbent material configured to wick moisture relatively quickly and allow it to disperse quickly therethrough. The absorbent material may be hydrophilic, including cotton, non-woven cotton linter paper, felt, cellulose, or hydrophilic polymers. The pads 270 may be formed of thin sheets of layered material.

The configuration of the pads 270 in which the opening formed therebetween is generally aligned with the central channel 2015 and off-axis from the opening 254 of the mouthpiece 252 may result in the capture of large particles yet allow smaller particles through to the opening 254. In some implementations, a large particle may have a diameter of at least about 10 microns. In some implementations, a large particle may have a dimeter of at least about 8 microns, about 9 microns, about 10 microns, about 11 microns, up to about 12 microns. As larger particles have more inertia, the larger particles will hit the pad 270 whereas smaller particles will curl around the central, upper element 2052 to exit the mouthpiece 252, as further described below.

FIG. 15A illustrates an example of the cartridge body assembly 292, consistent with implementations of the current subject matter. The cartridge body assembly 292 may include the cartridge body 256 (which as noted above, may include the proximal end region 256A, the central region 256B, and the distal end region 256C). The cartridge body 256 may include the tank or reservoir body 258A, a wick housing 288, a heater 166, and the mouthpiece seal 277. The wick housing 288, which is described in more detail below, may include the central, upper element 2052, a central, lower element 2053, a central cannula 272 defining the vaporization chamber 2005 extending between the central, upper element 2052 and the central, lower element 2053, and a proximal wick housing base 2051.

As described above with respect to the cartridge 150, the cartridge 250 may include a vaporizing assembly of vapor-generating components. The vapor-generating components may include the heater 266, which is configured to heat the vaporizable material to a sufficient temperature that it may vaporize. The heater 266 may have the same or similar properties and/or features as the heater 166. Generally, as noted above, vaporizers for use with liquid vaporizable materials (e.g., neat liquids, suspensions, solutions, mixtures, etc.) typically include an atomizer in which a wicking element (also referred to herein as a wick 268, which may have the same or similar properties and/or features as the wick 168), which may include any material capable of causing passive fluid motion, (for example, by capillary pressure) conveys an amount of a liquid vaporizable material to a part of the atomizer that includes the heating element. The wicking element is generally configured to draw liquid vaporizable material from the reservoir configured to contain (and that may in use contain) the liquid vaporizable material such that the liquid vaporizable material may be vaporized by heat delivered from the heating element.

The heater 166 may be or include one or more of a conductive heater, a radiative heater, and a convective heater. One type of vaporizing heating element is a resistive heating element, which may be constructed of or at least include a material (e.g., a metal or alloy, for example a nickel-chromium alloy, or a non-metallic resistor) configured to dissipate electrical power in the form of heat when electrical current is passed through one or more resistive segments of the heating element. In some implementations of the current subject matter, an atomizer may include a vaporizing heating element that includes resistive coil or other heating element wrapped around, positioned or otherwise embedded within, integrated into a bulk shape of, pressed into thermal contact with, or otherwise arranged to deliver heat to a wicking element to cause a liquid vaporizable material drawn by the wicking element from a reservoir to be vaporized for subsequent inhalation by a user in a gas and/or a condensed (e.g., aerosol particles or droplets) phase. Other wicking element, heating element, and/or atomizer assembly configurations are also possible, as discussed further below.

Certain vaporizers may also or alternatively be configured to create an inhalable dose of gas-phase and/or aerosol-phase vaporizable material via heating of a non-liquid vaporizable material, such as for example a solid-phase vaporizable material or plant material containing the vaporizable material. In such vaporizers, a resistive heating element may be part of or otherwise incorporated into or in thermal contact with the walls of an oven or other heating chamber into which the non-liquid vaporizable material is placed. Alternatively, a resistive heating element or elements may be used to heat air passing through or past the non-liquid vaporizable material to cause convective heating of the non-liquid vaporizable material. In still other examples, a resistive heating element or elements may be disposed in intimate contact with plant material such that direct conductive heating of the plant material occurs from within a mass of the plant material (e.g., as opposed to only by conduction inward from walls of an oven).

Still with respect to FIGS. 13A-15B, the heater 266 may be configured to heat and/or vaporize at least a portion of the vaporizable material drawn towards the heater 266 from the reservoir 258. The central cannula 272 of the wick housing 288 is configured to couple to the heater 266 to generate heat to vaporize the vaporizable material contained in the reservoir 258. In some implementations, the heater 266 may include a resistive element such as a heating coil 267 in thermal contact with a wick 268. The heating coil 267 and the wick 268 may include the same or similar properties and features as the heating coil 267 and the wick 268 described above with respect to the cartridge 150.

The wick 268 may be formed of any of a variety of materials, including metals, polymer, natural fibers, synthetic fibers, or combinations of these. For example, the wick 268 may be formed of silica fibers, cotton, ceramic, hemp, stainless steel mesh, rope cables, and/or any porous medium, such as for example sintered glass beads. The wick 268 is porous and provides a capillary pathway for fluid within the reservoir 258 through and into the wick 268. The capillary pathway is generally large enough to permit wicking of sufficient material to replace vaporized liquid transferred from the reservoir 258 by capillary action (wicking) during vaporization, but may be small enough to prevent leakage of the vaporizable material out of the cartridge during normal operation, including when pressure is applied to outside the cartridge 250.

The wick 268 may have a size configured to handle high viscosity liquids. In some implementations, the wick 268 may have a diameter that is at least about 1.5 mm. The wick 268 may be larger than 1.5 mm in diameter (e.g., about 1.9 mm or larger, about 2.0 mm or larger, about 2.1 mm or larger, about 2.2 mm or larger, about 2.3 mm or larger, about 2.4 mm or larger, about 2.5 mm or larger, etc., including between about 1.8 mm and about 5 mm, between about 1.9 mm and about 4 mm, between about 2 mm and about 4 mm, etc.). The material of the wick 268 is configured to draw the liquid vaporizable material from the reservoir 258 into the vaporization chamber 2005 without the need for a pump or other mechanical moving part. In some implementations, the tension of the heating coil 267 wound around the wick 268 may vary. Winding the heating coil 267 tighter and/or with additional windings may create a larger heating surface area to create more intense or concentrated heating of the vaporizable material. Likewise, reducing the diameter of the wick may also create more intense or concentrated heating of the vaporizable material.

Consistent with implementations of the current subject matter and as shown in FIGS. 14-15B and 18, the wick 268 may be made of a porous material, such as ceramic, in which the pores of the porous material facilitate wicking of the vaporizable material along the length of the wick 268. A central bore 2069 may extend through a length of the wick 268 to further facilitate wicking. Additionally and/or alternatively, the wick 268 may include one or more side bores along at least a portion of the length of the wick 268 that extend orthogonal to the central bore 2069 and/or at other angles relative to the central bore 2069 to further facilitate wicking.

The heating coil 267 may be a resistance wire wrapped around the wick 268 and may be connected to a positive and negative pole of a current source. The heating coil 267 may increase in temperature as a result of the current flowing through the wire to generate heat. The heat may be transferred to at least a portion of the vaporizable material through conductive, convective, and/or radiative heat transfer such that at least a portion of the vaporizable material vaporizes. Air drawn into the vaporization chamber 2005 may carry the vapor away from the heater 266.

FIGS. 13A-23 illustrate an example of the heater 266 consistent with implementations of the current subject matter in which the wick 268 includes end caps 2068 that provide a connection between the heating coil 267 and the power source. The end caps 2068 may include respective leads 2067 (e.g., for facilitating the electrical connection of the heating coil 267 with the vaporizer body 110). In some implementations, the end caps 2068 are separately formed and coupled to the wick 268 and/or heating coil 267. In other implementations, the end caps 2068 may be integrally formed with the heating coil 267 and/or the leads 2067. Additionally and/or alternatively, the end caps 2068, the heating coil 267, the leads 2067, and/or the reservoir body 258A may be integrally formed. In other words, the end caps 2068, the heating coil 267, the leads 2067, and/or the reservoir body 258A may all be formed from a single piece of material, such as a sheet metal or other desired material. Such configurations may help to prevent or reduce leaking of the vaporizable material from the wick 268.

The end caps 2068 may be made of various materials, such as copper, stainless steel, other metals, or combinations thereof. The end caps 2068 may securely and snugly fit over respective ends of the wick 268 (e.g., opposing ends 2065a, b). For example, the end caps 2068 may be thin sleeves that fit over the respective ends of the wick 268. End portions of each of the end caps 2068 have an opening that aligns with the central bore 2069. The openings may be of a larger diameter than that of the central bore 2069 to further promote wicking of the vaporizable material along the length of the wick 268. In some implementations, the end portions of each of the end caps 2068 may also include at least one (e.g., one, two, three, four, five, six, seven, eight, or more) outer openings 2068A (see FIG. 23), defining one or more vents. In some implementations, the one or more outer openings 2068A may additionally and/or alternatively extend through all or a portion of a length of the wick 268, such as from one end 2065a to the other end 2065b The number of outer openings, the shape of the outer openings, the position of the outer openings, and/or the size of the outer openings may be adjusted to increase, decrease, or otherwise improve transfer of the vaporizable material from the reservoir 258 to the wick 268, which helps to ensure that the wick 268 remains saturated.

The heater 266 may extend across the air path within the vaporization chamber 2005, such as in a transverse direction. Still with respect to FIGS. 15A-15B and 18, the central cannula 272 of the wick housing 288 may be arranged coaxial with the longitudinal axis A of the device and the wick 268 may extend orthogonal to the longitudinal axis A through the central cannula 272. The wick 268 is preferably positioned near a distal-most end region of the reservoir 258 such that the vaporizable material in the reservoir 258 may be fully used. A pair of lateral openings 2074a,b may extend through the walls of the central cannula 272 of the wick housing 288 near its base where the central cannula 272 couples to an inner distal surface of the reservoir body 258A. The pair of lateral openings 2074a,b may be aligned across from one another on opposing sides of the central cannula 272. The openings 2074a,b are provided and sized for coupling to the heater 266.

In some implementations, the wick 268 of the heater 266 may include a central portion 2060 and opposing ends 2065a,b positioned on opposite sides of the central portion 2060. The heating coil 267 may be wrapped around the central portion 2060 of the wick 268, which in turn may be positioned within the vaporization chamber 2005. The opposing ends 2065a,b of the wick 268 may be positioned outside the vaporization chamber 2005 by extending laterally outward through the lateral openings 2074a,b of the central cannula 272. As such, the opposing ends 2065a,b may be positioned within the internal volume of the reservoir 258 whereas the central portion 2060 of the wick 268 wrapped by the heating coil 267 may be positioned inside the vaporization chamber 2005 of the central cannula 272. The leads 2067 of the heating coil 267 may extend away from the central portion 2060 of the wick 268 and down through respective openings in an interior surface of the reservoir body 258A, out of the vaporization chamber 2005. The leads 2067 may extend into the distal end region 256C of the cartridge body 256 where the leads 2067 may electrically couple with the power pin receptacles 260a,b.

As noted above, the wick housing 288 includes the central, upper element 2052, a central, lower element 2053, the central cannula 272 defining the vaporization chamber 2005 extending between the central, upper element 2052 and the central, lower element 2053, and a proximal wick housing base 2051 positioned adjacent to the central, upper element 2052 and surrounding at least a portion of the central cannula 272 (see FIGS. 15A and 18). In some implementations, the central, upper element 2052, the central, lower element 2053, the central cannula 272, and the proximal wick housing base 2051 may be integrally formed to define a single component.

As noted above, the pair of lateral openings 2074a,b may extend through the walls of the central cannula 272 and/or the central, lower element 2053 of the wick housing 288. The pair of lateral openings 2074a,b may be aligned across from one another on opposing sides of the central cannula 272 and receive or otherwise house at least a portion of the wick 268, such as the central portion 2060 of the wick 268 and the heater 266.

Figure 16A:
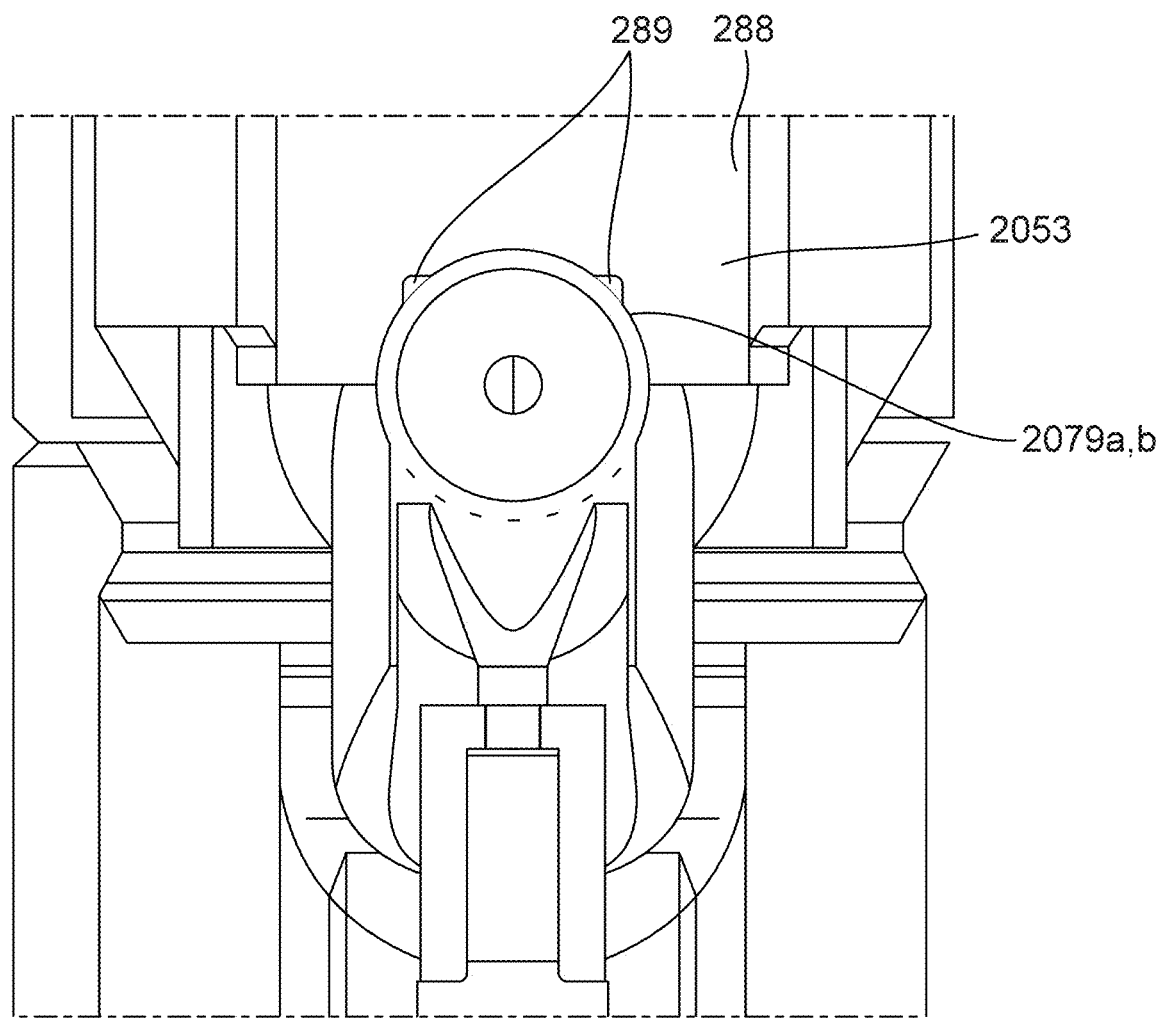
FIGS. 16A-16B illustrate partial views of a cartridge consistent with implementations of the current subject matter.
Figure 16B:
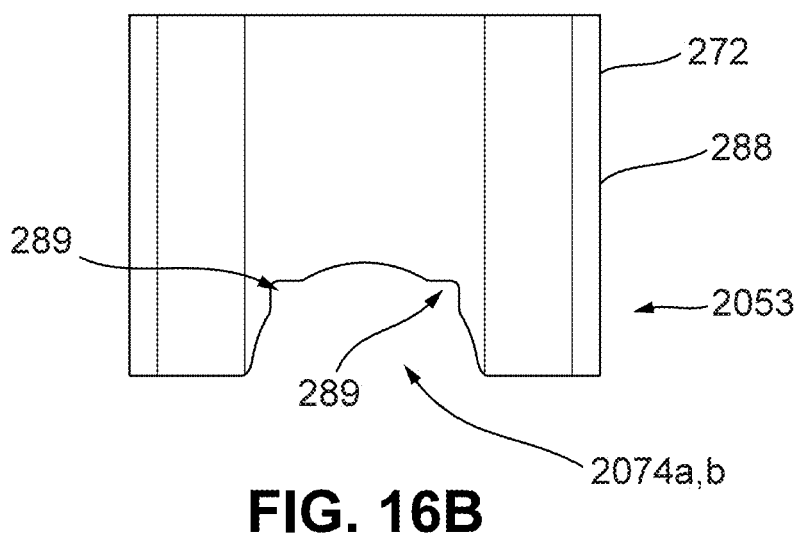

FIG. 16A illustrates a close-up side view of the central, lower element 2053 engaged with the heater 266, consistent with implementations of the current subject matter. FIG. 16B illustrates a close-up side view of the central, lower element 2053, consistent with implementations of the current subject matter. As shown in FIGS. 16A-16B, each of the pair of lateral openings 2074a,b may include one or more (e.g., one, two, three, four, or more) vents 289. The vents 289 may be curved, form a semi-circular shape, or other shape, such as oval, square, rectangular, and/or the like. The vents 289 may define recesses in the central, lower element 2053 that extend inwardly from an edge of the lateral openings 2074*a,b*. The recesses form openings between the edge of the lateral openings 2074*a,b* and an outer surface of the end caps 2068.

The vents 289 may prevent or reduce the likelihood of leaking of the vaporizable material from the reservoir 258, help to maintain a consistent level of saturation of the wick 268 with vaporizable material, and/or help to prevent flooding of the wick 268. For example, as vaporizable material is vaporized by the heating coil 267 from the wick 268, air may enter the reservoir 258 to prevent a vacuum from occurring within the cartridge 250, and to prevent leakage of the vaporizable material. Generally, the vaporizable material would fill the openings formed by the vents 289. The vents 289 may break the surface tension of the vaporizable material to allow air to enter the reservoir 258 to counteract the transfer of vaporizable material to the wick 268 and relieve the pressure caused by the transfer of vaporizable material to the wick 268. Thus, the vents may desirably prevent leaking of the vaporizable material. The vents 289 may additionally and/or alternatively control vapor performance and/or provide a predictable experience to the user from puff to puff, at least because the vents 289 help to control the amount of air entering the reservoir 258 as the vaporizable material is displaced from the reservoir 258. In some implementations, the vents 289 have a radius of approximately 1 to 2 mm, 2 to 3 mm, 3 to 4 mm, and/or greater. The number of vents 289, the shape of the vents 289, the position of the vents 289, and/or the size of the vents 289 may be adjusted to increase, decrease, or otherwise improve transfer of the vaporizable material from the reservoir 258 to the wick 268, and/or to control the transfer of air into the reservoir 258 during, before, or after a puff. Additionally and/or alternatively, the vents 289 (or outer openings of the end caps 2068) may be positioned along various portions of the end caps 2068 (see FIG. 23) to help control the amount of air entering the reservoir 258 to provide more consistent vapor production.

Referring to FIGS. 15A-15B and 18, the central cannula 272 extends from the central, lower element 2053 to the central, upper element 2052 and defines the vaporization chamber 2005. When the wick housing 288 is coupled with the reservoir body 258A, the central cannula 272 may extend through the reservoir body 258A from near the distal end region 256C of the cartridge body 256 to the proximal end region 256A of the cartridge body 256. The proximal end region 256A of the cartridge body 256 defines a central channel 2015 that extends to an opening that may be coaxially aligned with the opening 254 through the proximal end surface of the mouthpiece 252.

As noted above, the central cannula 272 extending through the reservoir body 258A defines the vaporization chamber 2005 that together with the central channel 2015 directs vapor flow from the heater 266 towards the mouthpiece 252. The central cannula 272 defining the vaporizing chamber may be a generally rectangular element extending from the central, lower element 2053 to the central, upper element 2052. The central cannula 272 may extend coaxial with the longitudinal axis A of the cartridge 250 up through the reservoir body 258A such that the reservoir body 258A surrounds the central cannula 272. Vapor from the vaporization chamber 2005 may flow through the central cannula 272 into the central channel 2015 and out the one or more openings 254 of the mouthpiece 252.

The rectangular cross-sectional shape of the central cannula 272 may lead to less clogging of vaporizable material within the vapor path that flows through the central cannula 272. For example, the central cannula 272 may have a depth of approximately 3.3 mm and a width of approximately 5.4 mm. In other implementations, the central cannula 272 has a depth of approximately 2 to 3 mm, 3 to 4 mm, 4 to 5 mm, 5 to 6 mm, and/or the like, and a width of approximately 3 to 4 mm, 4 to 5 mm, 5 to 6 mm, 6 to 7 mm, 7 to 8 mm, and/or the like. The rectangular cross-sectional shape allows the central cannula 272 to provide a greater volume through which the vaporized vaporizable material may travel, which reduces clogging of the vaporized vaporizable material within the vapor path. Such configurations may improve the user experience by providing more consistent and controlled amounts of vapor each puff. Additionally and/or alternatively, the cross-sectional shape of the central cannula 272 may provide a desired amount (e.g., approximately 1 mm, 2 mm, 3 mm, and/or the like) of clearance around the heater 166 (e.g., the heating coil 267 and the wick 268), which may prevent or reduce the likelihood that the central cannula 272 will melt or otherwise become damaged due to the heat from the heater 166.

Referring to FIGS. 15A, 17-18, and 21A-22A, the central, upper element 1052 extends across a major axis of the upper, proximal surface 2050 of the cartridge body 256, consistent with implementations of the current subject matter. As shown, the central, upper element 2052 is positioned above the top end portion of the central cannula 272 in the central channel 2015. In some implementations, the central, upper element 2052 is about 0 mm, about 0.1 mm, about 0.2 mm, about 0.3 mm, about 0.4 mm, about 0.5 mm, about 0.6 mm, about 0.7 mm, about 0.8 mm, about 0.9 mm, about 1.0 mm, about 1.1 mm, about 1.2 mm, about 1.3 mm, about 1.4 mm, about 1.5 mm, about 1.6 mm, about 1.7 mm, about 1.8 mm, about 1.9 mm, up to about 2.0 mm above the top end portion of the central cannula 272.

The size and shape of the central, upper element 2052 may aesthetically block off the internal components from a user (e.g., through the opening 254 of the mouthpiece 252) as well as direct or split vapor flow around it. By directing the flow around the central, upper element 2052, larger particles may become trapped in the pads 270 due to their inherent inertial properties described above. The central, upper element 2052 thus splits the vapor flow to allow for flow around the central, upper element 2052 and thereby reduces the amount of excess material that is collected on the central, upper element 2052 and elsewhere in the cartridge body 256.

In an implementation, as shown in FIG. 15B, the central, upper element 2052 has a side cross-sectional profile with a sharpened end, curved and angled sides, and a blunt top that splits. Due to the sharpened end and the curved and angled sides, the flow of vapor around the central, upper element 2052 provides for larger particles to be captured and entrained by the pads 270, which are off-axis with respect to direction of the vapor flow. The central, upper element 2052 may be an airfoil with a leading edge and a closed trailing edge. At least a central portion of the side cross-sectional profile of the central, upper element 2052 may be parabolic or triangular, with a flat top surface 2052*c* and with angled side portions 2052*a* and 2052*b* that meet at the sharpened end. The central, upper element 2052 may also have extensions that extend laterally away from the central portion. This configuration may prevent vapor impaction on surfaces within the cartridge body 256 (including the central, upper element 2052 itself), which can lead to a build-up of oil condensation. In some implementations, the angled side portions 2052*a,b* may be, with respect to the flat top surface 2052*c*, at an angle of about 45 degrees, about 50 degrees, about 55 degrees, about 60 degrees, about 65 degrees, about 70 degrees, about 75 degrees, up to about 80 degrees. A bounding box defining the side cross-sectional area of the central, upper element 2052 may have a length of about 1.5 mm, about 1.6 mm, about 1.7 mm, about 1.8 mm, about 1.9 mm, up to about 2.0 mm, and may have a height of about 2.0 mm, about 2.1 mm, about 2.2 mm, about 2.3 mm, about 2.4 mm, about 2.5 mm, about 2.6 mm, up to about 2.7 mm.

In some implementations, other side cross-sectional profiles as well as variations of those described herein may be used for the central, upper element 2052, where such profiles aid in the splitting and directing of the flow of vapor, such as other shapes with a sharpened or pointed end, including for example a diamond, a teardrop, an arrow, or a round or rounded edge profile.

Referring to the FIGS. 15A, 17-18, and 21A-22A, the wick housing 288 may also include the proximal wick housing base 2051 that is positioned adjacent to the central, upper element 2052 and surrounding at least a portion (e.g., a proximal portion) of the central cannula 272. The proximal wick housing base 2051 may include a body portion 2051A and a distal end portion 2051B. The body portion 2051A and the distal end portion 2051B may each have an exterior surface. The exterior surface of the distal end portion 2051B may be approximately parallel to the exterior surface of the body portion 2051A. The exterior surface of the distal end portion 2051B may be positioned inwardly relative to the exterior surface of the body portion 2051A. In some implementations, the distal end portion 2051B is configured to be connected with the body portion 2051A by a distally-facing portion 2051C. The distally-facing portion 2051C may extend between the distal end portion 2051B and the body portion 2051A. Accordingly, the distally-facing portion 2051C may be integrally formed with the body portion 2051A and the distal end portion 2051B. The distally-facing portion 2051C may be orthogonal relative to the exterior surface of the body portion 2051A and/or the exterior surface of the distal end portion 2051B. As explained in more detail below, when the wick housing 288 is coupled with the reservoir body 258A, the proximal end of the reservoir body 258A may contact and/or otherwise engage with at least an exterior surface of the distally-facing portion 2051C and/or the distal end portion 2051B of the proximal wick housing base 2051.

In some implementations, the proximal wick housing base 2051 may be configured to, at least temporarily, couple with the mouthpiece 252. For example, the proximal wick housing base 2051 may include one or more wick housing grooves 263, formed along at least a portion of an exterior surface of the proximal wick housing base 2051, which may receive the inwardly-projecting feature 298. The one or more wick housing grooves 263 may be spaced apart from one another and may be positioned about a perimeter of the proximal wick housing base 2051, adjacent a distal end portion of the proximal wick housing base 2051. In some implementations, the proximal wick housing base 2051 includes six wick housing grooves 263 that are configured to receive at least a portion of the inwardly-projecting feature 298. For example, at least two wick housing grooves 263 may be positioned on each of the longer sides of the proximal wick housing base 2051 and at least one wick housing groove 263 may be positioned on each of the shorter sides of the proximal wick housing base 2051. The wick housing grooves 263 may be shaped and/or sized to secure the mouthpiece 252 to the wick housing 288 of the cartridge body 256. In some implementations, the wick housing grooves 263 may be shaped and/or sized to allow the inwardly-projecting feature 298 of the mouthpiece 252 to slide over a proximal side and/or a distal side of each groove in one direction (e.g., in a distal direction) and prevent the inwardly-projecting feature 298 of the mouthpiece 252 to slide over the proximal side and/or the distal side of each groove in an opposite direction (e.g., in a proximal direction).

Figures 22A, 22B:
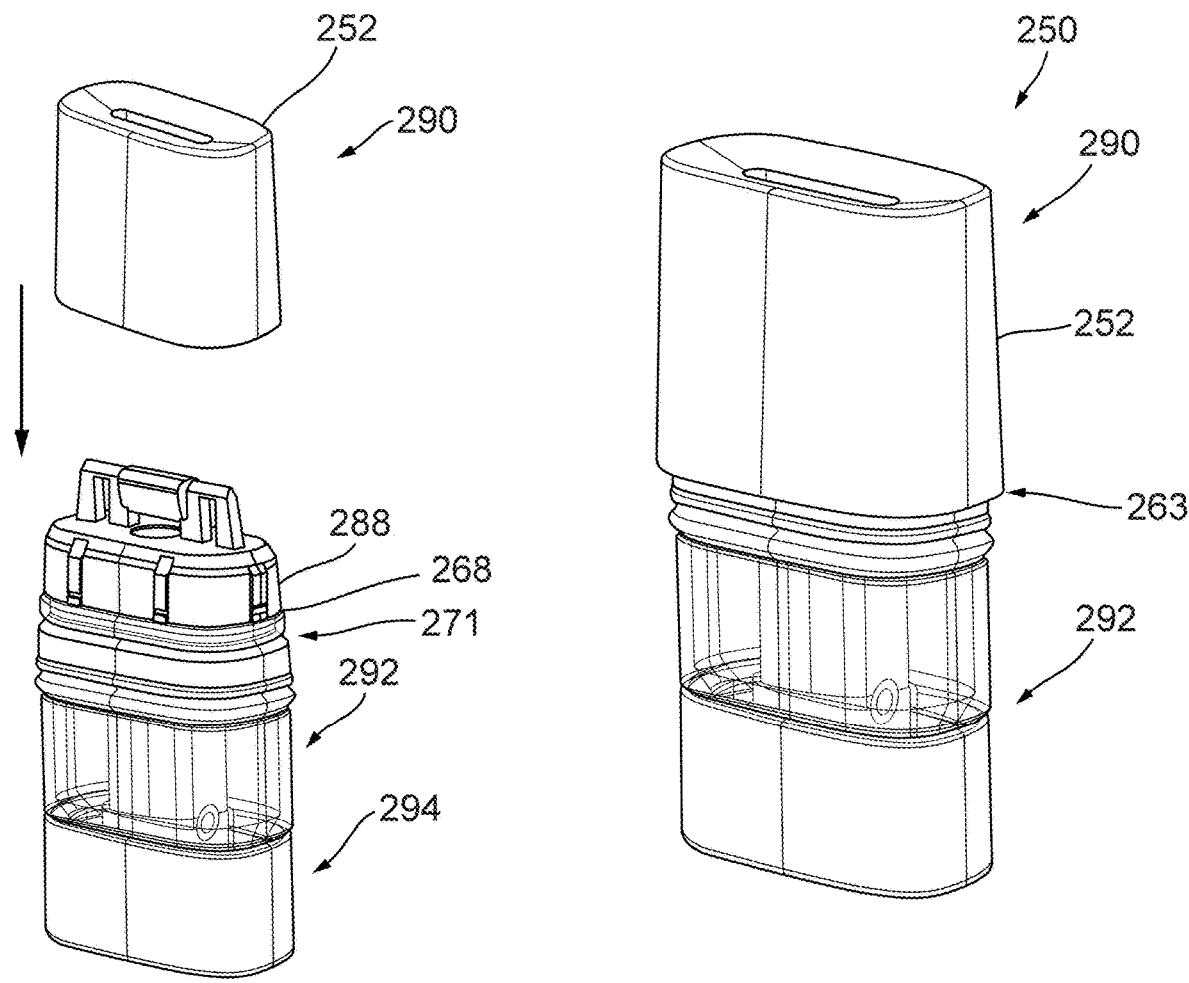
FIGS. 22A-22B illustrate examples of assembling a cartridge consistent with implementations of the current subject matter.
Figure 23:
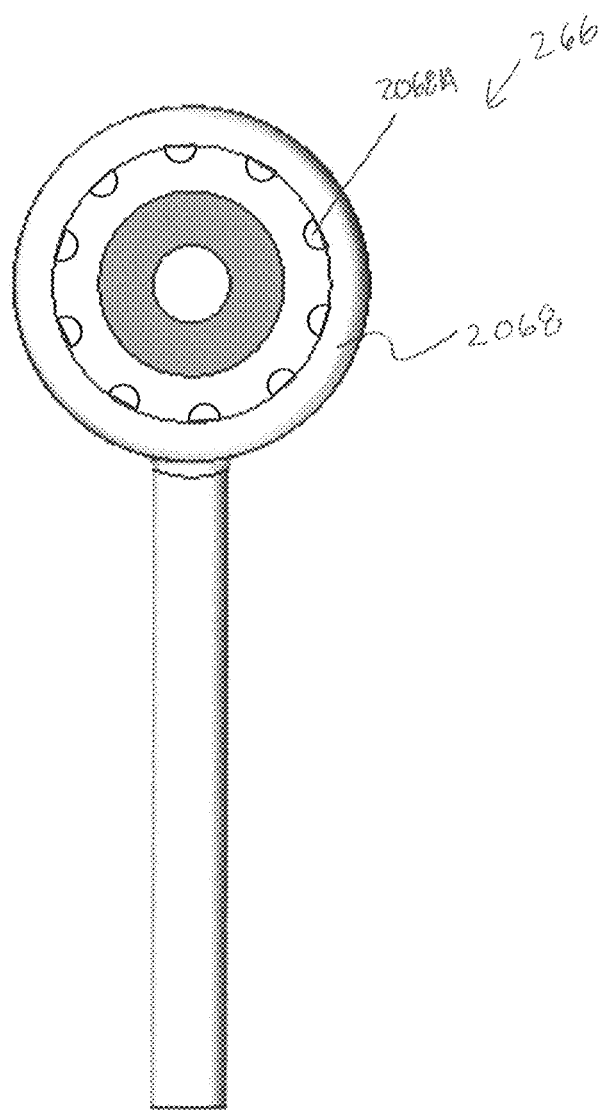
FIG. 23 illustrates an example heater of a cartridge consistent with implementations of the current subject matter.

As noted above, the proximal wick housing base 2051 may be configured to, at least temporarily, couple with the mouthpiece 252. For example, as shown in FIGS. 22A-22B illustrate a method of assembling the cartridge 250 including coupling the mouthpiece 252 to the proximal wick housing base 2051 of the cartridge body 256. As shown, the mouthpiece 252 slide over at least a part of the proximal end region 256A of the cartridge body 256. For example, the mouthpiece 252 may slide over at least the proximal wick housing base 2051 of the wick housing 288. In other words, at least a portion of the cartridge body assembly 292, such as the proximal wick housing base 2051, may be inserted into the interior volume of the mouthpiece 252. After insertion of the proximal wick housing base 2051 into the mouthpiece 252, the inwardly-projecting feature 298 of the mouthpiece 252 may engage with the one or more wick housing grooves 263 to secure the mouthpiece 252 to the cartridge body assembly 292. In some implementations, when the inwardly-projecting feature 298 of the mouthpiece 252 is secured to the one or more wick housing grooves 263, the interior volume of the cartridge 250, such as the reservoir 258, may be filled with the vaporizable material, via the fill port 297. The reservoir 258 may be filled via the fill port 297 and/or the fill port seal 296.

In some implementations, after the reservoir 258 has been at least partially filled with the vaporizable material and/or after the inwardly-projecting feature 298 of the mouthpiece 252 is secured to the one or more wick housing grooves 263, the cartridge body assembly 292 may be further inserted into the interior volume of the mouthpiece 252. For example, the cartridge body assembly 292 may be further inserted into the interior volume of the mouthpiece 252 until the inwardly-projecting feature 298 engages with the reservoir body groove 271. As noted above, the reservoir body groove 271 may be formed on the cartridge body assembly 292 between the mouthpiece seal 277 and a proximal end portion (e.g., a proximal rib on the proximal end portion) of the reservoir body 258A and/or located on one side of the recessed portion formed in the exterior surface of the cartridge body 156. As a result, the mouthpiece may enclose the septum of the fill port seal 296, preventing or reducing oil and/or air leakage through the fill port 297 from within the cartridge 250. In some implementations, In some implementations, the wick housing grooves 263 and/or the reservoir body groove 271 may be shaped and/or sized to allow the inwardly-projecting feature 298 of the mouthpiece 252 to slide over a proximal side and/or a distal side of each groove in one direction (e.g., in a distal direction) and prevent the inwardly-projecting feature 298 of the mouthpiece 252 to slide over the proximal side and/or the distal side of each groove in an opposite direction (e.g., in a proximal direction). This helps to add additional security to the cartridge 250. For example, once the cartridge 250 is filled by an authorized filler and/or with an authorized and/or tested vaporizable material, in some implementations, the mouthpiece 252 may not be removed without damaging the cartridge 250. This may prevent the cartridge 250 from being refilled, such as with an unauthorized substance and/or by an unauthorized party. Such configuration may also help to improve the user experience, as the user may be aware that the cartridge 250 may include the authorized vaporizable material. Such configuration may additionally and/or alternative allow for a pre-cut septum to be used at the fill port to enable blunt needle filling.

In some implementations, the proximal wick housing base 2051 may at least partially surround the central cannula 272. Referring to FIG. 15A, an interior of the proximal wick housing base 2051 may include one or more lateral, upper elements 2049 that define an interior volume between the proximal wick housing base 2051 and a proximal portion of the central cannula 272. In the cross-sectional view of the cartridge 250 shown in FIG. 15A, the one or more lateral, upper elements 2049 appears to include two lateral, upper elements 2049 positioned on opposite sides of the central cannula 272. For example, as shown in FIG. 15A, the lateral, upper element 2049 may define an interior volume 288A. When the wick housing 288 is coupled to the reservoir body 258A, the interior volume 288A of the lateral, upper element 2049 may combine with the interior volume of the reservoir body 258A to define (and increase) an interior volume (or the reservoir 258) of the cartridge body 256 in which the vaporizable material may be stored. As described herein, the combined interior volume in which the vaporizable material may be stored may be approximately 1000 μL of vaporizable material. In some implementations, the interior volume in which the vaporizable material may be stored may be approximately 500 μL. In some implementations, the interior volume in which the vaporizable material may be stored may be approximately 200 μL to 300 μL, 300 μL to 400 μL, 400 μL, to 500 μL, 500 μL to 600 μL, 600 μL to 700 μL, 700 μL to 800 μL, 800 μL to 900 μL, 900 μL to 1000 μL, or more of vaporizable material. In some implementations, the interior volume 288A of the lateral, upper element 2049 may form approximately 25% of the combined interior volume capable of storing vaporizable material and the interior volume of the reservoir body 258A may form approximately 75% of the combined interior volume capable of storing vaporizable material within the cartridge body 256. In some implementations, various other ratios of the interior volume 288A to the interior volume of the reservoir body 258A may be contemplated, such as 15%: 85%, 20%: 80%, 30%: 70% of the combined interior volume, and/or the like.

To prevent leakage of vaporizable material from the combined interior volume of the cartridge body 256, the wick housing 288 and the reservoir body 258A may be coupled via laser-welding. In some implementations, however, other fastening may be implemented, such as via adhesive, a snap-fit arrangement, and/or the like. In some implementations, the wick housing 288 and the reservoir body 258A may be laser-welded at at least one, two, three, or more interfaces to reduce leaking of the vaporizable material.

For example, FIGS. 15A-15B and 17 shows at least two joining interfaces at which the reservoir body 258A may be laser-welded or otherwise joined to the wick housing 288. As shown, the reservoir body 258A may be laser-welded to the wick housing 288 at a first joining interface 279A and a second joining interface 279B. The first joining interface 279A may be formed between an interior surface of the reservoir body 258A, at the proximal end of the reservoir body 258A, and at least a portion of an exterior surface of the proximal wick housing base 2051, such as the distally-facing portion 2051C and/or the distal end portion 2051B of the proximal wick housing base 2051.

In some implementations, the reservoir body 258A may include a distal chamber portion 255. The distal chamber portion 255 may be positioned within the reservoir body 258A proximate to a distal end portion of the reservoir body 258A. The distal chamber portion 255 may include a curved surface 259 that defines at least a portion of the distal chamber portion 255. The curved surface 259 may be spaced apart form and/or or at least partially surround the heater 266 when the heater 266 is coupled to the reservoir body 258A. The distal chamber portion of the reservoir body 258A may also include a chamber coupling portion 257. The chamber coupling portion 257 may be positioned adjacent to the curved surface 259. The chamber coupling portion 257 may include an inwardly-facing surface 261 and a proximally-facing surface 265. The inwardly-facing surface 261 may be positioned approximately parallel to the longitudinal axis A of the cartridge 250. The proximally-facing surface 265 may be positioned approximately orthogonal to the inwardly-facing surface 261 and extend between the inwardly-facing surface 261 and the curved surface 259. In some implementations, the second joining interface 279B may be formed between an interior surface of the reservoir body 258A, at or near the distal end of the reservoir body 258A, such as the proximally-facing surface 265 and/or the inwardly-facing surface 261 of the chamber coupling portion 257 and at least a portion of an exterior surface of wick housing 288, such an exterior surface of the central, lower element 2053 of the wick housing 288.

Together, the central, lower element 2053 and the distal chamber portion 255 of the reservoir body 258A may form at least a portion of the atomization chamber that houses and/or otherwise surrounds at least a portion of the heater 266, such as at least a portion of the wick 268 and/or the heating coil 267. Joining the wick housing 288 to the reservoir body 258A at at least the first joining interface 279A and/or the second joining interface 279B may create an improved seal around the heater 266 (e.g., the wick 268 and/or the heating coil 267), which may prevent or reduce leaking and/or clogging of vaporizable material from the cartridge 250. This configuration may also help to prevent leakage of vaporizable material from other portions of the cartridge 250, such as at or near the mouthpiece 252. This configuration may also help to expand the size of the interior volume of the reservoir 258 to allow the reservoir 258 to contain a greater amount of vaporizable material to be vaporized. This may improve the user experience, as the user may use the cartridge 250 for a greater length of time, such as during a single session and/or over a series of sessions.

Referring to FIGS. 15A-15B, 17-18, and 21A-22B, the cartridge body 256 may include the reservoir body 258A. The reservoir body 258A may be arranged to surround the central cannula 272, which may be positioned coaxial with the longitudinal axis A of the cartridge 250. As noted above, the reservoir 258 may be formed at least partially by a combination of an interior volume of the reservoir body 258A and the interior volume 288A of the lateral, upper element 2049. The reservoir 258 may thereby be generally ring-shaped such that the outer wall(s) of the reservoir 258 are formed by the reservoir body 258A and the proximal wick housing base 2051 of the wick housing 288, and the inner wall(s) of the reservoir 258 are formed by the central cannula 272 of the wick housing 288 extending through the reservoir body 258A. The reservoir 158 need not be arranged symmetrically around the longitudinal axis A of the cartridge 250 with the central cannula 272 extending through it. Other configurations are considered herein.

As mentioned above, at least a portion of the cartridge body 256 may be transparent, translucent, opaque, or a combination thereof. The cartridge body 256 may include one or more regions formed of an opaque material such that the contents are not visible from outside the device as well as one or more regions formed of a translucent or transparent material such that the contents are visible from outside the device. For example, the central region 256B of the cartridge body 256 may be translucent to transparent such that the reservoir 258 contained within this portion of the cartridge body 256 may remain visible to a user from outside the cartridge 250. The distal end region 256C of the cartridge body 256 may be opaque such that a majority of the components within this region remain hidden from view. Similarly, the mouthpiece 252 positioned over the proximal end region 256A of the cartridge body 256 may be opaque.

As noted above, the volume of the reservoir 258 may vary, but is generally sized to hold sufficient vaporizable material for delivering at least one dose of the material. The volume of the reservoir 258 may be between about 0.2 mL to about 2 mL, in other implementations between 0.4 mL to about 1.2 mL, in other implementations between about 0.4 mL to about 0.8 mL, or in still other implementations between about 0.6 mL to about 1 mL. The reservoir 158 may be pre-filled or filled prior to, during, and after use as described above.

Referring to FIGS. 15A-15B, and 17-18, the reservoir body 258A may include a distal support structure 269 that be configured to couple the cartridge body assembly 292 to the base assembly 194. The distal support structure 269 may be positioned proximate and distal to the interior volume of the reservoir body 258A. The distal support structure 269 may include a base sealing rib 273, one or more receptacle housings 278, one or more reservoir body air inlets 282, and one or more connection features 283.

FIGS. 15A-15B, and 17-18 show an example of the base sealing rib 273 or internal sealing gasket of the distal support structure 269 of the reservoir body 258A. The base sealing rib 273 may be configured to engage with, such as via a snap-fit arrangement, a corresponding feature, such as a base recess 284 of the base assembly 294. Thus, engagement between the base sealing rib 273 and the base recess 284 of the base assembly 294 may secure the cartridge body assembly 292 to the base assembly 294. In some implementations, the base sealing rib 273 may seal the interior of the base assembly 294 and/or the air flow path throughout the cartridge body 256. For example, the base sealing rib 273 may prevent air from escaping through a proximal end of the base assembly 194. As a result, the base sealing rib 273 may improve the efficiency of the cartridge 250 by directing the air entering the cartridge 250 along the air flow path and maximizing the amount of air that remains along the air flow path after entering the cartridge 250.

The distal support structure 269 of the reservoir body 258A includes one or more receptacle housings 278. As noted above, the leads 2067 may extend into the distal end region 256C of the cartridge body 256, where the leads 2067 may electrically couple with the power pin receptacles 260a,b. Also as noted below, in some implementations, the receptacles 360a,b may extend into the distal end region 356C of the cartridge body 356 within the one or more receptacle housings 378. Each of the power pin receptacles 260a,b may be positioned within and/or surrounded at least in part by a corresponding receptacle housing 278 that extends in a distal direction from the reservoir body 258A. The receptacle housings 278 may help separate the power pin receptacles 260a,b from the air flow path and/or other internal components of the cartridge 250. This may help to reduce disruption on the air flow caused by the power pin receptacles 260a,b. This may additionally and/or alternatively help to reduce any temperature impact on the air passing the power pin receptacles 260a,b that may have otherwise been caused by heat emitted from the power pin receptacles 260a,b.

Referring to FIG. 17A, the distal support structure 269 of the reservoir body 258A may include one or more reservoir body air inlets 282. The reservoir body air inlets 282 may be formed in at least a portion of the distal support structure 269, such as through an extension 286 of the distal support structure 269. The extension 286 may connect the two receptacle housings 278. For example, the reservoir body air inlets 282 may form openings in the extension 286. The reservoir body air inlets 282 allows air to flow from the interior volume of the base assembly 294 into the atomization chamber, where the air passes the heater 166. When the air passes the heater 166, vaporized vaporizable material may become entrained in the air before exiting through the mouthpiece 252.

The distal support structure 269 may include one or more connection features 283. In some embodiments, the one or more connection features 283 may extend from the reservoir body 258A into the base assembly 294 and press against a 275 pad, compressing the pad 275 and ensuring a secure and sealed engagement between the base assembly 294 and the cartridge body assembly 292.

Figure 19:
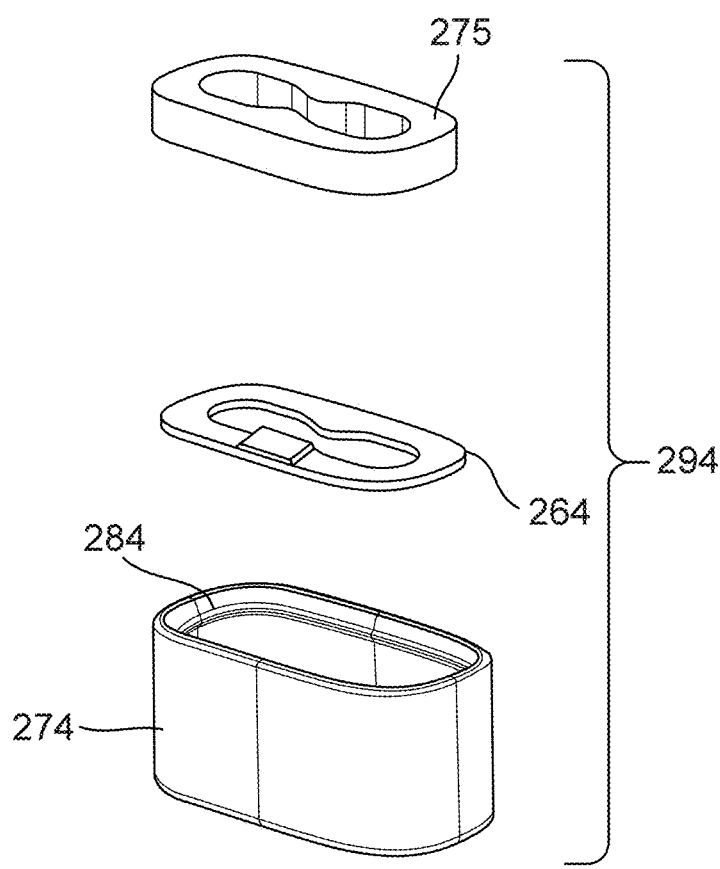
FIG. 19 illustrates a partial exploded view of a cartridge consistent with implementations of the current subject matter.

FIG. 19 shows an example of the base assembly 294. The base assembly 294 may include a base 287, an absorbent pad 275, and a tag 264. As noted above, the base assembly 294 may mate with the cartridge body assembly 292 via a snap-fit arrangement, such as between the base sealing rib 273 and the base recess 284 of the base assembly 194. The base recess 284 may extend around a perimeter of an internal surface of the base 287, proximate to a proximal end of the base 287.

As shown in FIG. 19, the tag 264, which is described in more detail below, may be positioned within an interior volume of the base 274, proximate to a distal face of the base. For example, the tag 264 may be positioned within the base 274 opposite the external distal face of the base. Positioning the tag 264 within the base 274 may protect the tag 264 rom user interference and/or other external conditions. As a result, positioning the tag 264 within the base 274 may improve the connection between the tag 264 and the vaporizer device 110. Additionally and/or alternatively, positioning the tag 264 within the base 274 may allow the tag 264 to be coupled with the cartridge 250 without the use of an adhesive, which may be used to secure the tag 264 to another portion of the cartridge 250, such as an external portion of the cartridge 250. Accordingly, this configuration may extend the usable life of the tag 264. In some implementations, this configuration may also help to may it more difficult for the tag 264 to be removed from the cartridge 250 and/or reduce the likelihood that the user or another party may remove the tag 264 from the cartridge 250, thereby improving the security and/or integrity of the cartridge 250.

Referring to FIG. 19, the base 274 may also include one or more absorbent pads 275 to prevent leakage of the vaporizable material from the reservoir 258 and/or to prevent vaporizable material from interfering with the electronics (e.g., receptacles 260a,b) of the cartridge 250. The pad 275, in addition and/or alternative to the base sealing rib 273, adds a layer of redundancy against vaporizable material leaking from the cartridge 250. The pad 275 may be oriented to prevent leakage in this region of the cartridge 250 without disrupting airflow or formation of vapor. For example, the absorbent pad 275 may be positioned and fitted within the base 274 off-axis from the air flow path. However, the configuration of the pad 275 may vary, such that a similar configuration as the pads 270 are applied in this region of the cartridge 250.

As shown in FIG. 19, for example, the pad 275 may include a flattened disk-shape defining a central opening and thus, has a ring-like shape, to allow air to pass through without disrupting airflow. It should be appreciated the pad 275 may have a ring shape, but need not be a circular ring-shaped object. Rather, the absorbent pad 275 may be a flat, non-circular ring having a perimeter in the shape of an oval, ellipse, or rectangle. The size and shape of the pad 275 may be configured to fit within open spaces of the base 274 thereby filling at least a portion of the base 274. As shown in FIG. 17A, the pad 275 may be wedged between or otherwise compressed between the tag 264 and the connection features 283 when the base assembly 294 is coupled with the cartridge body assembly 292.

The base 274 may include one or more (e.g., one, two, three, four, or more) air flow inlets 262a,b configured to remain in fluid communication with the atmosphere during use of the device. The distal end of the base 274 may define the air flow inlets 262a,b. The base 274 may include air flow channels 2085, which are defined by the region between the air flow inlets 262a,b and the reservoir body air inlets 282. Thus, the air flow inlets 262a,b form an entry point for air into the cartridge 250. From the air flow inlets 262a,b, the air may flow within the base 274, through the inlets 282, flow past the heater 266, through the central cannula 272, and out through the mouthpiece 252.

FIGS. 24A-29 illustrate features of a cartridge 350 of a vaporizer device, consistent with implementations of the current subject matter. The cartridge 350 may include the same or similar features as the cartridges 150, 250 described herein. For example, the cartridge 350 may include a cartridge body 356 defining, at least in part, a reservoir 358 configured to contain vaporizable material, a mouthpiece 352, and a vaporizing assembly of vapor-generating components positioned within the cartridge body 356 and configured to vaporize the vaporizable material, which are the same or similar to the cartridge body 156, 256, the reservoir 158, 258, and the mouthpiece 152, 252.

The cartridge 350 may include one or more assemblies that may be coupled together, such as via snap-fit, laser-welding, adhesives, and/or the like. For example, the cartridge 350 may include a mouthpiece assembly 390, a cartridge body assembly 392, and a base assembly 394. The cartridge body assembly 392 may include the cartridge body 356, which may be divided, generally, into a proximal end region 356A, a central region 356B, and a distal end region 356C. The proximal end region 356A of the cartridge body 356 can be coupled to the mouthpiece 352 configured to deliver the vapor to the user. A tank or reservoir body 358A is defined, at least in part by, the proximal end region 356A and the central region 356B of the cartridge body 356 and is configured to contain an amount of the vaporizable material. The distal end region 356C (alone or together with the central region 356B) of the cartridge body 356 may house one or more components configured to vaporize the material from the reservoir 358 into a vaporization chamber 3005 (see, e.g., FIGS. 24C-24D and FIGS. 25A-26F). The mouthpiece 352 is configured to interface with the user to release the vapor from the vaporization chamber 3005 to the user through one or more openings 354 in the mouthpiece 352, for example, upon the user drawing a breath through the vaporizer device. Each of these components will be described in more detail below, and as noted above, may have the same or similar features and/or properties as the components described above with respect to the cartridge 150 and/or the cartridge 250.

As described herein, the cartridge 350 may include a heater 366, which may be the same or similar to the heater 166, 266. The heater 366 may be configured to heat and/or vaporize at least a portion of the vaporizable material drawn towards the heater 366 from the reservoir 358. In some implementations, the heater 366 may include a resistive element such as a heating coil 367 in thermal contact with a wick 368. The heating coil 367 and the wick 368 may include the same or similar properties and features as the heating coil 167, 267 and the wick 168, 268 described above with respect to the cartridge 150, 250.

FIGS. 25A-25D illustrate an example of the heater 366 consistent with implementations of the current subject matter in which the wick 368 includes end caps 3068 that provide a connection between the heating coil 367 and the power source. In this example, the end caps 3068 may each be coupled (e.g., electrically coupled) to respective power pin receptacles 360a,b to facilitate the electrical connection of the heating coil 367 with the vaporizer body 110. In some implementations, the end caps 3068 are separately formed and coupled to the wick 268 and/or heating coil 367. In other implementations, the end caps 3068 may be integrally formed with the heating coil 367 and/or may be electrically and/or physically coupled to the heating coil 367 via welding and/or other mating processes. In some implementations, the heater 366 may be coupled to and/or include a carrier 323, which is described in more detail below.

Figure 24A:
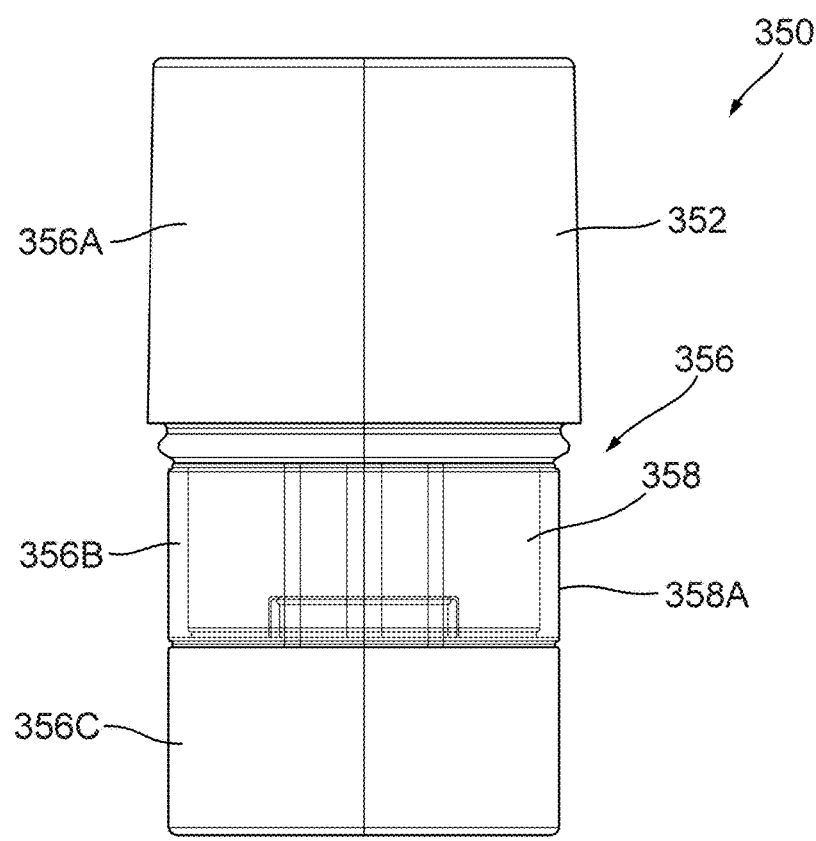
FIGS. 24A-24B illustrate an example of a cartridge of a vaporizer device consistent with implementations of the current subject matter.
Figure 24B:
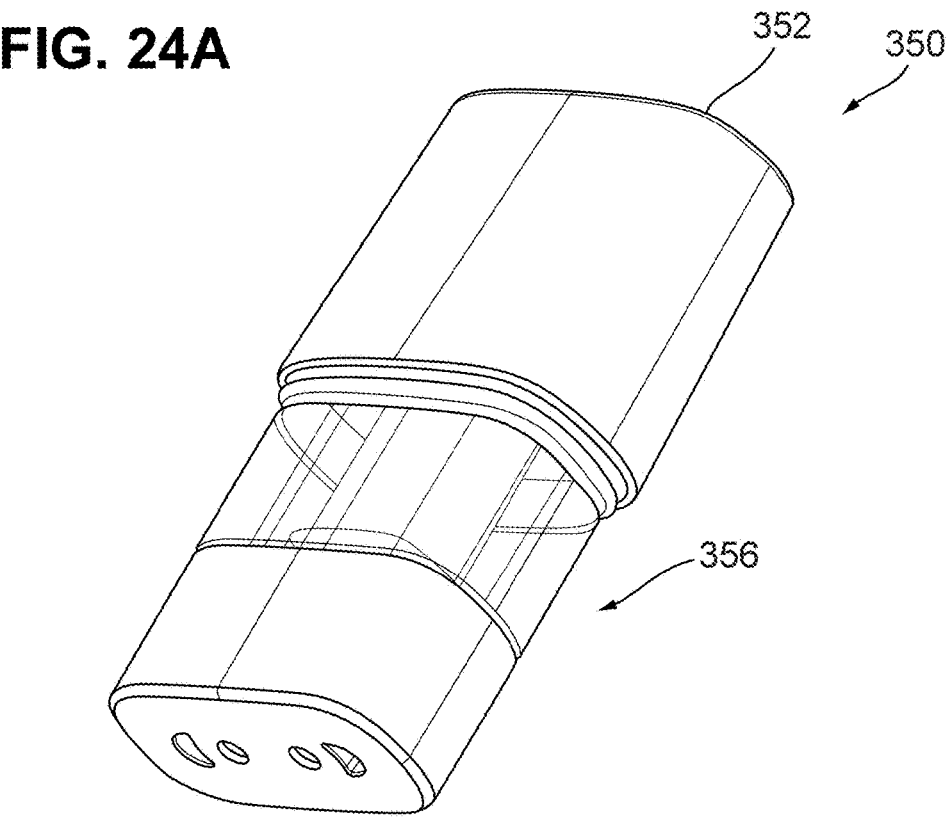
Figures 24C, 24D:
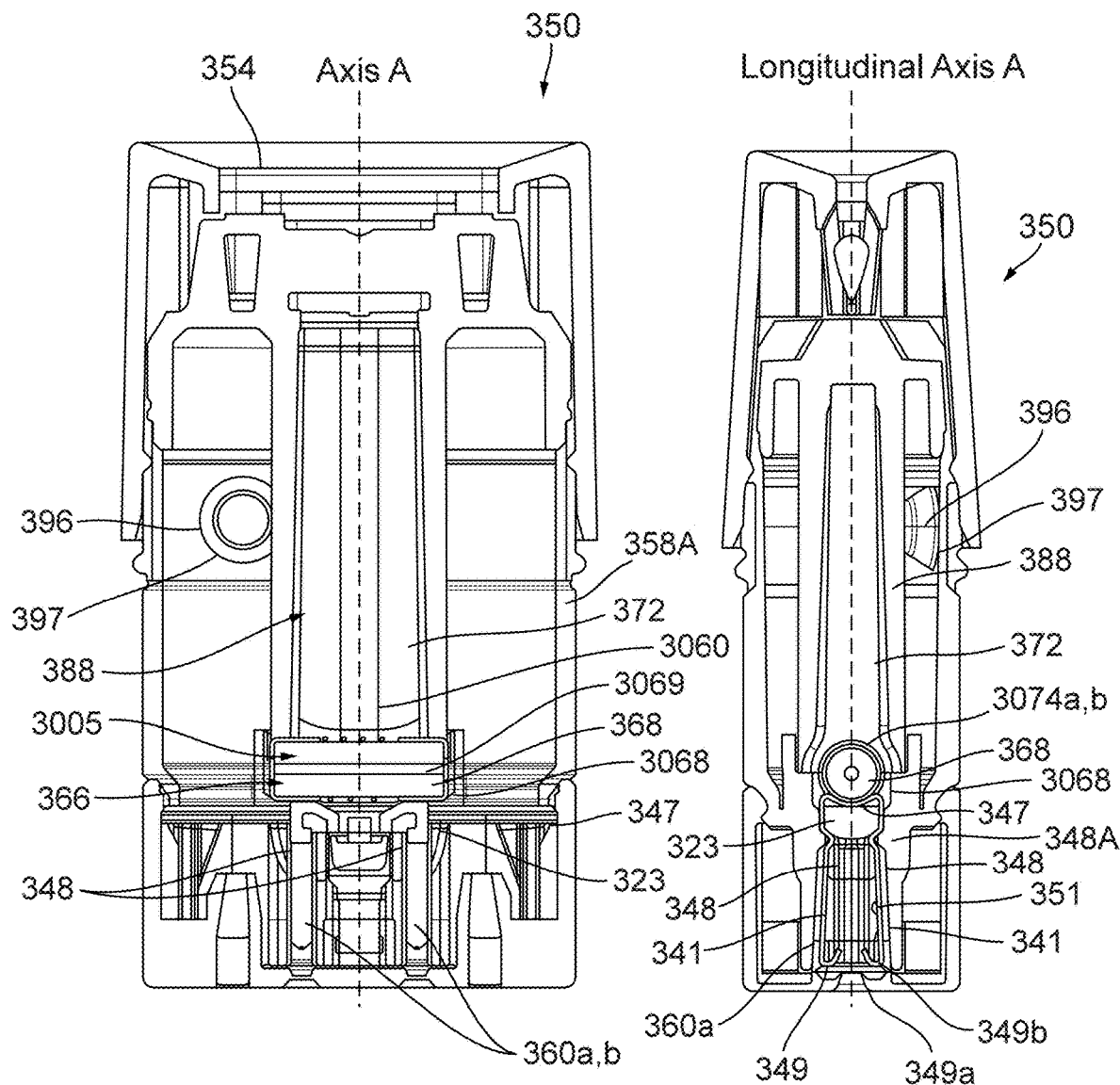
FIGS. 24C-24D illustrate cross-sectional views of a cartridge consistent with implementations of the current subject matter.
Figure 26F:
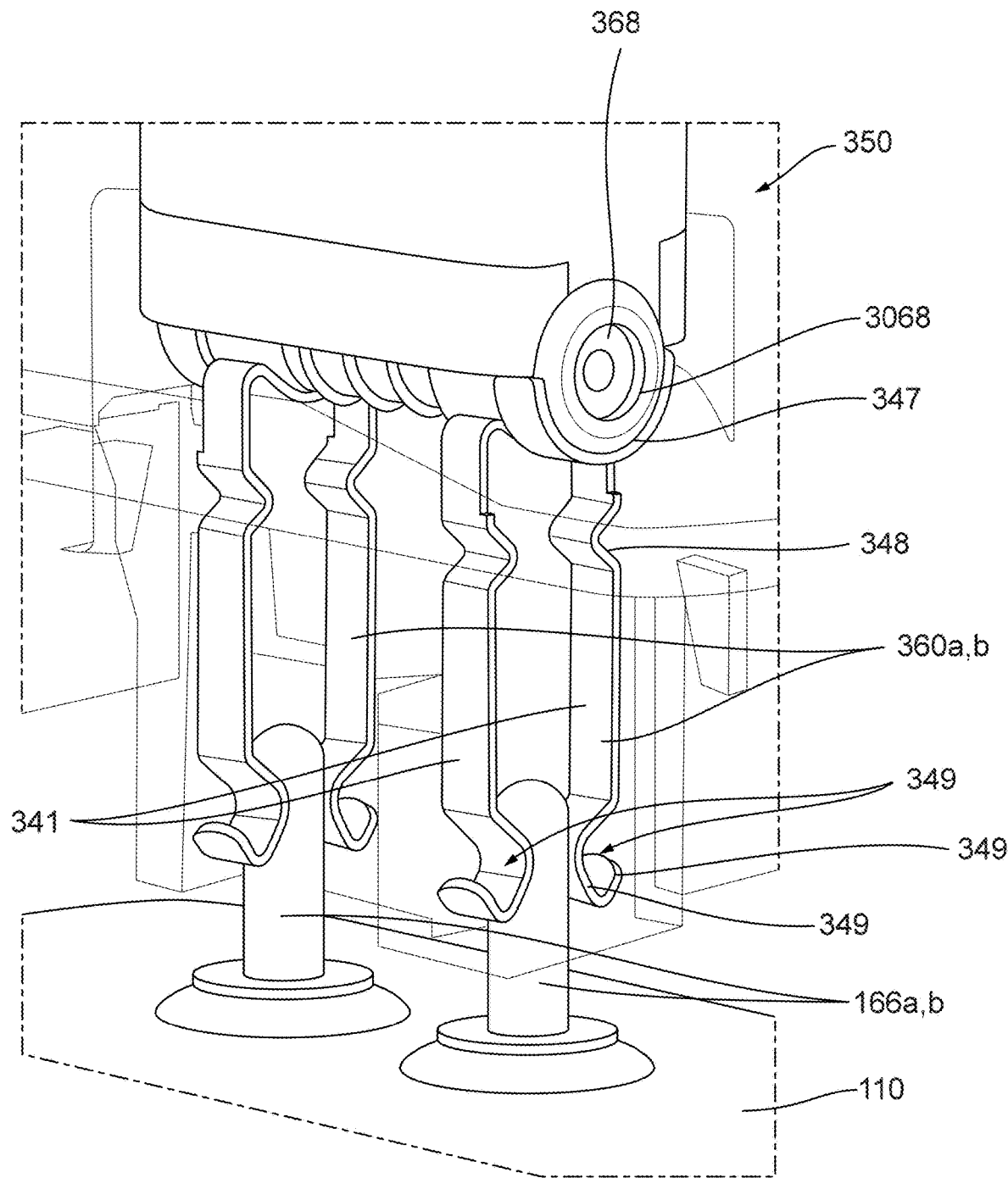
FIG. 26F illustrates a portion of a cartridge consistent with implementations of the current subject matter.

The end caps 3068 may be made of various materials, such as copper, stainless steel, other metals, or combinations thereof. The end caps 3068 may securely and snugly fit over respective ends of the wick 368 (e.g., opposing ends 3065a, b). For example, the end caps 3068 may be thin sleeves that fit over the respective ends of the wick 368. End portions of each of the end caps 3068 have an opening that aligns with a central bore 3069 of the wick 368. The openings may be of a larger diameter than that of the central bore 3069 to further promote wicking of the vaporizable material along the length of the wick 368. The heater 366 may extend across the air path within the vaporization chamber 3005, such as in a transverse direction. As shown in FIGS. 24C and 24D, a central cannula 372 of a wick housing 388 may be arranged coaxial with the longitudinal axis A of the device and the wick 368 may extend orthogonal to the longitudinal axis A through the central cannula 372. The wick 368 is preferably positioned near a distal-most end region of the reservoir 358 such that the vaporizable material in the reservoir 358 may be fully used. A pair of lateral openings 3074a,b may extend through the walls of the central cannula 372 of the wick housing 388 near its base where the central cannula 372 couples to an inner distal surface of the reservoir body 358A. The pair of lateral openings 3074a,b may be aligned across from one another on opposing sides of the central cannula 372. The openings 3074a,b are provided and sized for coupling to the heater 366.

In some implementations, the wick 368 of the heater 366 may include a central portion 3060 and opposing ends 3065a,b positioned on opposite sides of the central portion 3060. The heating coil 367 may be wrapped around the central portion 3060 of the wick 368, which in turn may be positioned within the vaporization chamber 3005. The opposing ends 3065a,b of the wick 368 may be positioned at least partially outside the vaporization chamber 3005 by extending laterally outward through and/or within the lateral openings 3074a,b of the central cannula 372. As such, the opposing ends 3065a,b may be positioned within or in contact with the internal volume of the reservoir 358 whereas the central portion 3060 of the wick 368 wrapped by the heating coil 367 may be positioned entirely inside the vaporization chamber 3005 of the central cannula 372. The receptacles 360a,b may be coupled (e.g., in electrical communication with) to the end caps 3068 and extend away from the wick 368 and down through respective openings in an interior surface of the reservoir body 358A, out of the vaporization chamber 3005. The receptacles 360a,b may extend into the distal end region 356C of the cartridge body 356 where the receptacles 360a,b may be configured to receive and/or couple with the power pins 166a,b.

FIG. 25A illustrates an example of a receptacle 360a, consistent with implementations of the current subject matter. FIG. 25B illustrates an example of the receptacles 360a,b coupled with the respective end caps 3068 and the carrier 323, consistent with implementations of the current subject matter. FIG. 25C illustrates a cross-sectional view of the receptacles 360a,b coupled with the respective end caps 3068 and the carrier 323, consistent with implementations of the current subject matter. As shown in FIG. 25A, the receptacle 360a may include at least one (e.g., one, two, three, four or more) contact arm 341, an end cap contact 347 positioned at one end (e.g., a proximal end) of the contact arm 341, and a power pin contact 349 positioned at another end (e.g., a distal end) of the contact arm 341. In some implementations, the receptacles 360a,b may include one or more materials. The material of the receptacles 360a,b may have a desired resistance to reduce or limit heat generated by the receptacles 360a,b and still transfer a sufficient amount of energy to the end caps 3068 and/or the heating coil 367 to heat the heating coil 367 to a desired temperature. In some implementations, at least a portion of the receptacles 360a,b includes gold-plated phosphor bronze, or other conductive materials as described herein. The receptacles 360a,b may therefore be configured to transfer power directly from the power pins 166a,b of the vaporizer body 110 to the end caps 3068, and then to the heating coil 367 coupled with the end caps 3068. Additionally and/or alternatively, the receptacles 360a,b may conduct heat away from the end caps 3068, and/or into the airflow through the airpath. This helps to prevent or limit the end caps 3068 and the heating coil 367 from over-heating and to maintain a consistent temperature at the heating coil 367, where the vaporizable material will be heated. This may also help to pre-heat the air passing through the air path, allowing the vaporizable material to be vaporized into vapor more quickly.

Referring to FIGS. 25A-25C, the end cap contact 347 may define a seat in which each end cap 3068 may be positioned and be in electrical communication with the respective receptacle 360a,b. Each end cap 3068 may rest on and/or within each end cap contact 347. For example, a surface of the end cap contact 347 may contact an outer surface of the end cap 3068. The surface of the end cap contact 347 may be shaped to correspond to a shape of the end cap 3068. For example, the surface of the end cap contact 347 may include a rounded and/or curved shape that corresponds to the rounded and/or curved shape of the end cap 3068. This helps to maintain contact between the end cap 3068 and the end cap contact 347. In some implementations, the end cap contact 347 includes an outer contact portion 347a and an inner contact portion 347b. The outer contact portion 347a may be integrally formed with the inner contact portion 347b. The outer contact portion 347a may be connected to the inner contact portion 347b at least a central region of the outer contact portion 347a and the inner contact portion 347b. The outer contact portion 347a may be positioned to contact an outer end region of the end cap 3068, while the inner contact portion 347b may be positioned to contact a region of the end cap 3068 positioned inwardly relative to the outer end region of the end cap 3068. The outer end region of the end cap 3068 may include ends that extend away from the contact arm 341 and are configured to surround at least a portion of an outer surface of the end cap 3068. This helps to secure the end cap 3068 within each end cap contact 347 and helps to limit or prevent lateral movement of the wick 368 and/or the end cap 3068 within each end cap contact 347. This configuration also helps to maintain electrical communication between each end cap 3068 and the respective receptacle 360a,b.

In some implementations, the outer contact portion 347a of the end cap contact has a semi-circular shape. The radius of curvature of the outer contact portion 347a may be the same as or less than a radius of curvature of the end cap 3068. As a result, the ends of the outer contact portion 347a may deflect outwardly when the end caps 3068 are positioned within the outer contact portion 347a, causing an opposite force on the end caps 3068 by at least the ends of the outer contact portion 347a. In some implementations, the size and/or shape of the end cap contacts 347 may allow the end caps 3068 to be snapped into and/or otherwise secured to the end cap contacts 347. In other implementations, such as when the radius of the curve formed by the outer contact portion 347a is the same as the radius of the end cap 3068, the ends of the outer contact portion 347a may not deflect outwardly when the end caps 3068 are positioned within the outer contact portion 347a. The configurations described herein further help to secure the end cap 3068 within each end cap contact 347 and help to limit or prevent lateral movement of the wick 368 and/or the end cap 3068 within each end cap contact 347. These configurations also helps to maintain electrical communication between each end cap 3068 and the respective receptacle 360a,b.

As noted above, each receptacle 360a,b may include at least one contact arm 341. In some implementations, each receptacle 360a,b includes at least two contact arms 341. The contact arms 341 may, at a proximal end, extend in a distal direction from the end cap contact 347 (e.g., from the inner contact portion 347b). In some implementations, the contact arms 341 may be positioned parallel to one another. In some implementations, the contact arms 341 may be positioned parallel to the longitudinal axis A of the cartridge 350. The contact arms 341 may be positioned at opposite lateral ends (e.g., in a direction transverse to the longitudinal axis A) of the end cap contact 347. For example, the contact arms 341 may define an interior volume 351 in which the power pins 122a,b of the vaporizer body 110 are inserted.

As shown in FIGS. 25A-25C, the contact arms 341 include a distal portion 341A. The distal portion 341A of each of the contact arms 341 may define planar and/or unbent portions of each of the contact arms 341. As noted above, at least the distal portion 341A of opposing contact arms 341 are parallel to one another. In some implementations, at least the opposing distal portions 341A of the contact arms 341 of each receptacle 360a,b are separated by the carrier 323. FIG. 25D illustrates an example of the carrier 323, consistent with implementations of the current subject matter. FIG. 25B illustrates an example of the carrier 323 coupled with the contact arms 341 of opposing receptacles 360a,b. As shown in at least FIGS. 25B and 25D, the carrier 323 includes a central opening 323A. The central opening 323A is aligned with the airflow path and along the longitudinal axis A of the cartridge 350 when the heater 366 is coupled with the cartridge 350. The carrier 323 may also include opposing lateral sides 325 and pairs of opposing front and rear sides 327A, 327B. The opposing lateral sides 325 may form flat surfaces that are configured to extend between the distal portions 341A of each of the contact arms 341 of each receptacle 360a,b. In some implementations, each of the front sides 327A and the rear sides 327B of the pairs of opposing front and rear sides 327A, 327B may include a recessed surface 329. The recessed surface 329 may be formed between two walls to receive at least the distal portion 341A of the opposing contact arms 341 of each receptacle 360a,b. The recessed surface 329 may be flat. Thus, when the receptacles 360a,b are coupled to the carrier 323, the recessed surface 329 contacts the inner surface of each of the distal portions 341A. As shown in FIG. 25B, the carrier 323 is configured to receive at least one of the receptacles 360a,b on one side of the central opening 323A and at least another one of the receptacles 360a,b on the other side of the central opening 323A. The positioning of the carrier 323 helps to reduce disruption on the air flow caused by the power pin receptacles 360a,b.

The carrier 323 may help to support the heater 366 and receptacles 360a,b and is configured to form a receptacle assembly together with the receptacles 360a,b. The carrier 323 allows the receptacles 360a,b to, as a single unit, be inserted into and coupled with the cartridge body 356. This may improve assembly of the cartridge 350 by reducing the number of components assembled within the cartridge 350, and reducing the number of steps for assembling the cartridge 350. The carrier 323 may also allow the receptacles 360a,b to be inserted into the cartridge body 356 more easily. For example, the carrier 323 may be coupled to a runner or other portion of a mold, which may be broken off, during insertion of the receptacle assembly into the cartridge body 356. Once the receptacle assembly is properly positioned within and/or coupled to the cartridge body 356, the runner may be broken off of and/or otherwise separated from the receptacle assembly.

In some implementations, the carrier 323 may be made of a material, including a non-conductive material. For example, the carrier 323 may be formed of plastic, liquid crystal polymer, and/or the like.

Referring to FIGS. 25A-25C, each of the contact arms 341 may include a locking feature 348. The locking feature 348 may be configured to couple with a portion of the cartridge body 356. The locking feature 348 may be defined by a portion 348a of the contact arm 341 along a length of the contact arm 341 that extends inwardly toward the interior volume 351. For example, the locking feature 348 may be defined by a recess along a portion of an outer surface of the contact arm 341. Alternatively and/or additionally, the locking feature 348 may defined by a protrusion along a portion of an inner surface of the contact arm 341 opposite the portion of the outer surface. The locking feature 348 may be formed at a proximal end of the distal portion 341A of the contact arm 341. The locking feature 348 is configured to receive a corresponding cartridge body locking feature 348b (e.g., a protrusion) within the cartridge body 356 (see FIG. 24D). The locking feature 348 may engage with the corresponding cartridge body locking feature 348b via a snap-fit or other mechanical engagement feature. Thus, the locking feature 348 may secure the receptacles 360a,b to the cartridge body 356. This helps to maintain contact between the receptacles 360a,b and the end caps 3068 (and thus, the heating coil 367). This configuration also helps to prevent movement of the receptacles 360a,b, such as in a distal and/or proximal direction, when the power pins 122a,b are inserted within and coupled to each receptacle 360a,b, by providing a counter-force in a direction opposite to the insertion direction.

Referring to FIGS. 25A-25C, each receptacle 360a,b may include a power pin contact 349 positioned at a distal end of each contact arm 341. The power pin contacts 349 are configured to contact and electrically communicate with a respective power pin 166a,b of the vaporizer body 110. The power pin contacts 349 may define an opening through which the power pins 166a,b may be inserted. The power pin contacts 349 may include a distal pin contact portion 349a and a proximal pin contact portion 349b. The proximal pin contact portion 349b of the power pin contact 349 forms a bend in the power pin contact 349 and the distal pin contact portion 349a extends inwardly towards the interior volume 351. The distal pin contact portion 349a may also extend in a proximal direction within the interior volume 351.

A distance F (e.g., 0.72 mm, 0.25 mm to 0.5 mm, 0.5 mm to 0.75 mm, 0.75 mm to 1.0 mm) between opposing distal pin contact portions 349a may be approximately equal to a width or diameter of each of the power pins 166a,b. In some implementations, the distance F between opposing distal pin contact portions 349a is less than the width and/or diameter of each of the power pins 166a,b. Such configurations may help to maintain contact between the receptacles 360a,b and respective power pins 166a,b. For example, upon insertion of each power pin 166a,b into the respective receptacle 360a,b, the power pins 166a,b contact at least the distal pin contact portions 349a of the power pin contacts 349, causing the contact arms 341 to deflect away from one another (and in a direction outwardly away from the interior volume 351). The deflection of the contact arms 341 causes an opposite force to be applied to the power pins 166a,b at the power pin contacts 349 (e.g., at the distal pin contact portions 349a) in an opposite direction towards the interior volume 351. This opposite force helps to maintain contact between the power pins 166a,b and the receptacles 360a,b in use. In some implementations, the opposing contact arms 341 are spaced apart by a distance E (e.g., approximately 2.2 mm, 1.0 to 1.5 mm, 1.5 to 2.0 mm, 2.0 to 2.5 mm or greater) such that the contact arms 341 do not deflect beyond a yield distance when the power pins 166a,b are coupled to the receptacles 360a,b. This helps to reduce wear on the receptacles 360a,b and allows the cartridge 250 to be coupled to the vaporizer body 110 for at least a desired number of cycles (e.g., 500, 1000, 1500, or 2000 or more cycles). In some implementations, the distal pin contact portions 349a as shown in at least FIGS. 25A-25C includes a distal edge 349c. The distal edge 349c may form at least a part of an end of the distal pin contact portion 349a. The distal edge 349c may contact at least a portion of the power pins 166a,b when the power pins 166a,b are inserted within the receptacles 360a,b. The distal edge 349c may help to cut through vaporizable material, or other debris that has built up on the power pins 166a,b or along an interior portion of the receptacles 360a,b. Thus, this configuration may help to ensure a clean and secure contact between the power pins 166a,b and receptacles 360a,b in use.

Additionally and/or alternatively, FIGS. 26A-26F illustrates another example of the receptacles 360a,b consistent with implementations of the current subject matter. In the example shown in FIGS. 26A-26F, the proximal pin contact portion 349b may extend inwardly towards the interior volume 351 and the distal pin contact portion 349a may extend outwardly away from the interior volume 351 (and outwardly away from the distal pin contact portion 349a). A distance D (e.g., 0.83 mm, 0.25 mm to 0.5 mm, 0.5 mm to 0.75 mm, 0.75 mm to 1.0 mm) between opposing proximal pin contact portions 349b may be approximately equal to a width or diameter of each of the power pins 166a,b. In some implementations, the distance D between opposing proximal pin contact portions 349b is less than the width and/or diameter of each of the power pins 166a,b. Such configurations may help to maintain contact between the receptacles 360a,b and respective power pins 166a,b. For example, upon insertion of each power pin 166a,b into the respective receptacle 360a,b (see FIG. 26F), the power pins 166a,b contact at least an inner surface of the proximal pin contact portions 349b of the power pin contacts 349, causing the contact arms 341 to deflect away from one another (and in a direction outwardly away from the interior volume 351). The deflection of the contact arms 341 causes an opposite force to be applied to the power pins 166a,b at the power pin contacts 349 (e.g., at the proximal pin contact portions 349b) in an opposite direction towards the interior volume 351. This opposite force helps to maintain contact between the power pins 166a,b and the receptacles 360a,b in use. In some implementations, the opposing contact arms 341 are spaced apart by a distance E (e.g., approximately 2.2 mm, 1.0 to 1.5 mm, 1.5 to 2.0 mm, 2.0 to 2.5 mm or greater) such that the contact arms 341 do not deflect beyond a yield distance when the power pins 166a,b are coupled to the receptacles 360a,b. This helps to reduce wear on the receptacles 360a,b and allows the cartridge 350 to be coupled to the vaporizer body 110 for at least a desired number of cycles. In some implementations, when the power pins 166a,b are coupled with the receptacles 360a,b, and the vaporizer device is in use, power may be supplied from the power pins 166a,b to the receptacles 360a,b, and transferred directly from the receptacles 360a,b to the end caps 3068, and then to the heating coil 367 coupled with the end caps 3068.

In some implementations, the receptacles 360a,b shown in FIGS. 24A-26F help to improve assembly of the cartridge body 356. For example, the receptacles 360a,b may be inserted through a proximal end of the cartridge body 356 (e.g., coupled to the carrier 323 as noted above) and locked into place relative to the cartridge body 356 via the locking features 348 (such as by a snap-fit arrangement). This allows the wick 368 (and the end caps 3068 coupled to the wick 368) to be inserted into the cartridge body 356 and coupled to the receptacles 360a,b, regardless of the rotational orientation of the wick 368. For example, the wick 368 may be inserted into the cartridge body 356 in any rotational orientation as long as the wick 368 is positioned in a transverse direction relative to the longitudinal axis A. This helps to ease and speed the assembly of the cartridge 350. The receptacles 360a,b also helps to reduce the number of steps for assembling the cartridge 350. For example, the receptacles 360a,b may be configured to directly contact the end caps 3068 without a separate securement means, such as laser welding. In some implementations, the wick 368 and end caps 3068 may be properly positioned (e.g., snapped into place) with respect to the receptacles 360a,b when the wick housing 388 is inserted into the cartridge body 356. For example, the wick housing 388 may contact the end caps 3068 and press the end caps 3068 into contact with the receptacles 360a,b, thereby locking the end caps 3068 into place.

FIG. 24E illustrates a partial exploded view of the cartridge 360, including the mouthpiece assembly 390, the base assembly 394, and the cartridge body assembly 392, consistent with implementations of the current subject matter. The mouthpiece assembly 390, the base assembly 394, and the cartridge body assembly 392 include the same or similar features and/or components as the mouthpiece assembly 290, the base assembly 294, and the cartridge body assembly 292, respectively. As shown in FIG. 24E, the mouthpiece assembly 390 is coupled to the cartridge body assembly 392. The mouthpiece 352 and the base 387 are shown as transparent to more clearly illustrate the depicted features.

Figure 27:
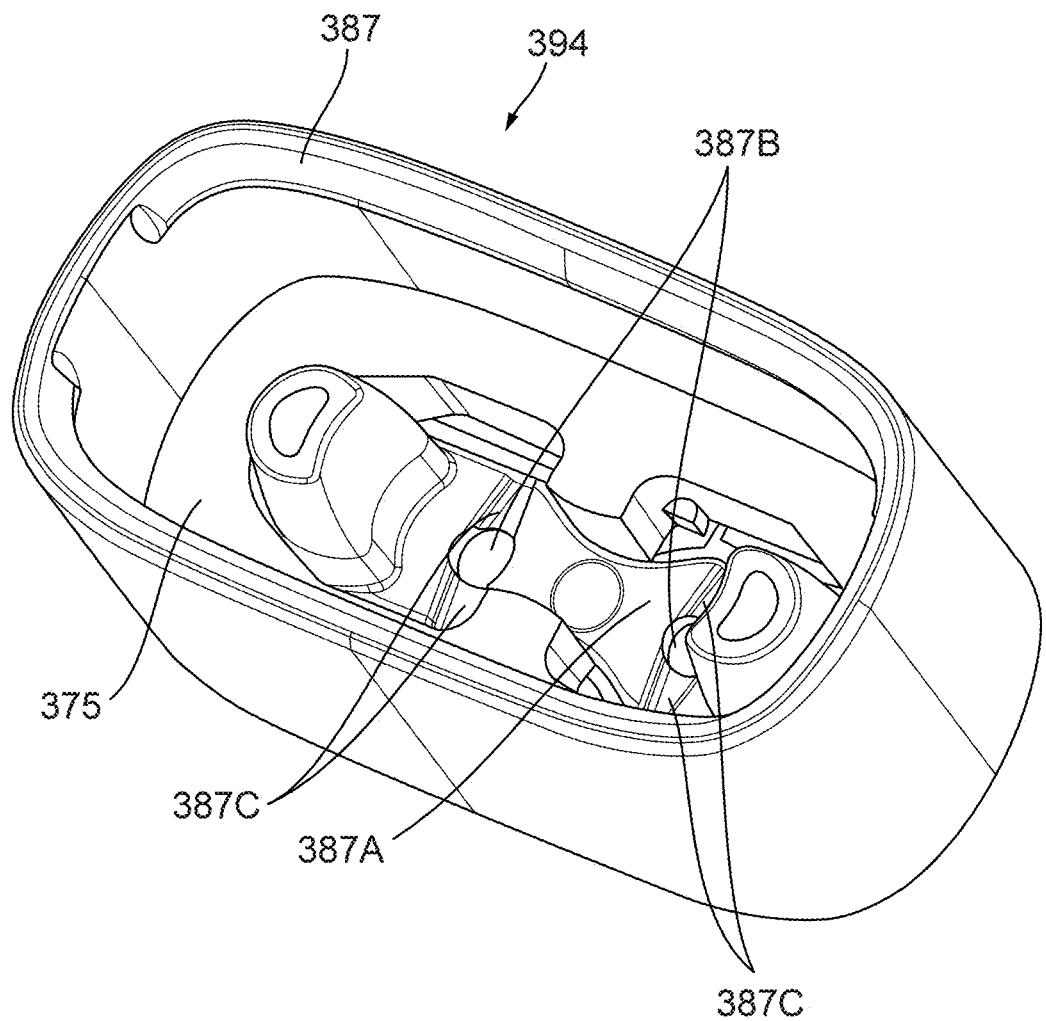
FIG. 27 illustrates a base assembly of a cartridge consistent with implementations of the current subject matter.

FIG. 27 illustrates a perspective view of the base assembly 394, including a base 387, an absorbent pad 375, and a tag 364 (see FIG. 24E). The base 387 includes a lower interior surface 387A upon which the absorbent pad 375 and the tag 364 rests. The lower interior surface 387A includes at least two openings 387B that align with the opening formed by the receptacles 360a,b that is configured to receive respective power pins (or contacts) 122a,b of the vaporizer body 110. The lower interior surface 387A includes base capillary channels 387C formed on opposing sides of each of the openings 387B. The base capillary channels 387C may include tapered and/or parallel walls. For example, as shown in FIG. 27, the base capillary channels 387C may have a width (e.g., 0.7 mm, 0.25 mm to 0.5 mm, 0.5 mm to 0.75 mm, 0.75 mm to 1.0 mm) that is wider adjacent to the openings 387B than a width (e.g., 0.6 mm, 0.25 mm to 0.5 mm, 0.5 mm to 0.75 mm, 0.75 mm to 1.0 mm) away from the openings 387B. The base capillary channels 387C are configured to direct vaporizable material that may be positioned on and/or near the receptacles 360a,b away from the receptacles 360a,b and/or the openings 387B, and towards the absorbent pad 375 to be absorbed by the absorbent pad 375. The width of the base capillary channels 387C causes capillary pressure to act on the vaporizable material, causing the vaporizable material to travel along the base capillary channels 387C to the absorbent pad 375. Such configurations may help to limit or prevent leakage of the vaporizable material out of the cartridge 350. Such configurations may also help to reduce the amount of vaporizable material that remains on the receptacles 360a,b. This helps maintain a consistent amount of power delivered to the heater 366 via the receptacles 360a,b, and helps improve the surface of the receptacles 360a,b that contacts the power pins 122a,b.

Figure 28A:
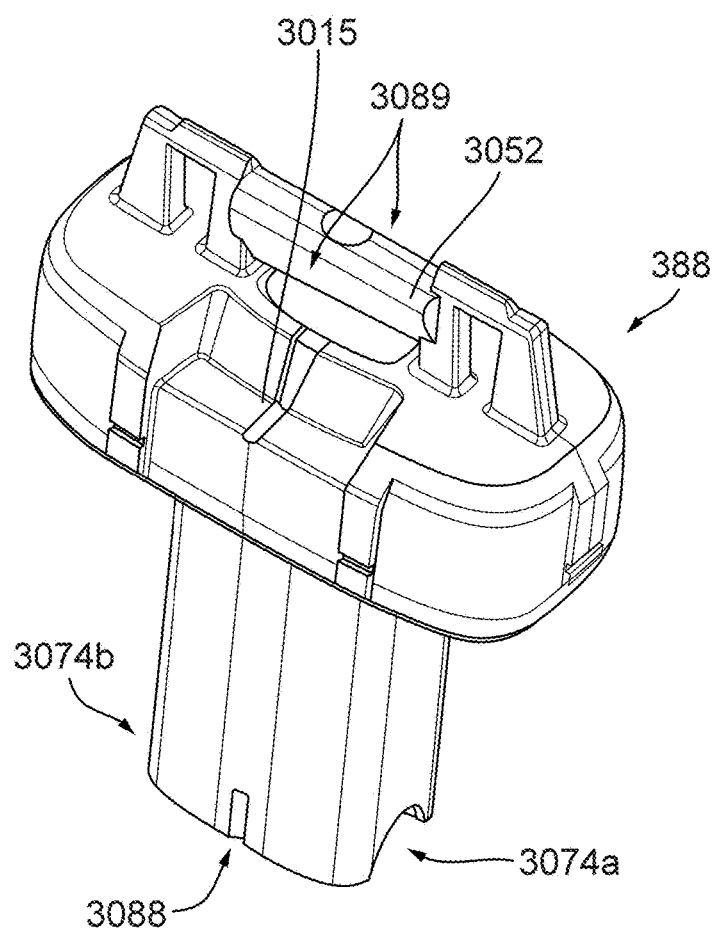
FIGS. 28A-28B illustrate a wick housing of a cartridge consistent with implementations of the current subject matter.
Figure 28B:
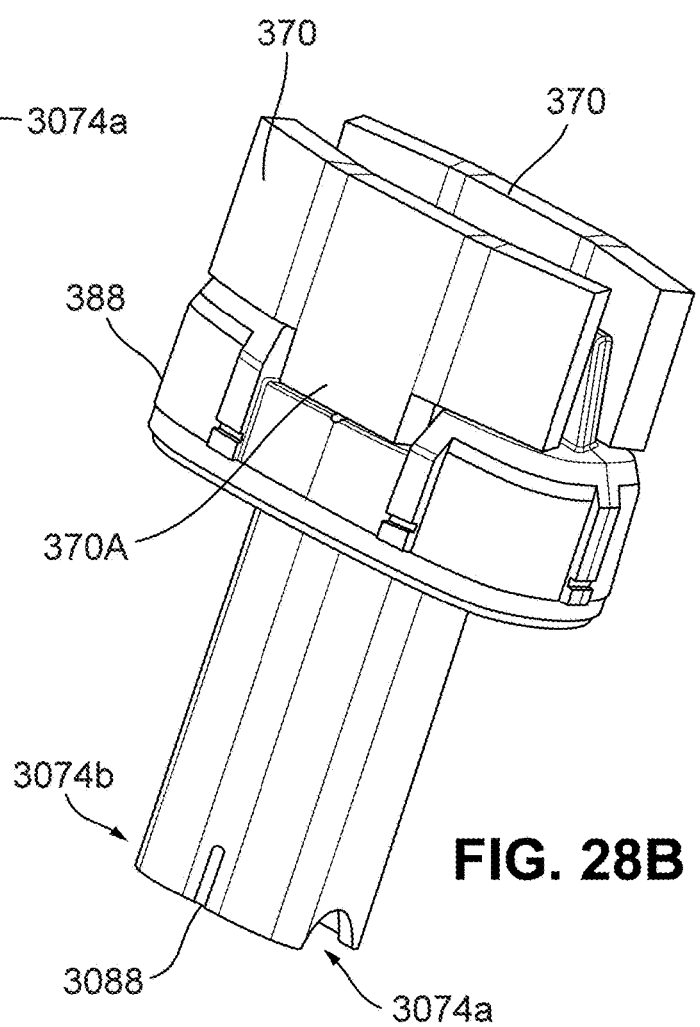
Figure 29:
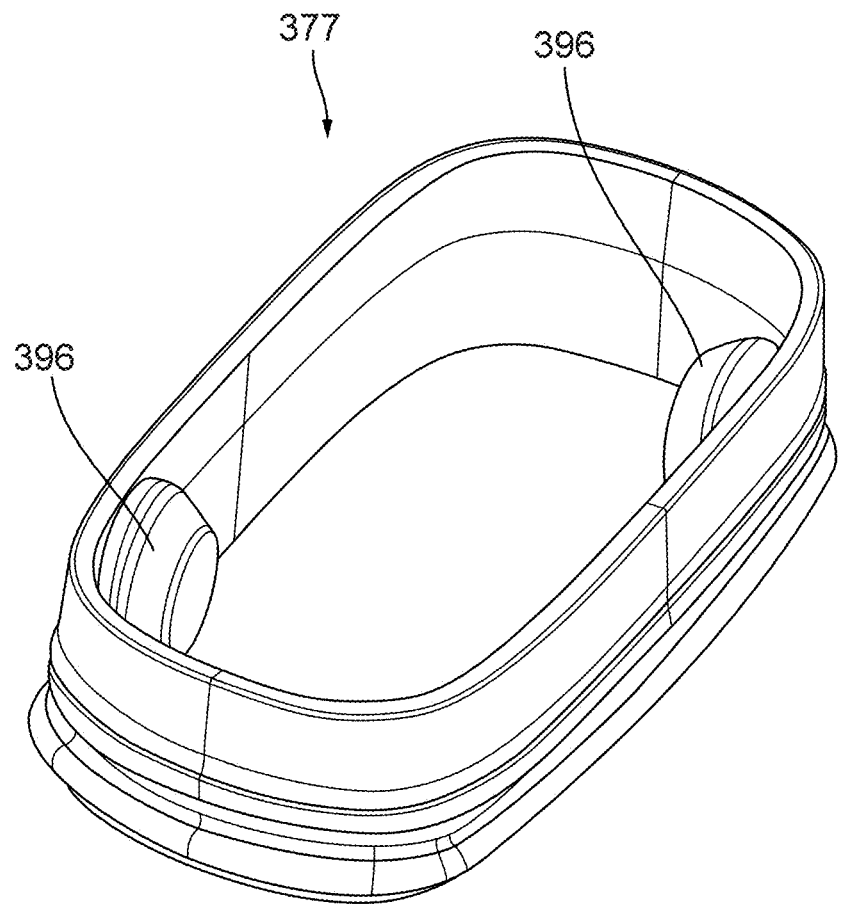
FIG. 29 illustrates a mouthpiece seal of a cartridge consistent with implementations of the current subject matter.

FIGS. 28A and 28B illustrate an example of the wick housing 388, which includes the same and/or similar features as the wick housing 288. In some implementations, the wick housing 388 includes a vent 3088. The vent 3088 may be positioned at a proximal end of the wick housing 388. The vent 3088 may define a recessed channel formed in an outer surface of the wick housing 388. The vent 3088 may be formed on one side (e.g., a side formed between opposing lateral sides of the wick housing 388 in which the lateral openings 3074a,b are formed) of the wick housing 388. The vent 3088 may allow air to flow or otherwise be transferred between the reservoir 358 and the vaporization chamber 3005 in which the heater 366 is located. For example, the vent 3088 allows air to replace the vaporizable material within the reservoir 358 via the vent 3088 when the vaporizable material saturates the wick 368. The vent 3088 may be shaped and/or sized to prevent or limit vaporizable material (e.g., of a certain surface tension) from flowing freely out of the reservoir 358 through the vent 3088. The size and/or shape of the vent 3088 may additionally and/or alternatively allow air to flow back into the reservoir 358 through the vent 3088 when a back pressure threshold (e.g., approximately −100 pa to −700 pa) is met. For example, the vent 3088 may have a semi-circular cross-sectional shape, among other shapes. The radios of the cross-sectional shape of the vent 3088 may be approximately 0.1 mm to 0.5 mm, 0.1 mm to 0.2 mm, 0.2 mm to 0.3 mm, 0.3 mm to 0.4 mm, 0.4 mm to 0.5 mm and/or the like. This helps to prevent or limit leaking of vaporizable material out of the reservoir 358. This also helps to ensure that the wick 368 remains saturated, helps to control the amount of air entering the reservoir 358, and/or the amount of vaporizable material saturating the wick 368, which provides a more consistent vapor production and improved user experience.

Again referring to FIGS. 28A and 28B, the wick housing 388 includes a pair of wick housing capillary channels 3089. The wick housing capillary channels 3089 may be formed in the proximal end portion of the wick housing 388. The wick housing capillary channels 3089 may be formed on opposing sides of the central channel 3015. In some implementations, at least a portion of the wick housing capillary channels 3089 may include tapered and/or parallel walls. For example, as shown in FIG. 28A, a portion of the wick housing capillary channels 3089 may be tapered away from the central channel 3015 and a portion of the wick housing capillary channels 3089 may include parallel walls. The wick housing capillary channels 3089 are configured to direct vaporizable material that may be positioned on and/or near the central channel 3015, and/or the central, upper element 3052 towards the pads 370 within the mouthpiece. The width (e.g., 0.7 mm, 0.25 mm to 0.5 mm, 0.5 mm to 0.75 mm, 0.75 mm to 1.0 mm) and/or shape of the wick housing capillary channels 3089 causes capillary pressure to act on the vaporizable material, causing the vaporizable material to travel along the wick housing capillary channels 3089 to the pads 370. Such configurations may help to limit or prevent the collection of the vaporizable material and/or condensed vaporizable material at the central channel 3015. This helps to reduce clogging and/or another disruption within the airflow path of the vapor leaving the cartridge 350. Such configurations may additionally and/or alternatively reduce and/or prevent leakage of the collected vaporizable material out of the mouthpiece of the cartridge 350.

In some implementations, such as is shown in FIG. 28B, the pads 370 may include an extension 370A that extends from a central region of the pads 370 and is configured to be positioned over at least a portion of the wick housing capillary channels 3089. Thus, the pads 370 may work together with the wick housing capillary channels 3089 to collect the vaporizable material and/or condensed vaporizable material, and prevent or limit the build-up and/or leakage of vaporizable material.

Referring again to FIG. 24E, the cartridge 350 may include a mouthpiece seal 377, which may be the same or similar to the mouthpiece seal 177, 277. The mouthpiece seal 377 may be incorporated between where the mouthpiece 352 and the proximal end region 356A of the cartridge body 356 couple together. The mouthpiece seal 377 may include a fill port seal 396 that aligns with at least one fill port 397 that extends through one or opposing sides of the reservoir body 358A (see FIG. 24C, 29). In some implementations, the reservoir body 358A and/or the cartridge body 356 includes two fill ports 397 positioned on opposing sides. The mouthpiece seal 377 includes two corresponding fill port seals 396 that are configured to align with each of the fill ports 397 (see FIG. 29). The fill ports 397 and the corresponding fill port seals 396 may be positioned such that the reservoir body 358A and/or the mouthpiece seal 377 has 180 degree rotational symmetry. The fill ports 397 and the corresponding fill port seals 396 allow the cartridge 350 to be filled from either side of the cartridge 350. This helps to speed and ease filling of the cartridge 350. In some implementations, the fill port seals 396 may be pre-cut. Pre-cutting the fill port seals 396 may improve safety in filling the cartridge 350, as it would allow a blunt needle to be used to fill the reservoir 358 with the vaporizable material.

FIGS. 30A-30E and 31A-31B illustrate features of a cartridge 450 of a vaporizer device, consistent with implementations of the current subject matter. The cartridge 450 may include the same or similar features as the cartridges 150, 250, 350 described herein. For example, the cartridge 450 may include a cartridge body 456 defining, at least in part, a reservoir 458 configured to contain vaporizable material, a mouthpiece 452, and a vaporizing assembly of vapor-generating components positioned within the cartridge body 456 and configured to vaporize the vaporizable material, which are the same or similar to the cartridge body 156, 256, 356, the reservoir 158, 258, 358, and the mouthpiece 152, 252, 352.

The cartridge 450 may include one or more assemblies that may be coupled together, such as via snap-fit, laser-welding, adhesives, and/or the like. For example, the cartridge 450 may include a mouthpiece assembly 490, a cartridge body assembly 492, and a base assembly 494. The cartridge body assembly 492 may include the cartridge body 456, which may be divided, generally, into a proximal end region, a central region, and a distal end region. The proximal end region of the cartridge body 456 can be coupled to the mouthpiece 452 configured to deliver the vapor to the user. A tank or reservoir body 458A is defined, at least in part by, the proximal end region and the central region of the cartridge body 456 and is configured to contain an amount of the vaporizable material. The distal end region (alone or together with the central region) of the cartridge body 456 may house one or more components configured to vaporize the material from the reservoir 458 into a vaporization chamber 4005 (see, e.g., FIGS. 30A-30B). The mouthpiece 452 is configured to interface with the user to release the vapor from the vaporization chamber 4005 to the user through one or more openings 454 in the mouthpiece 452, for example, upon the user drawing a breath through the vaporizer device. Each of these components will be described in more detail below, and as noted above, may have the same or similar features and/or properties as the components described herein with respect to the cartridge 150, the cartridge 250, and/or the cartridge 350.

As described herein, the cartridge 450 may include a heater 466, which may be the same or similar to the heater 166, 266, 366. The heater 466 may be configured to heat and/or vaporize at least a portion of the vaporizable material drawn towards the heater 466 from the reservoir 458. In some implementations, the heater 466 may include a resistive element such as a heating coil 467 in thermal contact with a wick 468. The heating coil 467 and the wick 468 may include the same or similar properties and features as the heating coil 167, 267, 367 and the wick 168, 268, 368 described herein with respect to the cartridge 150, 250, 350.

Figures 31A, 31B:
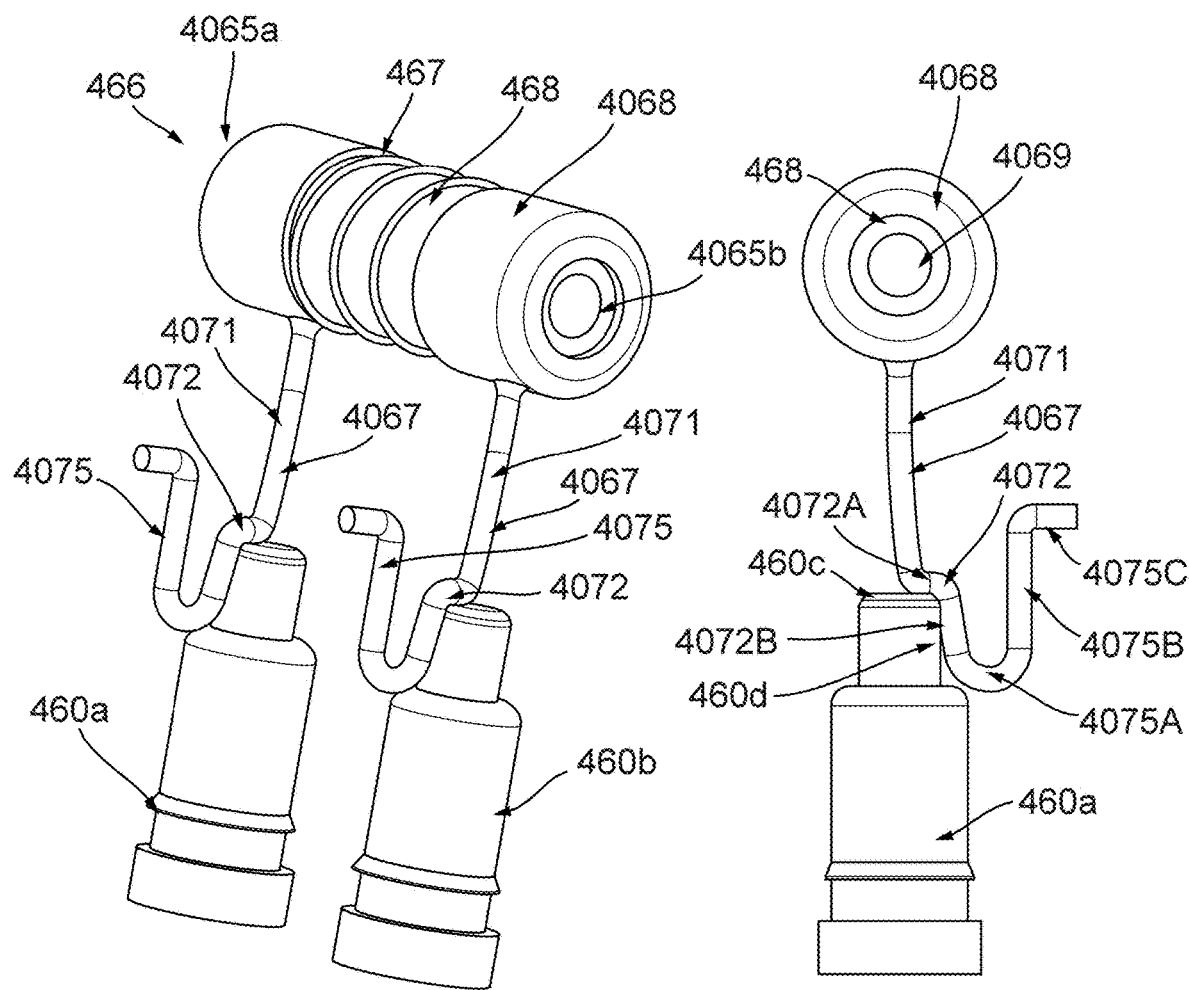
FIGS. 31A-31B illustrate features of a heater of a cartridge consistent with implementations of the current subject matter.

FIGS. 31A-31B illustrate an example of the heater 466 consistent with implementations of the current subject matter in which the wick 468 is coupled to end caps 4068 that provide a connection between the heating coil 467 and the power source. In this example, the end caps 4068 provide a connection between the heating coil 467 and respective leads 4067. For example, the end caps 4068 may facilitate the electrical connection of the coil 467 with respective power pin receptacles 460a,b. The power pin receptacles 460a,b may in turn electrically couple to the vaporizer body 110. In some implementations, the end caps 4068 are separately formed and coupled to the wick 468 and/or the heating coil 467. In other implementations, the end caps 4068 may be integrally formed with the heating coil 467 and/or may be electrically and/or physically coupled to the heating coil 467 via welding and/or other mating processes. In some implementations, the heater 466 may be coupled to and/or include the one or more power pin receptacles 460a,b, which are described in more detail below.

Figures 30A, 30B:
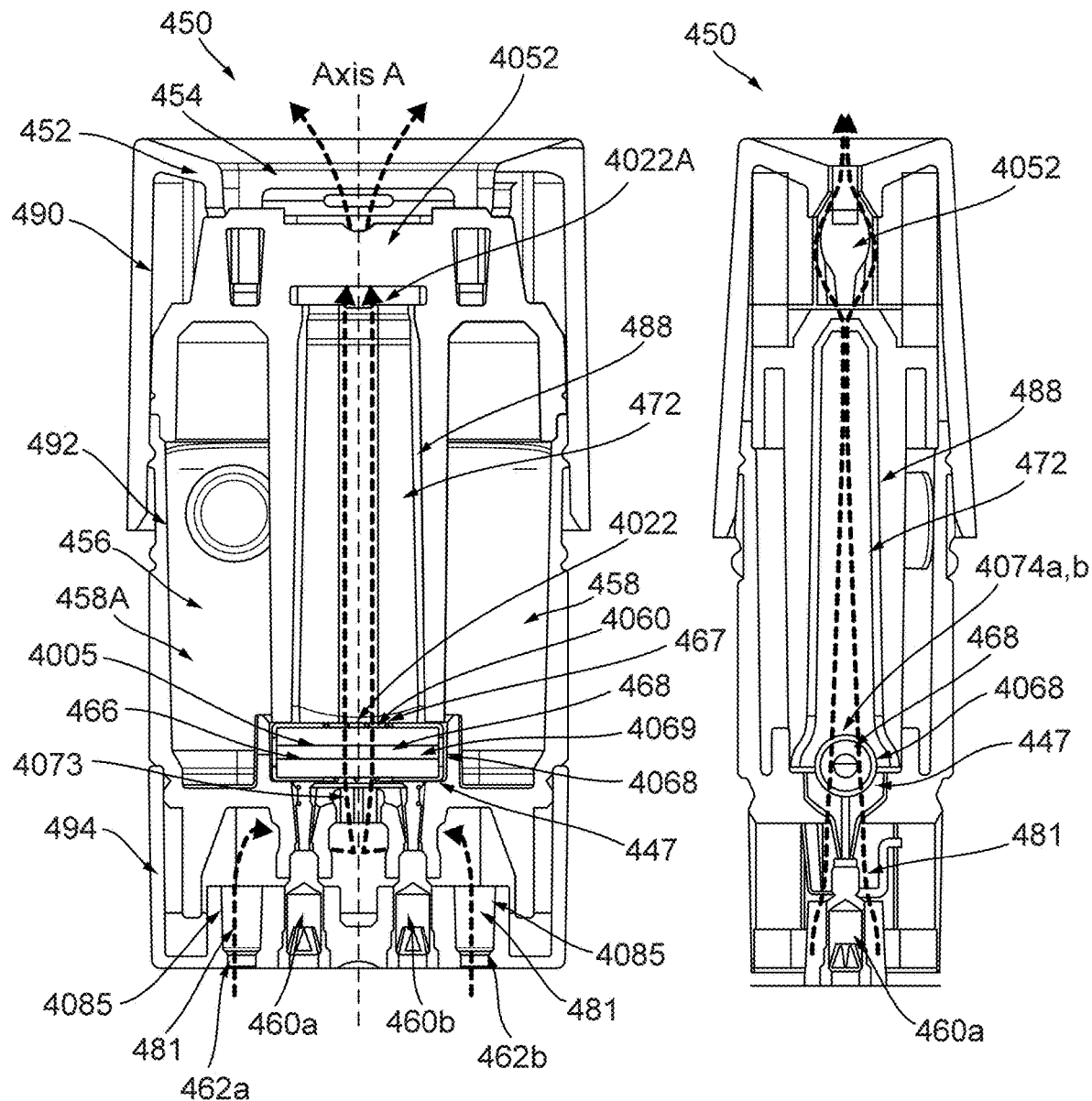
FIGS. 30A-30B illustrate cross-sectional views of a cartridge consistent with implementations of the current subject matter.

The end caps 4068 may be made of various materials, such as copper, stainless steel, other metals, or combinations thereof. The end caps 4068 may securely and snugly fit over respective ends of the wick 468 (e.g., opposing ends 4065a, b). For example, the end caps 4068 may be thin sleeves that fit over the respective ends of the wick 468. End portions of each of the end caps 4068 have an opening that aligns with a central bore 4069 of the wick 468. The openings may be of a larger diameter than that of the central bore 4069 to further promote wicking of the vaporizable material along the length of the wick 468. The heater 466 may extend across the air path within the vaporization chamber 4005, such as in a transverse direction. As shown in FIGS. 30A and 30B, a central cannula 472 of a wick housing 488 may be arranged coaxial with the longitudinal axis A of the device and the wick 468 may extend orthogonal to the longitudinal axis A through the central cannula 472. The wick 468 is preferably positioned near a distal-most end region of the reservoir 458 such that the vaporizable material in the reservoir 458 may be fully used. A pair of lateral openings 4074a,b may extend through the walls of the central cannula 472 of the wick housing 488 near its base where the central cannula 472 couples to an inner distal surface of the reservoir body 458A. The pair of lateral openings 4074a,b may be aligned across from one another on opposing sides of the central cannula 472. The openings 4074a,b are provided and sized for coupling to the heater 466.

In some implementations, the wick 468 of the heater 466 may include a central portion 4060 and opposing ends 4065a,b positioned on opposite sides of the central portion 4060. The heating coil 467 may be wrapped around the central portion 4060 of the wick 468, which in turn may be positioned within the vaporization chamber 4005. The opposing ends 4065a,b of the wick 468 may be positioned at least partially outside the vaporization chamber 4005 by extending laterally outward through and/or within the lateral openings 4074a,b of the central cannula 472. As such, the opposing ends 4065a,b may be positioned within or in contact with the internal volume of the reservoir 458 whereas the central portion 4060 of the wick 468 wrapped by the heating coil 467 may be positioned entirely inside the vaporization chamber 4005 of the central cannula 472. The leads 4067 of the heating coil 467 may extend away from the central portion 4060 of the wick 468 and down through respective openings 4073A in the distal support structure 469 of the reservoir body 458A out of the vaporization chamber 4005. The leads 4067 may extend into the interior of the base assembly 494 of the cartridge body 456 where the leads 4067 may contact and/or electrically couple with the power pin receptacles 460a,b.

FIGS. 31A and 31B illustrate an example of the heater 466 and power pin receptacles 460a,b consistent with implementations of the current subject matter. As noted above, the heater 466 includes end caps 4068 positioned on opposing sides of the heating coil 467 and a lead 4067 extending from each of the end caps 4068. In some implementations, the leads 4067 may include one or more materials which may be the same or different from the end caps 4068. The material of the leads 4067 may have a desired resistance to reduce or limit heat generated by the receptacles 460a,b and/or the leads 4067 and still transfer a sufficient amount of energy to the end caps 4068 and/or the heating coil 467 to heat the heating coil 467 to a desired temperature. In some implementations, at least a portion of the leads 4067 includes gold-plated phosphor bronze, or other conductive materials as described herein. The leads 4067 may therefore be configured to transfer power from the power pins 166a,b of the vaporizer body 110, via the receptacles 460a,b to the end caps 4068, and then to the heating coil 467 coupled with the end caps 4068. Additionally and/or alternatively, the leads 4067 may conduct heat away from the end caps 4068, and/or into the airflow through the airflow path. This helps to prevent or limit the end caps 4068 and the heating coil 467 from over-heating and to maintain a consistent temperature at the heating coil 467, where the vaporizable material will be heated. This may also help to pre-heat the air passing through the air path, allowing the vaporizable material to be vaporized into vapor more quickly.

As shown in FIGS. 31A and 31B, each of the leads 4067 includes an extension portion 4071, a contact portion 4072, and an end portion 4075. The extension portion 4071 may extend from an exterior surface of the corresponding end cap 4068. The extension portion 4071 may extend from the end cap 4068 in a direction that is generally perpendicular to a lateral axis that is centrally aligned with the opening of the end cap 4068. In some implementations, the extension portion 4071 is straight (e.g., unbent). In other implementations, the extension portion 4071 is curved. The extension portion 4071 may extend between the exterior surface of the end cap 4068 and the contact portion 4072 of the lead 4067.

The contact portion 4072 may extend from the extension portion 4071 and contact at least a portion of a respective receptacle of the receptacles 460a,b to establish an electrical connection between the receptacles 460a,b and the end caps 4068. The lead 4067 may be press fit, welded to, and/or otherwise coupled to the receptacle 460a to establish a secure electrical connection. Though the lead 4067 is described with respect to the receptacle 460a, the second lead 4067 may contact and/or communicate with the receptacle 460b in the same manner.

The contact portion 4072 may be bent relative to the extension portion 4071 and extend at an angle from the extension portion. 4071. In some implementations, at least a portion of the contact portion 4072, such as a first contact portion 4072A, extends at an angle that is approximately perpendicular relative to the extension portion 4071. In some implementations, at least a portion of the contact portion 4072, such as a second contact portion 4072B, additionally and/or alternatively is positioned approximately parallel relative to the extension portion 4071.

The contact portion 4072 of the lead 4067 may extend about at least a portion of the receptacle 460a. For example, the contact portion 4072 may contact the receptacle 460a at at least one, two, or more surfaces. As shown in FIG. 31B, for example, the contact portion 4072 contacts at least two surfaces, including an upper surface and a side surface, of the receptacle 460a. As noted above, the contact portion 4072 includes a first contact portion 4072A and a second contact portion 4072B. The first contact portion 4072A and the second contact portion 4072B are angled relative to one another, at an angle of approximately 90 degrees, 90 to 95 degrees, 95 to 100 degrees, 100 to 105 degrees, 105 to 110 degrees, 110 to 115 degrees, 115 to 120 degrees, or greater. This allows the first contact portion 4072A to contact a first surface 460c, such as an upper surface, of the receptacle 460a, and the second contact portion 4072B to contact a second surface 460d, such as a side surface, of the receptacle 460a. This configuration helps to secure the lead 4067 to the receptacle 460*a* and to ensure that the lead 4067 maintains contact and/or the electrical connection between the lead 4607 and the receptacle 460*a* in use.

Referring to FIGS. 31A and 31B, the lead 4067 may also include an end portion 4075. The end portion 4075 extends from the contact portion 4072. The end portion 4075 may include a bend, such as a 180 degree bend, that causes the lead 4067 to extend in an opposite direction, such as in a direction towards the end cap 4068, from an end of the contact portion 4072. The end portion 4075 may include a first portion 4075A that includes the bend, a second portion 4075B that extends in a direction towards the end cap 4068, and a third portion 4075C. The second portion 4075A may extend in a direction that is approximately parallel to a side surface of the end cap 4068 and/or the extension portion 4071. This third portion 4075C may extend in a direction that is approximately perpendicular to the second portion 4075B.

The end portion 4075 may help to secure the leads 4067 to the cartridge body 456. For example, as shown in FIGS. 30C-30E, the leads 4067 may extend away from the end caps 4068 and down through respective openings 4073A in the distal support structure 469 of the reservoir body 458A out of the vaporization chamber 4005. The leads 4067 may extend into the interior of the base assembly 494 of the cartridge body 456 where the leads 4067 may contact and/or electrically couple with the power pin receptacles 460*a,b*. The distal support structure 469 may include one or more (e.g., one, two, three, four, or more) lead guides 479*a,b* that corresponds to each of the leads 4067. The lead guides 479*a,b* are configured to extend into the interior of the base assembly 494 when the base assembly 494 is coupled to the cartridge body 456. The lead guides 479*a,b* are configured to support the leads 4067 and/or prevent or limit lateral movement of the leads 4067.

The lead guides 479*a,b* may include a bore extending through a thickness of the lead guides 479*a,b* from a generally circular opening 4073A on the upper surface of the distal support structure 469 to another generally circular opening 4082 leading towards the power pin receptacles 460*a,b*. The bore of the lead guides 479*a,b* may be cylindrical and have an inner diameter sized to receive and mate with the outer surface of the leads 4067 such that the leads 4067 are securely held within the lead guides 479*a,b*. The opening 4073A into the bore of the lead guides 479*a,b* on the upper surface may have an inner diameter that is slightly larger than the inner diameter of the bore. For example, the opening 4073A into the bore of the lead guides 479*a,b* may be funnel-shaped to ease insertion of each the leads 4067 into their respective lead guides 479*a,b*. The lead guides 479*a,b* may advantageously eliminate the cumbersome installation by hand of properly inserting the leads 4067 into contact with the receptacles 460*a,b*. Thus, the lead guides 479*a,b* are configured to receive and securely hold the leads 4067 as well as reduce the free space between the heater within the vaporization chamber 4005 and the power pin receptacles 460*a,b* to improve assembly. When the cartridge 450 is assembled, the receptacles 460*a,b* may be at least partially inserted through and/or plug the opening 4082 and/or within the bore of the lead guides 479*a,b* to limit or prevent vaporizable material from leaking from the reservoir into the base assembly.

The lead guides 479*a,b* may include an end portion recess 470 (see FIGS. 30C-30E) configured to enclose at least a portion of the end portion 4075 of each of the leads 4067. The end portion recess 470 is configured to limit or prevent movement of the leads 4067 to help maintain the electrical connection between the leads 4067 and the receptacles 460*a,b*. In some implementations, during assembly, the end portion 4075 of the lead 4067 is formed after the lead 4067 passes through the openings 4073A. For example, at least the end portion 4075 may be bent around at least a portion of the lead supports 469A and within the end portion recess 470 after the end portion 4075 of the lead 4067 passes through the opening 4073A.

Referring to FIGS. 30C-30E, the reservoir body 458A may include an end cap contact 447. The end cap contact 447 may be integrally formed with the reservoir body 458A, within an interior of the reservoir body 458A. The end cap contact 447 may include two or more end cap contacts 447 that correspond with and support each of the end caps 4068. The end cap contact 447 may define a seat in which each end cap 4068 is positioned. Each end cap 4068 may rest on and/or within each end cap contact 447. For example, a surface of the end cap contact 447 may contact an outer surface of the end cap 4068. The surface of the end cap contact 447 may be shaped to correspond to a shape of the end cap 4068. For example, the surface of the end cap contact 447 may include a rounded, curved, and/or semicircular shape that corresponds to the rounded, curved, and/or circular shape of the end cap 4068. This helps to limit or prevent movement of the end caps 4068 and/or the heater 466 within the reservoir body 458A, which helps to maintain electrical communication between each end cap 3068 and the corresponding receptacle 460*a,b*.

In some implementations, the wick 468 and end caps 4068 may be properly positioned within the reservoir body 458A and/the cartridge body 456 when the wick housing 488 is inserted into the cartridge body 456. For example, the wick housing 488 (e.g., the lateral openings 4074*a,b*) may contact the end caps 4068 and press the end caps 4068 into contact with the end cap contacts 447, thereby locking the end caps 4068 into place and/or sealing around an exterior surface of the end caps 4068.

Referring back to FIGS. 30A and 30B, air may flow along an airflow path 481, such as when the user puffs on the mouthpiece of the cartridge 450 and/or when the cartridge 450 is coupled to the vaporizer body 110. As described elsewhere herein, the outer shell 112 of the cartridge receptacle 114 of the vaporizer body 110 may include one or more side air inlets 116*a,b* (see also FIG. 1C and FIG. 1D). The air inlets 116*a,b* may be aligned with or positioned in fluid communication with the lower air flow inlets 462*a,b* leading into air flow channels 4085 of the base assembly 494. Air may enter the cartridge 450 through the air inlets 116*a,b* of the vaporizer body 110, between an exterior surface of the cartridge 450 and an interior surface of the cartridge receptacle 114, and through the lower air flow inlets 462*a,b* and into the air flow channels 4085 of the base assembly 494. Additionally and/or alternatively, air may enter the cartridge 450 through the air inlets 116*a,b* of the vaporizer body 110, and directly through the lower air flow inlets 462*a,b* and into the air flow channels 4085 of the base assembly 494. From the air flow channels 4085, the air may pass into an interior of the base assembly 494. For example, the base assembly 494 may act as a plenum for the air, which is then directed through the central aperture 4073, past the wick 468 and heating coil 467, where the vaporized vaporizable material becomes entrained within the air, and through the vaporization chamber 4005 of the central cannula 472. The airflow path 481 may continue through the opening 4022 of the wick housing 488, into the central channel 4015 and out an opposite opening 4022A of the central cannula 472 of the wick housing 488. The vapor may then be directed around the central, upper element 4052, which splits the vapor flow to allow for flow around the central, upper element 4052 and thereby reduces the amount of excess material that is collected on the central, upper element 4052 and elsewhere in the cartridge body 456. The central, upper element 4052 may additionally and/or alternatively allow the vapor to cool via a longer, turbulent flow path before entering the mouth of the user. The vapor may then flow through one or more openings 454 in the mouthpiece 452 to exit the cartridge 450.

FIGS. 32A-33C illustrate another example of the cartridge 450 of a vaporizer device, consistent with implementations of the current subject matter. The cartridge 450 shown in FIGS. 32A-33C may include the same or similar features, components, and/or properties as the cartridge 450 illustrated in FIGS. 30A-31C. For example, the cartridge 450 shown in FIGS. 32A-33C may also include the heater 466, which includes the heating coil 467, the wick 468, the end caps 4068, and the leads 4067. The end caps 4068 and the leads 4067 may facilitate the electrical connection of the coil 467 with respective power pin receptacles 560a,b, which include the same or similar properties and/or features as the power pin receptacles 160a,b, 260a,b, 360a,b, 460a,b, and may in turn electrically couple to the vaporizer body 110.

Figures 33A, 33B, 33C:
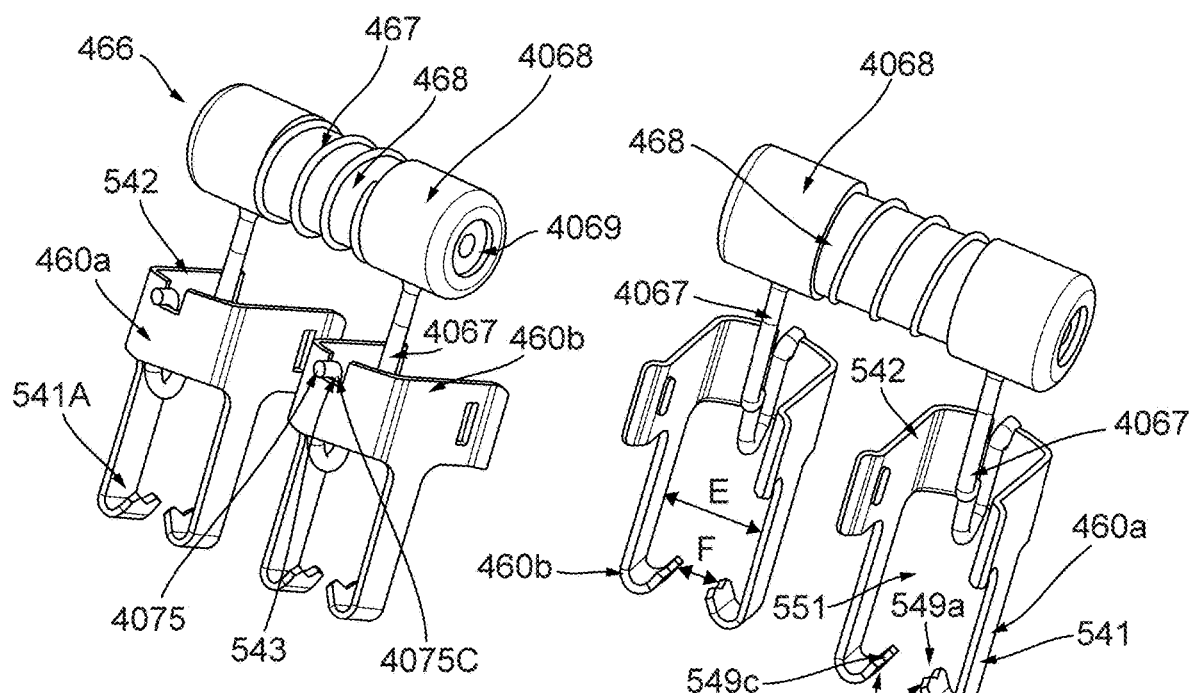
FIGS. 33A-33C illustrate features of a heater of a cartridge consistent with implementations of the current subject matter.

FIGS. 33A-33C illustrate an example of the heater 466 coupled with the receptacles 560a,b consistent with implementations of the current subject matter. The receptacles 560a,b include opposing contact arms 541 and a lead connector portion 542. The contact arms 541 may, at a proximal side of the lead connector portion 542, extend in a distal direction from the lead connector portion 542. In some implementations, the contact arms 541 may be positioned parallel to one another. In some implementations, the contact arms 541 may be positioned parallel to the longitudinal axis A of the cartridge 450. The contact arms 541 may be positioned adjacent opposite end portions of the lead connector portion 542. For example, the contact arms 541 may define an interior volume 551 in which the power pins 122a,b of the vaporizer body 110 are inserted.

As shown in FIGS. 33A-33C, the contact arms 541 include a distal portion 541A. The distal portion 541A of each of the contact arms 541 may define planar and/or unbent portions of each of the contact arms 541. As noted above, at least the distal portion 541A of opposing contact arms 541 are parallel to one another. Each receptacle 560a,b may include a power pin contact 549 positioned at a distal end of each contact arm 541. The power pin contacts 549 are configured to contact and electrically communicate with a respective power pin 166a,b of the vaporizer body 110. The power pin contacts 549 may define an opening through which the power pins 166a,b may be inserted. The power pin contacts 549 may include a distal pin contact portion 549a and a proximal pin contact portion 549b. The proximal pin contact portion 549b of the power pin contact 549 forms a bend in the power pin contact 549 and the distal pin contact portion 549a extends inwardly towards the interior volume 551. The distal pin contact portion 549a may also extend in a proximal direction within the interior volume 551.

A distance F (e.g., 0.72 mm, 0.25 mm to 0.5 mm, 0.5 mm to 0.75 mm, 0.75 mm to 1.0 mm) between opposing distal pin contact portions 549a may be approximately equal to a width or diameter of each of the power pins 166a,b. In some implementations, the distance F between opposing distal pin contact portions 549a is less than the width and/or diameter of each of the power pins 166a,b. Such configurations may help to maintain contact between the receptacles 560a,b and respective power pins 166a,b. For example, upon insertion of each power pin 166a,b into the respective receptacle 560a,b, the power pins 166a,b contact at least the distal pin contact portions 549a of the power pin contacts 549, causing the contact arms 541 to deflect away from one another (and in a direction outwardly away from the interior volume 551). The deflection of the contact arms 541 causes an opposite force to be applied to the power pins 166a,b at the power pin contacts 549 (e.g., at the distal pin contact portions 549a) in an opposite direction towards the interior volume 551. This opposite force helps to maintain contact between the power pins 166a,b and the receptacles 560a,b in use. In some implementations, the opposing contact arms 541 are spaced apart by a distance E (e.g., approximately 2.2 mm, 1.0 to 1.5 mm, 1.5 to 2.0 mm, 2.0 to 2.5 mm or greater) such that the contact arms 541 do not deflect beyond a yield distance when the power pins 166a,b are coupled to the receptacles 560a,b. This helps to reduce wear on the receptacles 560a,b and allows the cartridge 450 to be coupled to the vaporizer body 110 for at least a desired number of cycles (e.g., 500, 1000, 1500, or 2000 or more cycles). In some implementations, the distal pin contact portions 549a as shown in at least FIGS. 33A-33C includes a distal edge 549c. The distal edge 549c may form at least a part of an end of the distal pin contact portion 549a. The distal edge 549c may contact at least a portion of the power pins 166a,b when the power pins 166a,b are inserted within the receptacles 560a,b. The distal edge 549c may help to cut through vaporizable material, or other debris that has built up on the power pins 166a,b or along an interior portion of the receptacles 560a,b. Thus, this configuration may help to ensure a clean and secure contact between the power pins 166a,b and receptacles 560a,b in use.

Referring to FIGS. 33A-33C, the lead connector portion 542 connects the opposing contact arms 541. The lead connector portion 542 is electrically couples the contact arms 541 with the leads 4067. The lead connector portion 542 may include three closed sides and an opened side. Thus, the lead connector portion 542 may form a generally U-shape, which helps to secure the lead connector portion 542 to the lead guides 479a,b. The lead connector portion 542 may include a shape to correspond to the shape of the lead guides 479a,b to secure the receptacles 560a,b to the reservoir body 458A. The lead connector portion 542 may include a recess 543, which may contact and/or support at least a portion of the lead 4067, such as the end portion 4075 of the lead 4067. For example, the third portion 4075C may reside within and/or be supported by the recess 543. In some implementations, contact between the end portion 4075 and the recess 543 establishes an electrical connection between the receptacles 460a,b and the corresponding lead 4067. The recess 543 may be positioned between opposing sides of the lead connector portion 542 from which each of the opposing contact arms 541 extend. Referring again to FIGS. 33A-33C, the lead connector portion 542 may include end portions 544 that are flared outwardly from the opposing sides of the lead connector portion 542. The end portions 544 of the lead connector portion 542 may help to guide the attachment between the lead connector portion 542 and the lead guides 479a,b.

Figures 32A, 32B:
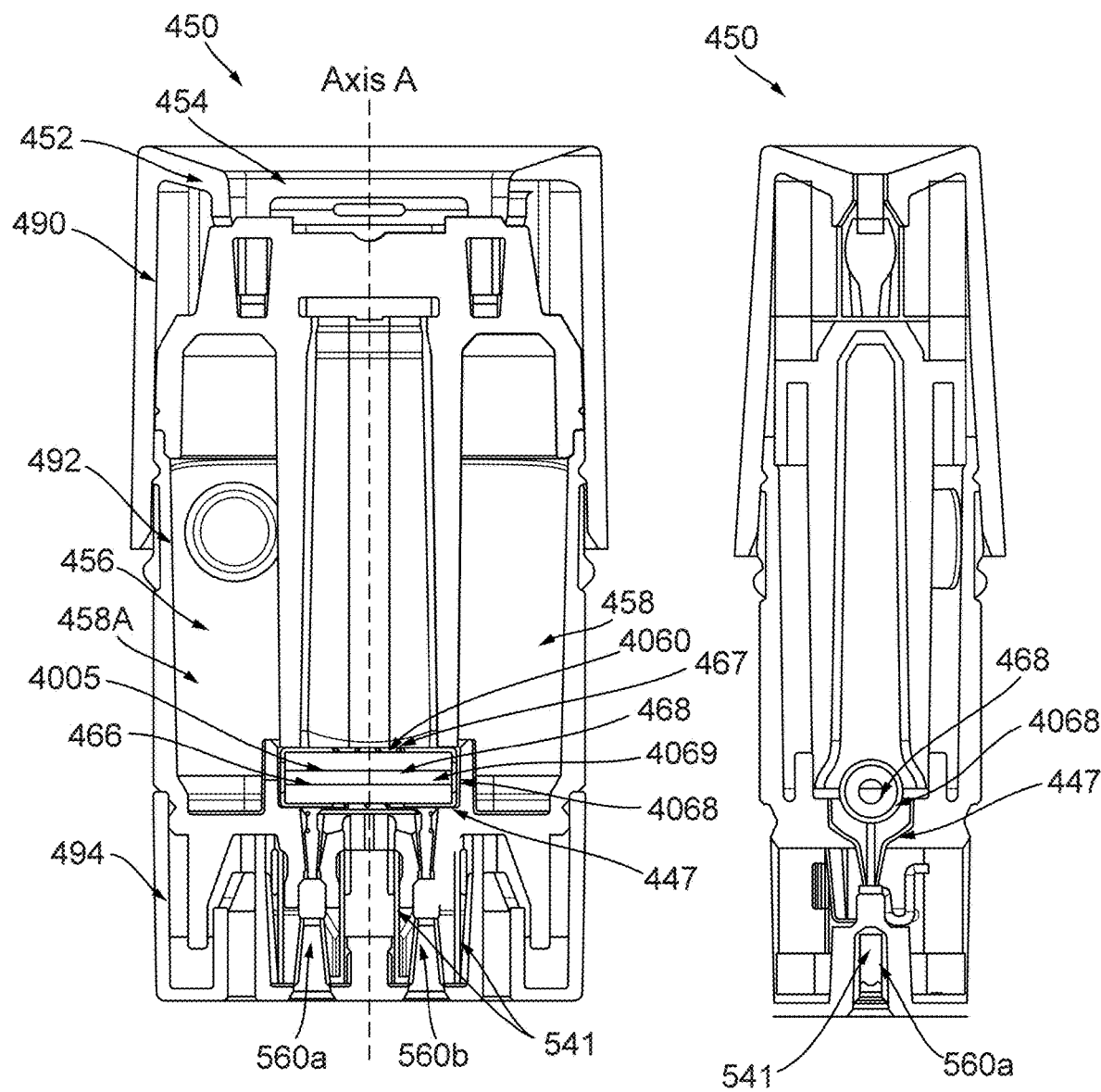
FIGS. 32A-32B illustrate cross-sectional views of a cartridge consistent with implementations of the current subject matter.
Figure 32C:
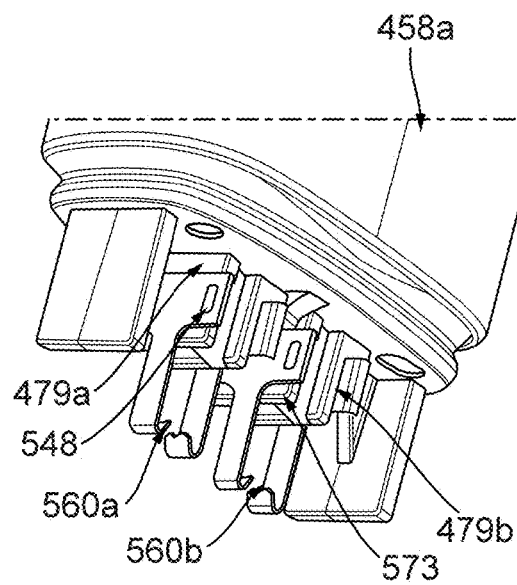
FIGS. 32C-32E illustrate partial views of a cartridge consistent with implementations of the current subject matter.
Figure 32D:
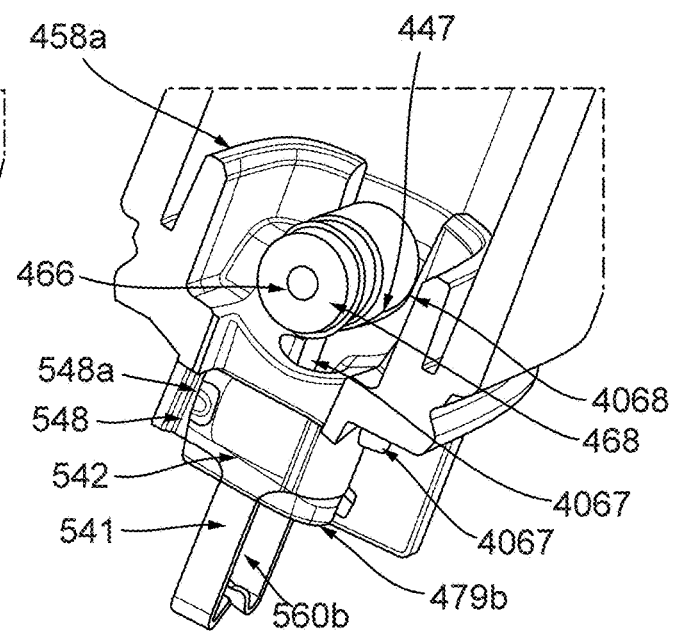
Figure 32E:
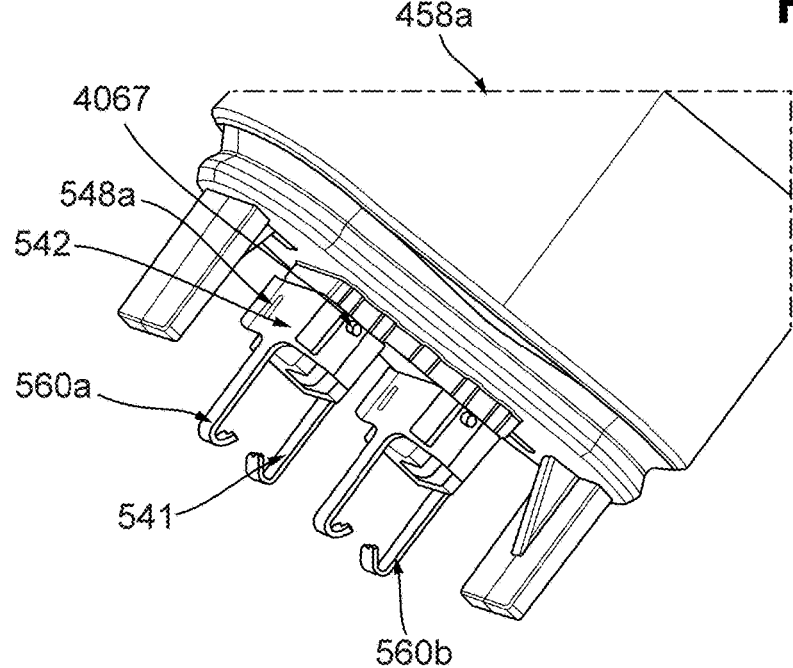

Referring again to FIGS. 33A-33C, the lead connector portion 542 may include a locking feature 548. The locking feature 548 may include one, two, or more locking features 548 positioned on opposing sides of the lead connector portion 542. The locking feature 548 may be positioned between the contact arm 541 and the end portion 544 on the opposing sides of the lead connector portion 542. The locking feature 548 may be configured to couple with a portion of the cartridge body 456, such as the lead guides 479a,b. The locking feature 548 may be defined by a hole formed through each of the opposing sides of the lead connector portion 542. The locking feature 548 is configured to receive a corresponding cartridge body locking feature 548a (e.g., a protrusion) formed on opposing sides of each of the lead guides 479a,b. FIGS. 32C-32E illustrate an example of the receptacles 560a,b coupled to the respective lead guides 479a,b in which the cartridge body locking feature 548a extends through and/or otherwise couples to each of the locking features 548 on the receptacles 560a,b. The locking feature 548 may engage with the corresponding cartridge body locking feature 548a via a snap-fit or other mechanical engagement feature. Thus, the locking feature 548 may secure the receptacles 560a,b to the cartridge body 456. This helps to maintain contact between the receptacles 560a,b and the leads 4067 (and thus, the heating coil 467). This configuration also helps to prevent or limit movement of the receptacles 560a,b, such as in a distal and/or proximal direction, when the power pins 122a,b are inserted within and coupled to each receptacle 560a,b, by providing a counter-force in a direction opposite to the insertion direction. As shown in FIGS. 32C-32E, the lead guides 479a,b may additionally and/or alternatively include a receptacle recess 573, which is positioned around at least a portion of the lead guides 479a,b and is configured to receive the lead connector portion 542. The receptacle recess 573 may additionally and/or alternatively help to secure the receptacles 560a,b to the cartridge body 456, maintain contact between the receptacles 560a,b and the leads 4067 (and thus, the heating coil 467), and prevent or limit movement of the receptacles 560a,b, such as in a distal and/or proximal direction, when the power pins 122a,b are inserted within and coupled to each receptacle 560a,b, by providing a counter-force in a direction opposite to the insertion direction.

FIGS. 34A-40B illustrate features of a cartridge 550 of a vaporizer device, consistent with implementations of the current subject matter. The cartridge 550 may include the same or similar features as the cartridges 150, 250, 350, 450 described herein. For example, the cartridge 350 may include a cartridge body 556 defining, at least in part, a reservoir 558 configured to contain vaporizable material, a mouthpiece 552, and a vaporizing assembly of vapor-generating components positioned within the cartridge body 556 and configured to vaporize the vaporizable material, which are the same or similar to the cartridge body 156, 256, 356, 456 the reservoir 158, 258, 358, 458, and the mouthpiece 152, 252, 352, 452 described herein.

The cartridge 550 may include one or more assemblies that are be coupled together, such as via snap-fit, laser-welding, adhesives, and/or the like. For example, the cartridge 550 may include a mouthpiece assembly 590, a cartridge body assembly 592, and a base assembly 594. The cartridge body assembly 592 may include the cartridge body 556, which may be divided, generally, into a proximal end region 556A, a central region 556B, and a distal end region 556C. The proximal end region 556A of the cartridge body 556 can be coupled to the mouthpiece 552 configured to deliver the vapor to the user. A tank or reservoir body 558A is defined at least in part by the proximal end region 556A and the central region 556B of the cartridge body 556 and is configured to contain an amount of the vaporizable material. The distal end region 556C (alone or together with the central region 556B) of the cartridge body 556 may house one or more components configured to vaporize the material from the reservoir 558 into a vaporization chamber 5005 (see, e.g., FIGS. 35A-35E, 36). The mouthpiece 552 is configured to interface with the user to release the vapor from the vaporization chamber 5005 to the user through one or more openings 554 in the mouthpiece 552, for example, upon the user drawing a breath through the vaporizer device. Each of these components will be described in more detail below, and as noted above, may have the same or similar features and/or properties as the components described above with respect to the cartridge 150, the cartridge 250, the cartridge 350, and/or the cartridge 450 and/or may be interchanged and/or used in combination with one or more of the components of the cartridge 150, the cartridge 250, the cartridge 350, and/or the cartridge 450.

As described herein, the cartridge 550 may include a heater 566, which may be the same or similar to the heater 166, 266, 366, 466. The heater 566 may be configured to heat and/or vaporize at least a portion of the vaporizable material drawn towards the heater 566 from the reservoir 558. In some implementations, the heater 566 may include a resistive element such as a heating coil 567 in thermal contact with a wick 568. The heating coil 567 and the wick 568 may include the same or similar properties and features as the heating coil 167, 267, 367, 467 and the wick 168, 268, 368, 468 described above with respect to the cartridge 150, 250, 350, 450.

FIGS. 37A-37D illustrate an example of the heater 566 consistent with implementations of the current subject matter in which the wick 568 is coupled to end caps 5068 that provide a connection between the heating coil 567 and the power source. In this example, the end caps 5068 provide a connection between the heating coil 567 and respective leads 5067. For example, the end caps 5068 may facilitate the electrical connection of the coil 567 with respective power pin receptacles 560a,b. The power pin receptacles 560a,b may in turn electrically couple to the vaporizer body 110. In some implementations, the end caps 5068 are separately formed and coupled to the wick 568 and/or the heating coil 567. In other implementations, the end caps 5068 may be integrally formed with the heating coil 567 and/or may be electrically and/or physically coupled to the heating coil 567 via welding and/or other mating processes. In some implementations, the heater 566 may be coupled to and/or include the one or more power pin receptacles 560a,b, which are described in more detail below.

Figure 35A:
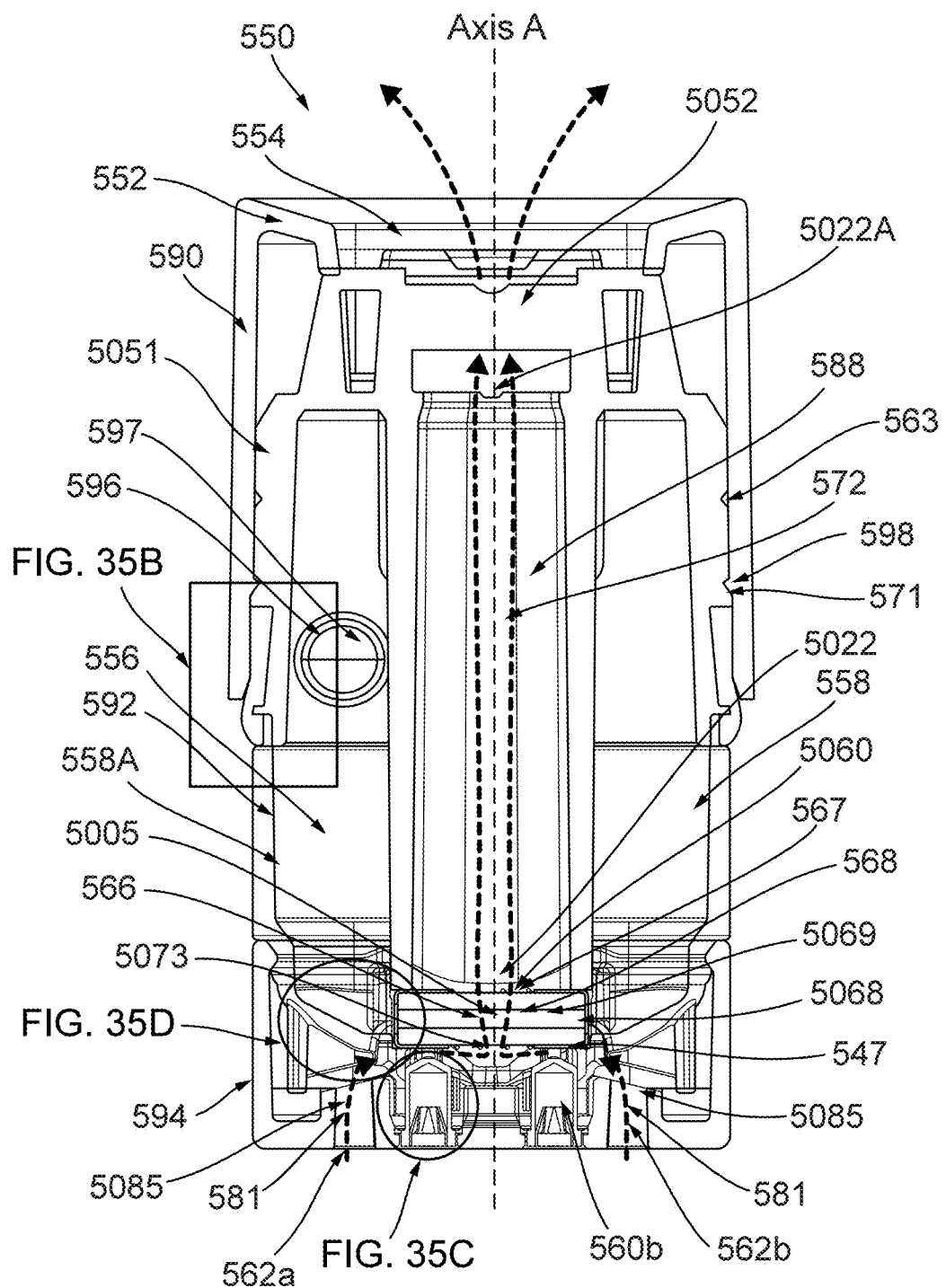

The end caps 5068 may be made of various materials, such as copper, stainless steel, other metals, or combinations thereof. The end caps 5068 may securely and snugly fit over respective ends of the wick 568 (e.g., opposing ends 5065a, b). For example, the end caps 5068 may be thin sleeves that fit over the respective ends of the wick 568. End portions of each of the end caps 5068 have an opening that aligns with a central bore 5069 of the wick 568. The openings may be of a larger diameter than that of the central bore 5069 to further promote wicking of the vaporizable material along the length of the wick 568. As shown in FIGS. 35A and 35D, the reservoir 558 may include a distal side 5058 that is tapered in a distal direction towards the opening of the end caps 5068. The tapered distal side 5058 may further encourage the vaporizable material towards the wick 568 from the interior of the reservoir 558. This configuration may help to improve wicking efficiency of the atomizer (e.g., the heater 566). For example, such configurations may help to ensure that the wick 568 is fully saturated and/or that the wick 568 is saturated or re-saturated more quickly. This may lead to an improved experience for the user, as a more consistent amount of vapor is produced by the atomizer and/or the vapor may be produced more quickly upon activation of the heater 566.

Referring to FIGS. 35A and 35E, the heater 566 may extend across the air path within the vaporization chamber 5005, such as in a transverse direction. A central cannula 572 of a wick housing 588 may be arranged coaxial with the longitudinal axis A of the cartridge 550 and the wick 568 may extend orthogonal to the longitudinal axis A through the central cannula 572. The wick 568 is preferably positioned near a distal-most end region of the reservoir 558 such that the vaporizable material in the reservoir 558 may be fully used. A pair of lateral openings 5075*a*,*b* may extend through the walls of the central cannula 572 of the wick housing 588 near its base where the central cannula 572 couples to an inner distal surface of the reservoir body 558A. The pair of lateral openings 5074*a*,*b* may be aligned across from one another on opposing sides of the central cannula 572. The openings 5074*a*,*b* are provided and sized for coupling to the heater 566.

As shown in FIGS. 35A and 35E, the heater 566, and thus the vaporization chamber 5005, may be positioned within the interior volume of the base assembly 594 when the cartridge body assembly 592 is coupled to the base assembly 594. Positioning the heater 566 at the distal end of the reservoir 558 and within the interior volume of the base assembly 594 increases the volume of the reservoir 558, thereby allowing the reservoir 558 to be capable of storing a greater amount (e.g., 0.5 g, 1.0 g, 0.5 g to 0.75 g, 0.75 g to 1.0 g, 1.0 g to 1.25 g, 1.25 g to 1.5 g, and/or other ranges therebetween, lesser, or greater) of vaporizable material. Positioning the heater 566 within the interior volume of the base assembly 594 and a greater distance away from the proximal side of the reservoir 558 also allows for a greater tolerance when filling the reservoir 558 of the cartridge 550 with the vaporizable material. For example, when the reservoir 558 is filled with the vaporizable material, such as via at least one of the fill ports 597, a filling tolerance may be up to approximately 1%, 5%, 10%, 15%, 20% or greater.

As an example, the intended amount of vaporizable material to be filled into the reservoir 558 may be approximately 1.0 g. Due to various tolerance factors, the actual amount of vaporizable material filled into the reservoir 558 may be up to approximately 1.1 g (e.g., a 10% filling tolerance). Positioning the heater 566 within the interior volume of the base assembly 594 and a greater distance away from the proximal side of the reservoir 558 helps to account for the filling tolerance. In other words, the position of the heater 566 allows for greater error in filling the cartridge 550, as the reservoir 558 has a greater total interior volume and may accommodate for a greater amount of vaporizable material to be filled into the reservoir 558. The position of the heater 566 also allows the heater 566 to be at least partially hidden when viewed from a position external to the cartridge 550, which may improve the overall aesthetic appearance of the cartridge 550, and/or help to more clearly display to the user the amount of vaporizable material remaining in the reservoir 558 during use. Additionally and/or alternatively, the position of the heater 566 increases the efficiency of vaporizing the vaporizable material as the vaporizable material can pass more easily into the wick 568 due at least in part to gravity. Additionally and/or alternatively, the position of the heater 566 improves the manufacturability of the cartridge, as it simplifies the mating (e.g., welding) process when joining the wick housing 588 and the cartridge body assembly 592. For example, before the base assembly 594 is coupled to the cartridge body assembly 592, a proximal end of the wick housing 588 may be coupled with (e.g., laser-welded to) the reservoir body 558A on either size of the heater 566.

Referring again to FIGS. 35A and 35E, the wick 568 of the heater 566 may include a central portion 5060 and opposing ends 5065*a*,*b* positioned on opposite sides of the central portion 5060. The heating coil 567 may be wrapped around the central portion 5060 of the wick 568, which in turn may be positioned within the vaporization chamber 5005. The opposing ends 5065*a*,*b* of the wick 568 may be positioned at least partially outside the vaporization chamber 5005 by extending laterally outward through and/or within the lateral openings 5074*a*,*b* of the central cannula 572. As such, the opposing ends 5065*a*,*b* may be positioned within or in contact with the internal volume of the reservoir 558 whereas the central portion 5060 of the wick 568 wrapped by the heating coil 567 may be positioned entirely inside the vaporization chamber 5005 of the central cannula 572. The leads 5067 may extend away from the central portion 5060 of the wick 568 and from the end caps 5068 and down through respective openings 5073A in the distal support structure 569 of the reservoir body 558A out of the vaporization chamber 5005. As the heater 566 is positioned within the interior volume of the base assembly 594, the leads 5067 may extend further into the interior of the base assembly 594 of the cartridge body 556 where the leads 5067 contact and/or electrically couple with the power pin receptacles 560*a*,*b*.

FIGS. 37A and 37B illustrate an example of the heater 566 and power pin receptacles 560*a*,*b* consistent with implementations of the current subject matter. As noted above, the heater 566 includes end caps 5068 positioned on opposing sides of the heating coil 567 and a lead 5067 extending from each of the end caps 5068. In some implementations, the leads 5067 include one or more materials which may be the same or different from the end caps 5068. The material of the leads 5067 may have a desired resistance to reduce or limit heat generated by the receptacles 560*a*,*b* and/or the leads 5067 and still transfer a sufficient amount of energy to the end caps 5068 and/or the heating coil 567 to heat the heating coil 567 to a desired temperature. In some implementations, at least a portion of the leads 5067 includes gold-plated phosphor bronze, or other conductive materials as described herein. The leads 5067 may therefore be configured to transfer power from the power pins 166*a*,*b* of the vaporizer body 110, via the receptacles 560*a*,*b* to the end caps 5068, and then to the heating coil 567 coupled with the end caps 5068. Additionally and/or alternatively, the leads 5067 may conduct heat away from the end caps 5068, and/or into the airflow through the airflow path. This helps to prevent or limit the end caps 5068 and the heating coil 567 from over-heating and to maintain a consistent temperature at the heating coil 567, where the vaporizable material will be heated. This may also help to pre-heat the air passing through the air path, allowing the vaporizable material to be vaporized into vapor more quickly.

As shown in FIGS. 37A and 37B, each of the leads 5067 includes an extension portion 5071 and a contact portion 5072. The extension portion 5071 may extend from an exterior surface of the corresponding end cap 5068. The extension portion 5071 may extend from the end cap 5068 in a direction that is generally perpendicular to a lateral axis that is centrally aligned with the opening of the end cap 5068. In other implementations, as shown in FIGS. 37A and 37B, the extension portion 5071 may extend at from the end cap 5068 in a distal direction at an angle, such as towards a side surface of each corresponding receptacle 560*a*,*b*. In some implementations, the extension portion 5071 is straight (e.g., unbent). In other implementations, the extension portion 5071 is curved. The extension portion 5071 may extend between the exterior surface of the end cap 5068 and the contact portion 5072 of the lead 5067.

The contact portion 5072 extends from the extension portion 5071 and contacts at least a portion of a respective receptacle of the receptacles 560a,b to establish an electrical connection between the receptacles 560a,b and the end caps 5068. For example, the contact portion 5072 may extend in a direction that is parallel to the receptacles 560a,b. The contact portion 5072 may be configured to contact a side surface of the corresponding receptacle 560a,b. The lead 5067 may be press fit, welded to, and/or otherwise coupled to the receptacle 560a to establish a secure electrical connection. In some implementations, for example, the lead 5067 may be welded (e.g., laser-welded, resistance-welded, and/or the like) to the receptacle 560a. Welding the connection between the lead 5067 and the receptacle 560a provides a robust electrical connection and helps to ensure that the lead 5067 maintains contact with the receptacle 560a during assembly and/or during use of the cartridge 550. Though the lead 5067 is described with respect to the receptacle 560a, the second lead 5067 may contact and/or communicate with the receptacle 560b in the same manner.

The contact portion 5072 may be bent relative to the extension portion 5071 and extend at an angle from the extension portion. 5071. The contact portion 5072 of the lead 5067 may extend about at least a portion of the receptacle 560a. For example, as noted above, the contact portion 5072 may contact the receptacle 560a at at least one, two, or more surfaces, such as along a side surface of the receptacle 560a. This configuration helps to secure the lead 5067 to the receptacle 560a and to ensure that the lead 5067 maintains contact and/or the electrical connection between the lead 5067 and the receptacle 560a in use. Such configurations increase the length and/or area of engagement between the lead 5067 and the receptacle 560a, to improve the efficiency in transferring power between the receptacle 560a and the lead 5067.

To further improve the securement and/or electrical connection between the lead 5067 and the receptacle 560a, the distal support structure 569 may include a lead securement portion 5073B. For example, at least a portion of the lead 5067, such as the extension portion 5071 and/or the contact portion 5072 may extend through the openings 5073A of the distal support structure 569 into the lead securement portion 5073B. Thus, the lead securement portion 5073B may act as a lead guide that guides the lead 5067 into contact with the receptacle 560a. The lead securement portion 5073B may be shaped and/or sized to surround at least the portion of the lead 5067 extending through the openings 5073A and/or contact at least the portion of the lead 5067. Thus, the lead securement portion 5073B may help to reduce and/or limit heat radiating from the lead 5067 and/or may help to maintain contact between the lead 5067 and the receptacle 560a.

As noted above, the heater 566 and the distal end of the reservoir 558 may be positioned within the interior volume of the base assembly 594. This allows the receptacle 560a to be press-fit directly into the cartridge body assembly 592, such as at least partially through the openings 5073A of the distal support structure 569. Such configurations may increase the length of engagement between the receptacle 560a and the lead 5067, which improves the efficiency in transferring power between the receptacle 560a and the lead 5067 and/or ensures engagement between the lead 5067 and the receptacle 560a. This also helps to reduce variation in placement and/or movement of the lead 5067 with respect to the receptacle 560a, thereby further improving the power transfer efficiency and/or electrical connection. In some implementations, press-fitting the receptacle 560a into contact with the cartridge body assembly 592 (e.g., the distal support structure 569) improves the seal between the cartridge body assembly 592 and the base assembly 594. For example, the press-fit configuration (alone and/or together with a barb or other mating feature on the receptacle 560a,b) may help to reduce or limit vaporizable material from passing out of the reservoir 558, passing into contact with one or more internal components of the base assembly 594, and/or leaking out of the cartridge 550.

Figure 38A:
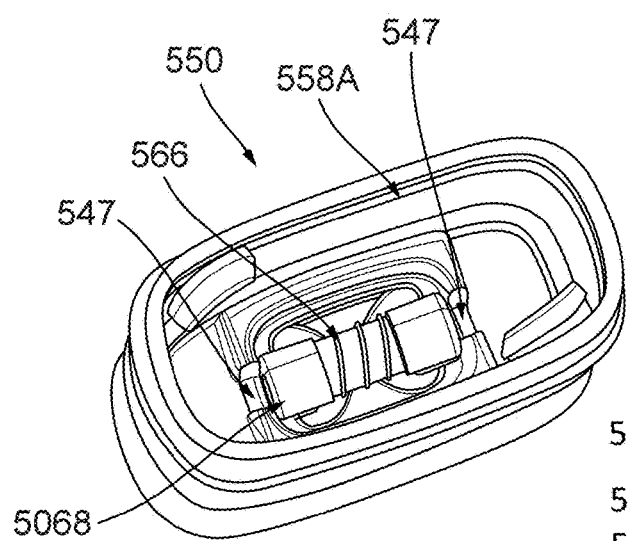
FIGS. 38A-38C illustrate partial views of a cartridge consistent with implementations of the current subject matter.
Figure 38B:
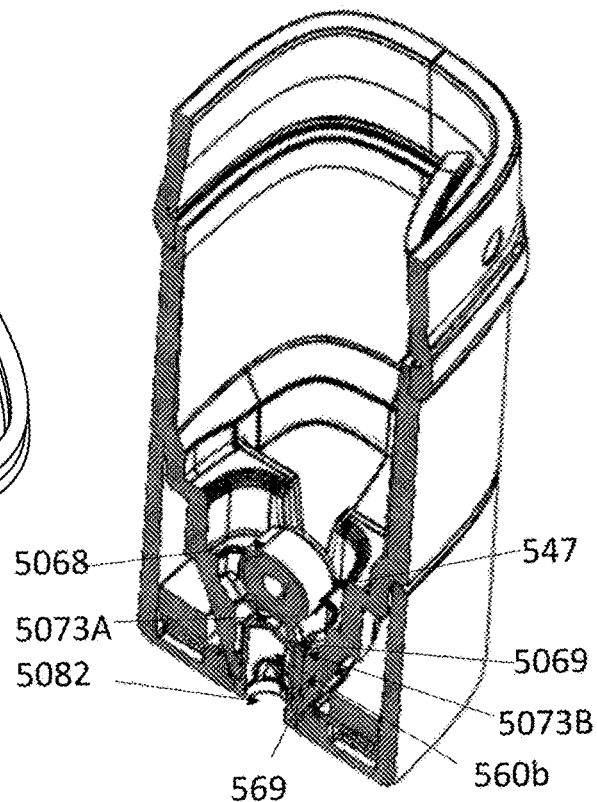
Figure 38C:
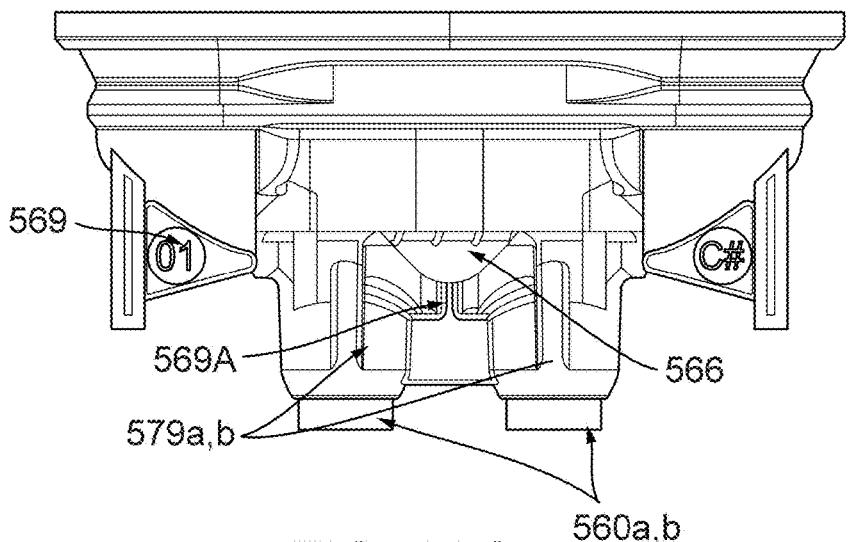

Referring to FIGS. 38A-38C, the reservoir body 558A (e.g., the distal support structure 569) may include an end cap contact 547. The end cap contact 547 may be integrally formed with the reservoir body 558A, within an interior of the reservoir body 558A. The end cap contact 547 may include two or more end cap contacts 547 that correspond with and support each of the end caps 5068. The end cap contact 547 may define a seat in which each end cap 5068 is positioned. Each end cap 5068 may rest on and/or within each end cap contact 547. For example, a surface of the end cap contact 547 may contact an outer surface of the end cap 5068. The surface of the end cap contact 547 may be shaped to correspond to a shape of the end cap 5068. For example, the surface of the end cap contact 547 may include a rounded, curved, and/or semi-circular shape that corresponds to the rounded, curved, and/or circular shape of the end cap 5068. This helps to limit or prevent movement of the end caps 5068 and/or the heater 566 within the reservoir body 558A, which helps to maintain electrical communication between each end cap 3068 and the corresponding receptacle 560a,b.

In some implementations, the wick 568 and end caps 5068 may be properly positioned within the reservoir body 558A and/the cartridge body 556 when the wick housing 588 is inserted into the cartridge body 556. For example, the wick housing 588 (e.g., the lateral openings 5074a,b) may contact the end caps 5068 and press the end caps 5068 into contact with the end cap contacts 547, thereby locking the end caps 5068 into place and/or sealing around an exterior surface of the end caps 5068.

As shown in FIGS. 38A-38C, the distal support structure 569 includes at least one (e.g., one, two, or more) guides 579a,b. The guides 579a,b include and/or form a part of the lead securement portion 5073B. The guides 579a,b may extend distally from a distal portion of the distal support structure 569. The guides 579a,b may include a bore extending through a thickness of the guides 579a,b from a generally circular opening 5073A on the upper surface of the distal support structure 569 to another generally circular opening 5082. The bore of the guides 579a,b may be cylindrical and have an inner diameter sized to receive and mate with the outer surface of the power pin receptacles 560a,b such that the power pin receptacles 560a,b are securely held within the guides 579a,b. The opening 5073A into the bore of the guides 579a,b on the upper surface may have an inner diameter that is slightly larger than the inner diameter of the bore. For example, the opening 5073A into the bore of the guides 579a,b may be funnel-shaped. Additionally, and/or alternatively, the opening 5082 shaped to receive the power pin receptacles 560a,b, which are press-fit into the bore of the guides 579a,b. As shown in FIGS. 35C, 37A, 37B, and 37D, for example, the power pin receptacles 560a,b may include a barb or other mating feature that retains the power pin receptacles 560a,b within the bore of the guides 579a,b when the power pin receptacles 560a,b are press-fit into the guides 579a,b. The mating feature may additionally and/or alternatively seal the power pin receptacles 560a,b within the bore such that vaporizable material may not pass through the bore, thereby limiting and/or preventing leakage of the vaporizable material out of the cartridge 550.

Referring back to FIGS. 38A-38C, the guides 579a,b may advantageously eliminate the cumbersome installation by hand of properly inserting the leads 5067 into contact with the receptacles 560a,b. For example, the power pin receptacles 560a,b may be press-fit into the bore of the guides 579a,b before and/or after the leads 5067 are positioned within the lead securement portion 5073B. Thus, the guides 579a,b are configured to receive and securely hold the leads 5067 and the power pin receptacles 560a,b, as well as reduce the free space between the heater within the vaporization chamber 5005 and the power pin receptacles 560a,b to improve assembly.

In some implementations, the distal support structure 569 may include a capillary feature 569A (see FIG. 38C). The capillary feature 569A may be positioned on one, two, three, or four sides (e.g., opposing sides) of the distal support structure 569. For example, the capillary feature 569A may be positioned on opposing sides of the distal support structure 569 and centrally aligned between the pair of guides 579a,b. The capillary feature 569A may include tapered and/or parallel walls. For example, as shown in FIG. 38C, the capillary feature 569A may have a width of approximately 0.6 mm, 0.25 mm to 0.5 mm, 0.5 mm to 0.75 mm, 0.75 mm to 1.0 mm. The capillary feature 569A may be configured to direct vaporizable material that may leak or otherwise pass from a central portion of the heater 566 (e.g., from a central portion of the wick). The capillary feature 569A may direct the vaporizable material towards the absorbent pad 575 to be absorbed by the absorbent pad 575 positioned within the base assembly 594. The width of the capillary feature 569A causes capillary pressure to act on the vaporizable material, causing the vaporizable material to travel along the capillary feature 569A to the absorbent pad 575. Such configurations may help to limit or prevent leakage of the vaporizable material out of the cartridge 550.

Figure 39A:
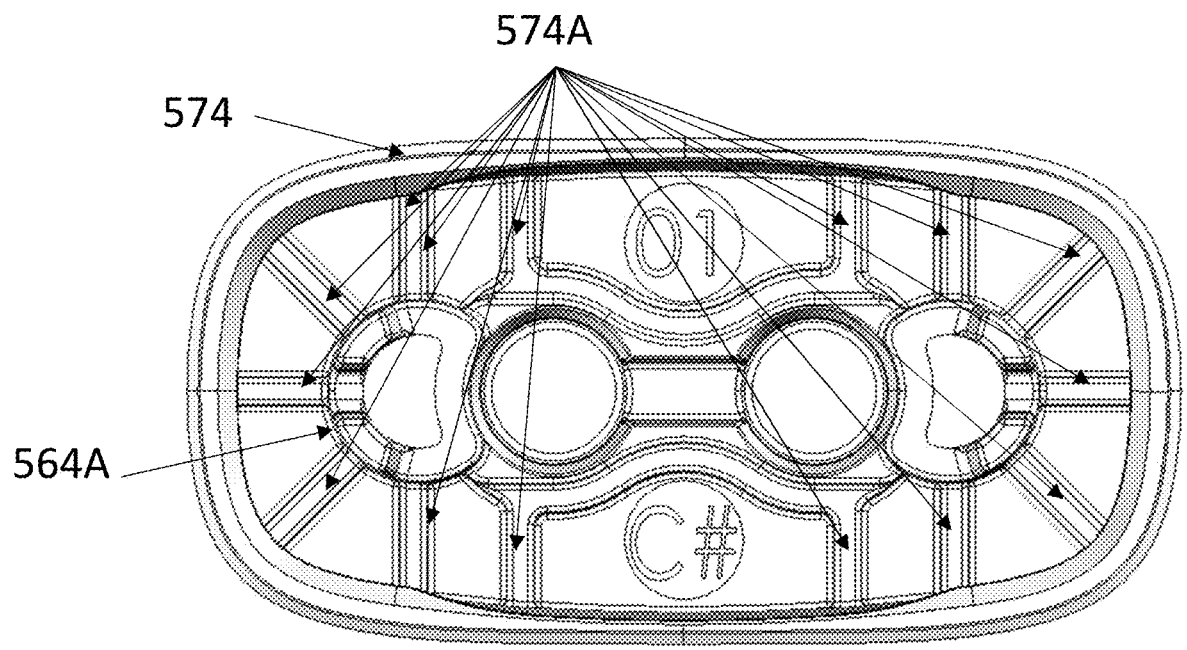
FIGS. 39A-39B illustrate partial views of a cartridge consistent with implementations of the current subject matter.
Figure 39B:
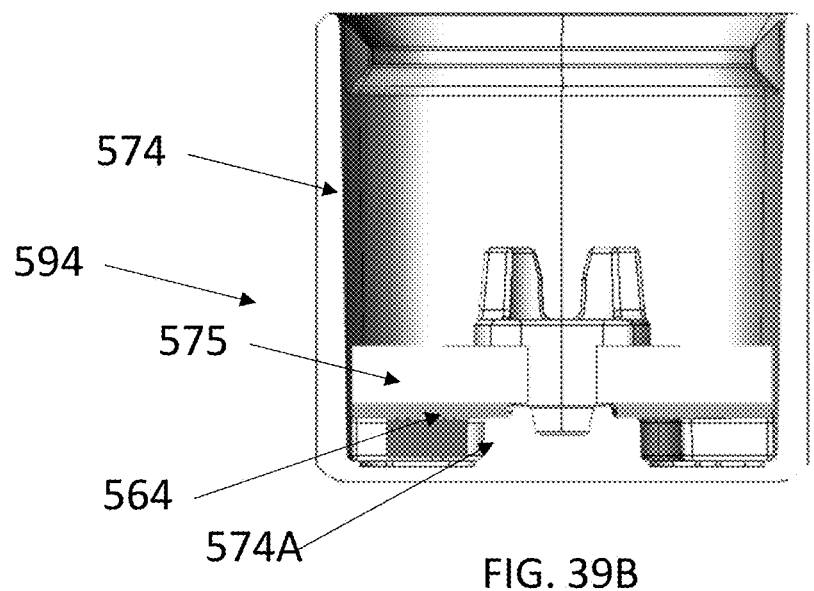

FIG. 39A illustrates a top view of an interior of the base 574, consistent with implementations of the current subject matter. FIG. 39B illustrates a side cross-sectional view of the base assembly 594, including the base 574, the absorbent pad 575, and the tag 564. The base assembly 594 may mate with the cartridge body assembly 592 via a snap-fit arrangement. Additionally, and/or alternatively, the base assembly 594 may mate with the cartridge body assembly 592 (e.g., the reservoir body 558A) via laser-welding or another mating process.

As shown in FIG. 38B, the tag 564, which is described in more detail below, may be positioned within an interior volume of the base 574, proximate to a distal face of the base. For example, the tag 564 may be positioned within the base 574 opposite the external distal face of the base. Positioning the tag 564 within the base 574 may protect the tag 564 from user interference and/or other external conditions. As a result, positioning the tag 564 within the base 574 may improve the connection between the tag 564 and the vaporizer device 110. To further improve RF performance and/or the connection between the tag 564 and the vaporizer device 110, the tag 564 may be positioned within the base 574 with a chip side of the tag 564 facing the distal wall of the base 574. This positions the chip of the tag 564 closer to the exterior of the cartridge 550 and within a greater proximity to the device 110 in use. This configuration may also help to reduce or limit interference in the connection between the tag 564 and the device 110. Additionally and/or alternatively, positioning the tag 564 within the base 574 may allow the tag 564 to be coupled with the cartridge 550 without the use of an adhesive. Accordingly, this configuration may extend the usable life of the tag 564. In some implementations, this configuration may also help to may it more difficult for the tag 564 to be removed from the cartridge 550 and/or reduce the likelihood that the user or another party may remove the tag 564 from the cartridge 550, thereby improving the security and/or integrity of the cartridge 550. In some implementations, to further improve the stability of the tag 564 and/or prevent movement of the tag 564 within the base 574, the base 574 may include a tag recess 564A. The tag recess 564A may be shaped and/or sized to correspond to the shape and/or size of the tag 564 and receive the tag 564. Thus, the tag 564 may be at least partially positioned within the tag recess 564A.

In some implementations, the base 574 includes one or more base ribs 574A upon which the tag 564 is positioned within the tag recess 564A. The base ribs 574A extend from a distal wall of the base 574 towards an interior volume of the base 574. The base ribs 574A space the tag 564 from the distal wall of the base 574. The base ribs 574A help to increase the structural integrity of the base 574 while reducing the amount of material used to form the base 574. The base ribs 574A provide a flat and/or stable surface upon which the internal components of the base assembly 594 (e.g., the tag 564 and the pad 575) may be positioned. In some implementations, the chip of the tag 564 may be positioned within the space formed between adjacent base ribs 574A to position the chip of the tag 564 closer to the exterior of the cartridge 550, which further improves RF performance and limits or reduces interference in the connection between the tag 564 and the vaporizer device 110.

Referring to FIG. 39B, the base 574 may also include one or more absorbent pads 575 to prevent leakage of the vaporizable material from the reservoir 558 and out of the cartridge 550 and/or to prevent vaporizable material from interfering with the electronics (e.g., receptacles 560a,b) of the cartridge 550. The pad 575 adds a layer of redundancy against vaporizable material leaking from the cartridge 550. The pad 575 may be oriented to prevent leakage in this region of the cartridge 550 without disrupting airflow or formation of vapor. In some implementations, the pad 575 has a thickness of approximately 1.0 mm, 0.25 mm to 0.5 mm, 0.5 mm to 0.75 mm, 0.75 mm to 1.0 mm, 1.0 mm to 1.25 mm, 1.25 mm to 1.5 mm or other ranges therebetween, greater, or lesser. The pad 575 may be sufficiently thick to absorb the vaporizable material while preventing or limiting the vaporizable material from passing to the tag 564 and/or out of the cartridge 550.

Figure 36:
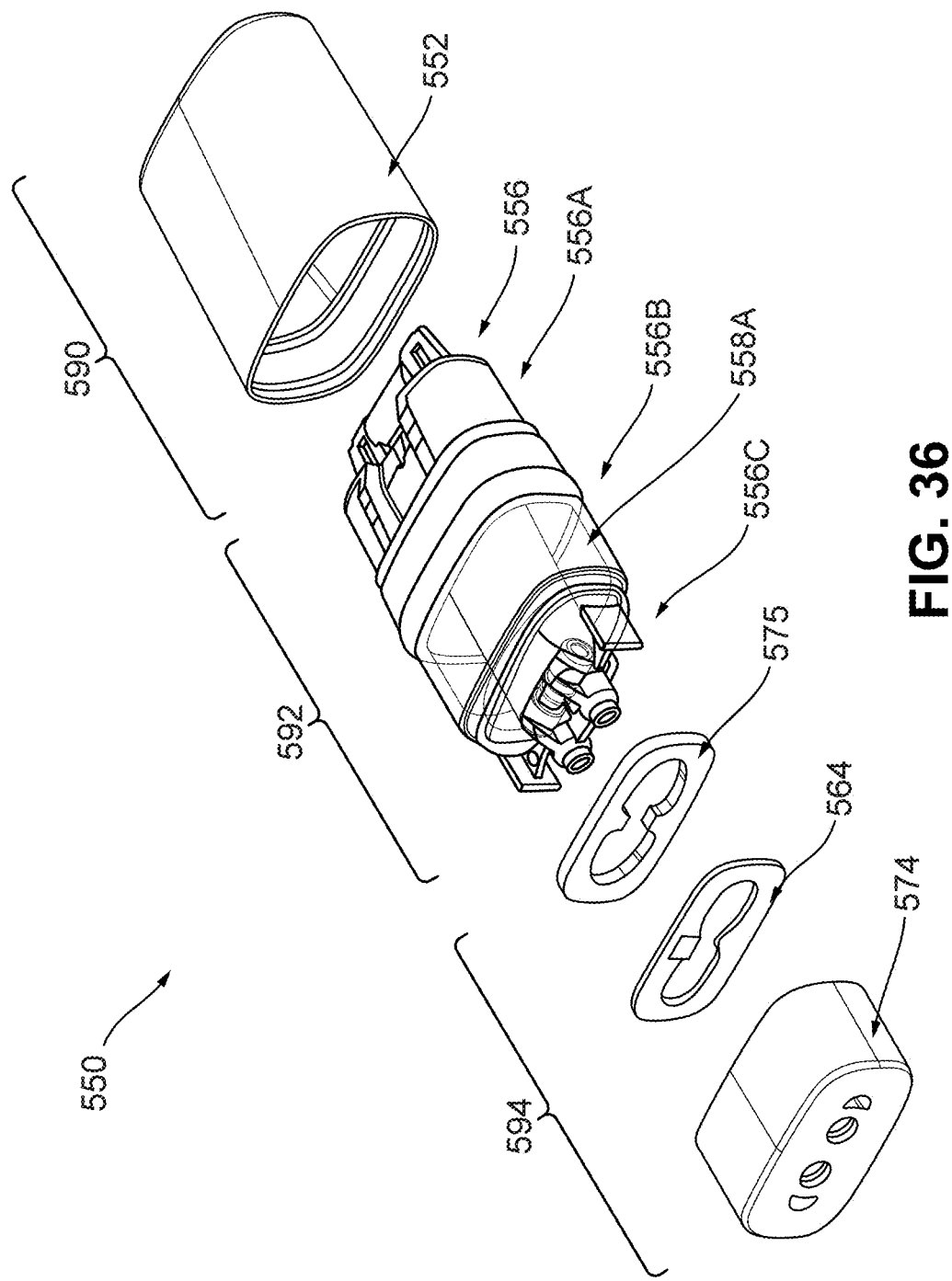
FIG. 36 illustrates an exploded view of a cartridge consistent with implementations of the current subject matter.

As shown in FIGS. 36 and 39B, for example, the pad 575 may include a flattened disk-shape defining a central opening and thus, has a ring-like shape, to allow air to pass through without disrupting airflow. It should be appreciated the pad 575 may have a ring shape, but need not be a circular ring-shaped object. Rather, the absorbent pad 575 may be a flat, non-circular ring having a perimeter in the shape of an oval, ellipse, or rectangle. The size and shape of the pad 575 may be configured to fit within open spaces of the base 574 thereby filling at least a portion of the base 574. The pad 575 may be wedged between or otherwise compressed between the tag 564 and the connection features 583 of the distal support structure 569 when the base assembly 594 is coupled with the cartridge body assembly 592.

Referring back to FIGS. 35A-35E, the cartridge 550 includes the mouthpiece 552. The mouthpiece 552 may have an overall length of approximately 19 mm, 10 to 15 mm, 15 to 20 mm, 20 to 25 mm, and/or the like. The length of the mouthpiece 552 may indicate an amount of vaporizable material stored within the reservoir 558 of the cartridge 550. For example, a mouthpiece 552 having a greater length may indicate that the reservoir 558 has a greater maximum capacity (e.g., for storing vaporizable material than a mouthpiece 552 having a lesser length. In some implementations, a mouthpiece 552 having a lesser length may indicate that the reservoir 558 has a lesser maximum capacity for storing vaporizable material than a mouthpiece 552 having a greater length. For example, FIGS. 41A-41D illustrate an example of the cartridge 550 having a mouthpiece with a length of approximately 15.6 mm, 10 to 15 mm, 15 to 20 mm, 20 to 25 mm, and/or the like. Thus, the shorter mouthpiece 552 of the cartridge 550 shown in FIGS. 41A-41D relative to the mouthpiece of the cartridge 550 shown in FIGS. 34A-40B may indicate that the reservoir 558 of the cartridge 550 shown in FIGS. 41A-41D is configured to hold a maximum volume (e.g., 0.5 g, among other ranges described herein) of vaporizable material that is less than the maximum volume (e.g., 1.0 g, among other ranges described herein) of vaporizable material stored in the reservoir 558 of the cartridge 550 shown in FIGS. 34A-40B.

As described herein, the mouthpiece 552 may be coupled to the cartridge body assembly 592. For example, the mouthpiece 552 may be first coupled to a first portion of the cartridge body assembly 592, such as a first portion of the wick housing 588, leaving the fill port 597 exposed for filling the reservoir 558 of the cartridge 550. Once the filling process is complete, the mouthpiece 552 may slide along an exterior surface of the wick housing 588 in a distal direction. The mouthpiece 552 may then be coupled to a second portion of the cartridge body assembly 592, such as a second portion of the wick housing 588, to secure and/or cover the fill port.

For example, as described herein the proximal wick housing base 5051 of the wick housing 588 may be configured to, at least temporarily, couple with the mouthpiece 552. The mouthpiece 552 may slide over at least a part of the proximal end region 556A of the cartridge body 556. For example, the mouthpiece 552 may slide over at least the proximal wick housing base 5051 of the wick housing 588. In other words, at least a portion of the cartridge body assembly 592, such as the proximal wick housing base 5051, may be inserted into the interior volume of the mouthpiece 552. After insertion of the proximal wick housing base 5051 into the mouthpiece 552, the inwardly-projecting feature 598 of the mouthpiece 552 may engage with one or more proximal wick housing grooves 563 to secure the mouthpiece 552 to the cartridge body assembly 592. In some implementations, when the inwardly-projecting feature 598 of the mouthpiece 552 is secured to the one or more proximal wick housing grooves 563, the interior volume of the cartridge 550, such as the reservoir 558, may be filled with the vaporizable material, via the fill port 597. The reservoir 558 may be filled via the fill port 597 and/or the fill port seal 596.

In some implementations, after the reservoir 558 has been at least partially filled with the vaporizable material and/or after the inwardly-projecting feature 598 of the mouthpiece 552 is secured to the one or more proximal wick housing grooves 563, the cartridge body assembly 592 may be further inserted into the interior volume of the mouthpiece 552. For example, the cartridge body assembly 592 may be further inserted into the interior volume of the mouthpiece 552 until the inwardly-projecting feature 598 engages with the distal wick housing groove 571. As described herein, the distal wick housing groove 571 may be formed on the wick housing 588 on one side of the mouthpiece seal 577 and distally relative to the proximal wick housing groove 563. As a result, the mouthpiece may enclose the septum of the fill port seal 596, preventing or reducing oil and/or air leakage through the fill port 597 from within the cartridge 550. In some implementations, the proximal wick housing grooves 563 and/or the proximal wick housing groove 571 may be shaped and/or sized to allow the inwardly-projecting feature 598 of the mouthpiece 552 to slide over a proximal side and/or a distal side of each groove in one direction (e.g., in a distal direction) and prevent the inwardly-projecting feature 598 of the mouthpiece 552 to slide over the proximal side and/or the distal side of each groove in an opposite direction (e.g., in a proximal direction). This helps to add additional security to the cartridge 550. For example, once the cartridge 550 is filled by an authorized filler and/or with an authorized and/or tested vaporizable material, in some implementations, the mouthpiece 552 may not be removed without damaging the cartridge 550. This may prevent the cartridge 550 from being refilled, such as with an unauthorized substance and/or by an unauthorized party. Such configuration may also help to improve the user experience, as the user may be aware that the cartridge 550 may include the authorized vaporizable material. Such configuration may additionally and/or alternatively allow for a pre-cut septum to be used at the fill port to enable blunt needle filling.

In some implementations, to prevent leakage of vaporizable material from the interior volume of the cartridge body assembly 592 (e.g., from the interior volume of the cartridge body 556, the wick housing 588 and the reservoir body 558A), one or more components of the cartridge body assembly 592 may be joined by a mating process, such as laser-welding and/or by application of an adhesive, a snap-fit arrangement, and/or the like. For example, the wick housing 588 and the reservoir body 558A may be laser-welded at at least one, two, three, or more interfaces to reduce leaking of the vaporizable material.

For example, FIGS. 35A and 35B show at least two joining interfaces at which the reservoir body 558A may be laser-welded or otherwise joined to the wick housing 588. As shown, the reservoir body 558A may be laser-welded to the wick housing 588 at a joining interface 579A. The joining interface 579A may be formed between an interior surface of the reservoir body 558A, such as at a portion that extends from the proximal end of the reservoir body 558A, and at least a portion of an exterior surface of the wick housing 588 (e.g., the proximal wick housing base 5051). Joining the wick housing 588 to the reservoir body 558A at at least the joining interface 579A may create an improved seal to define the reservoir 558 and to prevent or reduce leaking of vaporizable material from the cartridge 550. This configuration may also help to expand the size of the interior volume of the reservoir 558 to allow the reservoir 558 to contain a greater amount of vaporizable material to be vaporized (e.g., a maximum of approximately 1.0 g, 0.1 g to 0.25 g, 0.25 g to 0.5 g, 0.5 g to 0.75 g, 0.75 g to 1.0 g, 1.0 g to 1.25 g, 1.0 g to 2.0 g, and/or other ranges therebetween, greater, or lesser). This may improve the user experience, as the user may use the cartridge 550 for a greater length of time, such as during a single session and/or over a series of sessions.

Additionally and/or alternatively, in some implementations, such as in the cartridge 550 shown in FIGS. 41A-41D, the reservoir 558 may have a volume that is lesser than the volume of the reservoir 558 shown in FIGS. 34A-40B and is thus capable of containing a lesser amount of the vaporizable material. For example, the wick housing 588 shown in FIGS. 41A-41D may have a maximum internal height max h (e.g., from the proximal-most end of the wick housing to the distal-most point within the interior of the wick housing) of approximately 15.8 mm, whereas the wick housing 588 shown in FIGS. 34A-40B may have a maximum internal height max h (e.g., from the proximal-most end of the wick housing to the distal-most point within the interior of the wick housing) of approximately 22.6 mm Additionally and/or alternatively, the wick housing 588 shown in FIGS. 41A-41D may have an internal height h (e.g., from a surface 559 of the wick housing 588 where the reservoir body 558A couples to the wick housing 588 to the distal-most point within the interior of the wick housing) of approximately 6.5 mm, whereas the wick housing 588 shown in FIGS. 34A-40B may have an internal height h (e.g., from a surface 559 of the wick housing 588 where the reservoir body 558A couples to the wick housing 588 to the distal-most point within the interior of the wick housing) of approximately 13.3 mm Additionally and/or alternatively, the reservoir 558 shown in FIGS. 41A-41D may have a maximum height (e.g., from the proximal-most end of the wick housing to the distal-most point of the reservoir) of approximately 17.5 mm, whereas the wick reservoir 558 shown in FIGS. 34A-40B may have a maximum internal height (e.g., from the proximal-most end of the wick housing to the distal-most point of the reservoir) of approximately 24.3 mm Thus, the reservoir 558 of the cartridge 550 shown in FIGS. 41A-41D may contain a maximum amount of vaporizable material to be vaporized of approximately 0.5 g, 0.1 g to 0.25 g, 0.25 g to 0.5 g, 0.5 g to 0.75 g, and/or other ranges therebetween, greater, or lesser.

In some implementations, the mouthpiece seal 577 may be positioned over at least a portion of the joining interface 579A. For example, as shown in FIG. 35B, the mouthpiece seal 577 is positioned around at least a portion of the wick housing 588 and the reservoir body 558A. This prevents access to the joining interface 579A. This configuration may also improve the seal between the wick housing 588 and the reservoir body 558A to improve the ability of the joined components to prevent or limit leakage of vaporizable material from the reservoir 558. Such configurations may improve the structural integrity and/or stiffness of the joined components at at least the joining interface 579A by increasing the overall thickness of the components surrounding the joining interface 579A, which decreases bending around the joining interface 579A. Additionally and/or alternatively, positioning the mouthpiece seal 577 over at least the portion of the joining interface 579A helps limit bending or other movement of the wick housing 288, the reservoir body 558A, and/or the mouthpiece seal 577 during filling, such as when a needle is inserted into and/or removed from the fill port 597 and/or the fill port seal 596. Such configurations may also help to prevent the fill port seal 596 (e.g., the septum) from bending into or from being pulled into the interior of the reservoir 558 when the filling needle is inserted into the fill port 597 for filling the reservoir 558.

In some implementations, the placement of the mouthpiece seal 577, the shape of the mouthpiece seal 577, the position of the joining interface 579A, and/or the shape of the wick housing 588, for example, may improve the structural integrity of the cartridge 550 and help to improve the ability of the cartridge 550 to withstand a greater force during insertion and/or removal of the cartridge 550 from the device 110 and/or to withstand insertion and/or removal of the cartridge 550 for a greater number of insertions and/or removals. For example, the wick housing 588 may include a joining rib 579B (see FIG. 35B) that extends about all or a portion of a perimeter of the wick housing 588. The joining rib 579B may extend laterally outwards from the wick housing 588. The joining rib 579B may be coupled to a corresponding joining recess 577A formed along an interior surface of the mouthpiece seal 577. For example, the joining rib 579B may be press-fit into the joining recess 577A.

The joining rib 579B and/or the joining recess 577A may improve the seal formed between the wick housing 588 and the reservoir body 558A. For example, the joining rib 579B and/or the joining recess 577A may prevent or limit rolling and/or wrinkling of the mouthpiece seal 577, such as during insertion of the cartridge 550 into the vaporizer device 110, during removal of the cartridge 550 from the vaporizer device, and/or during filling of the cartridge 550. The joining rib 579B may additionally and/or alternatively absorb and/or concentrate the force applied on the mouthpiece seal 577 to further strengthen the mouthpiece seal 577. For example, the joining rib 579B may reduce the angle of the pressure exerted by the vaporizer device 100 during insertion and/or removal of the cartridge 550, thereby reducing the impact of the force applied to the mouthpiece seal 577. In some implementations, the joining rib 579B also concentrates the force applied by the edge of the vaporizer device 110 to a distal side of the joining rib 579B to reduce the impact of the force applied to the mouthpiece seal 577.

In some implementations, the mouthpiece seal 577 may additionally and/or alternatively include a region of increased thickness 577B surrounding the joining rib 579B and/or the joining recess 577A to improve the strength and/or stiffness of the mouthpiece seal 577 surrounding the joining rib 579B and/or the joining interface 579A. The region of increased thickness 577B may extend from a distal end of the mouthpiece seal 577 (e.g., positioned distally relative to the joining rib 579B and/or the joining recess 577A) in a proximal direction to at least a portion of the mouthpiece seal 577 that contacts a distal edge of the mouthpiece 552 (e.g., positioned proximally relative to the joining rib 579B and/or the joining recess 577A). Such configurations may also prevent or limit rolling and/or wrinkling of the mouthpiece seal 577, such as during insertion of the cartridge 550 into the vaporizer device 110, during removal of the cartridge 550 from the vaporizer device, and/or during filling of the cartridge 550. The region of increased thickness 577B may also help to prevent rolling or rocking of the cartridge 550 when the cartridge is fully inserted into the vaporizer device 110. This improves the seal formed between the cartridge 550 and the vaporizer device 110 and thus, improves airflow and/or heating efficiency.

FIGS. 40A-40B and 41C-41D illustrate examples of the wick housing 588, absorbent pads 570, and heater 566. In some implementations, a proximal portion of the wick housing 588 includes a plurality of cutouts 587 (see FIGS. 40A and 41C-41D). The cutouts 587 of the wick housing 588 may reduce the amount of material used to form the wick housing 588, while still maintaining the structural integrity of the wick housing 588. Thus, the cutouts 587 may reduce the overall weight of the cartridge 550. In some implementations, the cutouts 587 help to make the formation (e.g., molding) of the wick housing 588 more consistent and have an improved quality by, for example, reducing the thickness of the proximal end of the wick housing 588.

Figure 40A:
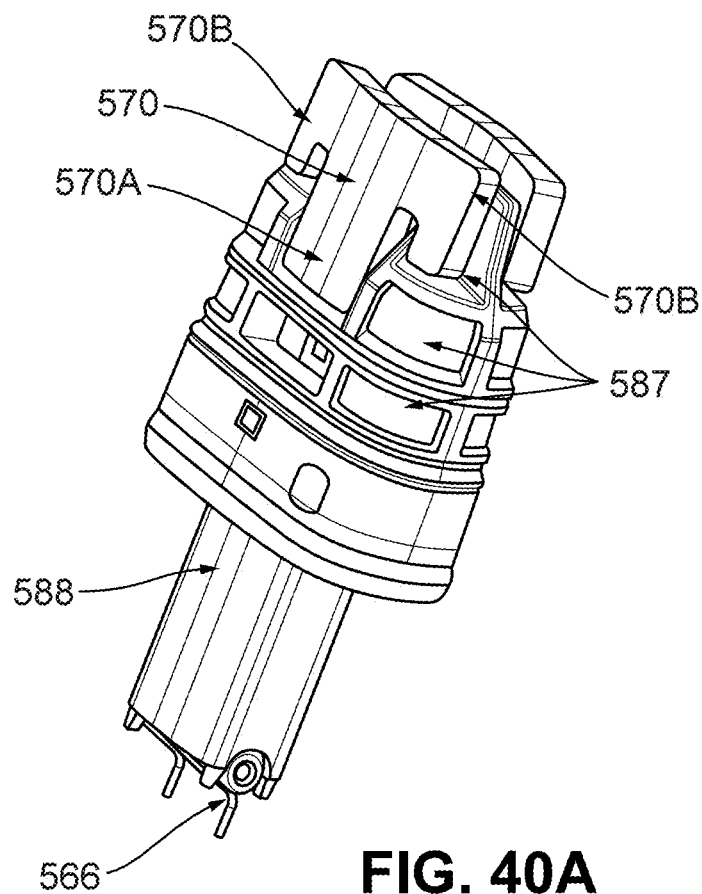
FIGS. 40A-40B illustrate partial views of a cartridge consistent with implementations of the current subject matter.
Figure 40B:
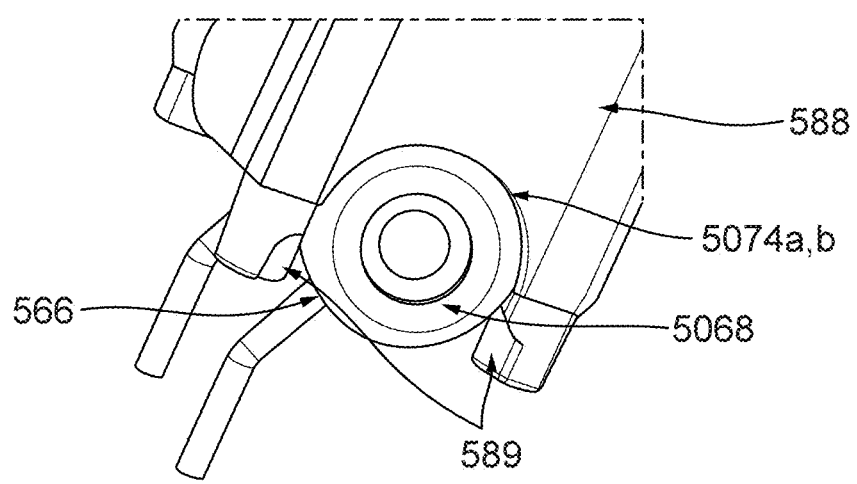
Figure 41A:
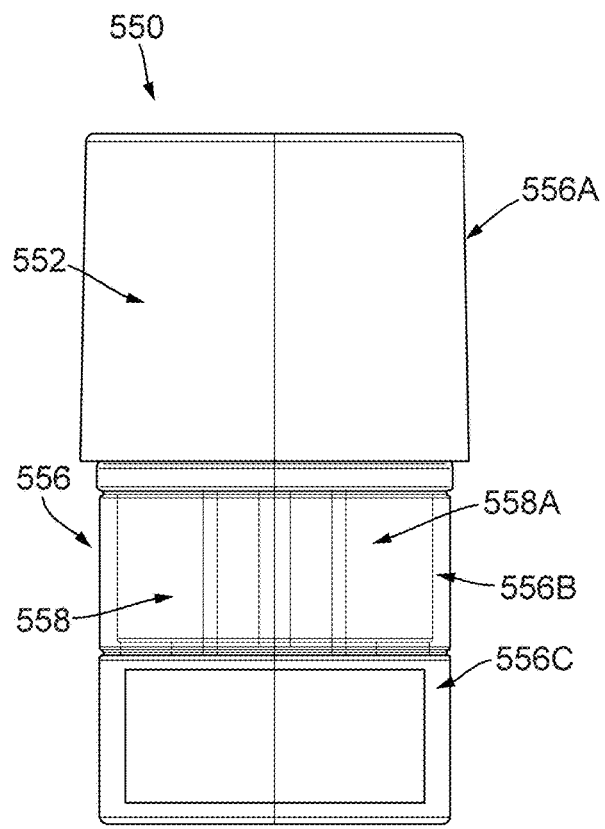
FIGS. 41A-41D illustrate an example of a cartridge of a vaporizer device consistent with implementations of the current subject matter.
Figure 41B:
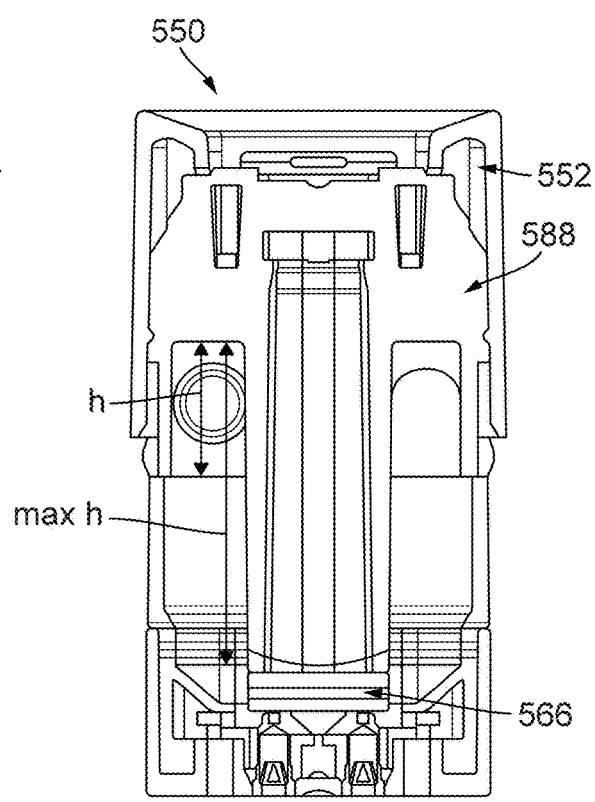
Figure 41C:
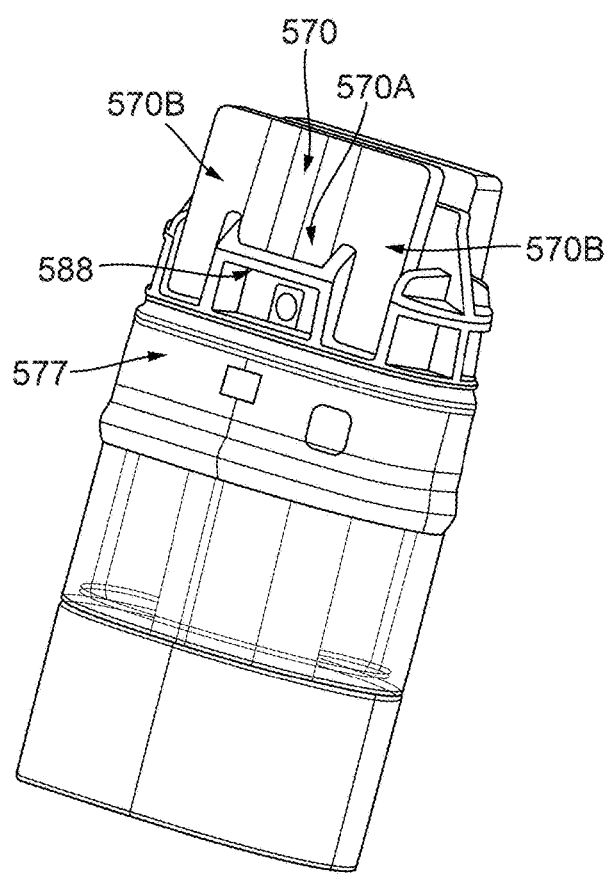
Figure 41D:
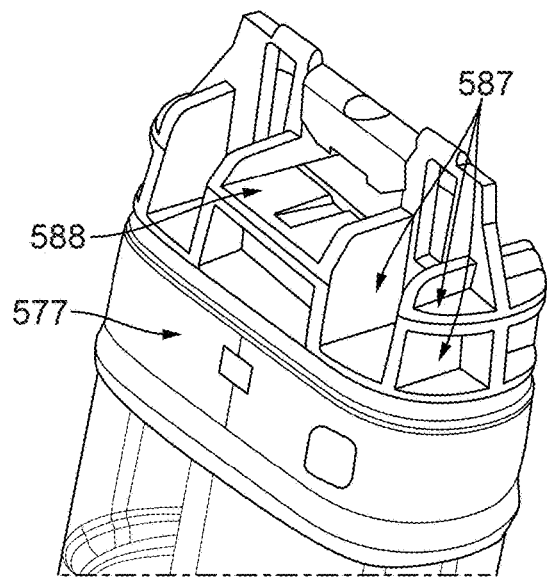

In some implementations, such as is shown in FIGS. 40A-40B and 41C, the pads 570 may be generally "T-shaped." For example, the pads 570 may each include an extension 570A that extends from a central region of the pads 570 and is configured to be positioned over at least a portion of the wick housing capillary channels (not shown). Thus, the pads 570 may work together with the wick housing capillary channels to collect the vaporizable material and/or condensed vaporizable material, wick vaporizable material away from the opening in the mouthpiece, prevent clogging of vaporizable material at a narrow opening at the proximal end of the wick housing 588, and/or prevent or limit the build-up and/or leakage of vaporizable material. Additionally, and/or alternatively, the pads 570 may include side extensions 570B that extend laterally outwardly from the central region of the pads 570. The side extensions 570B may also include a proximally extending portion that extends in a proximal direction. The proximally extending portion may be shaped to conform to and/or fill a cutout on the proximal side of the wick housing 588. Thus, the proximally extending portion may help to prevent or limit the build-up and/or leakage of vaporizable material via the cutout.

As shown in FIG. 40B, the wick housing 588 includes a pair of lateral openings 5074a,b, which may be aligned across from one another on opposing sides of the central cannula 572. Generally, the pair of lateral openings 5074a,b are shaped to correspond to and mate with the end caps 5068 to direct the flow of vaporizable material through the opening in the end caps 5068 and prevent or limit flow of the vaporizable material along the outer edges of the end caps 5068. In some implementations, the wick housing 588 includes a pair of crush ribs 589 on opposing ends of each of the pair of lateral openings 5074a,b The pair of crush ribs 589 may be tapered inwardly. The pair of crush ribs may deform on installation to create a seal between the wick housing 588, the end caps 5068, and/or another component of the cartridge 550. This helps to create a seal against the sides of the end caps 5068 in a semi-cylindrical region and to more easily mate the wick housing 588 with the reservoir body 558A. Thus, the crush ribs 589 help to prevent or limit leakage of vaporizable material from the interior of the reservoir 558.

Referring back to FIGS. 35A and 35B, air may flow along an airflow path 581, such as when the user puffs on the mouthpiece of the cartridge 550 and/or when the cartridge 550 is coupled to the vaporizer body 110. As described herein, the outer shell 112 of the cartridge receptacle 114 of the vaporizer body 110 may include one or more side air inlets 116a,b (see also FIG. 1C and FIG. 1D). The air inlets 116a,b may be aligned with or positioned in fluid communication with the lower air flow inlets 562a,b leading into air flow channels 5085 of the base assembly 594. Air may enter the cartridge 550 through the air inlets 116a,b of the vaporizer body 110, between an exterior surface of the cartridge 550 and an interior surface of the cartridge receptacle 114, and through the lower air flow inlets 562a,b and into the air flow channels 5085 of the base assembly 594. Additionally and/or alternatively, air may enter the cartridge 550 through the air inlets 116a,b of the vaporizer body 110, and directly through the lower air flow inlets 562a,b and into the air flow channels 5085 of the base assembly 594. From the air flow channels 5085, the air may pass into an interior of the base assembly 594. For example, the base assembly 594 may act as a plenum for the air, which is then directed through the central aperture 5073, past the wick 568 and heating coil 567, where the vaporized vaporizable material becomes entrained within the air, and through the vaporization chamber 5005 of the central cannula 572. The airflow path 581 may continue through the opening 5022 of the wick housing 588, into the central channel 5015 and out an opposite opening 5022A of the central cannula 572 of the wick housing 588. The vapor may then be directed around the central, upper element 5052, which splits the vapor flow to allow for flow around the central, upper element 5052 and thereby reduces the amount of excess material that is collected on the central, upper element 5052 and elsewhere in the cartridge body 556. The central, upper element 5052 may additionally and/or alternatively allow the vapor to cool via a longer, turbulent flow path before entering the mouth of the user. The vapor may then flow through one or more openings 554 in the mouthpiece 552 to exit the cartridge 550.

Figure 42A:
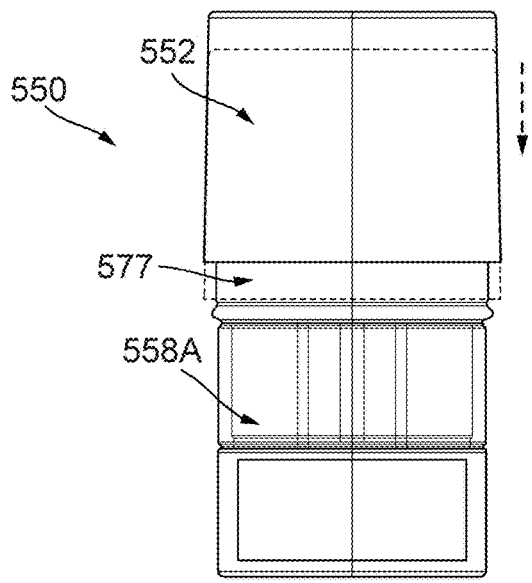
FIGS. 42A-42C illustrate an example method of filling a cartridge of a vaporizer device consistent with implementations of the current subject matter.
Figure 42B:
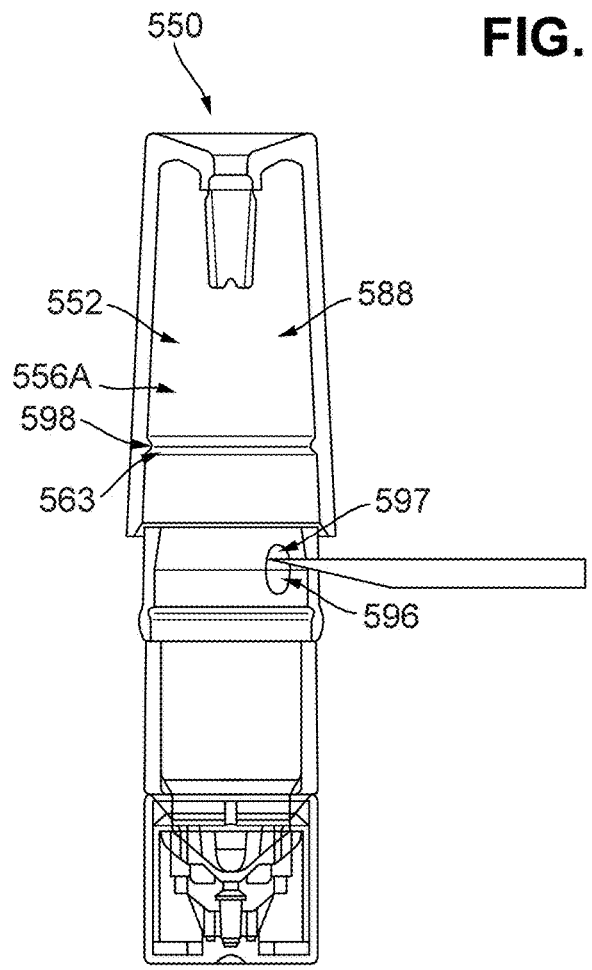
Figure 42C:
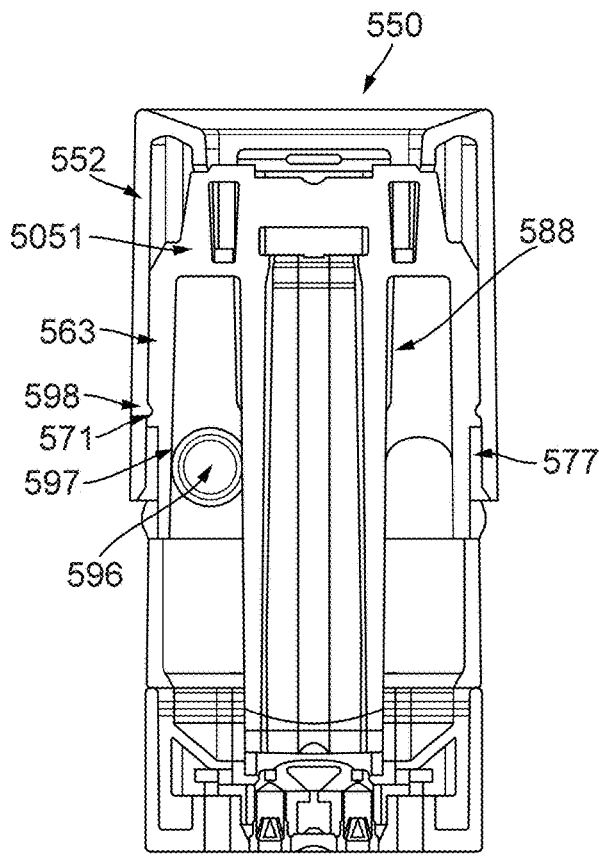
Figure 43:
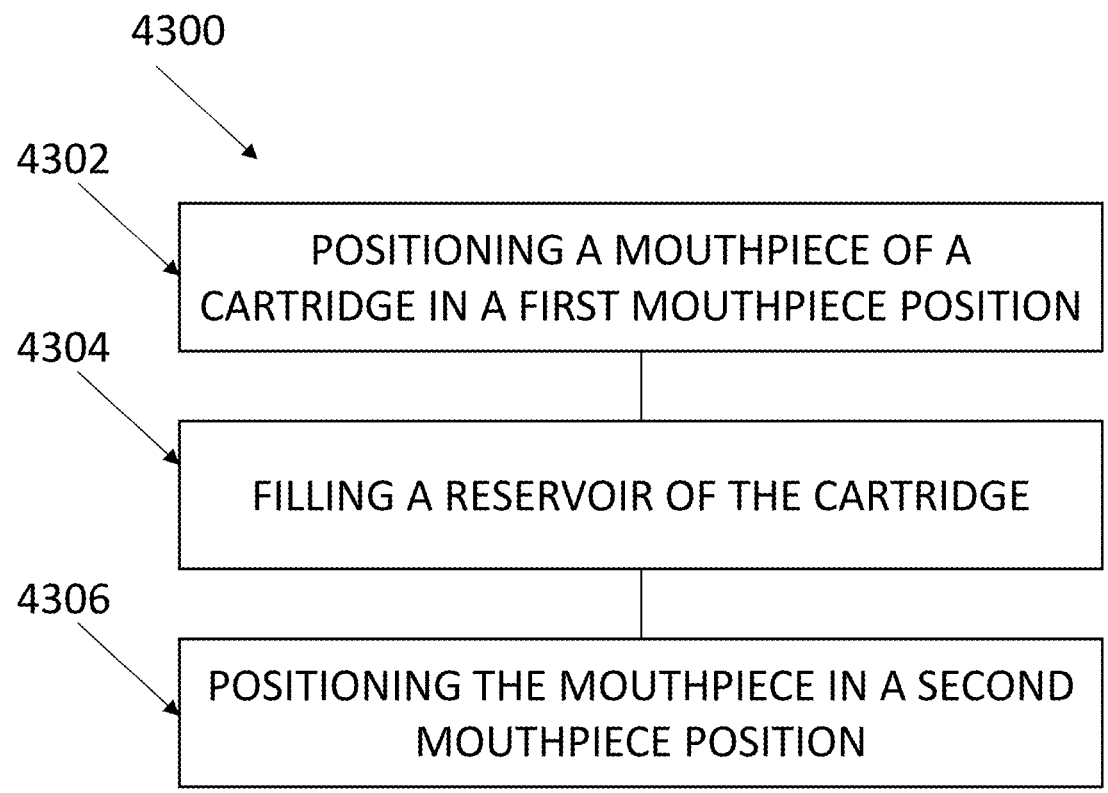
FIG. 43 is a chart illustrating a method of filling a cartridge of a vaporizer device consistent with implementations of the current subject matter.

FIGS. 42A-42C illustrate an example method of filling and assembling the cartridge 550, consistent with implementations of the current subject matter. FIG. 43 is a chart depicting the example method 4300 of filling and assembling the cartridge 550 consistent with implementations of the current subject matter. Although the method is illustrated with respect to the cartridge 550 of FIGS. 34A-40B, the method may be used to fill and/or assembly any of the cartridge configurations described herein, including the cartridge 150, 250, 350, and 450. In FIG. 42B, at least a portion of the wick housing 588 has been removed for clarity.

At 4302, the mouthpiece 552 is positioned in a first mouthpiece position (see FIG. 42A). In the first mouthpiece position, the fill port 597 (and fill port seal 596) are accessible for filling the cartridge 550. In the first mouthpiece position, the proximal wick housing base 5051 of the wick housing 588 may be, at least temporarily, coupled with the mouthpiece 552. To reach the first mouthpiece position, the mouthpiece 552 may slide over at least a part of the proximal end region 556A of the cartridge body 556. For example, the mouthpiece 552 may slide over at least the proximal wick housing base 5051 of the wick housing 588. In other words, at least a portion of the cartridge body assembly 592, such as the proximal wick housing base 5051, may be inserted into the interior volume of the mouthpiece 552. In the first mouthpiece position, the inwardly-projecting feature 598 of the mouthpiece 552 may engage with one or more proximal wick housing groove 563 to secure the mouthpiece 552 to the cartridge body assembly 592.

At 4304, the reservoir 558 of the cartridge 550 may be at least partially filled with the vaporizable material. For example, a needle may be used to fill the reservoir 558 via the fill port 597. The reservoir 558 may be filled via the fill portion 597 positioned on one or both sides of the cartridge 550. In such configurations, the needle may pierce or otherwise pass through the fill port seal 596 to fill the reservoir 558 (see FIG. 42B). When the needle is removed after filling the reservoir 558, the fill port seal may re-seal and/or otherwise prevent vaporizable material from leaking out of the reservoir 558.

At 4306, the mouthpiece 552 may be positioned in a second mouthpiece position. In the second mouthpiece position, the fill port 597 (and fill port seal 596) are inaccessible for filling the cartridge 550. For example, the cartridge body assembly 592 may be further inserted into the interior volume of the mouthpiece 552. In some implementations, the mouthpiece 552 slides in a distal direction along the exterior of the reservoir body 558A, the wick housing 558, and/or the mouthpiece seal 577, such as along a distance of approximately 4 mm, 1 to 2 mm, 2 to 3 mm, 3 to 4 mm, 4 to 5 mm, 5 to 6 mm, 6 to 7 mm, and/or the like. As shown in FIG. 42C, the cartridge body assembly 592 may be further inserted into the interior volume of the mouthpiece 552 until the inwardly-projecting feature 598 engages with the distal wick housing groove 571. As described herein, the distal wick housing groove 571 may be formed on the wick housing 588 on one side of the mouthpiece seal 577. As a result, the mouthpiece 552 may enclose the septum of the fill port seal 596, preventing or reducing oil and/or air leakage through the fill port 597 from within the cartridge 550. In some implementations, the proximal wick housing groove 563 and/or the distal wick housing groove 571 may be shaped and/or sized to allow the inwardly-projecting feature 598 of the mouthpiece 552 to slide over a proximal side and/or a distal side of each groove in one direction (e.g., in a distal direction) and prevent the inwardly-projecting feature 598 of the mouthpiece 552 to slide over the proximal side and/or the distal side of each groove in an opposite direction (e.g., in a proximal direction). This helps to add additional security to the cartridge 550. For example, once the cartridge 550 is filled by an authorized filler and/or with an authorized and/or tested vaporizable material, in some implementations, the mouthpiece 552 may not be removed without damaging the cartridge 550. This may prevent the cartridge 550 from being refilled, such as with an unauthorized substance and/or by an unauthorized party. Such configuration may also help to improve the user experience, as the user may be aware that the cartridge 550 may include the authorized vaporizable material. Such configuration may additionally and/or alternatively allow for a pre-cut septum to be used at the fill port to enable blunt needle filling.

Figure 44:
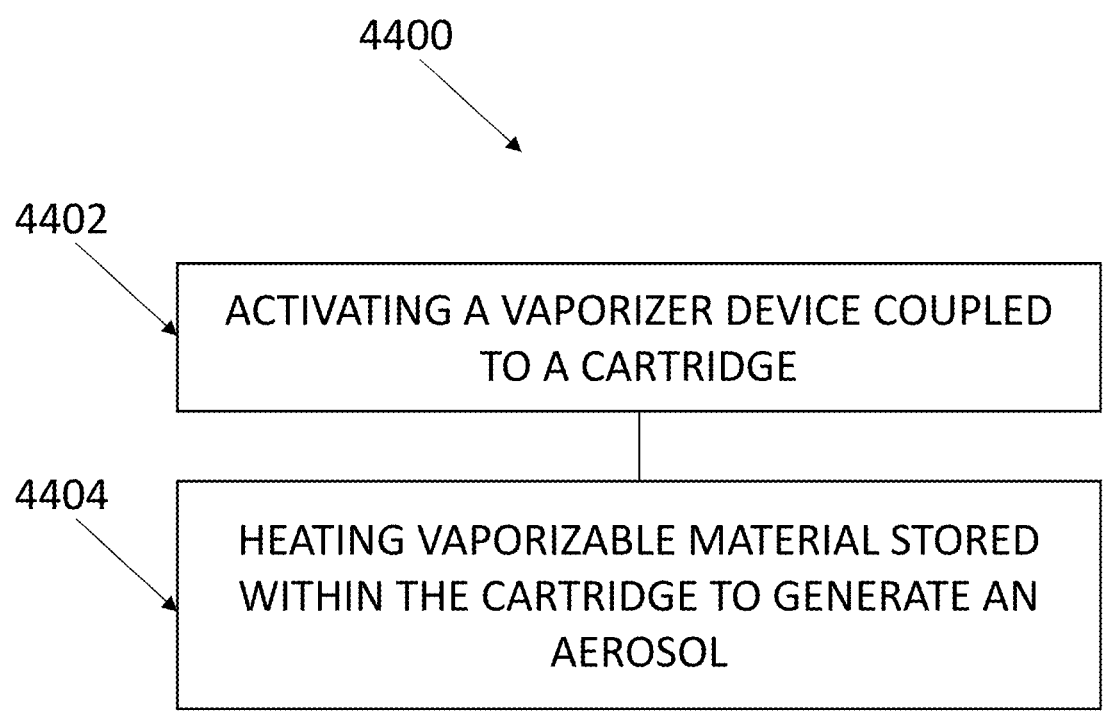
FIG. 44 is a chart illustrating a method of generating an aerosol consistent with implementations of the current subject matter.

FIG. 44 is an example method of generating an aerosol consistent with implementations of the current subject matter. At 4402, a vaporizer device (e.g., the vaporizer device 100) is activated. For example, the vaporizer device may be activated by drawing (e.g., inhaling) through the mouthpiece. The device may detect a draw (e.g., using a pressure sensor, flow sensors, and/or the like, including a sensor configured to detect a change in temperature or power applied to a heater element) and may increase the power to a predetermined temperature preset. The power may be regulated by the controller by detecting the change in resistance of the heating coil and using the thermal coefficient of resistance to determine the temperature.

At 4404, a heater (e.g., the heater 166, 266, 366, 466, 566) may heat at least a portion of the vaporizable material stored within the cartridge (e.g., the cartridge 150, 250, 350, 450, 550) to generate an aerosol. For example, the heater may heat at least a portion of the vaporizable material stored within the wick of the heater to generate the aerosol to be delivered to the user through the mouthpiece of the cartridge.

Any of a variety of materials may be used for the cartridge 150. Though these materials are described with respect to the cartridge 150, the cartridge 250, the cartridge 350, the cartridge 450, and/or the cartridge 550 may include the same or similar materials, features, and/properties. Portions of the cartridge 150 may be made of harder plastic materials configured to be strong and resist cracking, compression, or other damage when placed under pressure. For example, one or more regions of the cartridge body 156 such as the region defining the reservoir 158 may be formed of hard plastic materials, such as, for example, Trogamid CX7323 (BPA free). Other plastic materials for the cartridge body 156 and the mouthpiece 152 may include, for example, Veradel A-301 (BPA free). Other regions of the cartridge 150 such as the regions intended to provide for sealing with other harder regions of the cartridge 150 may be made of any of a variety of resilient or elastomeric materials. For example, the bottom tank seal 176 and the internal sealing gasket 173 may be made from a variety of materials including rubber, such as, for example, fluorosilicone rubber (SHIN-ETSU FE-251-U). The mouthpiece seal 177 may also be made from a variety of materials including rubber, such as, for example, clear liquid silicone rubber (LSR). The seals 176 and 177, the sealing ring 171, the internal sealing gasket 173, and the lower support structure 174 may be made from a variety of materials, such as Polypropylene and materials in the Nylon 6/3 or Polyethersulfone-based (PESU) classes, including but not limited to PESU, Nylon, Silicone, Nitrile, ethylene propylene diene monomer (EPDM), PTFE, Fluorocarbons, and Polyethylene Terephthalate (PET). The portions of the cartridge 150 including the reservoir 158, the cartridge body 156, the mouthpiece 152, the sealing ring 171, the internal sealing gasket 173, the bottom tank seal 176, the mouthpiece seal 177, and the lower support structure 174 are formed of durable materials that are suitable for the functions they perform. A variety of materials, including glass, aluminum, stainless steel, titanium, gold, bronze, gold-plated phosphor bronze, mullite, nickel chromium, and/or ceramic, may be used for the components of the cartridge 150, including but not limited to the reservoir 158, the cartridge body 156, the mouthpiece 152, the sealing ring 171, the internal sealing gasket 173, the bottom tank seal 176, and the mouthpiece seal 177.

As described above, a data tag 164 (and/or data tag 264) may be incorporated within a region of the cartridge 150, 250, 350, 450, 550 to transmit, receive, and/or store relevant information about the cartridge 150, 250, 350, 450, 550 and/or the vaporizable material contained within. Though the tag is described with respect to the tag 164 of the cartridge 150, the tag 264 may have the same or similar properties and/or features. The tag 164, 264 may be positioned within and/or otherwise used with the cartridge 350. For example, the tag 164 may allow for communication between the cartridge 150 and the vaporizer body 110 as well as between the cartridge 150 and an external computing device, such as a user device 305 (e.g., a smartphone, tablet, laptop), or a remote server 307. The communication between the cartridge 150 provided by the tag 164 may be independent of the vaporizer body 110 such that the cartridge 150 may communicate with an external computing device even when the cartridge 150 is not coupled to the vaporizer body 110, as described elsewhere herein.

In some implementations, the tag 164 is a near-field communication (NFC) tag positioned near a bottom region of the cartridge 150. In the example implementations of the cartridge 250, 350, 450, 550 shown in FIGS. 13A-42C, the tag 264 is positioned near a bottom region of the cartridge 150 within an interior of the cartridge (e.g., within the base of the cartridge 250, 350, 450, 550). In the example implementation shown in FIGS. 4-12C, the tag 164 may be positioned over a bottom plate of the lower support structure 174. In the example shown in FIGS. 4-12C, the tag 164 may be adhered to the bottom plate of the lower support structure 174, for example, by using a bottom base plate or base. The base may be an adhesive, such as a pressure sensitive adhesive (PSA) that is formed from an acrylic material or the like, and may have a thickness of, for example, about 0.06 mm, 0.07 mm, 0.08 mm, 0.09 mm, or 0.10 mm.

The tag 164 may be an antenna trace made of copper or a similar material and may have a thickness of, for example, about 0.05 mm, 0.06 mm, 0.07 mm, 0.08 mm, 0.09 mm, or 0.10 mm. The tag 164 may be protected by a protective layer, such as, for example, a plastic cover made of polyethylene terephthalate (PET) plastic or other plastics. A variety of non-conductive materials, such as glass or ceramic, may be used for the protective layer. The protective layer may have a thickness of, for example, about 0.08 mm, 0.09 mm, 0.10 mm, 0.11 mm, or 0.12 mm. The overall thickness of the tag 164, with or without the base 184 and/or with or without the protective layer 185, may be, for example, about 0.05 mm, 0.06 mm, 0.07 mm, 0.08 mm, 0.10 mm, 0.12 mm, 0.14 mm, 0.16 mm, 0.18 mm, 0.20 mm, 0.22 mm, 0.24 mm, 0.26 mm, 0.28 mm, 0.30 mm, 0.32 mm, 0.34 mm, 0.36 mm, 0.38 mm, 0.40 mm, 0.42 mm, 0.44 mm, 0.46 mm, 0.48 mm, or 0.50 mm.

The tag 164 may be a variety of shapes, including the generally planar element with an upper surface, a lower surface and an outer perimeter such as that shown in the figures. In the example cartridge 150 shown in FIGS. 4-12C, the outer perimeter of the tag 164 may be identical to the outer perimeter of the cartridge 150 at its distal end 1020 such that its shape resembles the cross-sectional shape of the distal end 1020 of the cartridge 150 so as not to interfere with coupling between the cartridge 150 and the vaporizer body 110. The upper surface of the tag 164 is configured to abut flush against the bottom plate of the lower support structure 174. The lower surface is similarly planar. As mentioned above, the tag 164 may be positioned on the cartridge 150 in any of a number of configurations, such as between the power pin receptacle 160a,b or encircling the power pin receptacles 160a,b. Additionally, and/or alternatively, the tag 264 (and/or the tag 364) may be positioned within the cartridge 250, 350, 450, 550 such as within the interior of the base 274, 374, 474, 574 of the cartridge 250, 350, 450, 550.

In some implementations, the tag 164 has a circular or partially circular shape. The tag 164 may include at least one aperture extending through its thickness such that the tag 164 surrounds the power pin receptacles 160a,b and air flow inlets 162a,b at the distal end of the cartridge 150.

Figure 45A:
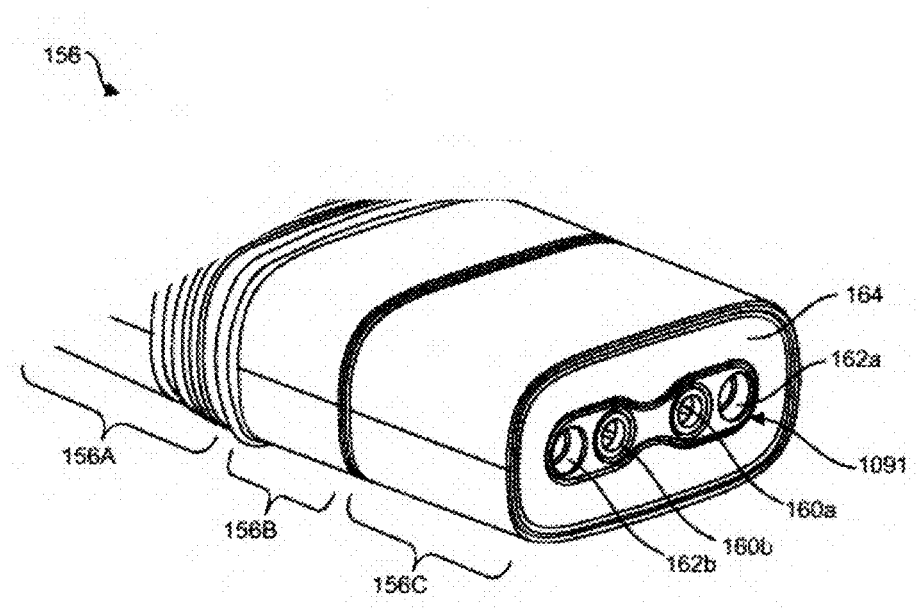
FIGS. 45A-45D illustrate an example of a cartridge having a tag consistent with implementations of the current subject matter.

In an implementation in which the tag is coupled with an exterior of the cartridge, as shown in FIG. 45A which is a bottom perspective view of the cartridge body 156, the tag 164 may include a single aperture 1091 extending through its thickness such that the single aperture 1091 surrounds the power pin receptacles 160a,b and the air flow inlets 162a,b. The single aperture 1091 may dip or extend slightly between the power pin receptacles 160a,b to provide more usable area of the tag 164 (e.g., providing more room for additional antennae coils). Moreover, the air flow inlets 162a,b may be moved inward to also provide additional usable area of the tag 164.

Similarly, in an implementation in which the tag is coupled with an interior of the cartridge, as shown in FIG. 19 the tag 264, 364 may include also a single aperture 2091 extending through its thickness such that the single aperture 2091 surrounds the power pin receptacles 260a,b and the air flow inlets 262a,b.

Figure 45B:
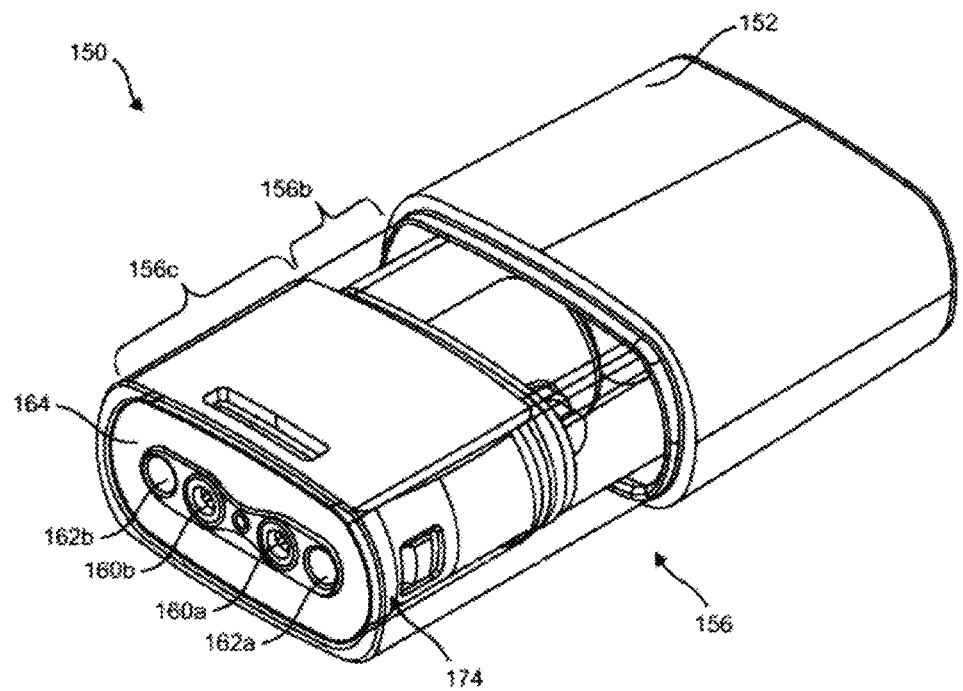
Figure 45C:
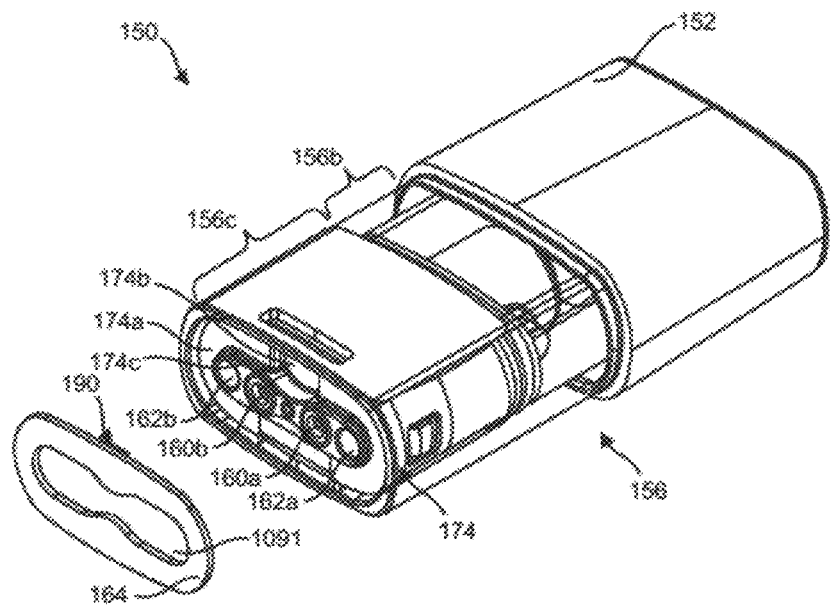
Figure 45D:
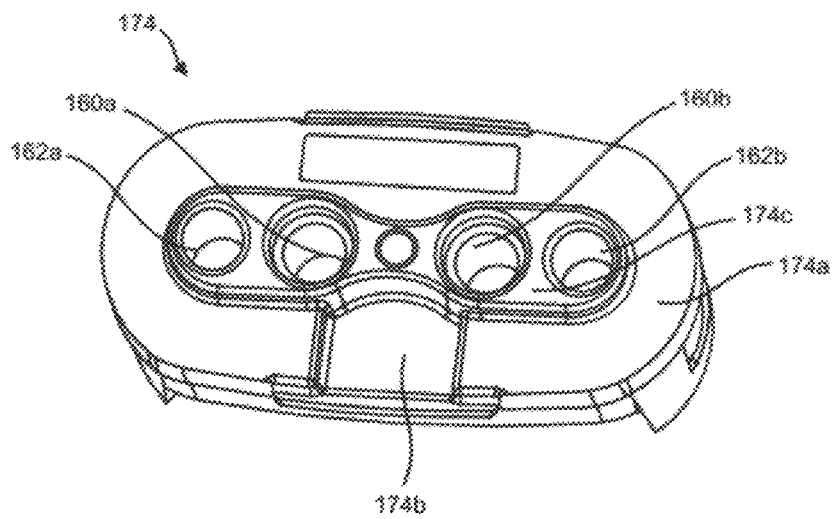

FIG. 45B-FIG. 45D illustrate details of an additional implementation of the cartridge 150 with the tag 164 configured to be attached to the bottom plate of the lower support structure 174 of the cartridge 150. FIG. 45B is a bottom perspective view of the cartridge 150 illustrating the central region 156B and the distal end region 156C of the cartridge body 156, with the mouthpiece 152 coupled to the proximal end region 156A of the cartridge body 156 and the tag 164 coupled or otherwise attached to the lower support structure 174 at the distal end region 156C. FIG. 45C is a bottom perspective view of the cartridge 150 and the tag 164, illustrating placement of the tag 164 with respect to the cartridge 150. FIG. 45D is a perspective view of a portion of the lower support structure 174 without the tag 164 adhered thereto. As described elsewhere herein, the placement of the tag 164 on a bottom portion of the cartridge 150 (such as on an exterior of the cartridge or with the interior of the cartridge, such as within a base of the cartridge) may provide for communication with the vaporizer body 110 via the first antenna 143 at the proximal end of the vaporizer body 110 when the cartridge 150 is engaged with the vaporizer body 110. However, the tag 164 may be positioned at other portions of the cartridge 150.

As shown in the bottom perspective views of the cartridge 150 in FIG. 45B and FIG. 45C, the cartridge body 156 may have a profile or shape that varies from that of the cartridge body 156 shown in, for example, FIG. 45A. For example, the outer and inner perimeters of the cartridge body 156 of the cartridge 150 shown in FIG. 45B and FIG. 45C may include a more rounded shape or cross section at side portions (e.g., the shorter, opposing side portions) of the cartridge body 156 compared to that of the cartridge body 156 shown in FIG. 45A. Some portions of the cartridge body 156 may be opaque while other portions are clear. Moreover, the power pin receptacles 160a,b and the air flow inlets 162a,b formed through the lower support structure 174 may be spaced apart with respect to one another with distances that vary from that of the cartridge body 156 shown in FIG. 45A.

As shown in FIG. 45C, the tag 164 consistent with implementations of the current subject matter may be sized and shaped to accommodate the shape of the bottom plate of the lower support structure 174, which may be sized and shaped to accommodate the shape of the distal end region 156C of the cartridge body 156. The tag 164 may include the single aperture 1091 extending through its thickness such that the single aperture 1091 surrounds the power pin receptacles 160a,b and the air flow inlets 162a,b of the lower support structure 174. The single aperture 1091 may dip or extend slightly between the power pin receptacles 160a,b to provide more usable area of the tag 164 (e.g., providing more room for additional antennae coils). In some implementations, two apertures (one for each set of receptacle and air flow inlet) may be provided in the tag 164.

As shown in FIG. 45C and FIG. 45D, the bottom plate of the lower support structure 174 may include a recessed region 174a sized and shaped to accommodate the tag 164. The tag 164 and the recessed region 174a may be the same size and shape, or substantially the same size and shape, as one another. In some implementations, the shapes of the tag 164 and the recessed region 174a mirror or substantially mirror one another. In some implementations, the size of the tag 164 is slightly smaller than that of the recessed region 174a to provide for placement of the tag 164 on the recessed region 174a. The recessed region 174a may include an indentation or pocket 174b to accommodate the microcontroller unit (MCU) 190 and a tuning capacitor 3802 of the tag 164 (see FIG. 46B and FIG. 46C). The bottom plate of the lower support structure 174 may include a raised region 174c surrounded by the recessed region 174a and through which the power pin receptacles 160a,b and the air flow inlets 162a,b are formed.

Consistent with implementations of the current subject matter, the size and shape of the tag 164 may vary to accommodate variations of the size and shape of the cartridge body 156. For example, the cartridge body 156 may have a circular, oval, square, rectangular, or other polygonal cross section, and the tag 164 may be sized and shaped to attach to a distal end of the cartridge body 156. The tag 164 may be of various shapes and sizes and is not limited to a shape that mirrors that of the bottom plate fitted within the cartridge body 156. For example, in some implementations, the tag 164 may be of a variety of polygonal shapes to accommodate the antenna 192.

Figure 46A:
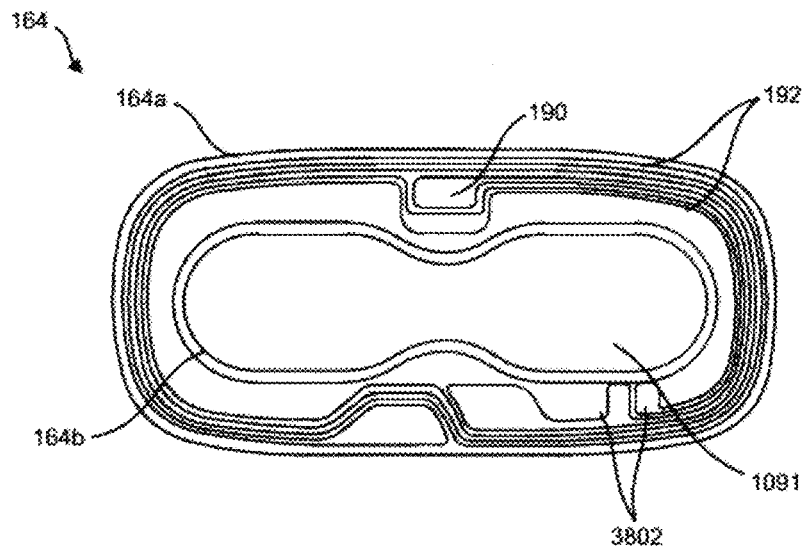
FIGS. 46A-46C illustrate an example of a tag consistent with implementations of the current subject matter.

FIG. 46A illustrates features of the tag 164, consistent with some implementations of the current subject matter. As described elsewhere herein and with respect to FIG. 2, the tag 164 may include a microcontroller unit (MCU) 190 and an antenna 192. Shown in FIG. 46A are the MCU 190 and the antenna 192. Also included is the tuning capacitor 3802 that is configured to tune the wireless signal from the antenna 192. Pockets sized and shaped to accommodate the microcontroller unit (MCU) 190 and the tuning capacitor 3802 may be formed on the bottom plate of the lower support structure 174. For example, the pocket 174b shown in FIG. 45C may accommodate the microcontroller unit (MCU) 190 and the tuning capacitor 3802 when the microcontroller unit (MCU) 190 and the tuning capacitor 3802 are positioned side-by-side as in FIG. 46B. In implementations in which the microcontroller unit (MCU) 190 and the tuning capacitor 3802 are not side-by-side but are instead spaced apart at different regions of the tag 164, as in FIG. 46A, separate indentations or pockets on the bottom plate of the lower support structure 174 may be provided to accommodate the microcontroller unit (MCU) 190 and the tuning capacitor 3802.

In some implementations, the antenna 192 may be traced or etched onto the tag 164 on the usable area of the tag 164 between an outer perimeter 164a and an inner perimeter 164b of the tag 164. The outer perimeter 164a may be of the same or similar size as that of the bottom plate of the cartridge body 156. The inner perimeter 164b may define the single aperture 1091. In one implementation, as shown in FIG. 46A, the antenna 192 may have a racetrack-like configuration in which the antenna 192 is etched on the tag 164 in a plurality of concentric traces. The concentric traces may be shaped to mirror the shape of the outer perimeter of the tag 164 or the inner perimeter of the tag 164. Variations of the concentric traces may be incorporated, such as concentric traces with right angles as opposed to the curved implementation shown in FIG. 46A. The antenna 192 may have a variety of other alternative configurations to enable communication with the vaporizer body 110 or other devices (e.g., the user device 305, the remote server 307, etc.). The other configurations of the antenna 192 may include, for example, helical, parabolic, spiral, zig zag, linear, or circular configurations. As the tag 164 may be of a variety of shapes and sizes, the traces of the antenna 192 may be configured to match, in size or shape, one or more usable areas of the tag 164.

Figure 46B:
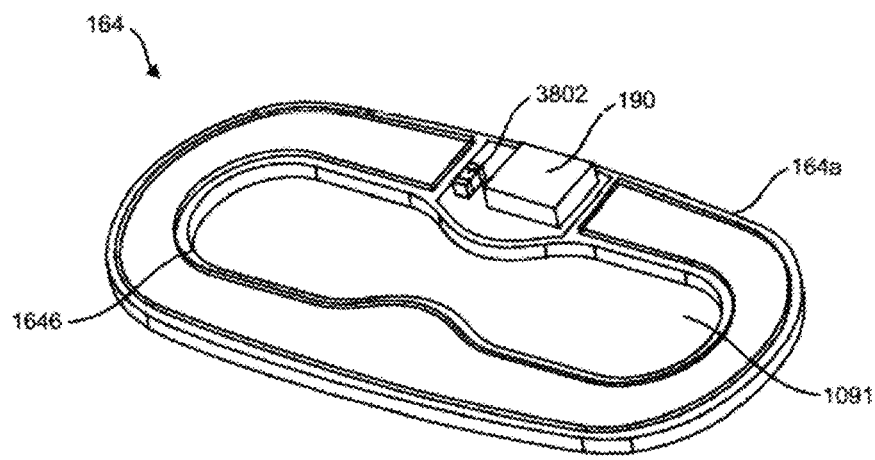
Figure 46C:
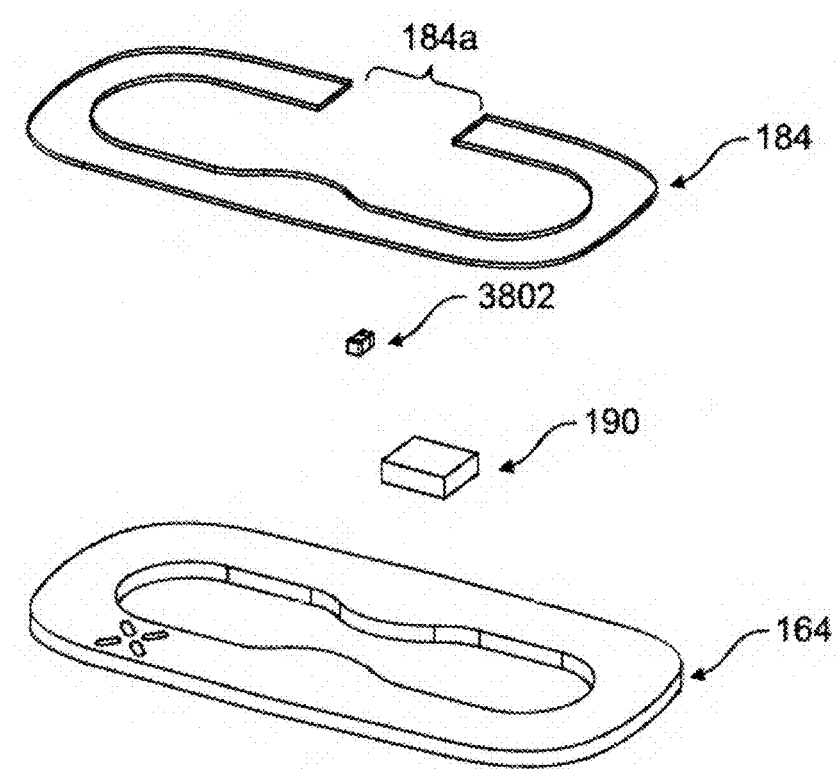

FIG. 46B and FIG. 46C illustrate features of the tag 164 consistent with additional implementations of the current subject matter. FIG. 46B is a bottom perspective view of the tag 164. On a bottom surface of the tag 164, the microcontroller unit (MCU) 190 and the tuning capacitor 3802 are provided on an area of the tag 164 that corresponds to, for example, the pocket 174b formed on the bottom plate of the lower support structure 174; although the pocket 174b is not required to accommodate such an arrangement of the microcontroller unit (MCU) 190 and the tuning capacitor 3802. The tag 164 may be a printed circuit board with an antenna (i.e., the antenna 192) with the outer perimeter 164a and the inner perimeter, where the inner perimeter 164b defines the single aperture 1091.

FIG. 46C is an exploded view from a bottom perspective of the tag 164 of FIG. 46B. Shown are the tag 164 (that includes, in some implementations, a printed circuit board with an antenna), the microcontroller unit (MCU) 190, the tuning capacitor 3802, and the base 184 that may be an adhesive for adhering the tag 164 to the bottom plate of the lower support structure 174. The base 184 may be sized and shaped to align with at least a portion of the tag 164. In some implementations, the base 184 aligns with at least a portion of the tag 164 and is of the same general shape of the tag 164 but is slightly smaller to allow for proper placement of the tag 164 on the base 184. In some implementations, the base 184 is of the same size and shape of the tag 164. In some implementations, the base 184 includes a gap or a cut-out region 184a to accommodate the microcontroller unit (MCU) 190 and the tuning capacitor 3802 on the tag 164. The base 184 may be of various other sizes and shapes and may include multiple pieces, such as two or more strips.

As shown in FIG. 46B and FIG. 46C, the arrangement of the microcontroller unit (MCU) 190 and the tuning capacitor 3802 is such that the microcontroller unit (MCU) 190 and the tuning capacitor 3802 are adjacent or near one another. However, other arrangements, such as that provided in FIG. 46A where the microcontroller unit (MCU) 190 and the tuning capacitor 3802 are spaced apart from one another, are possible consistent with implementations of the current subject matter. The arrangement of the microcontroller unit (MCU) 190 and the tuning capacitor 3802 may be based on various factors, such as tuning, manufacturing considerations, and placement/fitting on the cartridge 150.

The tag 164 may be encased in plastic during injection molding of the mating plastics, or an ultrasonic welding process may be implemented in which the protective layer is welded to mating plastics. The tag 164 may be manufactured like a flexible printed circuit (FPC). In some implementations, the tag 164 may be formed like a rigid printed circuit board. Alternatively, an air coil may be used as a coiled wire for the tag 164, rather than being printed like a FPC. The air coil is conductive with an increased range of performance compared to the FPC method. As another alternative, the tag 164 may be printed or directly etched onto a base, such as for example the PSA base 184, using a laser direct structuring (LDS) method or the like.

In some implementations, the tag 164 may include one or more substrate layers on which the antenna traces, made of copper or a similar material, are etched or formed. In one implementation, the tag 164 includes four traces on one substrate layer. In another implementation, the tag 164 includes two traces on a first substrate layer and 6 traces on a second substrate layer. Various other implementations consistent with the current subject matter are possible. For example, the tag 164 may include any number of traces on any number of layers to achieve desired properties with respect to size, frequency, tuning, range (i.e., range with one or more antennas such as the first antenna 143), and manufacturability.

In one implementation, the antenna traces have a width of about 75 microns and a thickness of 18 microns, and there may be a gap of about 75 microns between each antenna trace. The antenna traces may have a width of, for example, about 20 microns, 25 microns, 30 microns, 35 microns, 40 microns, 45 microns, 50 microns, 55 microns, 60 microns, 65 microns, 70 microns, 75 microns, 80 microns, 85 microns, 90 microns, or 95 microns. The antenna traces may have a thickness of, for example, about 8 microns, 10 microns, 12 microns, 14 microns, 16 microns, 18 microns, 20 microns, 22 microns, 24 microns, 26 microns, 28 microns, or 30 microns. The gap between the antenna traces may be, for example, about 20 microns, 25 microns, 30 microns, 35 microns, 40 microns, 45 microns, 50 microns, 55 microns, 60 microns, 65 microns, 70 microns, 75 microns, 80 microns, 85 microns, 90 microns, or 95 microns. The thickness of the antenna traces on a single substrate may differ from one another or may be the same as one another. The gap between the antenna traces may be the same on a single substrate or may differ such that one gap is larger than another gap.

Once assembled, the cartridge 150 may be difficult for a user to take apart. A feature may be incorporated on a region of the cartridge 150 to discourage tampering and disassembly and for internally securing components. The configuration of the feature may vary. In an implementation, the cartridge 150 may include an internal snap feature 180 on one or more outer edges of the lower support structure 174 (at the distal end of the cartridge 150) (see FIG. 9). The feature 180 may be an angled annular projection configured to mate with one or more complementary recesses 183 formed on an internal side of the cartridge body 156 (see FIG. 6 and FIG. 9). The feature 180 may have a proximal-facing ramped surface and a distal-facing flat surface. The lower support structure 174 may be inserted within the distal end region 156C of the cartridge body 156 from the distal end region. The ramped surface slides along the inner surface of the cartridge body 156. Upon proper seating within the distal end region 156C, the ramped surface of the feature 180 inserts within the recess 183 of the internal surface of the cartridge body 156. The distal-facing flat surface of the feature abuts against a corresponding proximal-facing flat surface preventing the lower support structure 174 from sliding in the opposite direction back out from the lower end of the cartridge body 156. Such an internal configuration makes it difficult for a user to take apart the cartridge 150. Additionally, and/or alternatively, other features may be incorporated on a region of the cartridge 150 to discourage tampering and disassembly and for internally securing components, such as features described above including the mating between the mouthpiece and the cartridge body assembly, the mouthpiece covering the fill port, the tag being positioned within the cartridge, and/or the like.

In operation, after the vaporizer device is fully charged, a user may activate the vaporizer device by drawing (e.g., inhaling) through the mouthpiece. The device may detect a draw (e.g., using a pressure sensor, flow sensors, and/or the like, including a sensor configured to detect a change in temperature or power applied to a heater element) and may increase the power to a predetermined temperature preset. The power may be regulated by the controller by detecting the change in resistance of the heating coil and using the temperature coefficient of resistivity to determine the temperature.

The heater may include a small heating element configured to heat and/or vaporize at least a portion of the vaporizable material and a wicking material that may draw a liquid vaporizable material into the atomizer (e.g., heater). The resistance wire may be a coil. When the resistance wire is activated, the resistance wire (or coil) may have a temperature increase as a result of the current flowing through the resistive wire to generate heat. The heat may be transferred to at least a portion of the vaporizable material through conductive, convective, and/or radiative heat transfer such that at least a portion of the vaporizable material vaporizes.

Air may be drawn into the vaporizer device to carry the vaporized aerosol away from the heating element, where it then cools and condenses to form liquid particles suspended in air, which may then be drawn out of the mouthpiece by the user.

In some examples, the vaporizable material may include a viscous liquid such as, for example a *cannabis* oil. In some variations, the *cannabis* oil comprises between 0.3% and 100% *cannabis* oil extract. The viscous oil may include a carrier for improving vapor formation, such as, for example, propylene glycol, glycerol, medium chain triglycerides (MCT) including lauric acid, capric acid, caprylic acid, caproic acid, etc., at between 0.01% and 25% (e.g., between 0.1% and 22%, between 1% and 20%, between 1% and 15%, and/or the like). In some variations the vapor-forming carrier is 1,3-Propanediol. A *cannabis* oil may include a cannabinoid or cannabinoids (natural and/or synthetic), and/or a terpene or terpenes derived from organic materials such as for example fruits and flowers. For example, any of the vaporizable materials described herein may include one or more (e.g., a mixture of) cannabinoid including one or more of: CBG (Cannabigerol), CBC (Cannabichromene), CBL (Cannabicyclol), CBV (Cannabivarin), THCV (Tetrahydrocannabivarin), CBDV (Cannabidivarin), CBCV (Cannabichromevarin), CBGV (Cannabigerovarin), CBGM (Cannabigerol Monomethyl Ether), Tetrahydrocannabinol, Cannabidiol (CBD), Cannabinol (CBN), Tetrahydrocannabinolic Acid (THCA), Cannabidioloc Acid (CBDA), Tetrahydrocannabivarinic Acid (THCVA), one or more Endocannabinoids (e.g., anandamide, 2-Arachidonoylglycerol, 2-Arachidonyl glyceryl ether, N-Arachidonoyl dopamine, Virodhamine, Lysophosphatidylinositol), and/or a synthetic cannabinoids such as, for example, one or more of: JWH-018, JWH-073, CP-55940, Dimethylheptylpyran, HU-210, HU-331, SR144528, WIN 55,212-2, JWH-133, Levonantradol (Nantrodolum), and AM-2201. The oil vaporization material may include one or more terpene, such as, for example, Hemiterpenes, Monoterpenes (e.g., geraniol, terpineol, limonene, myrcene, linalool, pinene, Iridoids), Sesquiterpenes (e.g., humulene, farnesenes, farnesol), Diterpenes (e.g., cafestol, kahweol, cembrene and taxadiene), Sesterterpenes, (e.g., geranylfarnesol), Triterpenes (e.g., squalene), Sesquarterpenes (e.g, ferrugicadiol and tetraprenylcurcumene), Tetraterpenes (lycopene, gamma-carotene, alpha- and beta-carotenes), Polyterpenes, and Norisoprenoids. For example, an oil vaporization material as described herein may include between 0.3-100% cannabinoids (e.g., 0.5-98%, 10-95%, 20-92%, 30-90%, 40-80%, 50-75%, 60-80%, etc.), 0-40% terpenes (e.g., 1-30%, 10-30%, 10-20%, etc.), and 0-25% carrier (e.g., medium chain triglycerides (MCT)).

In any of the oil vaporizable materials described herein (including in particular, the cannabinoid-based vaporizable materials), the viscosity may be within a predetermined range. The range may be between, at room temperature (23° C.) about 30 cP (centipoise) and 115 kcP (kilocentipoise), between 30 cP and 200 kcP, although higher viscosities and/or lower viscosities may be implemented as well. For example, the viscosity may be between 40 cP and 113 kcP at room temperature. Outside of this range, the vaporizable material may fail in some instances to wick appropriately to form a vapor as described herein. In particular, it is typically desired that the oil may be made sufficiently thin to both permit wicking at a rate that is useful with the apparatuses described herein, while also limiting leaking (e.g., viscosities below that of ~40 cP at room temperature might result in problems with leaking).

Although the disclosure, including the figures, described herein may described and/or exemplify these different variations separately, it should be understood that all or some, or components of them, may be combined.

Although various illustrative embodiments are described above, any of a number of changes may be made to various embodiments. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the claims.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. References to a structure or feature that is disposed "adjacent" another feature may have portions that overlap or underlie the adjacent feature.

Terminology used herein is for the purpose of describing particular embodiments only and is not intended to be limiting. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as, for example, "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings provided herein.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" "or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, are possible.

In the descriptions above and in the claims, phrases such as, for example, "at least one of" or "one or more of" may occur followed by a conjunctive list of elements or features. The term "and/or" may also occur in a list of two or more elements or features. Unless otherwise implicitly or explicitly contradicted by the context in which it used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

The implementations set forth in the foregoing description do not represent all implementations consistent with the subject matter described herein. Instead, they are merely some examples consistent with aspects related to the described subject matter. Although a few variations have been described in detail herein, other modifications or additions are possible. In particular, further features and/or variations can be provided in addition to those set forth herein. For example, the implementations described above can be directed to various combinations and sub-combinations of the disclosed features and/or combinations and sub-combinations of one or more features further to those disclosed herein. In addition, the logic flows depicted in the accompanying figures and/or described herein do not necessarily require the particular order shown, or sequential order, to achieve desirable results. The scope of the following claims may include other implementations or embodiments.

What is claimed is:

1. A cartridge configured to operatively couple with a vaporizer, the cartridge comprising:
    an atomizer assembly configured to heat a vaporizable material to generate an inhalable vapor;
    a reservoir configured to store the vaporizable material, the reservoir comprising:
        a wick housing configured to surround at least a portion of the atomizer assembly and form a proximal wall of the reservoir,
        wherein the wick housing further comprises a fill port configured to receive the vaporizable material to fill the reservoir with the vaporizable material, wherein the fill port comprises a self-healing septum; and
        a reservoir body coupled to the wick housing and configured to form a distal wall of the reservoir, the distal wall opposite the proximal wall;
        a base assembly coupled to the reservoir; and
    a mouthpiece configured to deliver the inhalable vapor, wherein the mouthpiece is slidable along an external surface of a side of the wick housing from a first position to a second position in a distal direction, wherein,
    in the first position, an inwardly projecting feature of the mouthpiece is positioned within a first wick housing groove on the wick housing and, in the second position, the inwardly projecting feature is positioned within a second wick housing groove on the wick housing, wherein the first wick housing groove and the second wick housing groove are shaped so as allow the inwardly projecting feature to slide over each of the first wick housing groove and the second wick housing groove in a first direction and to prevent the inwardly projecting feature of the mouthpiece from sliding over each of the first wick housing groove and the second housing groove in a second direction opposite the first direction,
    wherein when the mouthpiece is coupled to the wick housing in the first position, the fill port is accessible, and wherein when the mouthpiece is coupled to the wick housing in the second position, the fill port comprising the self-healing septum is inaccessible; and
    a mouthpiece seal, the mouthpiece seal coupled to the reservoir body, the mouthpiece seal configured to secure the cartridge to the vaporizer, and the mouthpiece seal configured to prevent air from passing through a side of the cartridge.

2. The cartridge of claim 1, wherein the atomizer assembly is positioned within an interior volume of the base assembly.

3. The cartridge of claim 2, wherein at least a portion of the reservoir is transparent and at least a portion of the base assembly is opaque, and wherein at least a portion of the atomizer assembly is hidden behind at least the portion of the base assembly from a position external to the cartridge.

4. The cartridge of claim 1, wherein the atomizer assembly comprises:
    a wick configured to passively draw the vaporizable material;
    a heating element in contact with the wick;
    an end cap positioned over an end of the wick, the end cap electrically coupled to the heating element;
    a lead extending from the end cap, the lead comprising a bend; and
    a receptacle configured to receive power from a power supply of the vaporizer.

5. The cartridge of claim 4, wherein the lead contacts a side surface of the receptacle.

6. The cartridge of claim 4, wherein the receptacle is press-fit into contact with the lead.

7. The cartridge of claim 1, wherein a distal side of the reservoir is tapered, the distal side configured to encourage the vaporizable material from within the reservoir towards the atomizer assembly.

8. The cartridge of claim 1, wherein the wick housing and the reservoir body are coupled at a joining interface via laser-welding.

9. The cartridge of claim 1, further comprising:
    at least two absorbent pads wedged within an interior volume of the mouthpiece, the at least two absorbent pads defining a central opening therebetween that aligns with at least one mouthpiece opening in the mouthpiece; and
    a central, upper element defining in part a top surface of the wick housing, wherein the central, upper element extends across a major axis of the cartridge between sidewalls of the cartridge and comprises a side cross-sectional profile having a sharpened end that is configured to split vapor flow around the central, upper element and to the mouthpiece such that particles within the generated inhalable vapor are entrained in the at least two absorbent pads.

10. The cartridge of claim 1, wherein the fill port comprises two fill ports positioned on opposing sides of the wick housing.

11. The cartridge of claim 10, wherein each of the opposing sides of the wick housing are mirrored about a longitudinal axis of the cartridge.

12. The cartridge of claim 10, wherein the wick housing comprises two opposing long sides and two opposing short sides, and wherein the two fill ports are positioned on the two opposing long sides.

13. A vaporizer device, comprising:
    a vaporizer body; and
    a cartridge configured to operatively couple with the vaporizer body, the cartridge comprising:
        an atomizer assembly configured to heat a vaporizable material when power is supplied by the vaporizer body to the cartridge to generate an inhalable vapor;
        a reservoir configured to store the vaporizable material, the reservoir comprising:

a wick housing configured to surround at least a portion of the atomizer assembly and form a proximal wall of the reservoir;

wherein the wick housing further comprises a fill port configured to receive the vaporizable material to fill the reservoir with the vaporizable material, wherein the fill port comprises a self-healing septum; and a reservoir body coupled to the wick housing and configured to form a distal wall of the reservoir, the distal wall opposite the proximal wall; and a mouthpiece configured to deliver the inhalable vapor;

wherein the mouthpiece is slidable along an external surface of a side of the wick housing from a first position to a second position in a distal direction, wherein, in the first position, an inwardly projecting feature of the mouthpiece is positioned within a first wick housing groove on the wick housing and, in the second position, the inwardly projecting feature is positioned within a second wick housing groove on the wick housing, wherein the first wick housing groove and the second wick housing groove are shaped so as allow the inwardly projecting feature to slide over each of the first wick housing groove and the second wick housing groove in a first direction and to prevent the inwardly projecting feature of the mouthpiece from sliding over each of the first wick housing groove and the second housing groove in a second direction opposite the first direction, wherein when the mouthpiece is coupled to the wick housing in the first position, the fill port is accessible, and wherein when the mouthpiece is coupled to the wick housing in the second position, the fill port comprising the self-healing septum is inaccessible; and a mouthpiece seal, the mouthpiece seal coupled to the reservoir body, the mouthpiece seal configured to secure the cartridge to the vaporizer, and the mouthpiece seal configured to prevent air from passing through a side of the cartridge.

14. The vaporizer device of claim 13, wherein the cartridge further comprises a base assembly coupled to a distal end of the reservoir, the base assembly comprising:

a base;

an absorbent pad positioned within the base.

15. The cartridge of claim 1, wherein the wick housing comprises a joining rib extending from an exterior surface of the wick housing, the joining rib configured to engage a corresponding joining recess on the mouthpiece seal to thereby strengthen the mouthpiece seal.

16. The cartridge of claim 1, wherein a length of the mouthpiece indicates a volume of the vaporizable material stored within the reservoir.

17. The cartridge of claim 16, wherein the length of the mouthpiece is 19 mm.

18. The cartridge of claim 1, wherein the wick housing and the reservoir body are coupled at a joining interface, the mouthpiece seal surrounds at least a portion of the joining interface.

19. The cartridge of claim 18, wherein the mouthpiece seal is positioned in contact with a portion of the reservoir body opposite the joining interface.

20. The cartridge of claim 19, wherein the mouthpiece seal comprises a region having a thickness positioned in contact with the portion of the reservoir body opposite the joining interface configured to increase a strength of the mouthpiece seal.

* * * * *